(12) United States Patent
Zhong et al.

(10) Patent No.: US 8,754,252 B2
(45) Date of Patent: Jun. 17, 2014

(54) ASYMMETRIC CYCLIZATION PROCESSES USING UNSATURATED NITRO COMPOUNDS

(75) Inventors: Guofu Zhong, Singapore (SG); Bin Tan, Singapore (SG); Pei Juan Chua, Singapore (SG); Zugui Shi, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/541,648

(22) Filed: Jul. 3, 2012

(65) Prior Publication Data

US 2013/0096338 A1 Apr. 18, 2013

Related U.S. Application Data

(63) Continuation of application No. 12/782,704, filed on May 18, 2010, now abandoned.

(60) Provisional application No. 61/179,552, filed on May 19, 2009.

(51) Int. Cl.
*C07C 201/12* (2006.01)
(52) U.S. Cl.
USPC .......................................................... 560/21
(58) Field of Classification Search
None
See application file for complete search history.

(56) References Cited

PUBLICATIONS

Allenmark, Chiroptical methods in the stereochemical analysis of natural products. Nat Prod Rep. Apr. 2000;17(2):145-155.
Bartoli et al., Organocatalytic Asymmetric Friedel-Crafts Alkylation of Indoles with Simple α,β-Unsaturated Ketones. Org Lett. Mar. 29, 2007;9(7):1403-1405.
Bernardi et al., Enantioselective aza-Henry reaction using cinchona organocatalysts. Tetrahedron 2006;62:375-380.
Biaggio et al., Synthesis and Biological Activity of Prostaglandin Analogs Containing Heteroatoms in the Cyclopentane Ring. Curr Org Chem. 2005;9(5):419-457.
Enders et al., Organocatalytic One-Pot Asymmetric Synthesis of Functionalized Tricyclic Carbon Frameworks from a Triple-Cascade/Diels—Alder Sequence. Angew Chem Int Ed Engl. 2007;46(3):467-469.
Enders et al., Control of four stereocentres in a triple cascade organocatalytic reaction. Nature Jun. 15, 2006;441 (7095):861-863.
France et al., Bifunctional Lewis Acid-Nucleophile-Based Asymmetric Catalysis: Mechanistic Evidence for Imine Activation Working in Tandem with Chiral Enolate Formation in the Synthesis of β-Lactams. J Am Chem Soc. Feb. 2, 2005;127(4):1206-1215.
Harper et al., Stereochemical Analysis by Solid-State NMR: Structural Predictions in Ambuic Acid. J Org Chem. Jun. 13, 2003;68(12):4609-4614.
Hayashi, et al, Diphenylprolinol Silyl Ether as a Catalyst in an Enantioselective, Catalytic, Tandem Michael/Henry Reaction for the Control of Four Stereocenters. Angew Chem Int Ed Engl. 2007;46(26):4922-4925.
Ihara and Fukumoto, Syntheses of Polycyclic Natural Products Employing the Intramolecular Double Michael Reaction. Angew Chem Int Ed Engl. 1993;32:1010-1022.
Lautens et al., Transition Metal-Mediated Cycloaddition Reactions. Chem Rev. Feb. 1, 1996;96(1):49-92.
Li et al., Enantioselective Nitroaldol Reaction of a.-Ketoesters Catalyzed by Cinchona Alkaloids. J Am Chem Soc. Jan. 25, 2006;128(3):732-733.
Marcelli et al., Asymmetric Organocatalytic Henry Reaction. Angew Chem Int Ed Engl. Jan. 30, 2006;45(6):929-931.
Masse and Panek, Diastereoselective Reactions of Chiral Allyl- and Allenylsilanes with Activated C=X pi-Bonds. Chem Rev. 1995;95(5):1293-1316.
Mattson et al., Direct Nucleophilic Acylation of Nitroalkenes Promoted by a Fluoride Anion/Thiourea Combination. J Am Chem Soc. Apr. 19, 2006;128(15):4932-4933.

(Continued)

*Primary Examiner* — Janet L Andres
*Assistant Examiner* — Timothy R Rozof
(74) *Attorney, Agent, or Firm* — Sam K. Tahmassebi; TechLaw LLP

(57) ABSTRACT

Disclosed are processes of forming a compound (33), (35) or (37)

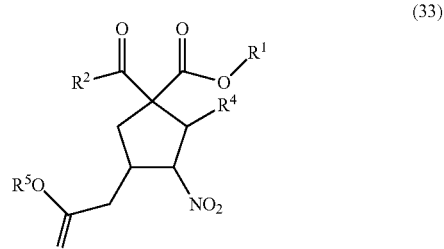

(33)

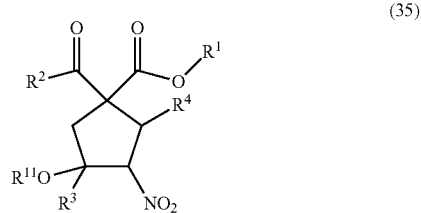

(35)

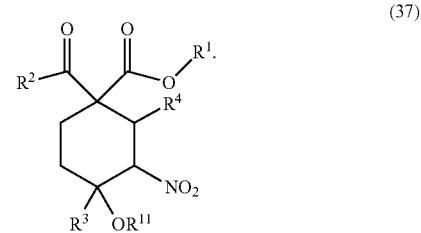

(37)

11 Claims, 96 Drawing Sheets

(56) References Cited

PUBLICATIONS

McCooey and Connon, Urea- and Thiourea-Substituted Cinchona Alkaloid Derivatives as Highly Efficient Bifunctional Organocatalysts for the Asymmetric Addition of Malonate to Nitroalkenes: Inversion of Configuration at C9 Dramatically Improves Catalyst Performance. Angew Chem Int Ed Engl. Oct. 7, 2005;44(39):6367-6370.

McCooey and Connon, Readily Accessible 9-epi-amino Cinchona Alkaloid Derivatives Promote Efficient, Highly Enantioselective Additions of Aldehydes and Ketones to Nitroolefins. Org Lett. Feb. 15, 2007;9(4):599-602.

Okino et al., Enantio- and Diastereoselective Michael Reaction of 1,3-Dicarbonyl Compounds to Nitroolefins Catalyzed by a Bifunctional Thiourea. J Am Chem Soc. Jan. 12, 2005;127(1):119-125.

Palomo et al., Recent Advances in the Catalytic Asymmetric Nitroaldol (Henry) Reaction. Eur J Org Chem. 2007:2561-2574.

Riccio et al., Stereochemical analysis of natural products. Approaches relying on the combination of NMR spectroscopy and computational methods. Pure Appl Chem. 2003;75(2-3):295-308.

Silva, Construction of cyclopentyl units by ring contraction reactions. Tetrahedron 2002;58:9137-9161.

Song et al., The Mannich Reaction of Malonates with Simple Imines Catalyzed by Bifunctional Cinchona Alkaloids: Enantioselective Synthesis of β-Amino Acids. Am Chem Soc. May 10, 2006;128(18)-6049:6048.

Taggi et al., Catalytic, Asymmetric Synthesis of beta-Lactams. J Am Chem Soc. 2000;122(32):7831-7832.

Tan et al., Organocatalytic Asymmetric Tandem Michael-Henry Reactions: A Highly Stereoselective Synthesis of Multifunctional Cyclohexanes with Two Quaternary Stereocenters, Org Lett. Jun. 19, 2008;10(12):2437-2440.

Tillman et al., Direct enantio- and diastereoselective Mannich reactions of malonate and β-keto esters with N-Boc and N-Cbz aldimines catalysed by a bifunctional cinchonine derivative. Chem Commun (Camb). Mar. 21, 2006;(11):1191-1193.

Vakulya et al., Highly Enantioselective Conjugate Addition of Nitromethane to Chalcones Using Bifunctional Cinchona Organocatalysts. Org Lett. May 12, 2005;7(10):1967-1969.

Xie et al., Highly Asymmetric Michael Addition to α,β-Unsaturated Ketones Catalyzed by 9-Amino-9-deoxyepiquinine. Angew Chem Int Ed Engl. 2007;46(3):389-392.

Xie et al., Highly Enantioselective Michael Addition of Cyclic 1,3-Dicarbonyl Compounds to α,β-Unsaturated Ketones. Org. Lett. Feb. 1, 2007;9(3):413-415.

Ye et al., Enantioselective organocatalytic Michael addition of malonate esters to nitro olefins using bifunctional cinchonine derivatives. Chem Commun (Camb). Sep. 21, 2005;(35):4481-4483.

Zheng et al., Highly enantioselective direct aldol reaction catalyzed by cinchona derived primary amines. Org Biomol Chem. Sep. 21, 2007;5(18):2913-2915.

| entry | cat. | solvent | time (h) | yield[b] (%) | dr[c] | ee[d] (%) |
|---|---|---|---|---|---|---|
| 1 | I | neat | 3 | 85 | 92:8 | 80 |
| 2 | I | toluene | 8 | 88 | 93:7 | 78 |
| 3[e] | I | neat | 8 | 86 | 93:7 | 77 |
| 4 | II | neat | 3 | 95 | 85:15 | 26 |
| 5 | III | neat | 3 | 94 | 82:18 | 23 |
| 6 | IV | neat | 10 | 92 | 78:22 | 65 |
| 7 | V | neat | 18 | 90 | 95:5 | 92 |
| 8 | VI | neat | 10 | 92 | 95:5 | 92 |
| 9 | VI | toluene | 24 | 88 | 97:3 | > 99 |
| 10[f] | VI | toluene | 18 | 92 | 98:2 | > 99 |
| 11[f] | VI | Et$_2$O | 16 | 93 | 98:2 | > 99 |
| 12[f,g] | VI | Et$_2$O | 16 | 93 | 98:2 | > 99 |

| entry | R[4] | 3 | time (h) | yield[b] (%) | dr | ee[c] (%) |
|---|---|---|---|---|---|---|
| 1 | Ph | 3a | 16 | 93 | 98:2 | >99 |
| 2 | 4-MeO-C6H4 | 3b | 24 | 91 | 95:5 | 98 |
| 3 | 4-Me-C6H4 | 3c | 24 | 89 | 96:4 | 98 |
| 4 | 3-Me-C6H4 | 3d | 24 | 90 | 95:5 | 99 |
| 5 | 4-Br-C6H4 | 3e | 30 | 88 | 93:7 | >99 |
| 6 | 2-Br-C6H4 | 3f | 20 | 90 | 99:1 | 97 |
| 7 | 4-Cl-C6H4 | 3g | 24 | 87 | 93:7 | 97 |
| 8 | 2-Cl-C6H4 | 3h | 24 | 91 | 96:4 | 97 |
| 9 | 2-O2N-C6H4 | 3i | 24 | 94 | 98:2 | 97 |
| 10 | 4-CF3-C6H4 | 3j | 24 | 91 | 95:5 | 98 |

| entry | catalyst | solvent | t (h) | yield (%)[b] | dr[c] | ee (%)[d] |
|---|---|---|---|---|---|---|
| 1 | II | neat | 6 | 72 | 94:6 | 23 |
| 2 | I | neat | 5 | 73 | 96:4 | 79 |
| 3 | I | toluene | 8 | 91 | 96:4 | 82 |
| 4 | I | Et$_2$O | 8 | 90 | 97:3 | 83 |
| 5[e] | I | Et$_2$O | 24 | 88 | 97:3 | 83 |
| 6 | IV | Et$_2$O | 8 | 90 | 96:4 | 80 |
| 7 | VII | Et$_2$O | 8 | 87 | 96:4 | 95 |
| 8 | VI | Et$_2$O | 16 | 91 | >99:1 | 97 |
| 9 | V | Et$_2$O | 16 | 91 | 97:3 | 95 |
| 10[f] | VI | Et$_2$O | 30 | 85 | >99:1 | 97 |
| 11 | VI | toluene | 36 | 86 | 97:3 | 90 |
| 12[e] | VI | Et$_2$O | 24 | 87 | >99:1 | 96 |
| 13[g] | VI | Et$_2$O | 16 | 82 | >99:1 | 96 |

| entry | R[4] | 5 | t (h) | yield(%)[b] | dr[c] | ee (%)[d] |
|---|---|---|---|---|---|---|
| 1 | Ph (2a) | 5a | 16 | 91 | >99:1 | 97 |
| 2 | 4-MeC$_6$H$_4$ (2c) | 5c | 24 | 89 | 97:3 | 95 |
| 3 | 3-MeC$_6$H$_4$ (2d) | 5d | 24 | 85 | 96:4 | 95 |
| 4[e] | 4-MeOC$_6$H$_4$ (2b) | 5b | 30 | 83 | 96:4 | 94 |
| 5[e] | 2-MeOC$_6$H$_4$ (2l) | 5l | 30 | 81 | 98:2 | 90 |
| 6 | 4-BrC$_6$H$_4$ (2e) | 5e | 16 | 92 | >99:1 | 95 |
| 7 | 4-ClC$_6$H$_4$ (2g) | 5g | 16 | 88 | 98:2 | 95 |
| 8 | 2-naphthyl (2m) | 5m | 24 | 84 | 95:5 | 95 |
| 9 | 1-naphthyl (2n) | 5n | 24 | 87 | 97:3 | 97 |
| 10 | 3-furanyl (2o) | 5o | 24 | 86 | 98:2 | 97 |
| 11 | 2-furanyl (2p) | 5p | 24 | 87 | 95:5 | 96 |
| 12 | 2-thienyl (2q) | 5q | 18 | 91 | >99:1 | 96 |
| 13[e] | 4-O$_2$NC$_6$H$_4$ (2r) | 5r | 36 | 81 | 96:4 | 95 |

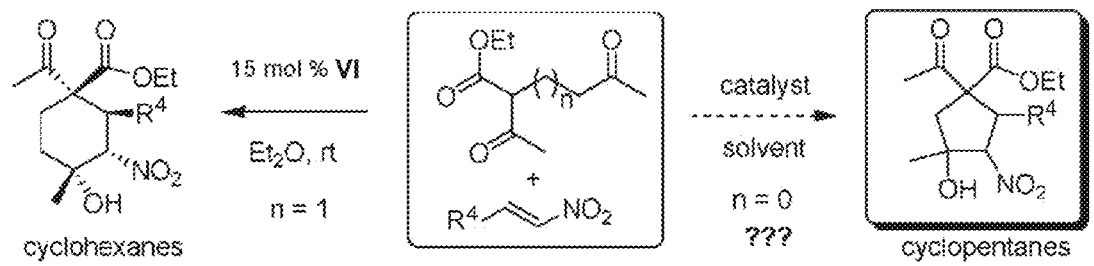
Fig. 10
Fig. 12
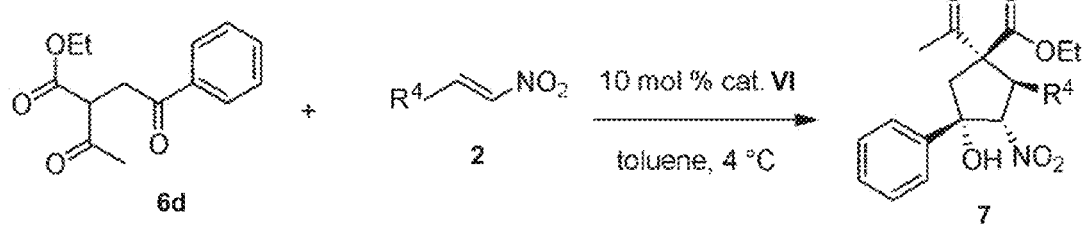
| entry | R[4] | 7 | time (h) | yield (%)[b] | ee (%)[c] |
|---|---|---|---|---|---|
| 1 | Ph | 7a | 36 | 93 | 95 |
| 2 | 3-MeO-C$_6$H$_4$ | 7w | 48 | 91 | 92 |
| 3 | 4-MeO-C$_6$H$_4$ | 7b | 60 | 93 | 92 |
| 4 | 2-Me-C$_6$H$_4$ | 7t | 48 | 90 | 90 |
| 5 | 4-Me-C$_6$H$_4$ | 7c | 48 | 91 | 95 |
| 6 | 4-Br-C$_6$H$_4$ | 7e | 40 | 94 | 91 |
| 7 | 4-Cl-C$_6$H$_4$ | 7v | 36 | 95 | 95 |
| 8 | 2-thienyl | 7q | 40 | 93 | 93 |
| 9 | 2-furyl | 7p | 48 | 91 | 92 |
| 10 | 1-naphthyl | 7n | 60 | 91 | 96 |
| 11 | 4-O$_2$N-C$_6$H$_4$ | 7r | 72 | 90 | 91 |
| 12 | 4-CF$_3$-C$_6$H$_4$ | 7j | 48 | 95 | 92 |

| entry | 6 | catalyst | solvent | time (h) | yield[b] (%) | ee[c] (%) |
|---|---|---|---|---|---|---|
| 1 | 6a | VI | Et$_2$O | 18 | 92 | 67 |
| 2 | 6a | I | neat | 3 | 94 | 71 |
| 3 | 6a | I | toluene | 10 | 92 | 80 |
| 4[d] | 6a | I | toluene | 18 | 90 | 82 |
| 5 | 6b | I | neat | 3 | 92 | 70 |
| 6 | 6c | I | neat | 3 | NR[e] | NA[f] |
| 7 | 6d | I | neat | 3 | 95 | 75 |
| 8 | 6e | I | neat | 3 | 94 | 75 |
| 9 | 6d | I | toluene | 10 | 92 | 80 |
| 10[d] | 6d | I | toluene | 18 | 93 | 83 |
| 11 | 6d | IV | toluene | 10 | 94 | 75 |
| 12 | 6d | III | toluene | 18 | 93 | 65 |
| 13 | 6d | VI | toluene | 18 | 93 | 90 |
| 14 | 6d | VI | Et$_2$O | 18 | 92 | 88 |
| 15[d] | 6d | VI | toluene | 36 | 93 | 95 |

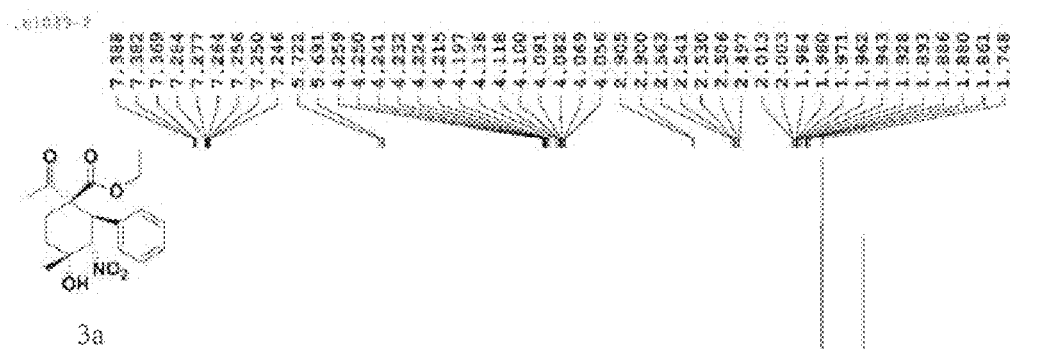
Fig. 18A
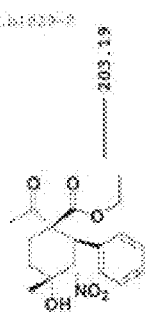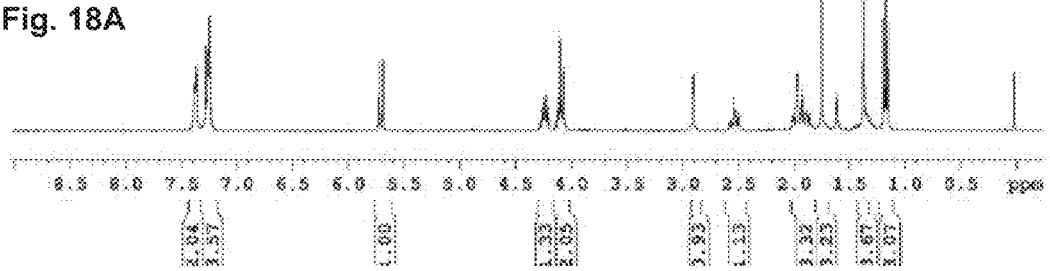
Fig. 18B

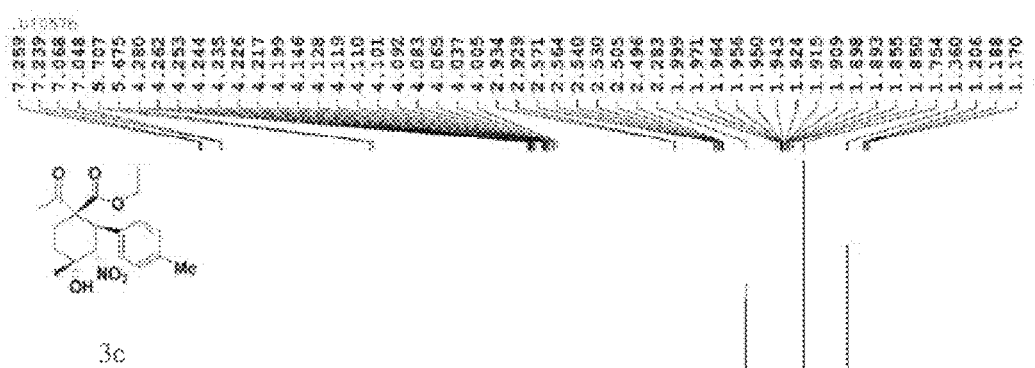
Fig. 20A
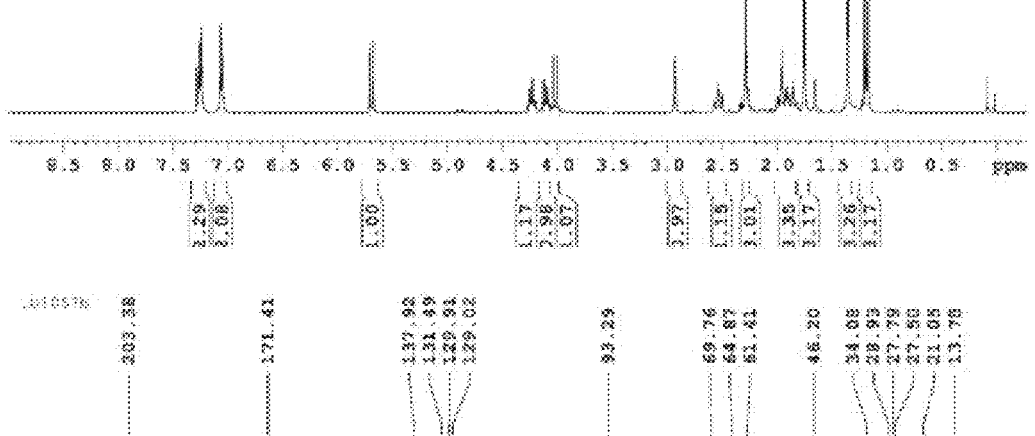
Fig. 20B
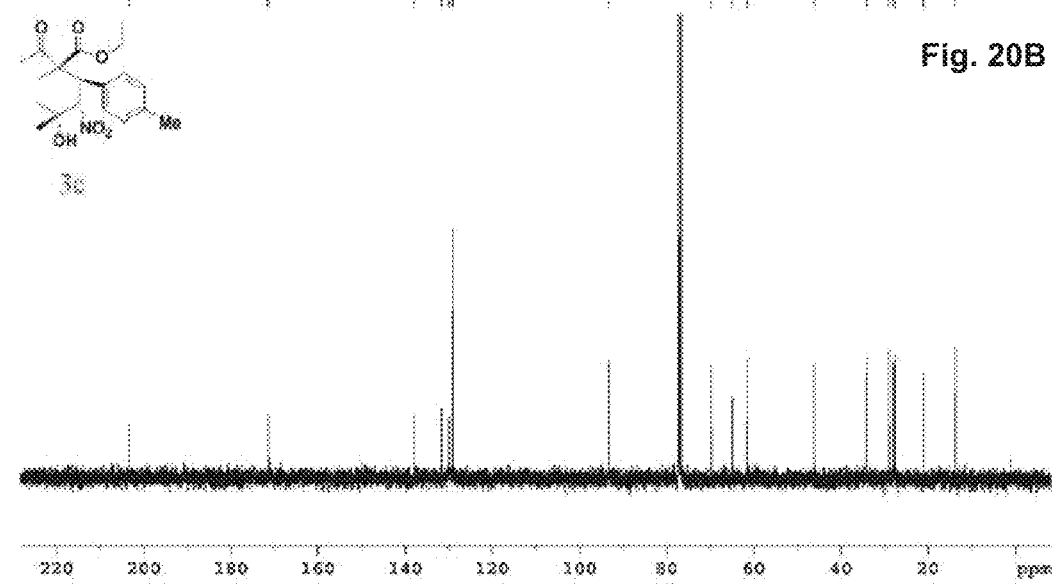

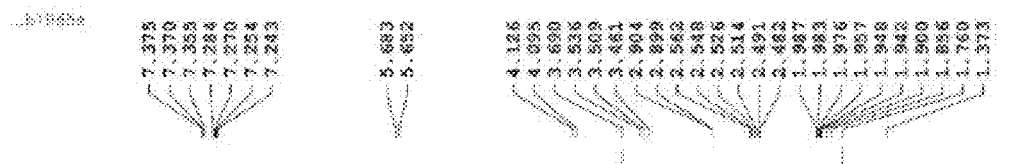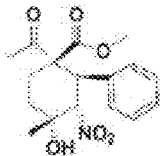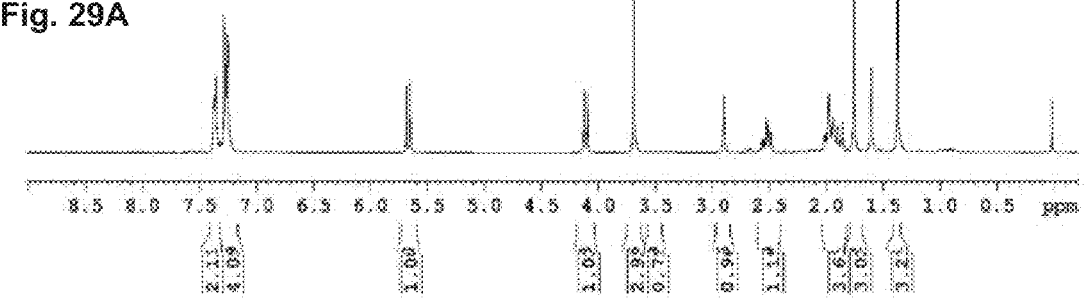
Fig. 29A
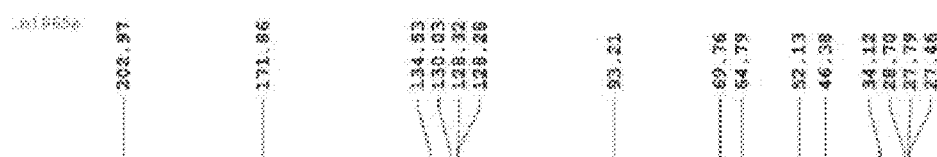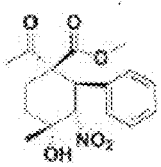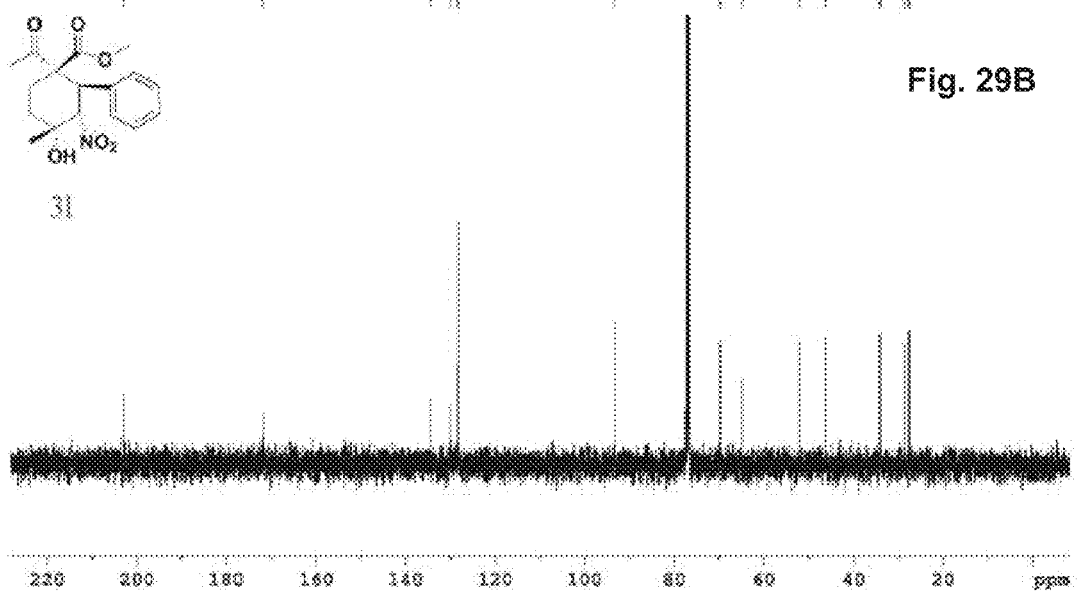
Fig. 29B

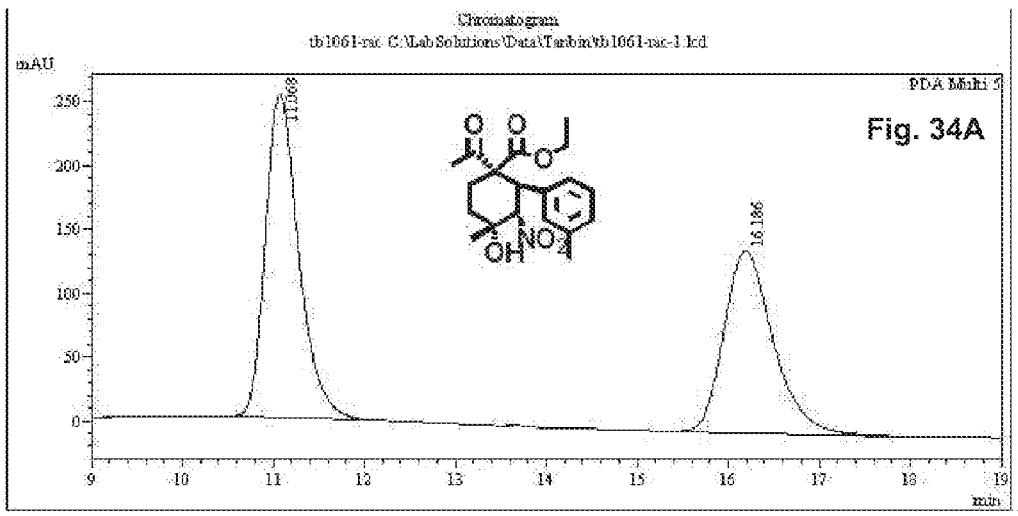
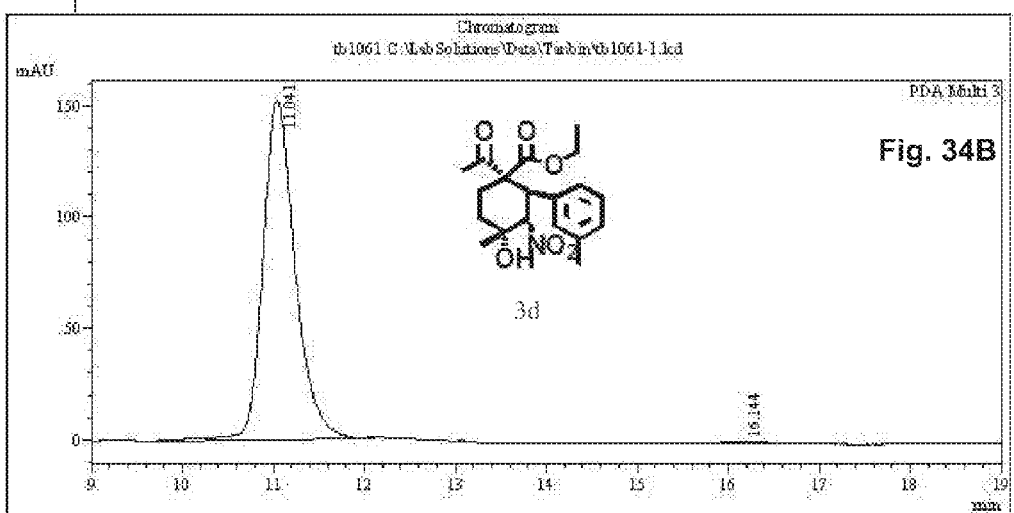

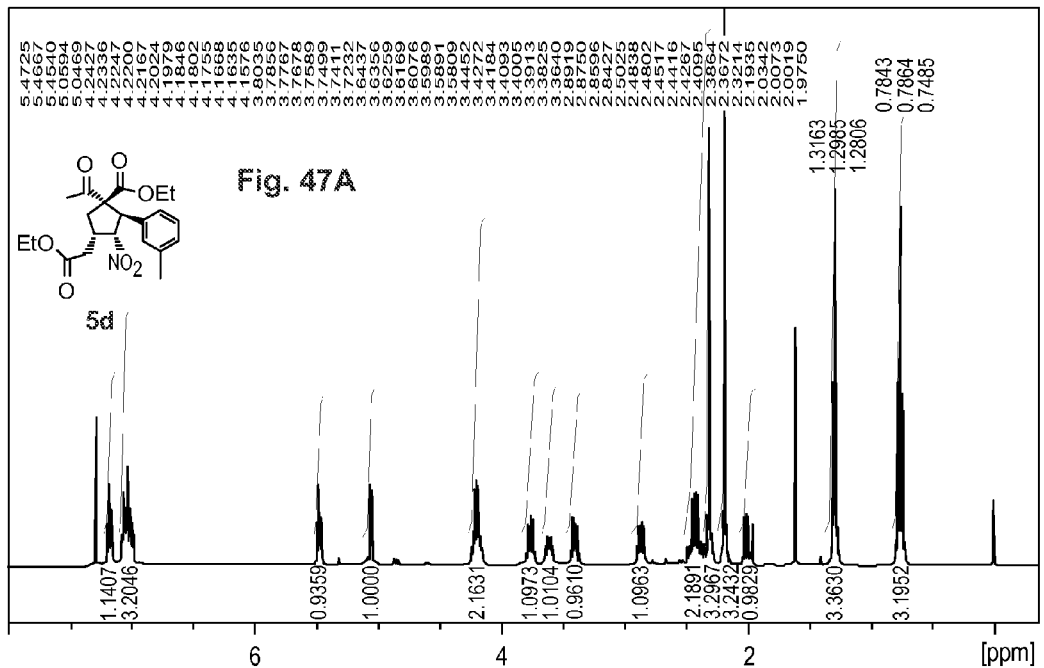
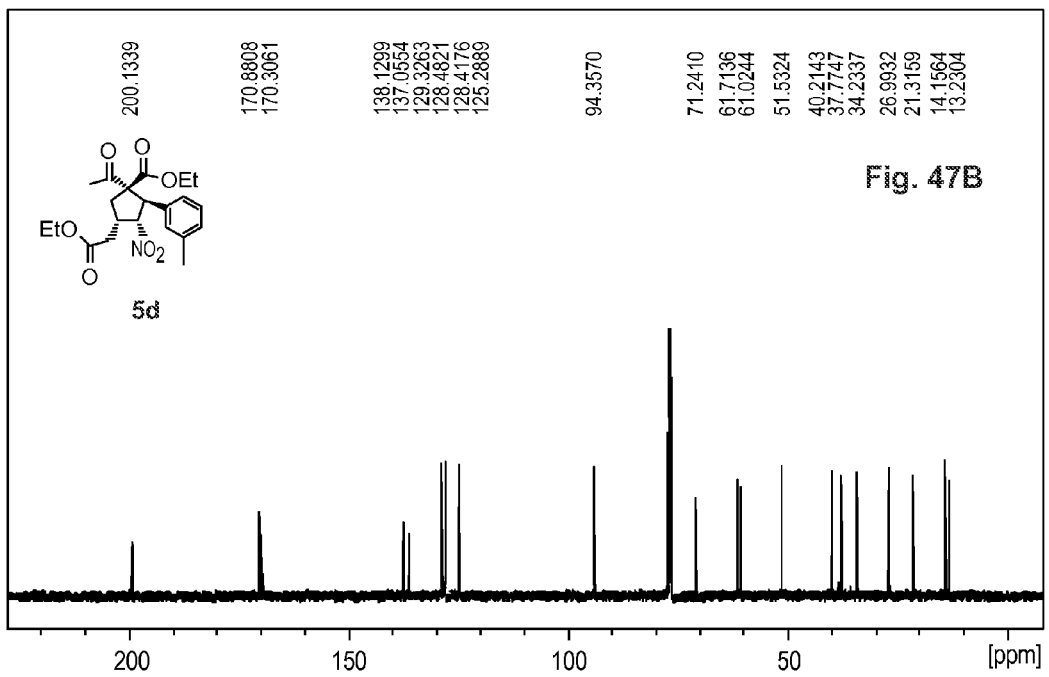

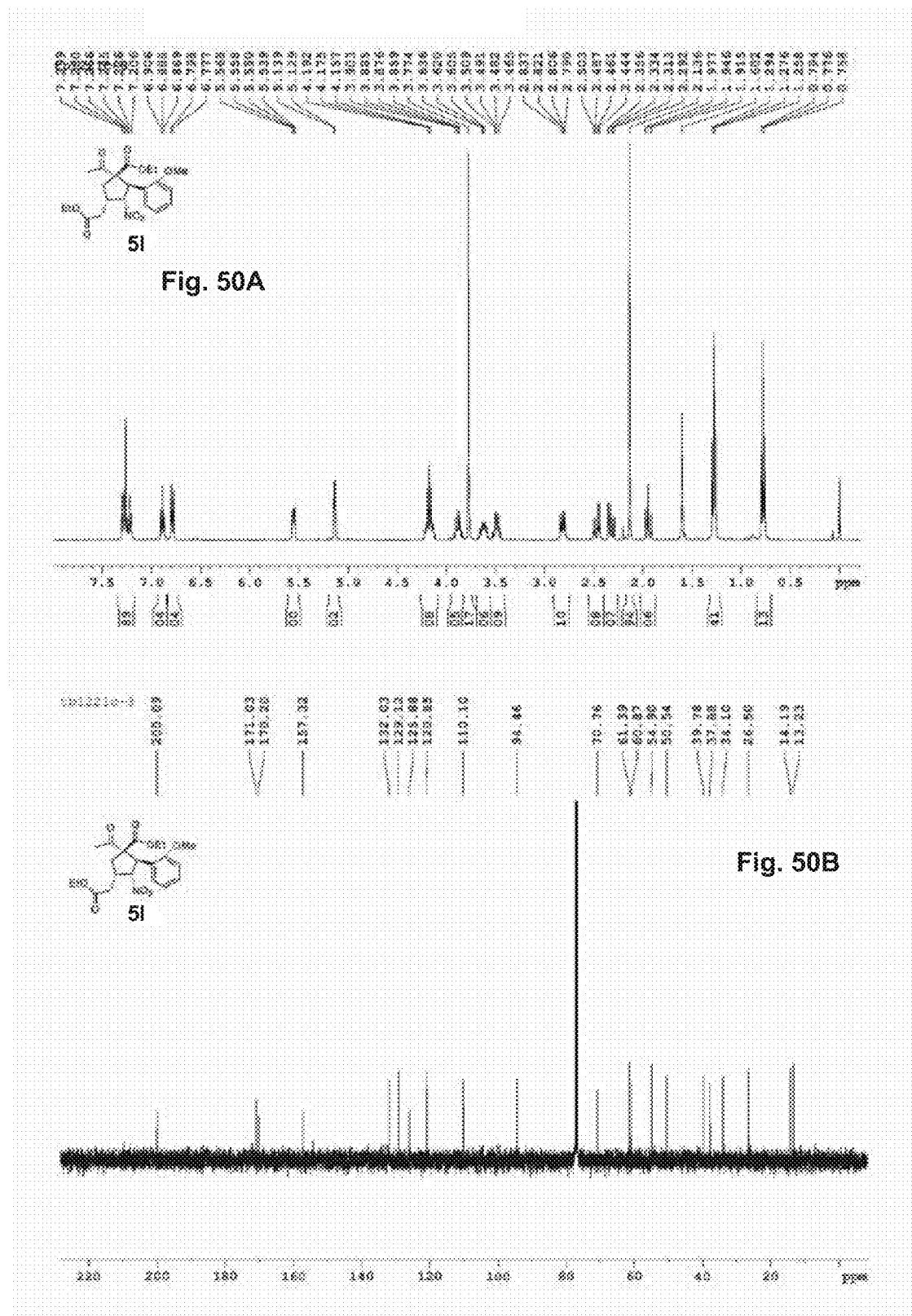

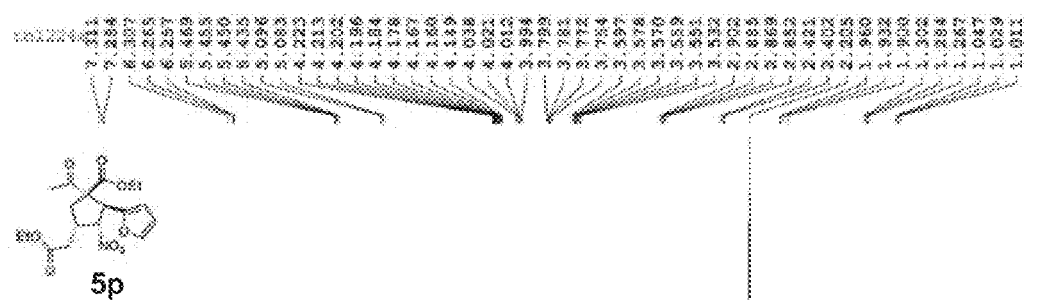
Fig. 54A
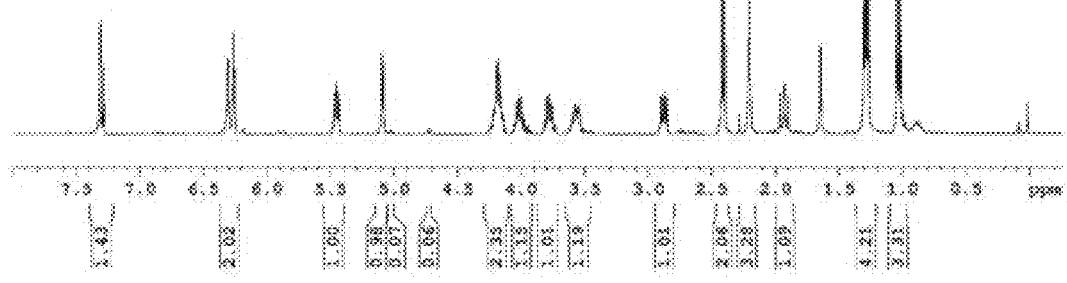
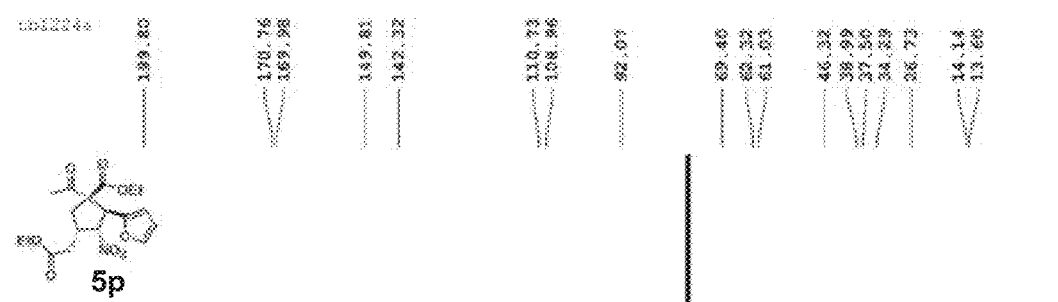
Fig. 54B
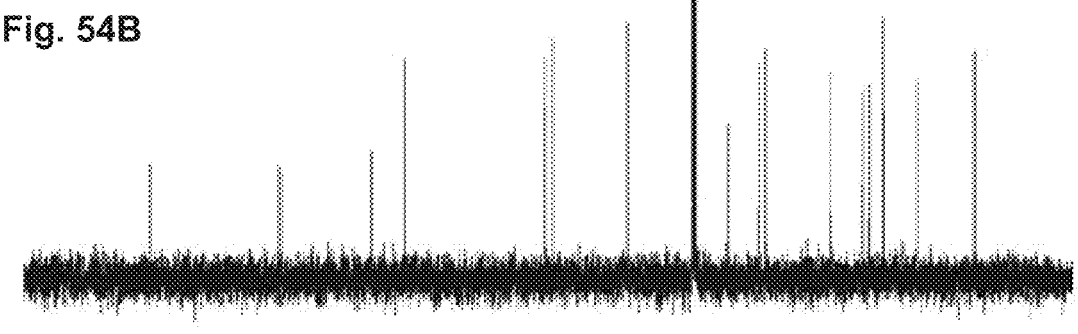

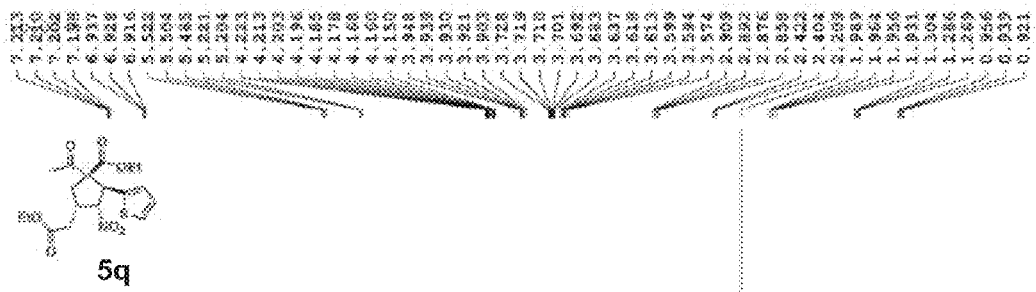
Fig. 55A
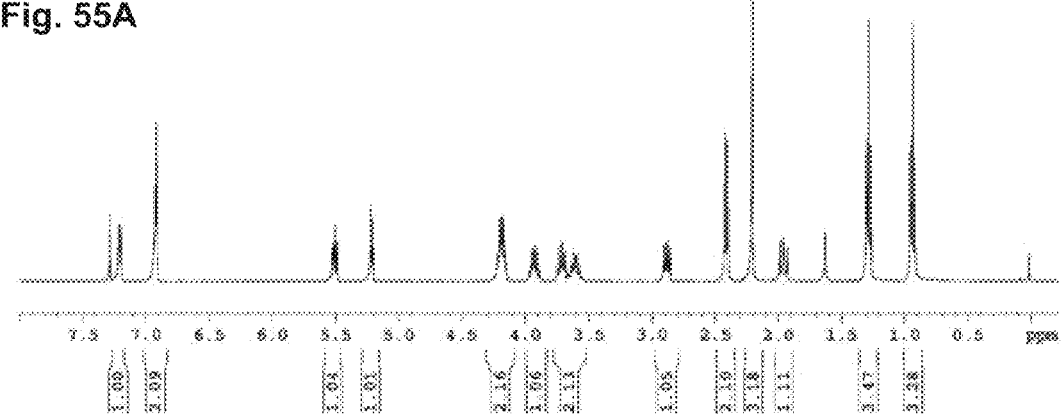
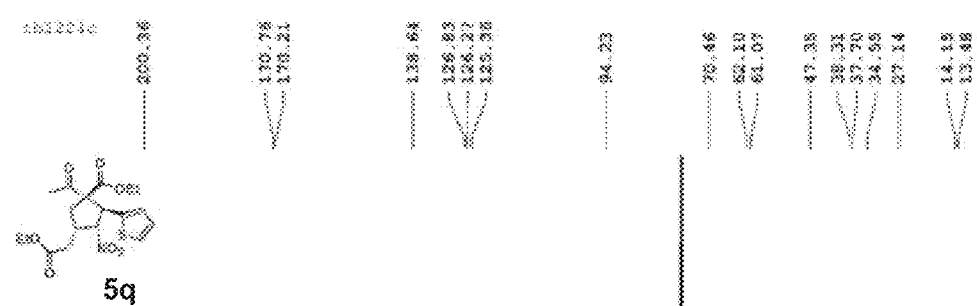
Fig. 55B
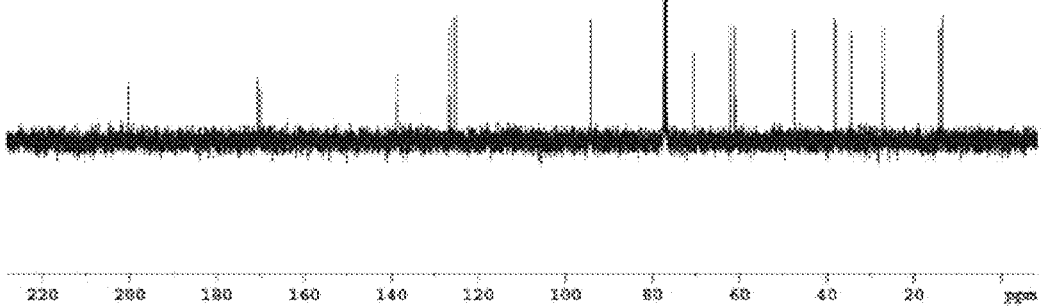

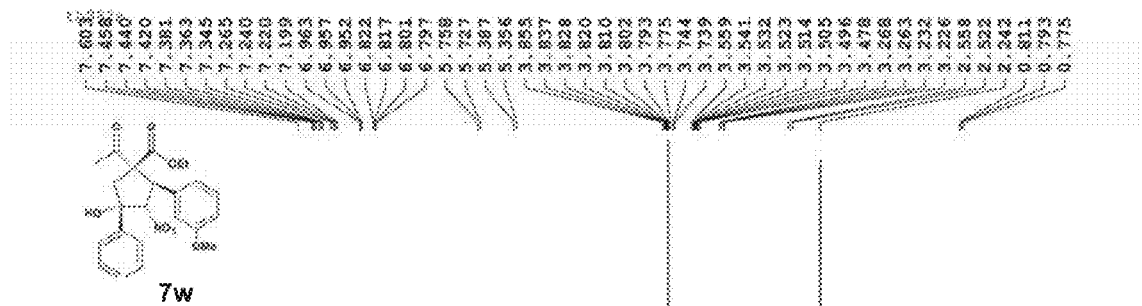
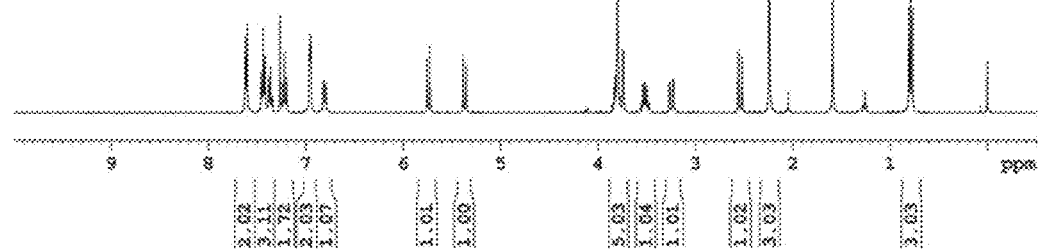
Fig. 75A
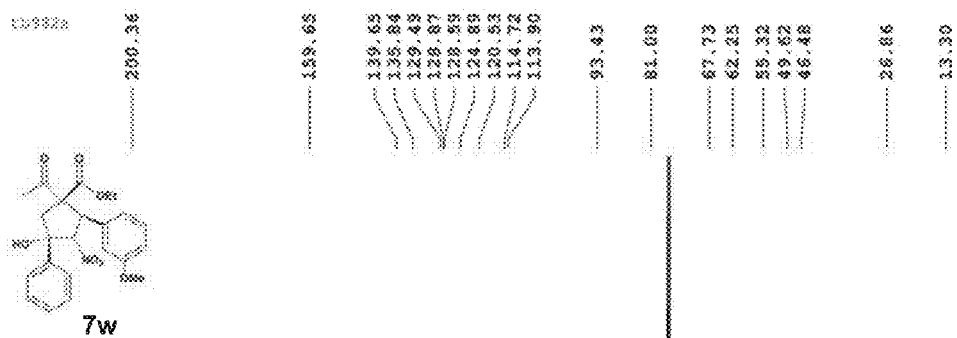
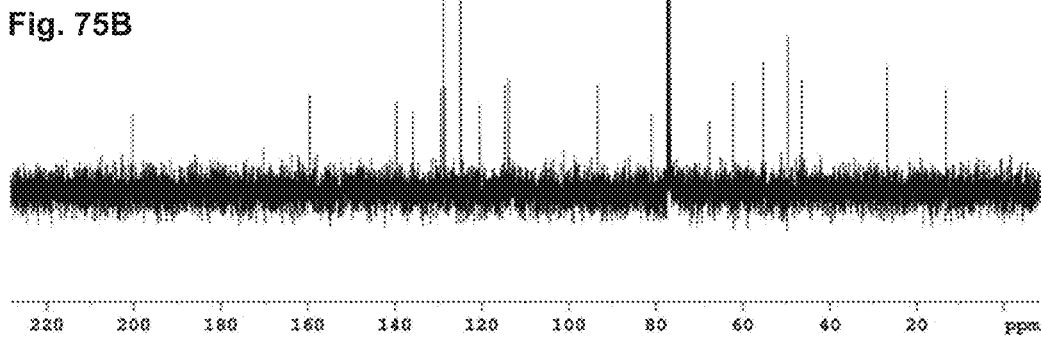
Fig. 75B

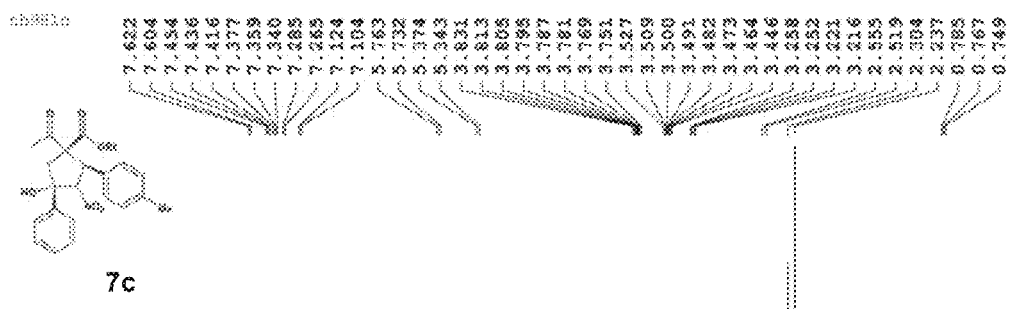
Fig. 78A
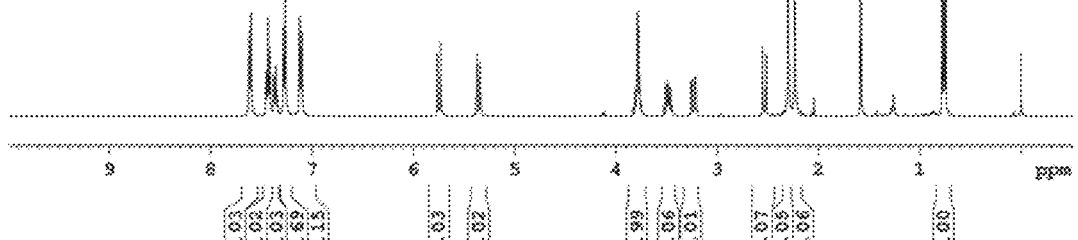
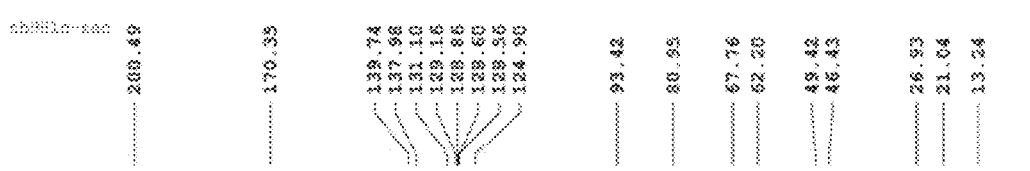
Fig. 78B
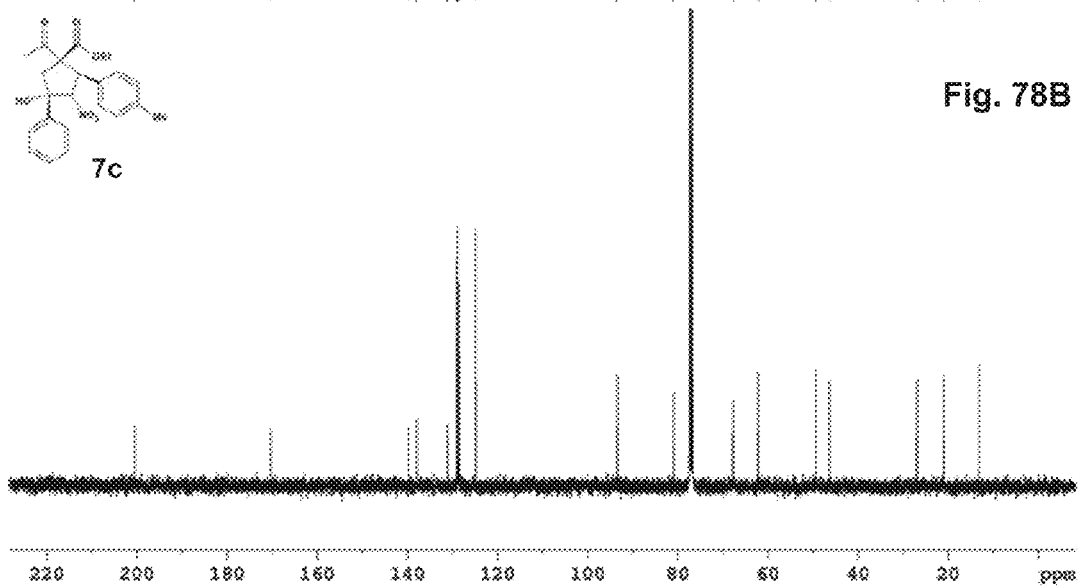

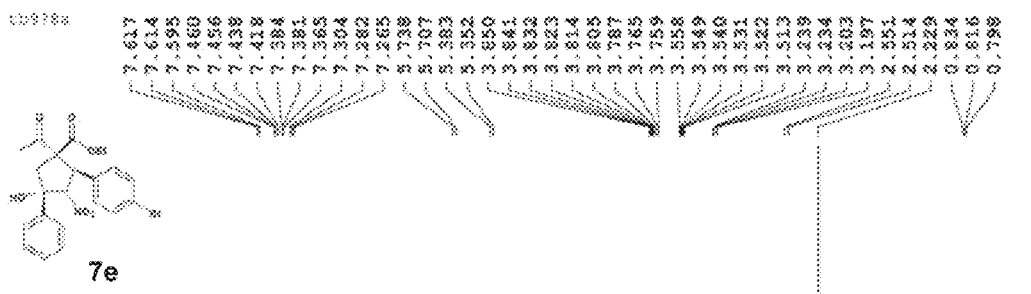
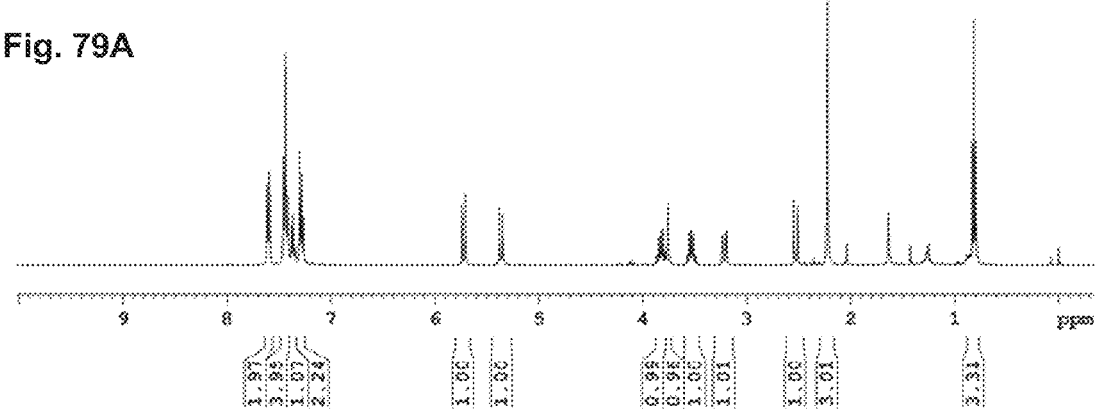
Fig. 79A
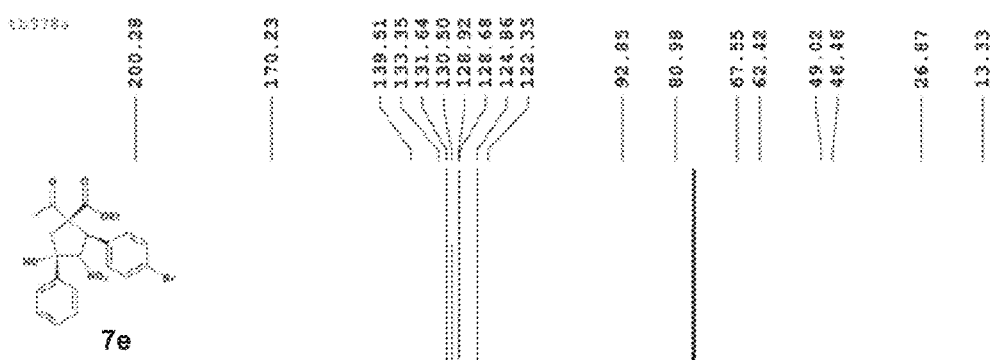
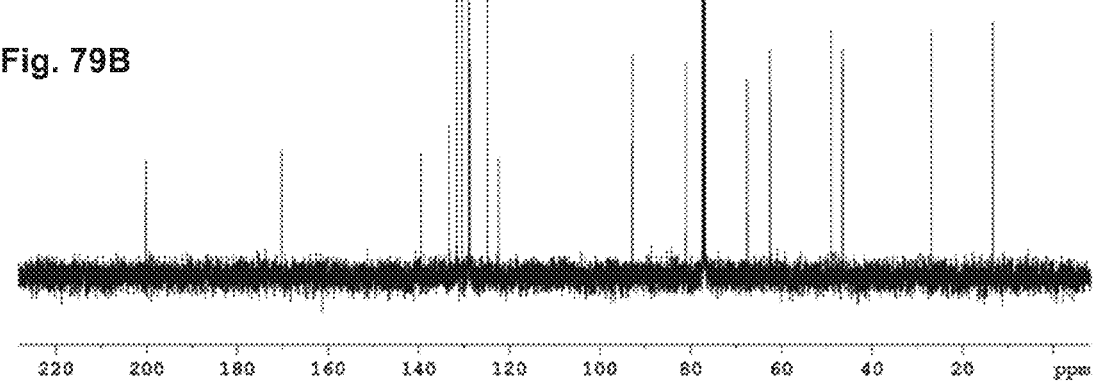
Fig. 79B

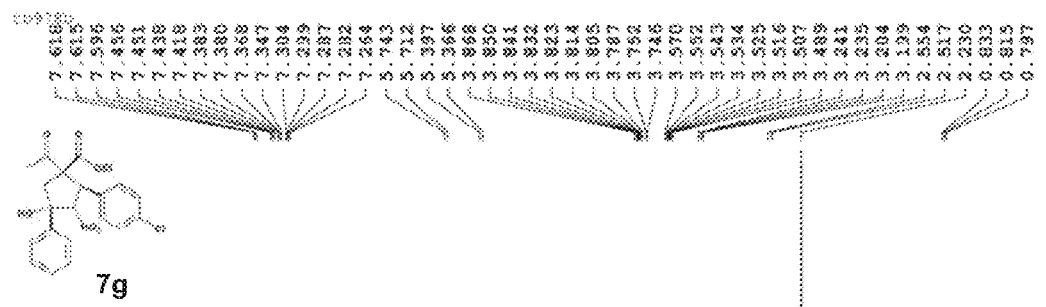
Fig. 80A
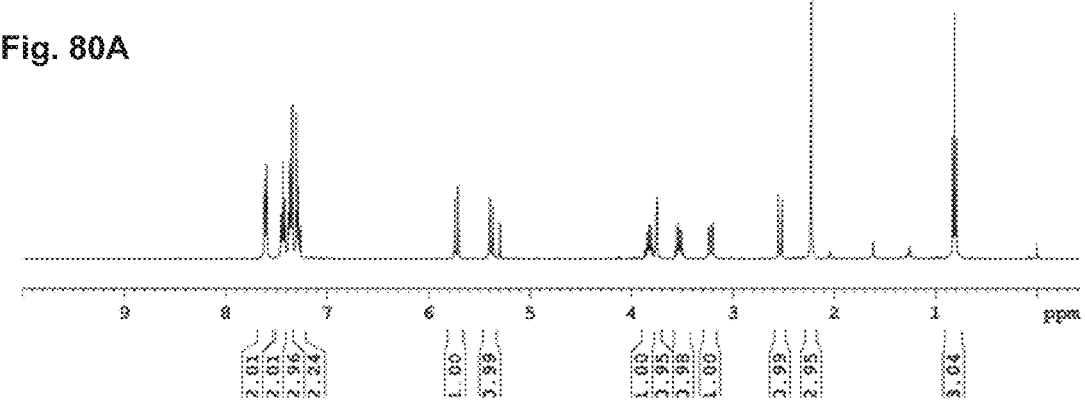
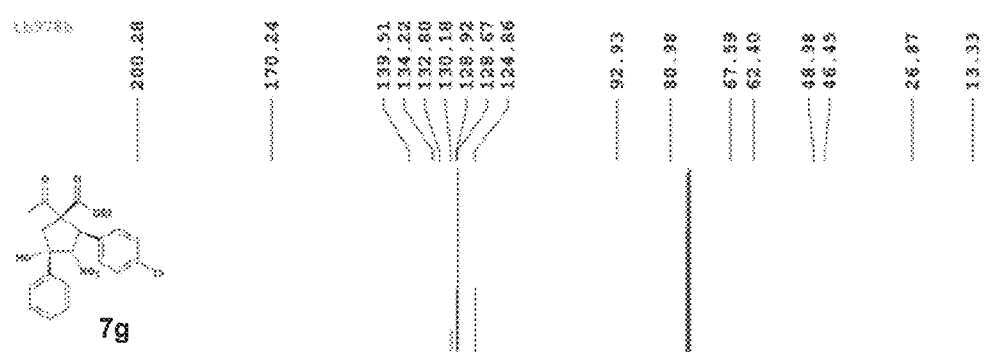
Fig. 80B
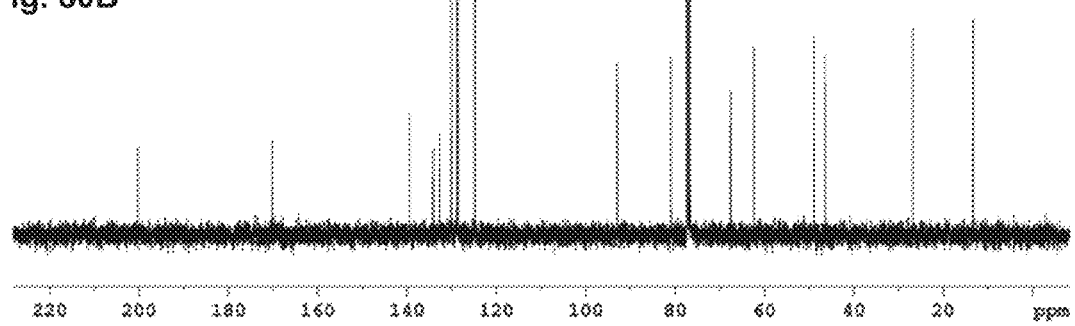

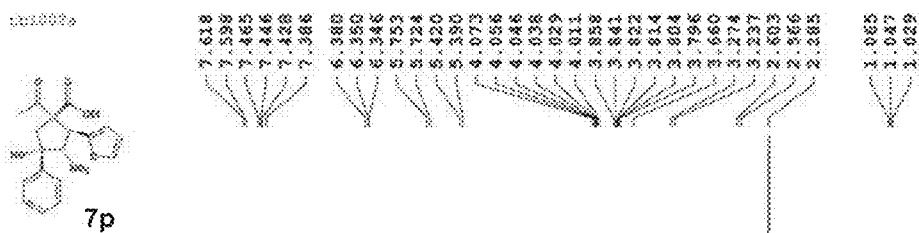
Fig. 82A
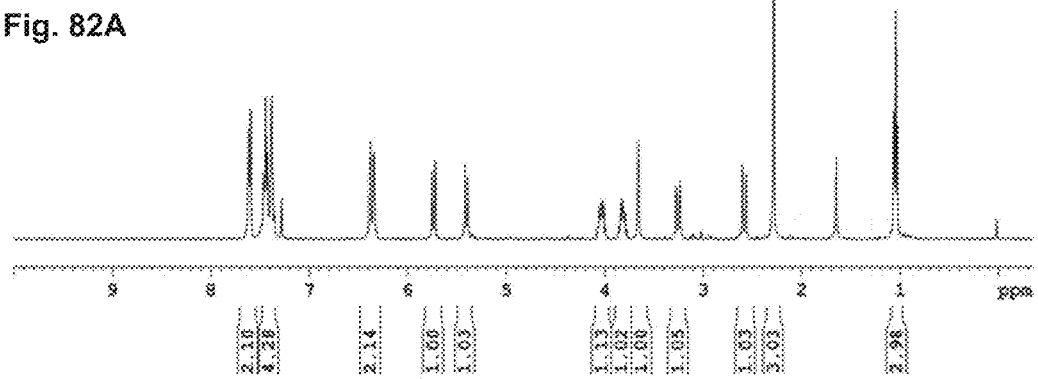
Fig. 82B
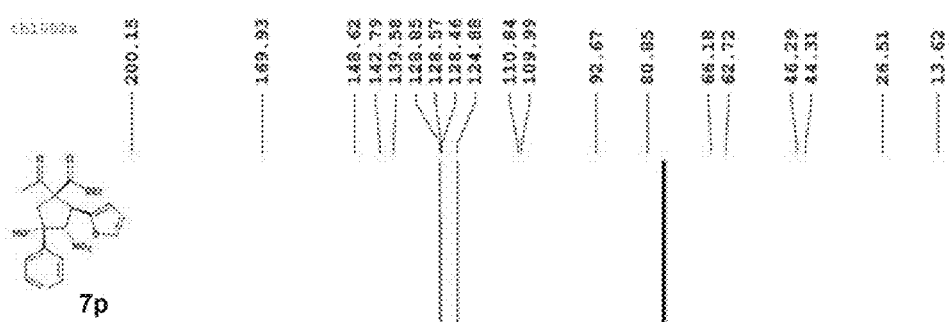
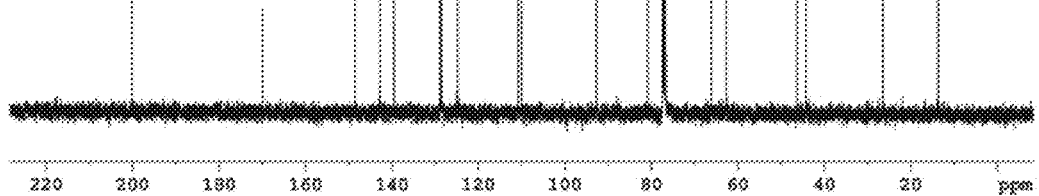

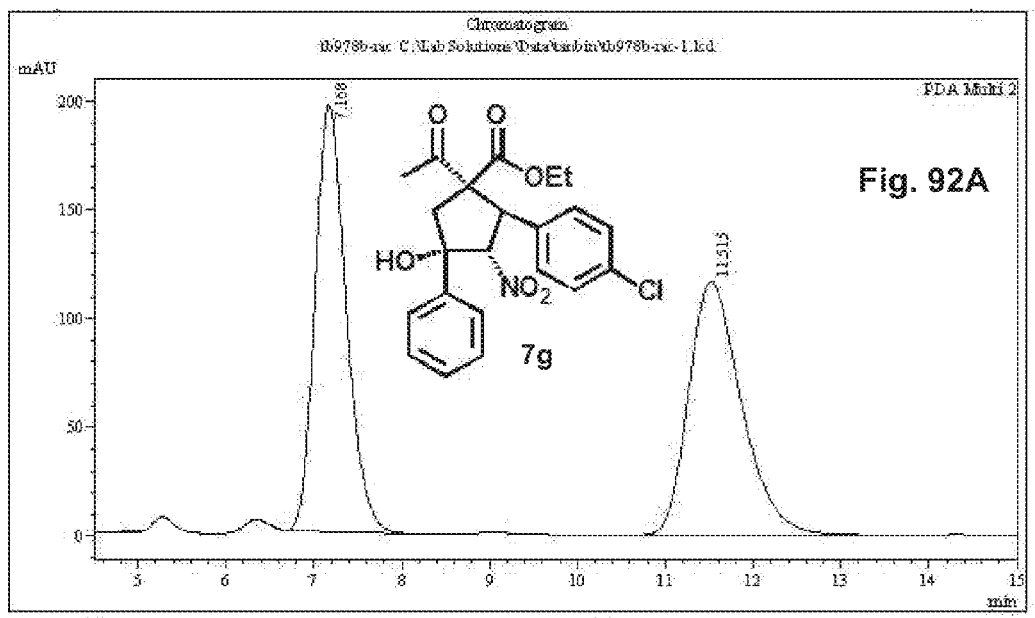
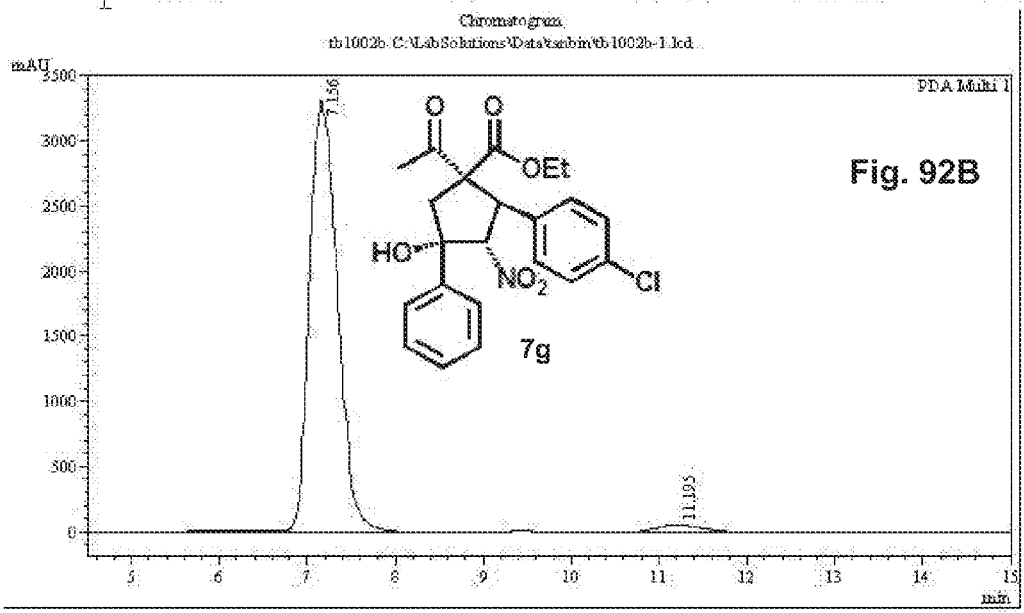

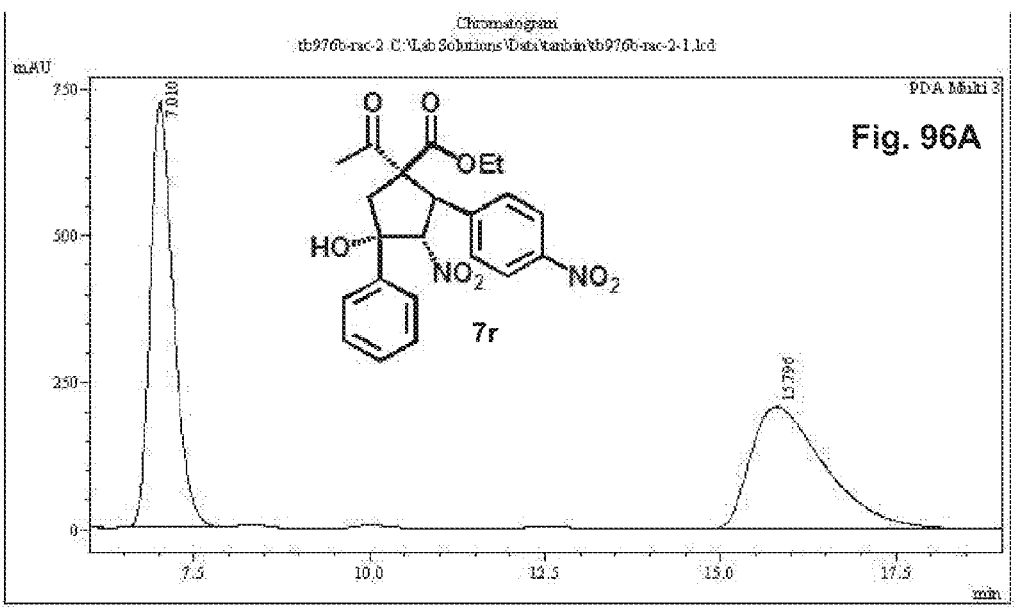
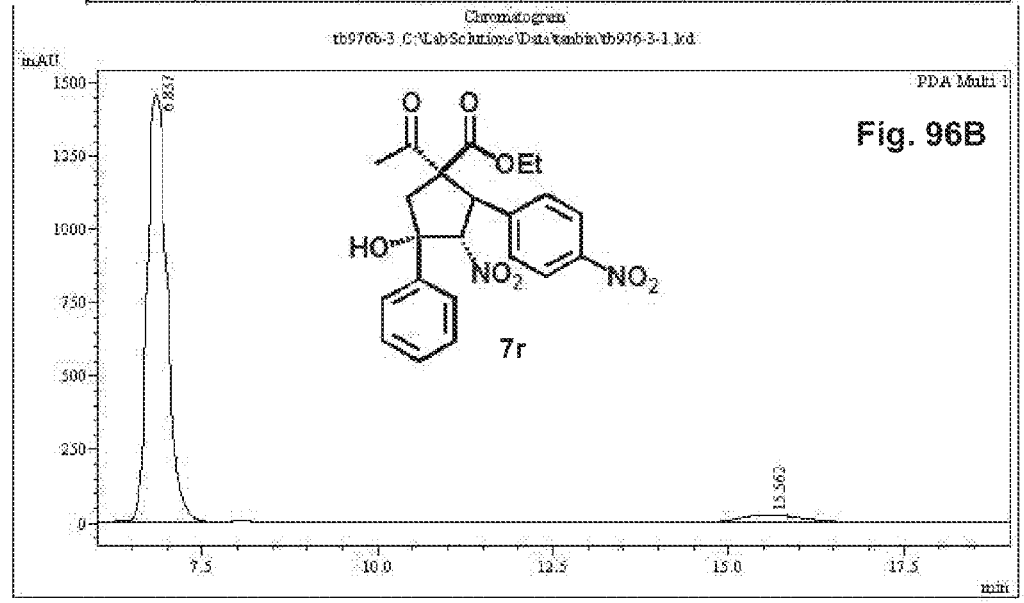

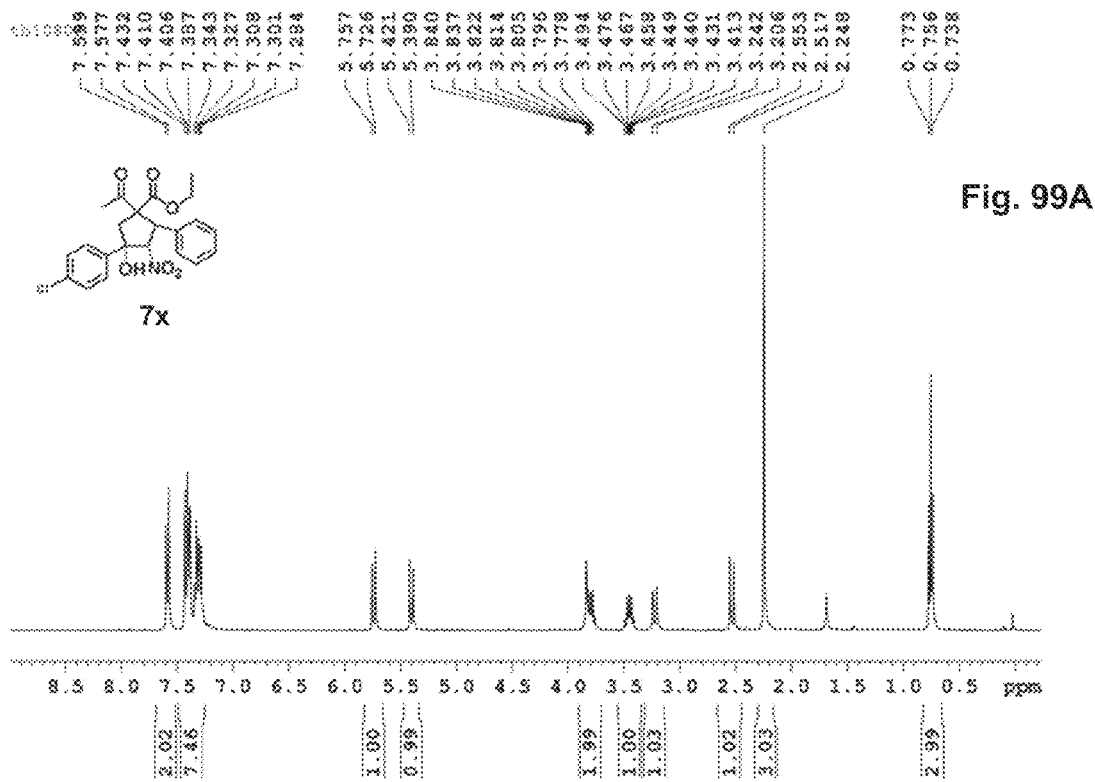
Fig. 99A
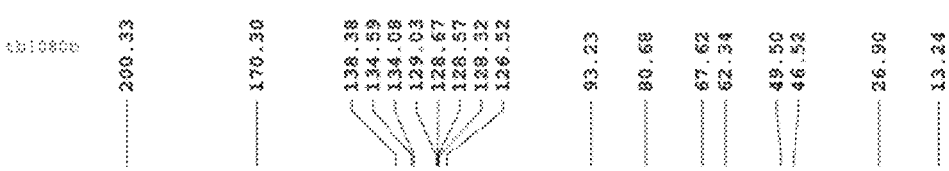
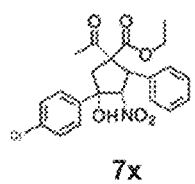
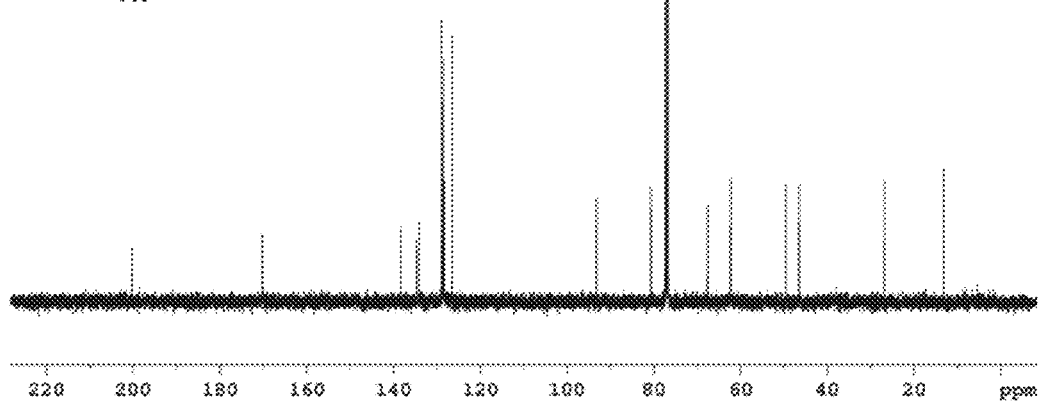
Fig. 99B

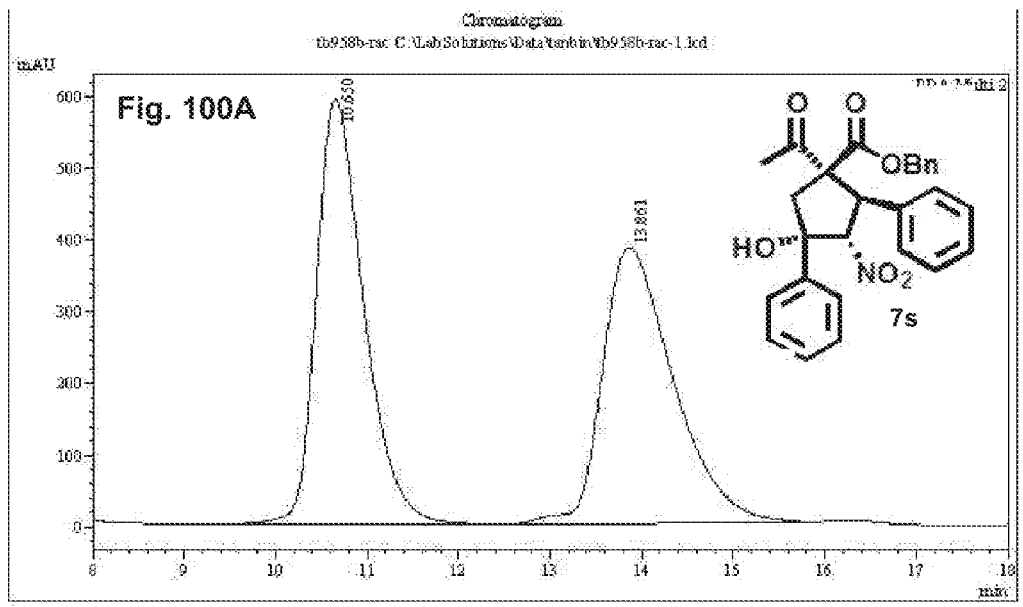
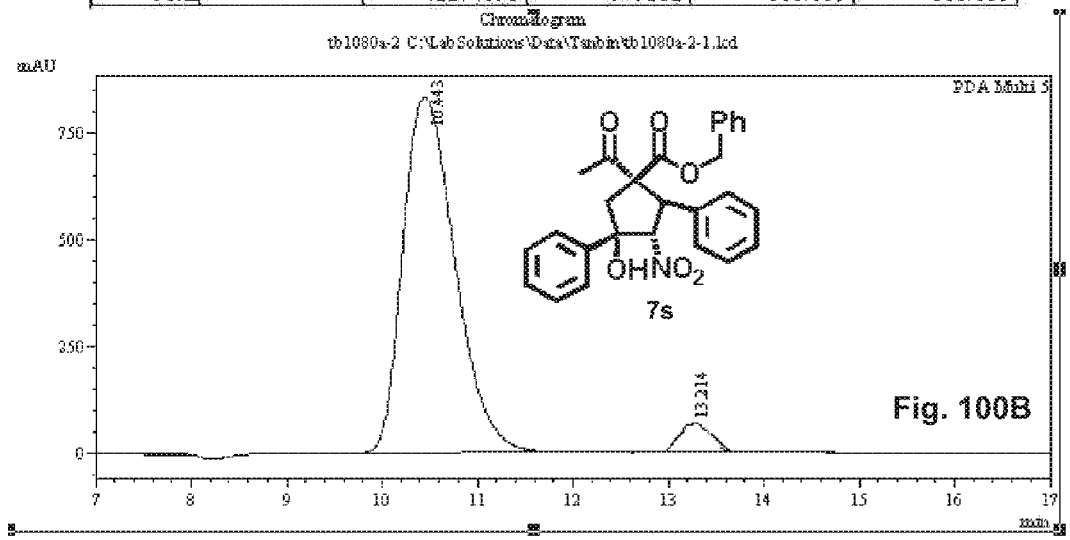

| Peak# | Ret. Time | Area | Height | Area % | Height % |
|---|---|---|---|---|---|
| 1 | 6.256 | 15970946 | 731794 | 50.350 | 63.253 |
| 2 | 9.440 | 15748919 | 425130 | 49.650 | 36.747 |
| Total | | 31719865 | 1156924 | 100.000 | 100.000 |

| Peak# | Ret. Time | Area | Height | Area % | Height % |
|---|---|---|---|---|---|
| 1 | 6.263 | 24086654 | 1152647 | 95.515 | 96.156 |
| 2 | 9.481 | 1131011 | 46085 | 4.485 | 3.844 |
| Total | | 25217664 | 1198732 | 100.000 | 100.000 |

ASYMMETRIC CYCLIZATION PROCESSES USING UNSATURATED NITRO COMPOUNDS

CROSS-REFERENCE TO RELATED APPLICATIONS

This application is a continuation of the U.S. application Ser. No. 12/782,704, filed May 18, 2010, which in turn makes reference to and claims the benefit of priority of an application for "Highly Recyclable Organocatalysis: Enantioselective Michael Addition of 1,3-Diaryl-1,3-propanedione to Nitroolefins" filed on May 19, 2009 with the United States Patent and Trademark Office, and there duly assigned Ser. No. 61/179,552. The above applications are incorporated herein by reference for all purposes in their entirety.

FIELD OF THE INVENTION

The present invention provides asymmetric cyclization processes using unsaturated nitro compounds. The obtained compounds have a cyclohexane or a cyclopentane structure with four stereogenic carbon atoms. Using a chiral catalyst, cyclic products can be obtained in high enantioselectivities.

BACKGROUND OF THE INVENTION

The asymmetric construction of a stereogenic carbon center with a quaternary carbon atom remains one of the most challenging and demanding topics in the synthesis of natural products and chiral drugs. The development of efficient asymmetric methods to access complex molecules with multiple stereogenic centers also continues to be a substantial challenge in both academic research and industrial applications.

One approach toward these challenges is the use of catalytic enantioselective cascade reactions, which have emerged as powerful tools to give a rapid increase in molecular complexity from simple and readily available starting materials, thus producing enantioenriched complex compounds in a single operation. Of the developed strategies for asymmetric tandem reactions, organocatalysis provided an efficient protocol. The syntheses of substituted cyclohexenes by applying a three-component domino reaction (Enders, D, et al., Nature (2006) 441, 861; Enders, D, et al., Angew. Chem. Int. Ed. (2007) 46, 467) and by a two-component multistep Michael-nitroaldol (Henry) sequence using pentane-1,5-dial and 2-substituted nitroalkenes (Hayashi, Y, et al, Angew. Chem. Int. Ed. (2007) 46, 4922) have been described.

Although several other elegant organocatalytic tandem reactions have also been reported recently, the development of new methods for the generation of molecules with multiple stereogenic carbons, including quaternary centers, in a cascade manner remains a big challenge at the forefront of synthetic chemistry. The Michael addition reaction, being one of the most general and versatile methods for formation of C—C bonds in organic synthesis, has received much attention in the development of enantioselective catalytic protocols. Domino Michael-Michael (also called "double Michael") reactions have been explored and demonstrated as a powerful tool in organic synthesis (for a review on double Michael reactions, see: Ihara, M, & Fukumoto, K, Angew. Chem. Int. Ed. (1993) 32, 1010). Efficient asymmetric double Michael processes have been achieved by relying on the use of chiral auxiliaries and chiral precursors for stereocontrol. However, the development of organocatalytic enantioselective versions of the reactions proved to be a challenging task, and there have been very few reports regarding the formation of quaternary and tertiary stereocenters with both excellent enantioselectivity and diastereoselectivity using α,β-unsaturated esters as Michael acceptors.

The nitroaldol reaction, also termed Henry reaction, also represents a powerful C—C bond forming tool, and the resulting nitro alcohol products can be transformed into a number of nitrogen and oxygen containing derivatives such as nitroalkenes, amino alcohols and amino acids (Palomo, C, et al., Eur. J. Org. Chem. (2007) 2561). In addition to substrate-controlled Henry reactions, organocatalytic systems that provide good stereoselectivity have been developed in recent years.

It is an object of the present invention to provide a further process that can be used to form organic molecules with multiple stereogenic carbon atoms, in particular quarternary carbon centers.

SUMMARY OF THE INVENTION

In a first aspect the invention relates to a process that involves forming a compound of general formula (33)

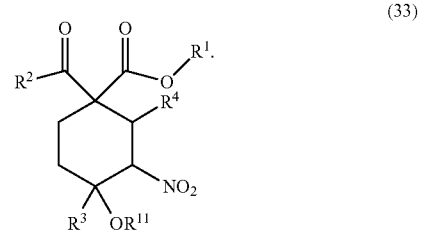

(33)

In formula (33) $R^1$ and $R^2$ are independently from one another one of a silyl group, an aliphatic group and an alicyclic group. A respective aliphatic group and an alicyclic group, as well as a silyl group, has a main chain that may have 1 to about 20 carbon atoms and 0 to about 7 heteroatoms. Such a heteroatom may be selected from the group consisting of N, O, S, Se and Si. $R^3$ is one of H, a silyl group, an aliphatic group, an alicyclic group, an aromatic group, an arylaliphatic group and an arylalicyclic group. A respective silyl group, aliphatic group, alicyclic group, aromatic group, arylaliphatic group or arylalicyclic group may have a main chain that may have 1 to about 20 carbon atoms and 0 to about 7 heteroatoms. Such a heteroatom is selected from the group consisting of N, O, S, Se and Si. $R^4$ may be the group —CH═CH—$R^9$. In this group $R^9$ is one of H, a silyl group, an aliphatic group, an alicyclic group, an aromatic group, an arylaliphatic group and an arylalicyclic group. A respective silyl group, aliphatic, alicyclic, aromatic, arylaliphatic or arylalicyclic group may have a main chain that may have 1 to about 20 carbon atoms and 0 to about 7 heteroatoms. Such a heteroatom may be selected from the group consisting of N, O, S, Se and Si. $R^4$ may also be one of an aromatic group, an arylaliphatic group and an arylalicyclic group. The aromatic, arylaliphatic or arylalicyclic group includes a main chain that may have 1 to about 20 carbon atoms and 0 to about 7 heteroatoms. Such a heteroatom may be selected from N, O, S, Se and Si. $R^{11}$ may be H. $R^{11}$ may also be a silyl group, an aliphatic group, an alicyclic group, an aromatic group, an arylaliphatic group or an arylalicyclic group. The aliphatic, alicyclic, aromatic, arylaliphatic or arylalicyclic group includes a main chain that may have 1 to about 20 carbon atoms and 0 to about 7 heteroatoms. Such a heteroatom may be selected from N, O, S, Se and Si. $R^{11}$ may also be one of a carbonate group —O—C(O)—O—$R^{17}$ and a carbamoyl group —O—C(O)—N($R^{17}$)—$R^{18}$. In such a carbonate group or carbamoyl group $R^{17}$ and $R^{18}$ are independent from one another H or one of an aliphatic, a alicyclic, an aromatic, an arylaliphatic, and an arylalicyclic group. A respective aliphatic, alicyclic, aromatic, arylaliphatic, or arylalicyclic group includes a main chain that may have a length of 1 to about 20 carbon atoms, which includes 0 to about 6 heteroatoms. Such a heteroatom may be selected from N, O, S, Se and Si. The process includes providing a first compound of the general formula (1)

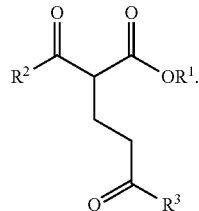
(1)

The process also includes providing a second compound of the general formula (2)

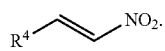
(2)

The process further includes providing a compound of the general formula (X)

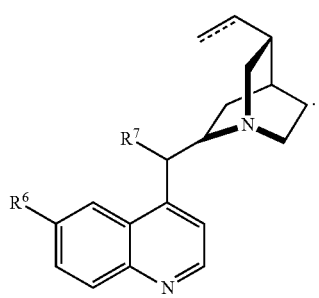
(X)

In formula (X) $R^6$ is one of H, —OMe, —OH, —OTf, —SH and —$NH_2$. $R^7$ is one of OH and —$N(R^8)H$. In this group $R^8$ is one of H, a carbamoyl group, and a thiocarbamoyl group. ⚌ represents one of a single and a double bond. Further, the process includes contacting the first compound of formula (1) and the second compound of formula (2) in the presence of the compound of general formula (X). Thereby a reaction mixture is formed. The process also includes allowing the first and the second compound to undergo—in the presence of the compound of the general formula (X)—a reaction for a sufficient period of time to allow the formation of a compound of general formula (23)

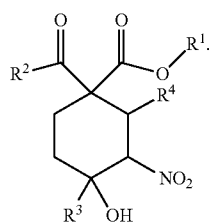
(23)

The compound of formula (23) may then be further reacted to a compound of formula (33).

In a second aspect the invention relates to a process that involves forming a compound of general formula (35)

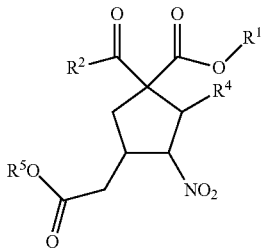
(35)

In formula (35) $R^1$ and $R^2$ are independent from one another one of a silyl group, an aliphatic group and an alicyclic group with a main chain that may have 1 to about 20 carbon atoms. The main chain may further have 0 to about 7 heteroatoms. Such a heteroatom may be selected from N, O, S, Se and Si. $R^4$ may be the group —CH=CH—$R^9$. In this group $R^9$ may be H. It may also be one of a silyl group, an aliphatic group, an alicyclic group, an aromatic group, an arylaliphatic group and an arylalicyclic group. A respective silyl group, aliphatic, alicyclic, aromatic, arylaliphatic or arylalicyclic group may have a main chain that has 1 to about 20 carbon atoms and 0 to about 7 heteroatoms. Such a heteroatom may be selected from the group consisting of N, O, S, Se and Si. $R^4$ may further be one of an aromatic group, an arylaliphatic group and an arylalicyclic group. The aromatic, arylaliphatic or arylalicyclic group includes a main chain that may have 1 to about 20 carbon atoms and 0 to about 7 heteroatoms. Such a heteroatom may be selected from N, O, S, Se and Si. $R^5$ is one of H, a silyl group, an aliphatic group, an alicyclic group, an aromatic group, an arylaliphatic group and an arylalicyclic group with a main chain that may have 1 to about 20 carbon atoms and 0 to about 7 heteroatoms. Such a heteroatom may be selected from N, O, S, Se and Si. The process includes providing a first compound of the general formula (4)

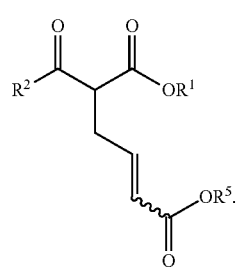
(4)

In formula (4) ⌇ indicates that the bond is in any configuration relative to the C=C bond, i.e. generally either an E- or a Z-configuration. The process also includes providing a second compound of the general formula (2)

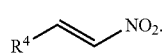
(2)

The process further includes providing a compound of the general formula (X)

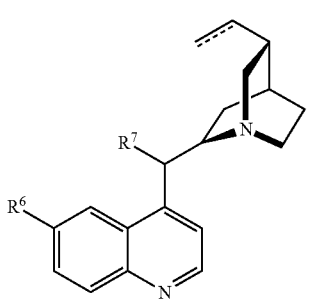

(X)

In formula (X) $R^6$ is one of H, —OMe, —OH, —OTf, —SH and —NH$_2$. $R^7$ is one of OH and —N($R^8$)H. In this group $R^8$ is one of H, a carbamoyl group, and a thiocarbamoyl group. ⚌ represents one of a single and a double bond. Further, the process includes contacting the first compound of formula (4) and the second compound of formula (2) in the presence of the compound of general formula (X). Thereby a reaction mixture is formed. The process also includes allowing the first and the second compound to undergo—in the presence of the compound of the general formula (X)—a reaction for a sufficient period of time to allow the formation of a compound of general formula (35).

In a third aspect the invention relates to a process that involves forming a compound of general formula (35)

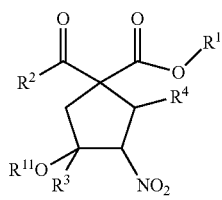

(37)

In formula (37) $R^1$ and $R^2$ are independent from one another one of a silyl group, an aliphatic group and an alicyclic group. A respective aliphatic group and an alicyclic group, as well as a silyl group, has a main chain that may have 1 to about 20 carbon atoms and 0 to about 7 heteroatoms. Such a heteroatom is selected from the group consisting of N, O, S, Se and Si. $R^3$ is one of a silyl group, an aliphatic group, an alicyclic group, an aromatic group, an arylaliphatic group and an arylalicyclic group. A respective silyl group, aliphatic group, alicyclic group, aromatic group, arylaliphatic group or arylalicyclic group may have a main chain that has 1 to about 20 carbon atoms and 0 to about 7 heteroatoms. Such a heteroatom may be selected from the group consisting of N, O, S, Se and Si. $R^4$ may be the group —CH=CH—$R^9$. In this group $R^9$ is one of H, a silyl group, an aliphatic group, an alicyclic group, an aromatic group, an arylaliphatic group and an arylalicyclic group. A respective silyl group, aliphatic, alicyclic, aromatic, arylaliphatic or arylalicyclic group may have a main chain that has 1 to about 20 carbon atoms and 0 to about 7 heteroatoms. Such a heteroatom may be selected from the group consisting of N, O, S, Se and Si. $R^4$ may also be one of an aromatic group, an arylaliphatic group and an arylalicyclic group. The aromatic, arylaliphatic or arylalicyclic group includes a main chain that may have 1 to about 20 carbon atoms and 0 to about 7 heteroatoms. Such a heteroatom may be selected from N, O, S, Se and Si. $R^{11}$ may be H. $R^{11}$ may also be a silyl group, an aliphatic group, an alicyclic group, an aromatic group, an arylaliphatic group or an arylalicyclic group. The aliphatic, alicyclic, aromatic, arylaliphatic or arylalicyclic group includes a main chain that has 1 to about 20 carbon atoms and 0 to about 7 heteroatoms. Such a heteroatom may be selected from N, O, S, Se and Si. $R^{11}$ may also be one of a carbonate group —O—C(O)—O—$R^{17}$ and a carbamoyl group —O—C(O)—N($R^{17}$)—$R^{18}$. In such a carbonate group or carbamoyl group $R^{17}$ and $R^{18}$ are independent from one another H or one of an aliphatic, a alicyclic, an aromatic, an arylaliphatic, and an arylalicyclic group. A respective aliphatic, a alicyclic, an aromatic, an arylaliphatic, and an arylalicyclic group includes a main chain of a length of 1 to about 20 carbon atoms, which may include 0 to about 6 heteroatoms. Such a heteroatom may be selected from N, O, S, Se and Si. The process includes providing a first compound of the general formula (6)

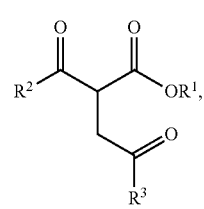

(6)

The process also includes providing a second compound of the general formula (2)

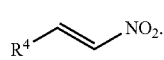

(2)

The process further includes providing a compound of the general formula (X)

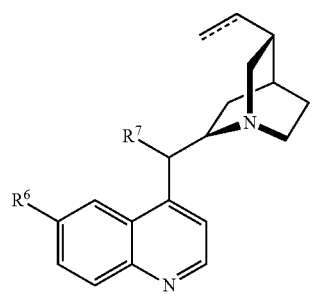

(X)

In formula (X) $R^6$ is one of H, —OMe, —OH, —OTf, —SH and —NH$_2$. $R^7$ is one of OH and —N($R^8$)H. In this group $R^8$ is one of H, a carbamoyl group, and a thiocarbamoyl group. ⚌ represents one of a single and a double bond. Further, the process includes contacting the first compound of formula (1) and the second compound of formula (2) in the presence of the compound of general formula (X). Thereby a reaction mixture is formed. The process also includes allowing the first and the second compound to undergo—in the presence of the compound of the general formula (X)—a reaction for a sufficient period of time to allow the formation of a compound of general formula (27)

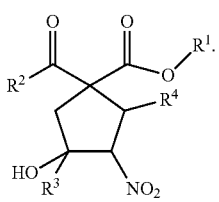

(27)

The compound of formula (27) may then be further reacted to a compound of formula (37).

BRIEF DESCRIPTION OF THE DRAWINGS

The invention will be better understood with reference to the detailed description when considered in conjunction with the non-limiting examples and the accompanying drawings.

FIG. 5 shows examples of a tandem Michael-Henry reactions of 1a with 2k and 1b/1c with 2a.

FIG. 10 illustrates schematically an organocatalytic synthesis of cycloalkanes using the tandem Michael-Henry reactions strategy.

FIG. 12 shows examples and data of domino Michael-Henry reactions of ethyl 2-acetyl-4-oxo-4-phenylbutanoate (6d) and nitroolefins catalyzed by catalyst VI. All the reactions were carried out using 6d (1.0 mmol, 2.0 equiv) and 2 (0.5 mmol, 1.0 equiv) in the presence of 10 mol % of VI at 4° C. with toluene (0.5 mL). b: Isolated yields. c: Determined by chiral HPLC analysis.

FIG. 18A depicts a $^1$H NMR spectrum and FIG. 18B a $^{13}$C NMR spectrum of compound 3a.

FIG. 20 depicts a $^1$H NMR spectrum (A) and a $^{13}$C NMR spectrum (B) of compound 3c.

FIG. 29 depicts $^1$H NMR (A) and $^{13}$C NMR (B) spectra of compound 3l.

FIG. 34 depicts an HPLC spectrum of a racemic mixture of compound 3d (A) in comparison to the obtained product 3d (B).

FIG. 44 depicts $^1$H NMR (A) and $^{13}$C NMR (B) spectra of compound 5a.

FIG. 47 depicts $^1$H NMR (A) and $^{13}$C NMR (B) spectra of compound 5d.

FIG. 50 depicts $^1$H NMR (A) and $^{13}$C NMR (B) spectra of compound 5l.

FIG. 54 depicts $^1$H NMR (A) and $^{13}$C NMR (B) spectra of compound 5p.

FIG. 55 depicts $^1$H NMR (A) and $^{13}$C NMR (B) spectra of compound 5q.

FIG. 74A depicts a $^1$H NMR spectrum and FIG. 74B a $^{13}$C NMR spectrum of compound 7a.

FIG. 75 depicts $^1$H NMR (A) and $^{13}$C NMR (B) spectra of compound 7w.

FIG. 78 depicts $^1$H NMR (A) and $^{13}$C NMR (B) spectra of compound 7c.

FIG. 79 depicts $^1$H NMR (A) and $^{13}$C NMR (B) spectra of compound 7e.

FIG. 80 depicts $^1$H NMR (A) and $^{13}$C NMR (B) spectra of compound 7g.

FIG. 82 depicts $^1$H NMR (A) and $^{13}$C NMR (B) spectra of compound 7p.

FIG. 92 depicts an HPLC spectrum of a racemic mixture of compound 7g (A), and in comparison the obtained product 7g (B).

FIG. 96 depicts an HPLC spectrum of a racemic mixture of compound 7r (A), and in comparison the obtained product 7r (B).

FIG. 99 depicts $^1$H NMR (A) and $^{13}$C NMR (B) spectra of compound 7x.

FIG. 100 depicts an HPLC spectrum of a racemic mixture of compound 7s (A), and in comparison the obtained product 7s (B).

DETAILED DESCRIPTION OF THE INVENTION

Figure 1A:
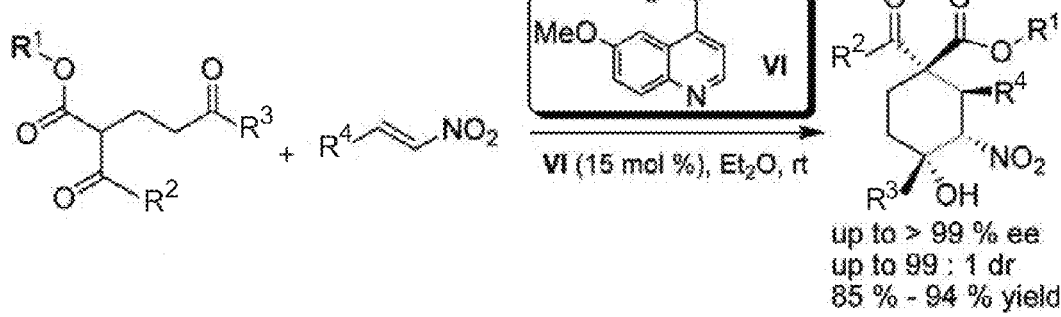
FIG. 1A depicts a scheme on an asymmetric tandem Michael-Henry reaction using exemplary Cinchona alkaloid catalyst VI, yielding a cyclohexane product.
Figure 1B:
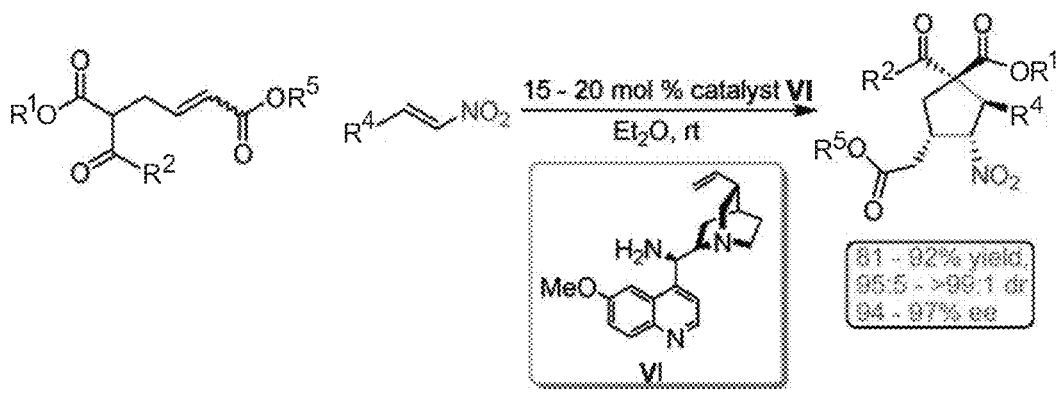
FIG. 1B depicts a scheme on an asymmetric domino double Michael reaction using exemplary Cinchona alkaloid catalyst VI, yielding a cyclopentane product.
Figure 1C:
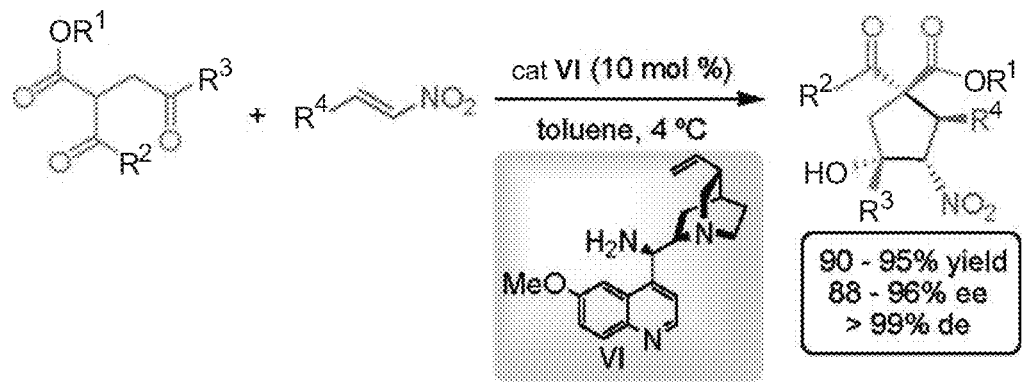
FIG. 1C depicts a scheme on an asymmetric domino Michael-Henry reaction using exemplary Cinchona alkaloid catalyst VI, yielding a cyclopentane product.

The invention relates to processes that involve cyclization reactions. The cyclization reactions proceed in an asymmetric fashion such that an asymmetric cyclization process is carried out if an asymmetric compound is used as further explained below. This asymmetric compound is, without being bound by theory, thought to act as a catalyst. The processes use an unsaturated nitro compound and a 2-substituted 3-ketoester or a corresponding aldehyde (i.e. a 2-substituted 2-formyl-ester) as reactants. The processes can, without being bound by theory, be taken as involving a Michael reaction. In the reaction that occurs in the process of the invention the compound that can be taken to define the Michael acceptor is an alkene substituted with a group $R^4$ and with a nitro group.

Accordingly, a compound of the general formula (2) is used in a process of the invention:

(2)

In formula (2) $R^4$ may in some embodiments be the group —CH═CH—$R^9$. In this group $R^9$ may be H. $R^9$ may also be one of a silyl group, an aliphatic group, an alicyclic group, an aromatic group, an arylaliphatic group and an arylalicyclic group. A respective aliphatic, alicyclic, aromatic or arylaliphatic moiety of $R^9$ typically has a main chain of about 1 to about 30 carbon atoms, such as 2 to about 30 carbon atoms or 3 to about 30 carbon atoms, including about 1 to about 25 carbon atoms, about 1 to about 20 carbon atoms, about 2 to about 20 carbon atoms, about 1 to about 15 carbon atoms, about 2 to about 15 carbon atoms, about 3 to about 15 carbon atoms, about 1 to about 10 carbon atoms, about 2 to about 10 carbon atoms or about 3 to about 10 carbon atoms, such as 1, 2, 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety further has 0 to about 6, e.g. 0 to about 5 or 0 to about 4, such as 0, 1, 2, 3, 4, 5 or 6 heteroatoms. A respective heteroatom may be one of N, O, S, Se and Si.

A respective silyl group may be represented as

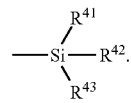

Each of $R^{41}$, $R^{42}$ and $R^{43}$ may be an independently selected aliphatic, alicyclic, aromatic, arylaliphatic or arylalicyclic group. A respective aliphatic, alicyclic, aromatic or arylaliphatic group may have a main chain of about 1 to about 30 carbon atoms, such as 2 to about 30 carbon atoms or 3 to about 30 carbon atoms, including about 1 to about 25 carbon atoms, about 1 to about 20 carbon atoms, about 2 to about 20 carbon atoms, about 1 to about 15 carbon atoms, about 2 to about 15 carbon atoms, about 3 to about 15 carbon atoms, about 1 to about 10 carbon atoms, about 2 to about 10 carbon atoms or about 3 to about 10 carbon atoms, such as 1, 2, 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety may further have 0 to about 6, e.g. 0 to about 5 or 0 to about 4, such as 0, 1, 2, 3, 4, 5 or 6 heteroatoms. A respective heteroatom may be one of N, O, S, Se and Si.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moieties may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl-, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3, 5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains, respectively, of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebis-benzene, 9-isopropylanthracene, 1,2,3-trimethylbenzene, 4-phenyl-2-buten-1-ol, 7-chloro-3-(1-methylethyl)-quinoline, 3-heptyl-furan, 6-[2-(2,5-diethyl-phenyl) ethyl]-4-ethyl-quinazoline or, 7,8-dibutyl-5,6-diethylisoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzene-sulfonyl, nitrobenzenesulfonyl, and methanesulfonyl.

An aliphatic, alicyclic, aromatic or arylaliphatic moiety may carry further moieties such as side chains. Such further moieties may be an aliphatic, alicyclic, aromatic, arylaliphatic or arylalicyclic group that typically is of a main chain length of 1 to about 10, to about 15 or to about 20 carbon atoms. These further moieties may also carry functional groups (supra).

$R^4$ may also be an aromatic group, an arylaliphatic group or an arylalicyclic group. The aromatic, arylaliphatic or arylalicyclic group includes a main chain that typically has 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aromatic, arylaliphatic or arylalicyclic moiety of $R^4$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si.

In one process according to the invention the compound of the general formula (2) is contacted with a compound of general formula (1)

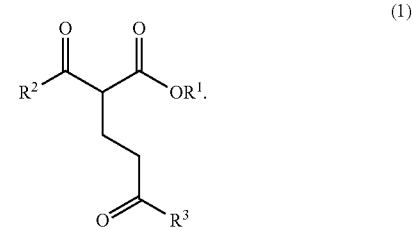

(1)

In formula (1) $R^1$ and $R^2$ may independently from one another be a silyl group (supra), an aliphatic group or an alicyclic group. A respective silyl group (supra), aliphatic or alicyclic group has a main chain that typically includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aliphatic group or alicyclic group of $R^1$ and/or $R^2$ (see above for a silyl group) may have 0 to about 8 heteroatoms, such as 0 to about 7 or 0 to about 6, e.g. 0 to about 5 or 0 to about 4, such as 0, 1, 2, 3, 4, 5 or 6 heteroatoms. Such a heteroatom may be selected from N, O, S, Se and Si.

$R^3$ in formula (1) may be a silyl group, an aliphatic group, an alicyclic group, an aromatic group, an arylaliphatic group or an arylalicyclic group. A respective silyl group may be as defined above. A corresponding aliphatic, alicyclic, aromatic, arylaliphatic or arylalicyclic group may have a main chain that typically includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aliphatic, alicyclic, aromatic, arylaliphatic or arylalicyclic group of $R^3$ (see above for a silyl group) may have 0 to about 8 heteroatoms, such as 0 to about 7 or 0 to about 6, e.g. 0 to about 5 or 0 to about 4, such as 0, 1, 2, 3, 4, 5 or 6 heteroatoms. Such a heteroatom may be selected from N, O, S, Se and Si.

In a further process according to the invention the compound of the general formula (2) is contacted with a compound of general formula (4)

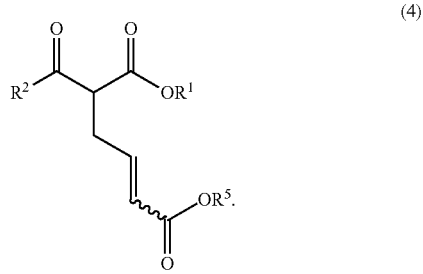

(4)

In formula (4) $R^1$ and $R^2$ are as defined above. $R^5$ may in some embodiments be H. $R^5$ may in some embodiments also be a silyl group, as defined above. In some embodiments $R^5$ may be an aliphatic group, an alicyclic group, an aromatic group, an arylaliphatic group and an arylalicyclic group. A respective aliphatic, alicyclic, aromatic, arylaliphatic or arylalicyclic group may have a main chain that that includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The main chain of the aliphatic, alicyclic, aromatic, arylaliphatic or arylalicyclic group of $R^5$ (see above for a silyl group) may have 0 to about 8 heteroatoms, such as 0 to about 7 or 0 to about 6, e.g. 0 to about 5 or 0 to about 4, such as 0, 1, 2, 3, 4, 5 or 6 heteroatoms. Such a heteroatom may be selected from N, O, S, Se and Si.

In a further process according to the invention the compound of the general formula (2) is contacted with a compound of general formula (6)

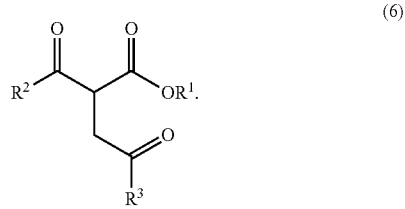

(6)

In formula (6) $R^1$ to $R^3$ are as defined above. In the following the compound of general formula (1), of general formula (4) or of general formula (6), which is reacted with the nitro compound of formula (2), is also called the first compound. The compound of formula (2) is also called the second compound. Accordingly, if the reaction is taken to be defined in terms of a Michael reaction or a Michael reaction step, the Michael donor is herein also referred to as the first compound and the Michael acceptor as the second compound.

The second compound, i.e. the compound of the general formula (2) and the first compound, i.e. the compound of general formula (1), the compound of general formula (4) or the compound of general formula (6), respectively, are allowed to react in the presence of a quinine-based or a quinidine-based compound. The compound is of the general formula (X)

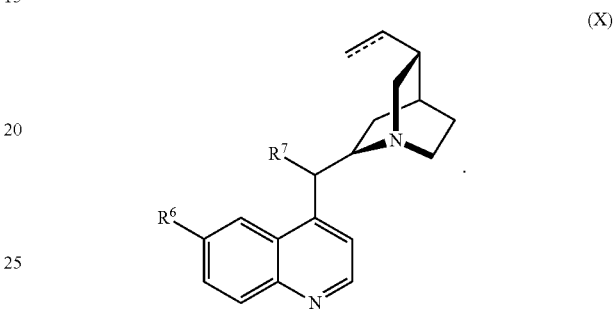

(X)

In formula (X) $R^6$ may in some embodiments be H. $R^6$ may also be —OMe, —OH, —OTf, —SH or —NH$_2$. $R^7$ may be —OH and —N($R^8$)H. The respective moiety $R^8$ may be H, a carbamoyl group or a thiocarbamoyl group. A respective carbamoyl group may be represented as —C(O)—N($R^{21}$)—$R^{12}$ and a respective thiocarbamoyl group as —C(S)—N($R^{21}$)—$R^{12}$. $R^{21}$ and $R^{12}$ in the carbamoyl group and the thiocarbamoyl group, respectively, are independent from one another H or one of an aliphatic, an alicyclic, an aromatic, an arylaliphatic, and an arylalicyclic group. A respective aliphatic, alicyclic, aromatic, arylaliphatic or arylcycloaliphatic group may have a main chain that typically includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aliphatic, alicyclic, aromatic, arylaliphatic or arylalicyclic group of $R^{21}$ and/or $R^{12}$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be selected from N, O, S, Se and Si. ═ in general formula (X) represents a single or a double bond. Hence, in some embodiments ═ in the context of the structural formula represents —CH$_2$—CH$_3$, and in some embodiments —CH═CH$_2$. Illustrative examples of moieties $R^6$ and $R^7$ can be taken from FIG. 2.

A number of corresponding compounds, such as cinchonidine, cinchonine, quinine or quinidine are commercially available. Modifications such as hydrations (e.g. dihydrocinchonidine) or conversions of functional groups can be carried out using standard procedures available in the art.

The first compound, the second compound and the compound of formula (X) may be used in any ratio relative to each other. For example, the compounds of formulas (1), (2) and (X) may be used in any ratio relative to each other. In some embodiments the first compound, e.g. compound (1), is used in an about similar, including about equal amount or higher compared to the amount of compound (2). In some embodiments compound (2) is used in an at least about equal amount or higher when compared to the amount of the first compound, e.g. compound (1). Accordingly the first compound may be provided in excess to the second compound. The first compound may for example be provided in a molar amount of about 1.1-fold, about 1.2-fold, about 1.5-fold, about 2-fold, about 2.5-fold, about 3-fold, about 3.5-fold, about 4-fold, about 4.5-fold or about 5-fold in comparison to the molar amount of the second compound.

In some embodiments compound (X) is used in an about similar or lower amount than the amount of one the first and the second compound, e.g. of compound (1) and compound (2). Compound (2) may for example be used in excess to compound (1). Compound (X) may then for instance be used in an about similar or lower amount relative to the amount of the first compound, e.g. compound (1). It may also be used in an about similar or lower amount relative to the amount of compound (2). In some embodiments compound (X) is used in a catalytic amount. The term "catalytic amount" as also used in the art refers to a substoichiometric amount relative to a reactant, in particular relative to a reactant that is used in a lower amount than another reactant. The catalytic amount of a particular compound (X) varies according to the concentration of the first and the second compound, e.g. compounds (1) and (2), as well as to reaction conditions such as temperature and time. As used herein, a catalytic amount means from about 0.0001 to about 90 mole percent relative to a reactant, such as from about 0.001 to about 50 mole percent, from about 0.001 to about 25 mole percent, from about 0.01 to about 10 mole percent, or from about 0.1 to about 5 mole percent relative to a reactant. In some embodiments the respective mole percent value is determined relative to that amount of the first or the second compound, e.g. compounds (1) and (2) that is lower. If in such an embodiment compound (2) is used in an excess relative to the first compound, e.g. compound (1), the mole percent value of the amount of compound (X) is determined relative to the amount of compound (1). The above said applies mutatis mutandis to the compounds of formulas (4), (2) and (X), and to the compounds of formulas (6), (2) and (X), where these compounds are used in a process according to the invention. For example, in some embodiments the compound of formula (X) is used in a substoichiometric amount relative to the compound of formula (4) or to the compound of formula (6), respectively.

A reaction mixture may be formed by contacting the second compound, i.e. the compound of formula (2), and the first compound, i.e. the compound of either formula (1), formula (4) or formula (6), in the presence of the compound of formula (X). The reaction mixture may be formed at any temperature at which the three compounds, i.e. either the two reactants of formulae (1) and (2), the two reactants of formulae (4) and (2) or the two reactants of formulae (6) and (2), and the compound of formula (X) are at least essentially stable enough to undergo a cyclization reaction. The reaction mixture may be formed at a temperature from about −200° C. to about 50° C., including from about −180° C. to about 40° C., from about −180° C. to about 30° C., from about −160° C. to about 50° C., from about −160° C. to about 40° C., from about −40° C. to about 40° C., from about −20° C. to about 40° C., from about −40° C. to about 30° C. or from about 0° C. to about 30° C., such as ambient temperature, e.g. about 18° C. or about 22° C. The first compound and the nitro compound of formula (2) may be allowed to react in the reaction mixture at the same temperature. In some embodiments the reaction temperature is altered, such as increased or lowered. The reaction may be allowed to proceed at a temperature from about −200° C. to about 50° C., including from about −180° C. to about 40° C., from about −180° C. to about 30° C., from about −160° C. to about 50° C., from about −160° C. to about 40° C., from about −100° C. to about 40° C., from about −40° C. to about 40° C., from about −20° C. to about 40° C., from about −20° C. to about 30° C. or from about 0° C. to about 30° C., such as ambient temperature, e.g. about 18° C. or about 22° C.

The present process of the invention may in some embodiments be carried out in the absence of any solvent. In some embodiments forming the reaction mixture includes adding a liquid. Thereby the first compound, the second compound and the compound of formula (X) may be dissolved in the liquid. Accordingly, the present process of the invention may be carried out in the liquid phase. Any solvent may be used, as long as the compounds can undergo a cyclization reaction therein to a desired extent. Solvents used may be polar or non-polar liquids, including aprotic non-polar liquids. Examples of non-polar liquids include, but are not limited to mineral oil, hexane, heptane, cyclohexane, benzene, toluene, dichloromethane, chloroform, carbon tetrachloride, carbon disulfide, and a non-polar ionic liquid. Examples of a non-polar ionic liquid include, but are not limited to, 1-ethyl-3-methylimidazolium bis[(trifluoromethyl)sulfonyl]amide bis (triflyl)-amide, 1-ethyl-3-methylimidazolium bis [(trifluoromethyl)sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsulfonyl)imide, trihexyl(tetradecyl)-phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris(pentafluoroethyl)trifluorophosphate, trihexyl(tetradecyl)phosphonium, N"-ethyl-N,N,N', N'-tetramethylguanidinium, 1-butyl-1-methylpyrroledinium tris(pentafluoroethyl)trifluorophosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium.

A polar solvent, such as a polar protic solvent, can be a solvent that has, for example, a hydrogen atom bound to an oxygen as in a hydroxyl group or a nitrogen as in an amine group. More generally, any molecular solvent which contains dissociable H$^+$, such as hydrogen fluoride, is called a protic solvent. The molecules of such solvents can donate an H$^+$ (proton). Examples of polar protic solvents include, but are not limited to, water or an alcohol, e.g. methanol, ethanol propanol, isopropanol or butanol, or a carboxylic acid such as acetic acid or formic acid. Other polar solvents are aprotic. Examples of such aprotic polar liquids include, but are not limited to, tetrahydrofuran, pyridine, dioxane, diethyl ether, diisopropylether, ethylene glycol monobutyl ether, pyridine, methyl propyl ketone, methyl isoamyl ketone, methyl isobutyl ketone, cyclo-hexanone, isobutyl isobutyrate, ethylene glycol diacetate, ethyl acetate, acetonitrile, dimethyl-formamide, N,N-dimethyl acetamide, N-methylpyrrolidone, formamide, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(penta-fluoroethyl)phosphinate, 1-butyl-3-methylimidazolium tetrakis(3,5-bis(trifluoromethylphenyl)-borate, tetrabutyl-ammonium bis(trifluoromethyl)imide, ethyl-3-methylimidazolium trifluoro-methanesulfonate, 1-butyl-3-methylimidazolium methylsulfate, 1-n-butyl-3-methylimidazolium ([bmim]) octylsulfate, and 1-n-butyl-3-methylimidazolium tetrafluoroborate.

In some embodiments the first compound, the second compound and the compound of formula (X) are provided in a coordinating solvent. A coordinating solvent may for instance include an ether or an amine, such as an alkylamine or a dialkylamine. In addition the solvent may in such an embodiment also include non-coordinating components such as an alkane or an alkene. Illustrative examples of an ether solvent include, but are not limited to, diethylether, methyl ethyl ether, methyl tert-butyl ether, dimethoxyethane, THF, dioxane or diphenyl ether.

The reaction of compound (1) and compound (2) yields a compound of general formula (23)

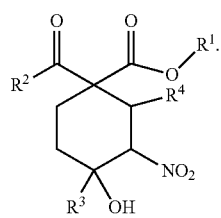

(23)

The moieties $R^1$ to $R^4$ are as defined above.

The reaction of compound (1) and compound (4) yields a compound of general formula (35)

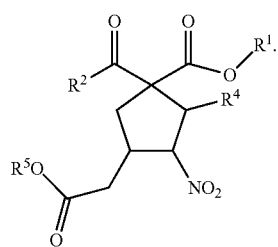

(35)

The moieties $R^1$ to $R^5$ are as defined above.

The reaction of compound (1) and compound (6) yields a compound of general formula (27)

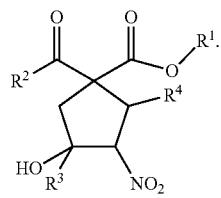

(27)

The moieties $R^1$ to $R^4$ are as defined above.

The reaction between the first and the second compound is allowed to proceed for a period of time sufficient to allow the formation of a product of formula (23), of formula (35) or of formula (27), respectively. In some embodiments the occurrence of the respective product is monitored using a suitable spectrometric and/or chromatographic technique. In some embodiments the reaction is allowed to proceed for a predetermined period of time. Such a predetermined period of time may for instance be based on optimization experiments carried out in advance. In some embodiments the compound of Formula (1) and the nitro compound of formula (2) are allowed to react for a period of time selected in the range from about 10 minutes to about 48 hours, such as from about 15 minutes to about 36 hours, from about 15 minutes to about 24 hours, from about 15 minutes to about 16 hours or from about 15 minutes to about 12 hours, such as e.g. about 1, about 2, about 3, about 4, about 5, about 6, about 10, about 14 hours or about 18 hours.

As indicated above, the reaction proceeds in an asymmetric manner in high enantioselectivities. The stereochemistry of the respective product may be analysed according to any method known in the art, such as for instance 2D-NMR based on homo- or heteronuclear J-coupling values (Riccio, R., et al., Pure Appl. Chem. (2003) 75, 2-3, 295-308), electron ionization mass spectrometry, polarimetry, circular dichroism spectroscopy (e.g. using the split Cotton-effect based on the Davydov splitting, see e.g. Allemark, S. G., Nat. Prod. Rep. (2000) 17, 145-155), enantioselective chromatography, derivatization in combination with standard analytical techniques such as NMR, including any suitable 2D-NMR technique, for example based on the nuclear Overhauser effect, as well as X-ray crystallography or solid state NMR (see e.g. Harper, J. K., et al., J. Org. Chem. (2003) 68, 4609-4614).

Carrying out a reaction of the invention using a chiral compound a cyclic product can be obtained in an enantiomerically enriched form, as well as at least essentially pure enantiomers of the corresponding product. The product may be obtained in an enantiomeric excess of at least 50% ee, at least 60% ee, at least 70% ee, at least 80% ee, at least 85% ee, at least 87% ee, at least 90% ee, at least 92% ee, at least 93% ee, at least 94% ee, at least 95% ee, at least 96% ee, at least 97% ee, at least 98% ee, at least 98.5% ee or at least 99% ee.

The compound of formula (X) may be used in racemic form. The compound of formula (X) may also be used in enantiomeric pure or enantiomerically enriched form, in particular when carrying out an asymmetric reaction. The compound of general formula (X) may be one of formulas (XA) and (XB)

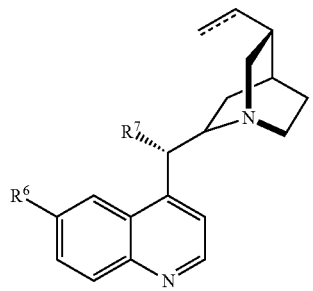

(XA)

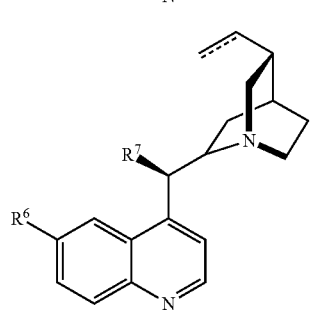

(XB)

Without being bound by theory the compound of general formula (X) may be used as a chiral catalyst. In such embodiments the catalyst employed in a process of the invention is a non-racemic chiral compound. Typically, the catalyst is in such embodiments of one of formulas (XA) and (XB).

Where the compound of formula (X) is used in the form of enantiomer (XA) the product of the reaction between the compound of the general formula (1) and the compound of the general formula (2) is at least essentially a compound of general formula (3)

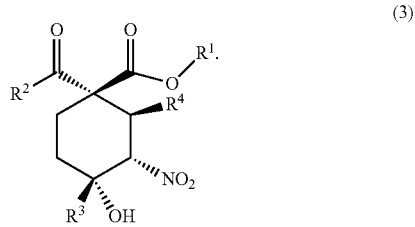

(3)

Where the compound of formula (X) is used in the form of enantiomer (XA) the product of the reaction between the compound of the general formula (4) and the compound of the general formula (2) is at least essentially a compound of general formula (5)

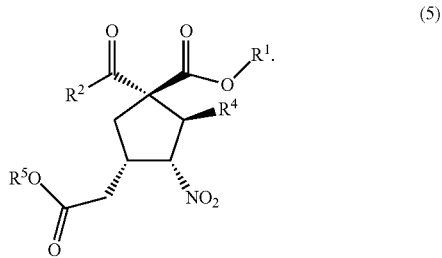

(5)

Where the compound of formula (X) is used in the form of enantiomer (XA) the product of the reaction between the compound of the general formula (6) and the compound of the general formula (2) is at least essentially a compound of general formula (7)

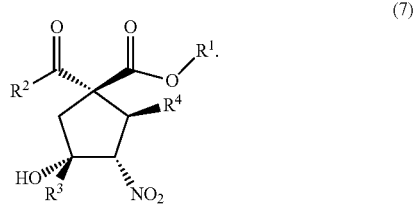

(7)

The hydroxyl group of the compound of formula (23) may be further converted to a derivative such as, but not limited to, an ether, a thioether, a selenoether, a silylether, an ester, a thioester, a selenoster, an amide, a carbonate or a carbamate. Thereby the compound of formula (23) may be converted to a compound of formula (33).

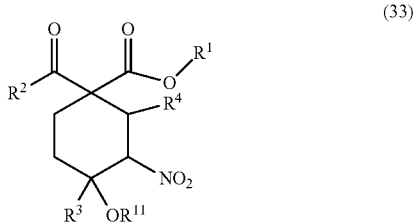

(33)

In formula (33) $R^{11}$ may accordingly be H or a moiety different from H. $R^{11}$ may be a silyl group as defined above. $R^{11}$ may also be one of an aliphatic group, an alicyclic group, an aromatic group, an arylaliphatic group and an arylalicyclic group. A respective aliphatic, alicyclic, aromatic, arylaliphatic or arylcycloaliphatic group may have a main chain that typically includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The respective main chain of the aliphatic, alicyclic, aromatic, arylaliphatic or arylalicyclic group of $R^{11}$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. $R^{11}$ may also be a carbonate group —O—C(O)—O—$R^{17}$ or a carbamoyl group —O—C(O)—N($R^{17}$)—$R^{18}$. $R^{17}$ and $R^{18}$ are independent from one another H or one of an aliphatic, an alicyclic, an aromatic, an arylaliphatic, and an arylalicyclic group. A respective aliphatic, alicyclic, aromatic, arylaliphatic or arylcycloaliphatic group may have a main chain that includes 1 to about 30 carbon atoms, such as 2 to about 30 carbon atoms or 3 to about 30 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 8 carbon atoms, such as 1, 2, 3, 4, 5, 6, 7, 8, 9, 10, 11, 12, 13, 14, 15, 16, 17, 18, 19 or 20 carbon atoms. The main chain of the aliphatic, alicyclic, aromatic, arylaliphatic or arylalicyclic group may include 0, 1, 2, 3, 4, 5 or 6 heteroatoms selected from N, O, S, Se and Si.

In some embodiments $R^{11}$ in formula (33), as well as $R^{11}$ in formulas (34), (37) and (24) below, may be a protective group such as an ether, a silyl ether, an ester, a sulfonate, a sulfenate, a sulfinate, a carbonate, a carbamate or a borate ester. Examples of an ether include, but are not limited to, a methoxymethyl ether, an ethoxyethyl ether, a 2-hydroxyethyl ether, a methylthiomethyl ether, a t-butyl ether, a triphenylmethyl ether, a t-butoxymethyl ether, a trimethylsilylethyl ether, a 1-[2-(trimethylsilyl)ethoxy]ethyl ether, a (phenyldimethylsilyl)methoxymethyl ether, a benzyl ether, a halobenzyl ether, a p-cyanobenzyl ether, a 2-trifluoromethylbenzyl ether, a p-nitrophenyl ether, a p-phenylbenzyl ether, a trimethylsilylxylyl ether, a p-(methyl-sulfinyl)benzyl ether, a p-siletanylbenzyl ether, a 2,3,5,6-tetrafluoro-4-(trifluoromethyl)phenyl ether, a benzyloxymethyl ether, a p-methoxybenzyl ether, a 3,4-dimethoxybenzy ether, a 2,6-dimethoxybenzyl ether, a p-nitrobenzyloxymethyl ether, a (4-methoxyphenoxy)methyl ether, a p-nitrobenzyl ether, a cyclohexyl ether, an allyl ether, a 2-phenylallyl ether, a prenyl ether, a cinnamyl ether, a propargyl ether, a (benzylthio)ethyl ether, an 1-methyl-1-benzyloxyethyl ether, a [3,4-dimethoxybenzyl]oxy)methyl ether, a tetrahydropyranyl ether, a tetrahydrothiopyranyl ether, a methoxycyclohexyl ether, a 1-[(2-chloro-4-methyl)phenyl}-4-methoxypiperidin-4-yl ether, a 1-[(2-fluorophenyl}-4-methoxypiperidin-4-yl ether, a 1,4-dioxan-2-yl ether, a tetrahydrofuranyl ether, a tetrahydrothiofuranyl ether, a 2,2,2-trichloroethyl ether, a 1,1-dianisyl-2,2,2-trichloroethyl ether, a 1,1,1,3,3,3-hexafluoro-2-phenylisopropyl ether, a pentadienylnitropiperonyl ether, a 2-naphtylmethyl ether, a 2-picolyl ether, a 1-pyrenylmethyl ether, a 2-quinolinylmethyl ether, a 5-dibenzosuberyl ether, a 4,4',4"-tris(4,5-dichlorophtalimidophenyl-diphenyl)methyl ether, a 4,4',4"-tris(levulinoyloxyphenyl) methyl ether, a 4,4'-dimethoxy-3"-[N-(imidazolylethyl) carbamoyl)-trityl ether, an anthryl ether and a 4,5-bis (ethoxycarbonyl)-[1,3]-dioxolan-2-yl ether.

Examples of a silyl ether include, but are not limited to, a trimethylsilyl ether, a triethylsilyl ether, a triisopropylsilyl ether, a triphenylsilyl ether, a dimethylisopropylsilyl ether, a diethylisopropylsilyl ether, a dimethylthexylsilyl ether, a t-butyldimethylsilyl ether, a norbornyl-dimethylsilyl ether, a t-butyldiphenylsilyl ether, a tribenzylsilyl ether, a tri-p-xylylsilyl ether, a diphenylmethylsilyl ether, a di-t-butylmethylsilyl ether, a bis(t-butyl)-1-pyernylmethoxysilyl ether, a tris(trimethylsilyl)silyl ether, a (2-hydroxystyryl)dimethylsilyl ether, a (2-hydroxystyryl)-diisopropylsilyl ether, a t-butylmethoxyphenylsilyl ether, a t-butoxydiphenylsilyl ether and a 1,1,3,3-tetraisopropyl-3-[2-(triphenylmethoxy)ethoxy]disiloxane-1-yl ether. Examples of an ester include, but are not limited to, an acetate group, a chloroacetate group, a trichloroacetate group, a 2,6-dichloro-4-methylphenoxyacetate group, a 2,6-dichloro-4-(1,1,3,3-tetramethylbutyl)phenoxyacetate group, a trifluoroacetate group, a chlorodiphenylacetate group, a 2,4-bis(1,1-dimethyl-propyl)phenoxyacetate group, a trichloroacetamidate group, a benzoate group, a 2-chlorobenzoate group, a p-phenylbenzoate group, a 2,4,6-trimethylbenzoate group, a 2,5-difluorobenzoate group, a p-nitrobenzoate group, an o-(methoxycarbonyl)benzoate group, a benzoylformate group, a methoxyacetate group, a phenoxyacetate group, a phenylacetate group, a diphenylacetate group, a 3-phenylpropionate group, a 4-penteneoate group, a 4-oxopentanoate group, a 4,4'-(ethylene-dithio)pentanoate group, a 5-[3-bis(4-methoxyphenyl)hydroxylmethylphenoxy]levulinate group, a pivalonate group, a 1-adamantoate group, a crotonate group, a 4-methoxycrotonate group, a picolinate group, a nicotinate group, an isobutyrate group, a monosuccinoate group, a Tigloate group and a naphtoate group.

Examples of a sulfonate include, but are not limited to, an allylsulfonate, a methanesulfonate, a benzylsulfonate, a tosylate, a 2-[4-nitrophenyl)ethyl]sulfonate and a 2-trifluoromethylsulfonate. Two illustrative examples of a sulfenate are 4-monomethoxytrityl-sulfenate and an alkyl-2,4-dinitrophenylsulfenate. Examples of a carbonate include, but are not limited to, an alkyl methyl carbonate, a methoxymethyl carbonate, an ethyl carbonate, a bromoethyl carbonate, a 2-(methylthiomethoxy)ethyl carbonate, a 2,2,2-trichloroethyl carbonate, a 1,1-dimethyl-2,2,2-trichloroethyl carbonate, a 2-(trimethylsilyl)ethyl carbonate, a 2-(dimethyl(2-naphtylmethyl)silyl]ethyl carbonate, a 2-(triphenylphosphonio)ethyl carbonate, a cis-[4-[[(meth-oxytrityl)sulfenyl]oxy]tetrahydrofuran-3-yl]oxy carbonate, a 9-fluorenylmethyl carbonate, a vinyl carbonate, an allyl carbonate, an isobutyl carbonate, a t-butyl carbonate, a cinnamyl carbonate, a propargyl carbonate, a phenacyl carbonate, a p-chlorophenyl carbonate, a p-nitrophenyl carbonate, a 4-ethoxy-1-naphthyl carbonate, a 6-bromo-7-hydroxycoumarin-4-ylmethyl carbonate, a o-nitrobenzyl carbonate, a p-nitrobenzyl carbonate, a p-methoxybenzyl carbonate, a 3,4-dimethoxybenzyl carbonate, an anthraquinon-2-ylmethyl carbonate, a dansylethyl carbonate, a 2-(4-nitrophenyl)ethyl carbonate, a 2-(2,4-nitrophenyl)ethyl carbonate, a 2-(2-nitrophenyl)propyl carbonate, a 2-(3,4-methylenedioxy-6-nitrophenyl)propyl carbonate, a 2-cyano-1-phenylethyl carbonate, a 2-(2-pyridyl)amino-1-phenylethyl carbonate, a 2-[N-methyl-N-(2-pyridyl)]amino-1-phenylethyl carbonate, a 3',5'-dimethoxybenzoin carbonate, a methyl dithiocarbonate and an S-benzyl thicarbonate. Three illustrative examples of a carbamate are a dimethylthiocarbamate, an N-phenylcarbamate and an N-methyl-N-(o-nitrophenyl) carbamate.

The compound of general formula (3) may accordingly be further converted to a compound of formula (34)

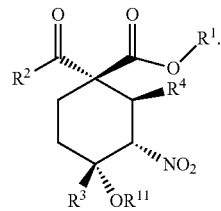

(34)

Likewise, the hydroxyl group of the compound of formula (27) may be further converted to a derivative such as, but not limited to, an ether, a thioether, a selenoether, a silylether, an ester, a thioester, a selenoster, an amide, a carbonate or a carbamate. Thereby the compound of formula (23) may be converted to a compound of formula (37).

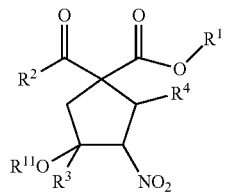

(37)

In formula (37) $R^{11}$ may accordingly be H or a moiety different from H. $R^{11}$ may be as defined above (cf. the explanations on formula (33)).

The compound of general formula (7) may accordingly be further converted to a compound of formula (24)

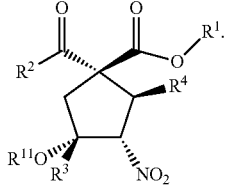

(24)

In order that the invention may be readily understood and put into practical effect, particular embodiments will now be described by way of the following non-limiting examples.

EXEMPLARY EMBODIMENTS OF THE INVENTION

General Information

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography was performed using Merck silica gel 60 with freshly distilled solvents. Columns were typically packed as slurry and equilibrated with the appropriate solvent system prior to use.

Proton nuclear magnetic resonance spectra ($^1$H NMR) were recorded on Bruker AMX 400 spectrophotometer (CDCl$_3$ as solvent). Chemical shifts for $^1$H NMR spectra are reported as δ in units of parts per million (ppm) downfield from SiMe$_4$ (δ 0.0) and relative to the signal of chloroform-d (δ 7.2600, singlet). Multiplicities were given as: s (singlet), d (doublet), t (triplet), dd (doublets of doublet) q (quartet) or m (multiplets). The number of protons (n) for a given resonance is indicated by nH. Coupling constants are reported as a J value in Hz. Carbon nuclear magnetic resonance spectra ($^{13}$C NMR) are reported as δ in units of parts per million (ppm) downfield from SiMe$_4$ (δ 0.0) and relative to the signal of chloroform-d (δ 77.03, triplet).

Enantioselectivities were determined by High performance liquid chromatography (HPLC) analysis employing a Daicel Chirapak AD-H or AS-H column. Optical rotations were measured in CH$_2$Cl$_2$ on a Schmidt+Haensch polarimeter (Polartronic MH8) with a 10 cm cell (c given in g/100 mL).

High resolution mass spectrometry (HRMS) was recorded on Finnigan MAT 95×P spectrometer.

Figure 2:
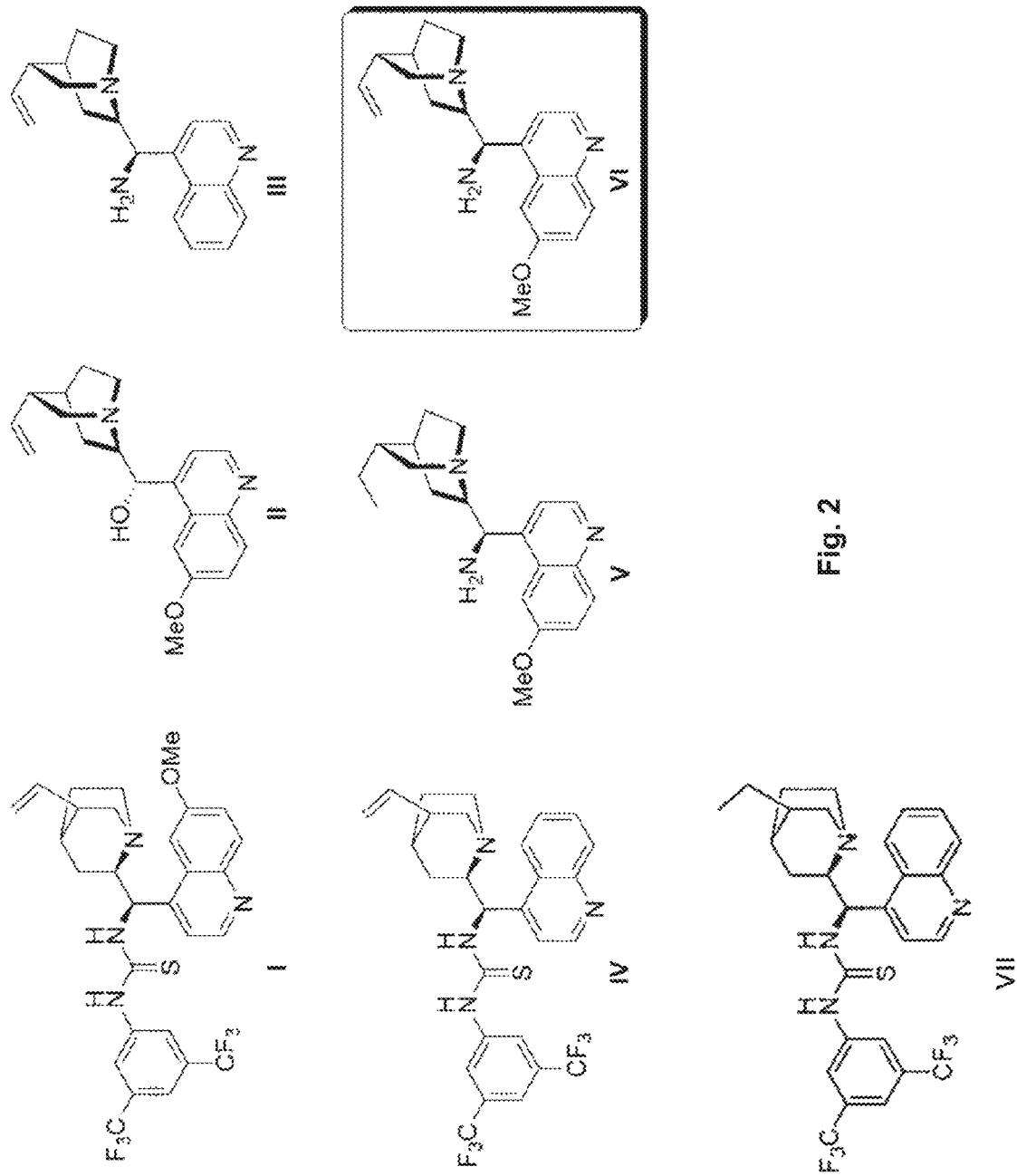
FIG. 2 depicts structures of exemplary Cinchona alkaloid catalysts that can be used in the processes of the invention.
Figure 3:
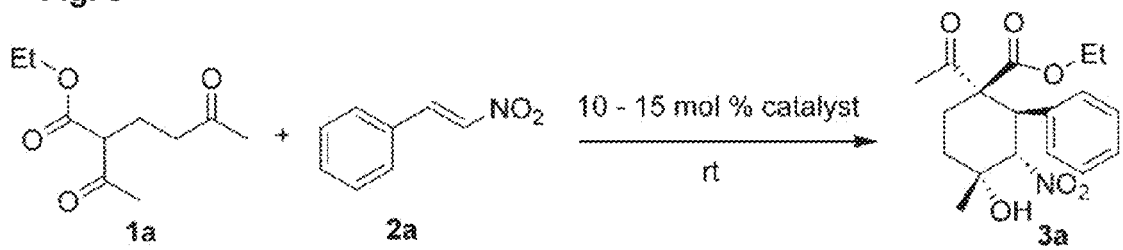
FIG. 3 depicts examples of organocatalytic Tandem Michael-Henry Reactions of ethyl 2-acetyl-5-oxohexanoate 1a and trans-β-Nitrostyrene 2a. Unless otherwise specified, all of the reactions were carried out using 1a (0.6 mmol, 1.5 equiv) and 2a (0.4 mmol, 1.0 equiv) with 10 mol % of catalyst at room temperature (23° C.). b: Isolated yields. c: Determined by crude NMR. d: Determined by chiral HPLC analysis (major isomer). e: Reaction at 4° C. f: 15 mol % of catalyst was used. g: 1a (0.4 mmol, 1.0 equiv) and 2a (0.6 mmol, 1.5 equiv) were used.

Readily accessible cinchona alkaloid and derivative catalysts, which were developed recently in several research groups, have been identified as efficient bifunctional organocatalysts in asymmetric Michael reactions (For developments and applications of cinchona-derived bifunctional catalysts, see: (a) McCooey, SH, & Connon, S J, Angew. Chem. Int. Ed. (2005) 44, 6367; (b) Ye, J, et al., Chem. Commun. (2005) 4481; (c) Vakulya, B, et al., Org. Lett. (2005) 7, 1967; (d) Tillman, A. L, et al., Chem. Commun. (2006) 1191; (e) Mattson, A E, et al., J. Am. Chem. Soc. (2006) 128, 4932. (f) Song, J, et al., Am. Chem. Soc. (2006) 128, 6048. (g) McCooey, SH, & Connon, S J, Org. Lett. (2007) 9, 599. (h) Bernardi, L, et al., Tetrahedron (2006) 62, 375; (i) France, S, et al, J. Am. Chem. Soc. (2005) 127, 1206; (j) Taggi, A E, et al., J. Am. Chem. Soc. (2000) 122, 7831) and nitroaldol reactions, also called Henry reactions (Marcelli, T, et al., Angew. Chem. Int. Ed. (2006) 45, 929; Li, H, et al., J. Am. Chem. Soc. (2006) 128, 732). The present inventors explored the feasibility of employing thiourea catalyst I (FIG. 2) to catalyze the tandem Michael-Henry reactions involving a nitroolefin and carbon nucleophiles 1a containing three carbonyl groups. Surprisingly, the tandem Michael-Henry reaction proceeded smoothly to yield the desired cyclohexane product in high yield (85%) and good enantioselectivity (80% ee) and diastereoselectivity (92:8 dr, FIG. 3, entry 1). To improve the results, different conditions were investigated. However, the results did not change significantly when the reaction was carried out in solvent or when the reaction temperature was decreased (FIG. 3, entries 2 and 3). Catalysts II-VI (FIG. 2) were screened at room temperature (23° C.) under neat conditions. V and VI were identified as excellent candidates to catalyze this tandem reaction with the highest stereoselectivity (92% ee, 95:5 dr) among all the tested cases, as shown in FIG. 3.

Catalyst VI (for pervious disclosures related to using this type of catalyst, see: (a) Xie, J-W, et al., Angew. Chem. Int. Ed. (2007) 46, 389; (b) Xie, J-W, et al., Org. Lett. (2007) 9, 413; (c) Barton, G, et al., Org. Lett. (2007) 9, 1403; (d) McCooey, SH, & Connon, S J, Org. Lett. (2007) 9, 599; (e) Zheng, B-L, et al., Org. Biomol. Chem. (2007) 5, 2913) was then chosen as catalyst due to the higher yield obtained and its easy synthesis. Further optimization of the reaction conditions revealed that solvents played a very important role in determining the selectivities of the reaction (in toluene or diethyl ether, >99% ee, 98:2 dr) (FIG. 3, entries 9-11).

With the optimized reaction conditions at hand, the scope of the tandem Michael-Henry process was expanded by using a variety of nitroolefins in diethyl ether at room temperature. Most of the reactions were found to be completed within 24 h with good to excellent yields (85%-94%), with excellent enantioselectivities (97% to >99% ee) and diastereoselectivities (93:7-98:2 dr). It appeared that the position and the electronic property of the substituents on aromatic rings have a very limited effect on the stereoselectivities.

Figure 4:
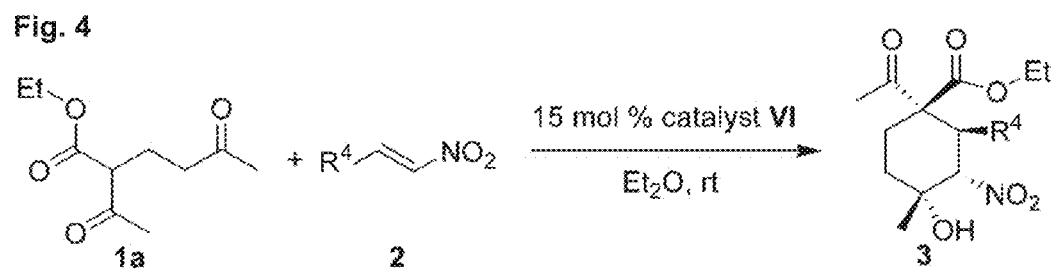
FIG. 4 illustrates an example of a tandem Michael-Henry reaction of diketo ester 1a and nitroolefin (2) Catalyzed by Catalyst VI.
Figure 5:
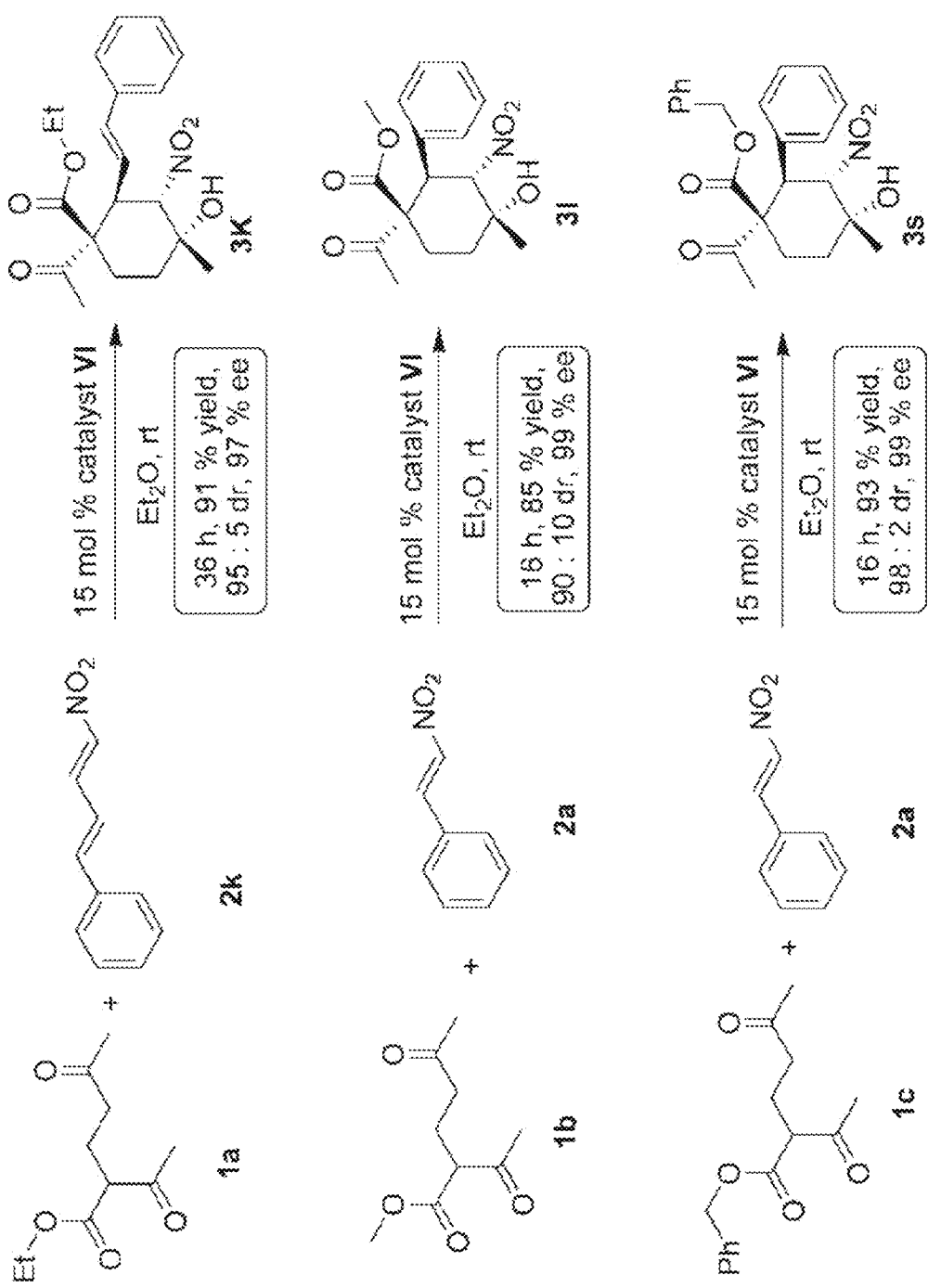

Regardless of the types of substituents on the aromatic rings, be it electron-withdrawing (FIG. 4, entries 9 and 10) or electron-donating (entries 2-4), neutral groups (entry 1) and substrates containing a variety of substitution patterns (para, meta, and ortho) participated in this reaction efficiently. The reactions proceeded to afford highly enantioselective adducts. Surprisingly, the presence of the nitro group on the aromatic ring did not cause the enantiomeric excess to decrease. Without being bound by theory, this may be attributed to the primary amine group in the catalyst that can selectively capture the two nitro groups. Notably, only one Michael-Henry adduct was obtained from the reaction of nitrodiene 2k in 97% ee (FIG. 5). Theoretically, both β- and δ-positions of 2k are possibly attacked due to the congruous two double bonds, showing the great regioselectivity and enantioselectivity of this method. Furthermore, the tandem reaction also proceeded smoothly when 1a was replaced by either 1b or 1c, giving excellent stereoselectivities (99% ee) as displayed in FIG. 5.

Figure 15:
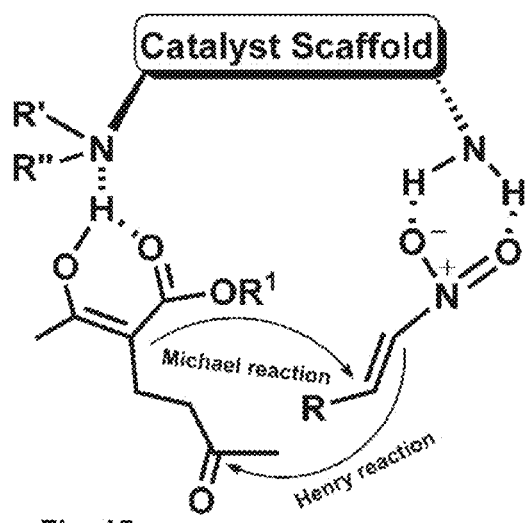
FIG. 15 illustrates the proposed action of the catalyst in a tandem Michael-Henry reaction yielding a cyclohexane compound.
Figure 16:
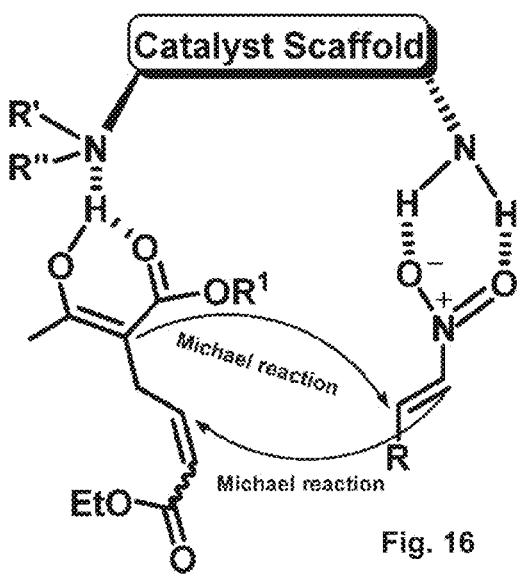
FIG. 16 illustrates the proposed action of the catalyst in a tandem double Michael reaction yielding a cyclopentane compound.

According to the dual activation model (Mattson, A E, et al., J. Am. Chem. Soc. (2006) 128, 4932), the two substrates involved in the reaction are activated simultaneously by catalyst VI as shown in FIG. 15. Nitroolefins are assumed to interact with the primary amine moiety of VI via multiple H-bonds, thus enhancing the electrophilic character of the reacting carbon center. The carboanion (adjacent to the nitro group) generated from the Michael addition then attacks the si-face of the carbonyl group to afford Henry products (FIG. 15). The stereochemistry was established by X-ray crystallographic determination of 3f (CCDC 670273) and analysis of NMR data of the products.

Typical Procedure for Michael-Henry Reactions Yielding Cyclohexane Products

To a solution of ethyl 2-acetyl-5-oxohexanoate 1a (0.4 mmol, 1.0 eq) and nitroolefin (0.6 mmol, 1.5 eq) in diethyl ether (0.4 mL) was added catalyst VI (Q-NH$_2$) (0.06 mmol, 0.15 eq) at room temperature (23° C.). The resulting mixture was stirred vigorously. After the reaction was completed (monitored by TLC or crude NMR), the product was afforded by flash chromatography over silica gel (EtOAc:Hexane=1: 10 to 1:5).

(1R,2R,3S,4R)-ethyl-1-acetyl-4-hydroxy-4-methyl-3-nitro-2-phenyl cyclohexane carboxylate (3a)

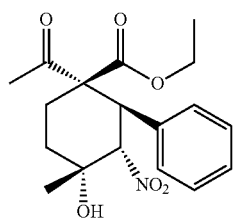 [SMILES: CCOC(=O)[C@]1(C(C)=O)CC[C@@](C)(O)[C@@H]([N+](=O)[O-])[C@@H]1c1ccccc1]

The title compound was prepared according to the typical procedure, as described above in 93% yield.

$^1$H-NMR (400 MHz, CDCl$_3$) δ 7.39-7.37 (m, 2H), 7.28-7.25 (m, 3H), 5.70 (d, J=12.4 Hz, 1H), 4.26-4.20 (m, 1H), 4.14-4.06 (m, 1H), 4.08 (d, J=12.4 Hz, 1H), 2.90 (d, J=2.0 Hz, 1H), 2.56-2.50 (m, 1H), 2.01-1.86 (m, 3H), 1.75 (s, 3H), 1.38 (s, 3H), 1.17 (t, J=7.2 Hz, 3H).

$^{13}$C-NMR (100 MHz, CDCl$_3$) δ 203.19, 171.37, 134.62, 130.07, 128.31, 128.23, 93.19, 69.77, 64.83, 61.44, 46.46, 34.08, 28.83, 27.81, 27.49, 13.75.

HPLC: Chiralpak AS-H (hexane/i-PrOH=80/20, flow rate 1 mL/min, λ=210 nm), t$_R$ (major)=10.4 min, t$_R$ (minor)=28.5 min; >99% ee.

[α]$_D^{25}$=−91.9 (c=1.0, CHCl$_3$).

HRMS (EI) calcd for C$_{18}$H$_{23}$O$_6$N, m/z 349.1521. found 349.1525.

(1R,2R,3S,4R)-ethyl-1-acetyl-4-hydroxy-2-(4-methoxyphenyl)-4-methyl-3-nitrocyclohexanecarboxylate (3b)

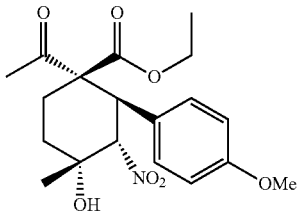 [SMILES: CCOC(=O)[C@]1(C(C)=O)CC[C@@](C)(O)[C@@H]([N+](=O)[O-])[C@@H]1c1ccc(OC)cc1]

The title compound was prepared according to the typical procedure, as described above in 91% yield.

$^1$H-NMR (400 MHz, CDCl$_3$) δ 7.30 (d, J=8.8 Hz, 2H), 6.78 (d, J=8.8 Hz, 2H), 5.67 (d, J=12.4 Hz, 1H), 4.27-4.21 (m, 1H), 4.14-4.09 (m, 1H), 4.00 (d, J=12.8 Hz, 1H), 3.77 (s, 3H), 2.94 (d, J=3.0 Hz, 1H), 2.57-2.50 (m, 1H), 2.07-1.83 (m, 3H), 1.76 (s, 3H), 1.37 (s, 3H), 1.20 (t, J=6.8 Hz, 3H).

$^{13}$C-NMR (100 MHz, CDCl$_3$) δ 203.49, 171.45, 159.28, 131.20, 126.45, 113.67, 93.34, 69.77, 64.91, 61.43, 55.13, 45.94, 34.07, 28.96, 27.77, 27.49, 13.81.

HPLC: Chiralpak AD-H (hexane/i-PrOH=90/10, flow rate 1 mL/min, λ=210 nm), t$_R$ (major)=18.7 min, t$_R$ (minor)=21.2 min; 98% ee.

[α]$_D^{25}$=−120.1 (c=1.0, CHCl$_3$).

HRMS (EI) calcd for C$_{19}$H$_{25}$O$_7$N, m/z 379.1626. found 379.1629.

(1R,2R,3S,4R)-ethyl-1-acetyl-4-hydroxy-4-methyl-3-nitro-2-p-tolylcyclohexane carboxylate (3c)

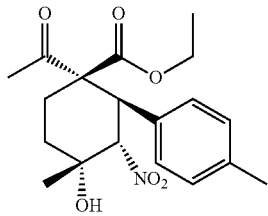 [SMILES: CCOC(=O)[C@]1(C(C)=O)CC[C@@](C)(O)[C@@H]([N+](=O)[O-])[C@@H]1c1ccc(C)cc1]

The title compound was prepared according to the typical procedure, as described above in 89% yield.

$^1$H-NMR (400 MHz, CDCl$_3$) δ 7.25 (d, J=8.0 Hz, 2H), 7.06 (d, J=8.0 Hz, 2H), 5.69 (d, J=12.8 Hz, 1H), 4.28-4.20 (m, 1H), 4.15-4.07 (m, 1H), 4.02 (d, J=12.8 Hz, 1H), 2.93 (d, J=2.0 Hz, 1H), 2.57-2.50 (m, 1H), 2.28 (s, 3H), 2.00-1.85 (m, 3H), 1.75 (s, 3H), 1.36 (s, 3H), 1.19 (t, J=7.2 Hz, 3H).

$^{13}$C-NMR (100 MHz, CDCl$_3$) δ 203.38, 171.41, 137.92, 131.49, 129.91, 129.02, 93.29, 69.76, 64.87, 61.41, 46.20, 34.08, 28.93, 27.79, 27.50, 21.05, 13.78.

HPLC: Chiralpak AD-H (hexane/i-PrOH=90/10, flow rate 1 mL/min, λ=220 nm), t$_R$ (major)=13.0 min, t$_R$ (minor)=16.3 min; 98% ee.

[α]$_D^{25}$=−94.1 (c=1.0, CHCl$_3$).

HRMS (EI) calcd for C$_{19}$H$_{25}$O$_6$N, m/z 363.1678. found 363.1676.

(1R,2R,3S,4R)-ethyl-1-acetyl-4-hydroxy-4-methyl-3-nitro-2-m-tolylcyclohexane carboxylate (3d)

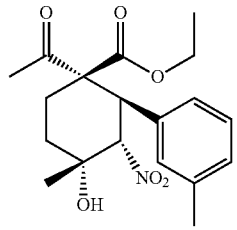 [SMILES: CCOC(=O)[C@]1(C(C)=O)CC[C@@](C)(O)[C@@H]([N+](=O)[O-])[C@@H]1c1cccc(C)c1]

The title compound was prepared according to the typical procedure, as described above in 90% yield.

$^1$H-NMR (400 MHz, CDCl$_3$) δ 7.21-7.13 (m, 3H), 7.04 (d, J=7.2 Hz, 1H), 5.70 (d, J=12.4 Hz, 1H), 4.26-4.19 (m, 1H), 4.12-4.08 (m, 1H), 4.04 (d, J=12.8 Hz, 1H), 2.90 (d, J=2.4 Hz, 1H), 2.56-2.49 (m, 1H), 2.30 (s, 3H), 2.00-1.88 (m, 3H), 1.75 (s, 3H), 1.36 (s, 3H), 1.19 (t, J=7.2 Hz, 3H).

$^{13}$C-NMR (100 MHz, CDCl$_3$) δ 203.25, 171.39, 137.78, 134.51, 130.89, 128.96, 128.15, 126.95, 93.22, 69.75, 64.80, 61.39, 46.35, 34.07, 28.87, 27.80, 27.49, 21.40, 13.75.

HPLC: Chiralpak AD-H (hexane/i-PrOH=90/10, flow rate 1 mL/min, λ=254 nm), t$_R$ (major)=11.0 min, t$_R$ (minor)=16.1 min; 99% ee.

[α]$_D^{25}$=−100.9 (c=1.0, CHCl$_3$).

HRMS (EI) calcd for C$_{19}$H$_{25}$O$_6$N, m/z 363.1678. found 363.1679.

(1R,2R,3S,4R)-ethyl-1-acetyl-2-(4-bromophenyl)-4-hydroxy-4-methyl-3-nitrocyclohexanecarboxylate (3e)

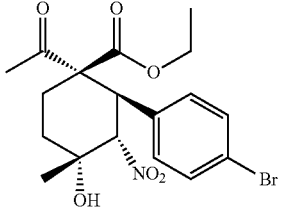 [SMILES: CCOC(=O)[C@]1(C(C)=O)CC[C@@](C)(O)[C@@H]([N+](=O)[O-])[C@@H]1c1ccc(Br)cc1]

The title compound was prepared according to the typical procedure, as described above in 88% yield.

$^1$H-NMR (400 MHz, CDCl$_3$) δ 7.39 (d, J=8.4 Hz, 2H), 7.26 (d, J=8.4 Hz, 2H), 5.59 (d, J=12.4 Hz, 1H), 4.27-4.22 (m, 1H), 4.12-4.06 (m, 1H), 4.10 (d, J=12.4 Hz, 1H), 2.85 (d, J=2.0 Hz, 1H), 2.50-2.44 (m, 1H), 2.00-1.91 (m, 3H), 1.83 (s, 3H), 1.36 (s, 3H), 1.19 (t, J=7.2 Hz, 3H).

¹³C-NMR (100 MHz, CDCl₃) δ 202.91, 171.26, 133.77, 131.82, 131.42, 122.43, 93.07, 69.75, 64.61, 61.61, 45.68, 34.06, 28.74, 27.74, 27.41, 13.77.

HPLC: Chiralpak AD-H (hexane/i-PrOH=90/10, flow rate 1 mL/min, λ=220 nm), $t_R$ (minor)=13.2 min, $t_R$ (major)=14.9 min; >99% ee.

$[\alpha]_D^{25}$=−82.0 (c=0.9, CHCl₃).

HRMS (EI) calcd for $C_{18}H_{22}O_6NBr$, m/z 429.0605. found 429.0591.

(R,2R,3S,4R)-ethyl-1-acetyl-2-(2-bromophenyl)-4-hydroxy-4-methyl-3-nitrocyclohexanecarboxylate (3f)

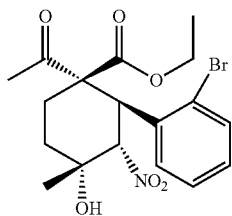 [SMILES: CCOC(=O)[C@]1(C(C)=O)CC[C@@](C)(O)[C@@H]([N+](=O)[O-])[C@@H]1c1ccccc1Br]

The title compound was prepared according to the typical procedure, as described above in 90% yield.

¹H-NMR (400 MHz, CDCl₃) δ 7.99 (dd, J=1.2, 8.0 Hz, 1H), 7.54 (d, J=8.0 Hz, 1H), 7.34-7.28 (m, 1H), 7.15-7.11 (m, 1H), 5.95 (d, J=12.4 Hz, 1H), 4.64 (d, J=12.4 Hz, 1H), 4.24-4.19 (m, 2H), 2.96 (d, J=2.0 Hz, 1H), 2.88-2.82 (m, 1H), 2.03-1.96 (m, 1H), 1.89-1.84 (m, 1H), 1.83 (s, 3H), 1.69-1.61 (m, 1H), 1.37 (s, 3H), 1.23 (t, J=7.2 Hz, 3H).

¹³C-NMR (100 MHz, CDCl₃) δ 202.07, 171.09, 134.58, 133.57, 130.53, 129.82, 127.84, 127.56, 93.28, 69.81, 64.69, 61.68, 44.25, 33.86, 28.90, 28.06, 27.43, 13.87.

HPLC: Chiralpak AD-H (hexane/i-PrOH=90/10, flow rate 1 mL/min, λ=210 nm), $t_R$ (minor)=16.0 min, $t_R$ (major)=20.3 min; 97% ee.

$[\alpha]_D^{25}$=−134.8 (c=1.1, CHCl₃).

HRMS (EI) calcd for $C_{18}H_{22}O_6NBr$, m/z 429.0605. found 429.0596.

(1R,2R,3S,4R)-ethyl-1-acetyl-2-(4-chlorophenyl)-4-hydroxy-4-methyl-3-nitrocyclohexanecarboxylate (3g)

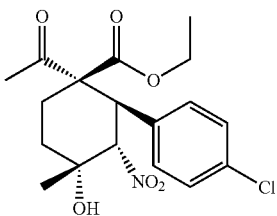 [SMILES: CCOC(=O)[C@]1(C(C)=O)CC[C@@](C)(O)[C@@H]([N+](=O)[O-])[C@@H]1c1ccc(Cl)cc1]

The title compound was prepared according to the typical procedure, as described above in 87% yield.

¹H-NMR (400 MHz, CDCl₃) δ 7.32 (d, J=8.8 Hz, 2H), 7.24 (d, J=8.8 Hz, 2H), 5.60 (d, J=12.4 Hz, 1H), 4.27-4.21 (m, 1H), 4.13-4.06 (m, 1H), 4.10 (d, J=12.8 Hz, 1H), 2.85 (s, 1H), 2.50-2.43 (m, 1H), 2.01-1.90 (m, 3H), 1.82 (s, 3H), 1.37 (s, 3H), 1.19 (t, J=7.2 Hz, 3H).

¹³C-NMR (100 MHz, CDCl₃) δ 202.93, 171.27, 134.19, 133.23, 131.48, 128.47, 93.13, 69.75, 64.66, 61.60, 45.63, 34.06, 28.74, 17.74, 27.42, 13.77.

HPLC: Chiralpak AD-H (hexane/i-PrOH=90/10, flow rate 1 mL/min, λ=210 nm), $t_R$ (minor)=9.2 min, $t_R$ (major)=10.7 min; 97% ee.

$[\alpha]_D^{25}$=−101.0 (c=1.0, CHCl₃).

HRMS (EI) calcd for $C_{18}H_{22}O_6NCl$, m/z 383.1131. found 383.1134.

(R,2R,3S,4R)-ethyl-1-acetyl-2-(2-chlorophenyl)-4-hydroxy-4-methyl-3-nitrocyclohexanecarboxylate (3h)

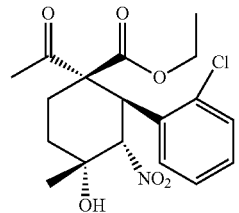

The title compound was prepared according to the typical procedure, as described above in 91% yield.

¹H-NMR (400 MHz, CDCl₃) δ 7.96 (d, J=7.6 Hz, 1H), 7.34 (d, J=7.6 Hz, 1H), 7.29-7.21 (m, 2H), 5.93 (d, J=12.0 Hz, 1H), 4.64 (d, J=12.4 Hz, 1H), 4.25-4.17 (m, 2H), 2.91 (d, J=2.4 Hz, 1H), 2.87-2.82 (m, 1H), 2.04-1.99 (m, 1H), 1.93-1.86 (m, 1H), 1.75 (s, 3H), 1.68-1.61 (m, 1H), 1.38 (s, 3H), 1.23 (t, J=7.2 Hz, 3H).

¹³C-NMR (100 MHz, CDCl₃) δ 202.16, 171.09, 136.23, 132.90, 130.48, 130.02, 129.52, 127.14, 93.18, 69.82, 64.71, 61.65, 41.47, 33.91, 28.60, 28.01, 27.47, 13.87.

HPLC: Chiralpak AD-H (hexane/i-PrOH=90/10, flow rate 1 mL/min, λ=210 nm), $t_R$ (minor)=15.0 min, $t_R$ (major)=18.5 min; 97% ee.

$[\alpha]_D^{25}$=−123.5 (c=1.2, CHCl₃).

HRMS (EI) calcd for $C_{18}H_{22}O_6NCl$, m/z 383.1131. found 383.1137.

(R,2R,3S,4R)-ethyl-1-acetyl-4-hydroxy-4-methyl-3-nitro-2-(4-(trifluoromethyl)phenyl)cyclohexanecarboxylate (3i)

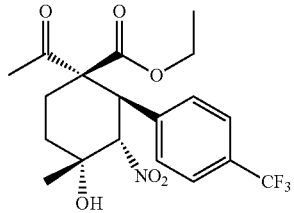 [SMILES: CCOC(=O)[C@]1(C(C)=O)CC[C@@](C)(O)[C@@H]([N+](=O)[O-])[C@@H]1c1ccc(C(F)(F)F)cc1]

The title compound was prepared according to the typical procedure, as described above in 91% yield.

¹H-NMR (400 MHz, CDCl₃) δ 7.52 (m, 4H), 5.60 (d, J=12.4 Hz, 1H), 4.26 (d, J=12.4 Hz, 1H), 4.26-4.21 (m, 1H), 4.08-4.03 (m, 1H), 2.82 (s, 1H), 2.49-2.42 (m, 1H), 2.04-1.98 (m, 3H), 1.84 (s, 3H), 1.38 (s, 3H), 1.15 (t, J=6.8 Hz, 3H).

¹³C-NMR (100 MHz, CDCl₃) δ 202.65, 171.17, 138.95, 130.54, 130.47, 125.09 (q, J=3.6 Hz), 122.49, 93.04, 69.76, 64.56, 61.66, 45.68, 34.09, 28.50, 27.73, 27.37, 13.66.

HPLC: Chiralpak AD-H (hexane/i-PrOH=90/10, flow rate 1 mL/min, λ=210 nm), $t_R$ (minor)=9.2 min, $t_R$ (major)=10.7 min; 97% ee.

$[\alpha]_D^{25}$=−79.6 (c=1.0, CHCl$_3$).

HRMS (EI) calcd for C$_{19}$H$_{22}$O$_6$NF$_3$, m/z 417.1394. found 417.1397.

(R,2R,3S,4R)-ethyl-1-acetyl-4-hydroxy-4-methyl-3-nitro-2-(2-nitrophenyl)cyclohexanecarboxylate (3j)

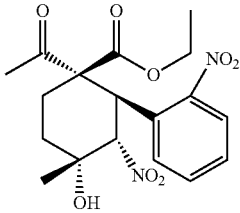 [SMILES: CCOC(=O)[C@]1(C(C)=O)CC[C@@](C)(O)[C@@H]([N+](=O)[O-])[C@@H]1c1ccccc1[N+](=O)[O-]]

The title compound was prepared according to the typical procedure, as described above in 94% yield.

$^1$H-NMR (400 MHz, CDCl$_3$) δ 7.82 (dd, J=1.2, 8.0 Hz, 1H), 7.69 (dd, J=0.8, 8.0 Hz, 1H), 7.53-7.49 (m, 1H), 7.42-7.38 (m, 1H), 5.65 (d, J=12.4 Hz, 1H), 4.14 (d, J=12.4 Hz, 1H), 4.28-4.20 (m, 1H), 4.07-3.99 (m, 1H), 3.08 (d, J=1.6 Hz, 1H), 2.41-2.37 (m, 1H), 2.13-2.09 (m, 2H), 2.02 (s, 3H), 1.39 (s, 3H), 1.14 (t, J=7.2 Hz, 3H).

$^{13}$C-NMR (100 MHz, CDCl$_3$) δ 202.11, 171.11, 151.62, 131.82, 129.77, 129.57, 128.94, 125.34, 93.23, 69.84, 63.90, 61.77, 38.34, 33.87, 27.88, 27.47, 21.19, 13.66.

HPLC: Chiralpak AD-H (hexane/i-PrOH=90/10, flow rate 1 mL/min, λ=210 nm), $t_R$ (minor)=25.9 min, $t_R$ (major)=37.9 min; 98% ee.

$[\alpha]_D^{25}$=−302.9 (c=0.5, CHCl$_3$).

HRMS (EI) calcd for C$_{18}$H$_{22}$O$_8$N$_2$, m/z 394.1371. found 394.1377.

(1R,2R,3S,4R,E)-ethyl-1-acetyl-4-hydroxy-4-methyl-3-nitro-2-styrylcyclohexane carboxylate (3k)

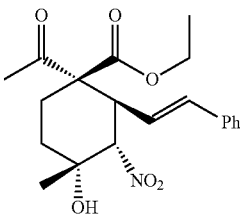 [SMILES: CCOC(=O)[C@]1(C(C)=O)CC[C@@](C)(O)[C@@H]([N+](=O)[O-])[C@@H]1/C=C/c1ccccc1]

To a solution of ethyl 2-acetyl-5-oxohexanoate 1a (0.4 mmol, 1.0 eq) and nitroolefin (2k) (0.6 mmol, 1.5 eq) in diethyl ether (0.4 mL) was added catalyst VI (0.06 mmol, 0.15 eq) at room temperature. The resulting mixture was stirred vigorously. After 36 hours the reaction was completed (monitored by TLC and crude NMR), the product was afforded by flash chromatography over silica gel in 91% yield.

$^1$H-NMR (400 MHz, CDCl$_3$) δ 7.33-7.24 (m, 6H), 6.51-6.39 (m, 2H), 5.10 (d, J=11.6 Hz, 1H), 4.31 (q, J=7.2 Hz, 1H), 3.51-3.26 (m, 1H), 3.29 ((d, J=2.4 Hz, 1H), 2.53-2.49 (m, 1H), 2.14 (s, 3H), 2.06-1.94 (m, 2H), 1.32 (s, 3H), 1.33 (t, J=7.2 Hz, 3H).

$^{13}$C-NMR (100 MHz, CDCl$_3$) δ 203.44, 171.29, 136.36, 136.08, 128.52, 128.11, 126.70, 122.76, 93.38, 69.22, 64.67, 61.69, 45.78, 34.37, 28.55, 27.38, 26.99, 14.06.

HPLC: Chiralpak AD-H (hexane/i-PrOH=90/10, flow rate 1 mL/min, λ=210 nm), $t_R$ (major)=15.2 min, $t_R$ (minor)=39.6 min; 97% ee.

$[\alpha]_D^{25}$=−35.4 (c=1.2, CHCl$_3$).

HRMS (EI) calcd for C$_{20}$H$_{25}$O$_6$N, m/z 375.1678. found 375.1675.

(R,2R,3S,4R)-methyl-1-acetyl-4-hydroxy-4-methyl-3-nitro-2-phenylcyclohexane carboxylate (3l)

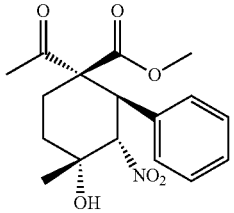

To a solution of Methyl 2-acetyl-5-oxohexanoate 1b (0.4 mmol, 1.0 eq) and nitroolefin (2a) (0.6 mmol, 1.5 eq) in diethyl ether (0.4 mL) was added catalyst VI (0.06 mmol, 0.15 eq) at room temperature. The resulting mixture was stirred vigorously. After 16 hours the reaction was completed (monitored by TLC and crude NMR), the product was afforded by flash chromatography over silica gel in 85% yield.

$^1$H-NMR (400 MHz, CDCl$_3$) δ 7.38-7.36 (m, 2H), 7.27-7.24 (m, 3H), 5.67 (d, J=12.4 Hz, 1H), 4.11 (d, J=12.4 Hz, 1H), 3.69 (s, 3H), 2.88 (d, J=2.0 Hz, 1H), 2.56-2.48 (m, 1H), 2.00-1.86 (m, 3H), 1.76 (s, 3H), 1.33 (s, 3H).

$^{13}$C-NMR (100 MHz, CDCl$_3$) δ 202.97, 171.86, 134.53, 130.03, 128.32, 128.28, 93.21, 69.76, 64.79, 52.13, 46.38, 34.12, 28.70, 27.79, 27.46.

HPLC: Chiralpak AD-H (hexane/i-PrOH=90/10, flow rate 1 mL/min, λ=210 nm), $t_R$ (major)=18.0 min, $t_R$ (minor)=31.5 min; 99% ee.

$[\alpha]_D^{25}$=−101.3 (c=1.0, CHCl$_3$).

HRMS (EI) calcd for C$_{17}$H$_{21}$O$_6$N, m/z 335.1365. found 335.1369.

(R,2R,3S,4R)-benzyl-1-acetyl-4-hydroxy-4-methyl-3-nitro-2-phenylcyclohexane carboxylate (3s)

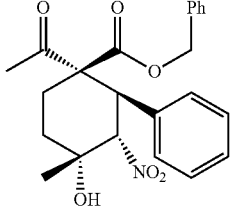

To a solution of benzyl 2-acetyl-5-oxohexanoate 1c (0.4 mmol, 1.0 eq) and nitroolefin (2a) (0.6 mmol, 1.5 eq) in diethyl ether (0.2 mL) was added catalyst VI (0.06 mmol, 0.15 eq) at room temperature. The resulting mixture was stirred vigorously. After 16 hours the reaction was completed (monitored by TLC and crude NMR), the product was afforded by flash chromatography over silica gel in 93% yield.

$^1$H-NMR (400 MHz, CDCl$_3$) δ 7.39-7.33 (m, 5H), 7.26-7.19 (m, 5H), 5.70 (d, J=12.4 Hz, 1H), 5.23 (d, J=12.0 Hz, 1H), 5.01 (d, J=12.0 Hz, 1H), 4.10 (d, J=12.4 Hz, 1H), 2.90 (s, 1H), 2.57-2.49 (m, 1H), 1.97-1.78 (m, 3H), 1.67 (s, 3H), 1.34 (s, 3H).

$^{13}$C-NMR (100 MHz, CDCl$_3$) δ 203.05, 171.15, 134.55, 134.35, 130.05, 128.79, 128.70, 128.57, 128.37, 128.27, 93.15, 69.76, 67.33, 64.94, 46.48, 33.98, 28.91, 27.80, 27.46.

HPLC: Chiralpak AS-H (hexane/i-PrOH=80/20, flow rate 1 mL/min, λ=210 nm), t$_R$ (major)=11.2 min, t$_R$ (minor)=38.7 min; 99% ee.

$[α]_D^{25}$=−83.8 (c=1.2, CHCl$_3$).

HRMS (EI) calcd for C$_{23}$H$_{25}$O$_6$N, m/z 411.1677. found 411.1682.

The stereochemistry of the tandem Michael-Henry reaction: The stereoselectivities of the tandem Michael-Henry reaction was established by determination of the X-ray crystal structure of 3f (the deposition number: CCDC 670273) together with NMR.

Further, the domino double Michael reaction was investigated. Thereby an organocatalytic diastereo- and enantioselective cascade double Michael reaction was developed, in which two C—C bonds and four contiguous stereogenic centers (containing one adjacent quaternary and tertiary stereocenters) were efficiently created in a one-pot operation with an efficient control of stereochemistry. This catalytic methodology serves as a facile approach to synthetically useful, highly functionalized chiral cyclopentanes (For reviews of the synthesis and bioactivities of cyclopentanes, see: (a) Biaggio, F C, et al., Curr. Org. Chem. (2005) 9, 419; (b) Silva, L F, Tetrahedron (2002) 58, 9137; (c) Lautens, M, et al., Chem. ReV. (1996) 96, 49; (d) Masse, C E, & Panek, J S, Chem. ReV. (1995) 95, 1293).

The design of a catalytic cascade double Michael addition reaction required the consideration of several factors. The reactivity of the α,β-unsaturated substrates that participates in the second conjugate addition reaction must be reactive enough to allow the intramolecular Michael reaction. In the meanwhile, these substrates should be less reactive than nitroolefins. Recognition of this reactivity profile allows the design of systems capable of undergoing efficient double Michael addition sequences. Furthermore, a carbon nucleophile should be sufficiently active to only engage in the first Michael addition reaction. To address this concern, we employed easily enolized acetoacetate ester to replace the α,β-unsaturated ester.

Figure 6:
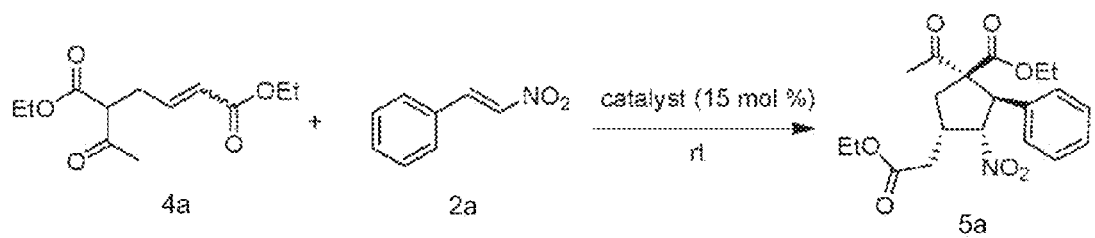
FIG. 6 shows examples and data of organocatalytic domino double Michael reactions of ethyl 2-acetyl-5-oxohexanoate 4a (E:Z) 6:1) and trans-β-Nitrostyrene 2a. Unless otherwise specified, all the reactions were carried out using 4a (0.3 mmol, 1.0 equiv) and 2a (0.45 mmol, 1.5 equiv) with 15 mol % of catalyst at room temperature (22° C.). b: Isolated yields. c: Determined by NMR and HPLC analysis. d: Determined by chiral HPLC analysis (major isomer). e: Reaction at 0° C. f: Catalyst (10 mol %) was used. g: 4a (0.45 mmol, 1.5 equiv) and 2a (0.3 mmol, 1.0 equiv) were used.

Since the cinchona alkaloid and derivatives thereof (supra) have been identified as efficient bifunctional organocatalysts in asymmetric Michael reactions, they were employed for the double Michael addition reaction. After reacting nitrostyene with diethyl 5-acetylhex-2-enedioate 2 (E:Z) 6:1) in the presence of cinchona alkaloid catalyst II (15 mol %) at room temperature (22° C.) the desired product could be isolated in 81% yield. Surprisingly a single diastereoisomer was isolated, albeit not enantiomerically pure (FIG. 6, entry 1). In attempts to improve the yield and enantioselectivity, several catalysts and reaction conditions were screened. Catalyst I proved to be a very efficient catalyst for Michael reaction. Therefore, I was chosen as the most promising catalyst to screen other conditions. However, the results were not improved significantly when the reaction was carried out in different solvents or at different reaction temperatures (FIG. 6, entries 2-5). As such, more catalysts were screened (in FIG. 2, IV-VII) to be at room temperature. Catalyst VI was found to be an excellent candidate to catalyze this domino reaction with the highest stereoselectivity (97% ee, >99:1 dr) among all the cases investigated, as shown in the FIG. 6, entry 10. Further optimization of the reaction conditions elucidated that solvents played a very important role in determining the selectivities of the reaction and yield (diethyl ether, >99:1 dr, 97% ee, 91% yield).

Figure 7:
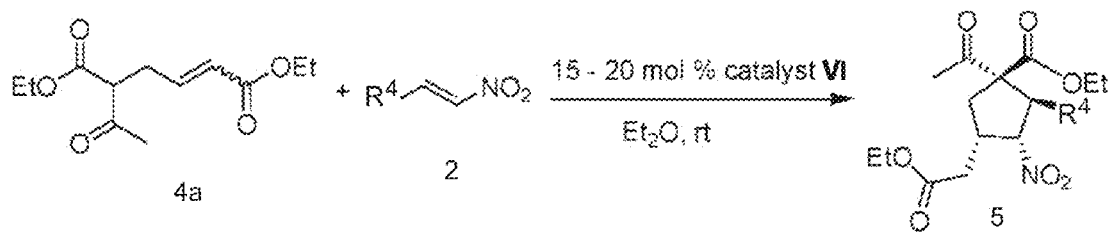
FIG. 7 depicts examples and data of a domino double Michael reaction of ethyl 2-acetyl-5-oxohexanoate 4a (E:Z) 6:1) and Nitroolefins (2) Catalyzed by Catalyst VI. Unless otherwise specified, the reactions were carried out using 4a (0.3 mmol, 1.0 equiv) and 2 (0.45 mmol, 1.5 equiv) in the presence of 15 mol % of VI at room temperature in diethyl ether (0.4 mL) (see the Examples). b: Isolated yields. c: Determined by NMR and HPLC analysis. d: Determined by chiral HPLC analysis (major isomer). e: 20 mol % catalyst and 2.0 equiv of 2 were used.
Figure 8A:
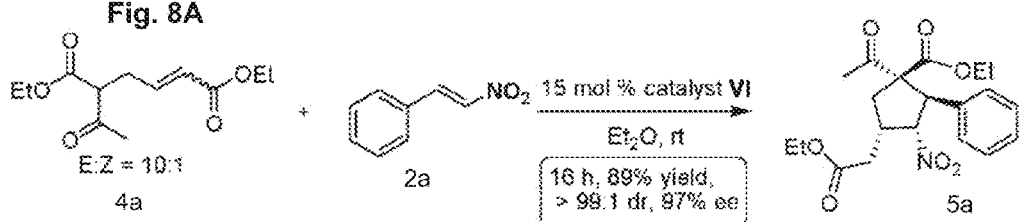
FIG. 8 illustrates domino double Michael reactions of 4a with 2a (E:Z) 10:1) and 4b with 2a/2k.
Figure 8B:
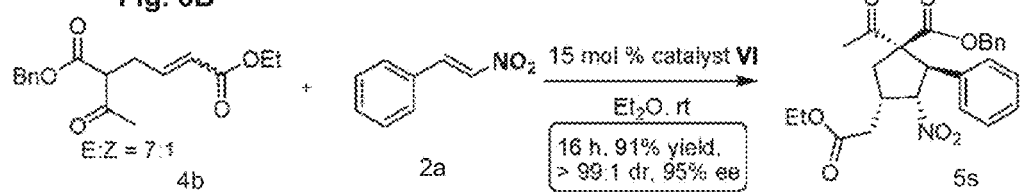
Figure 8C:
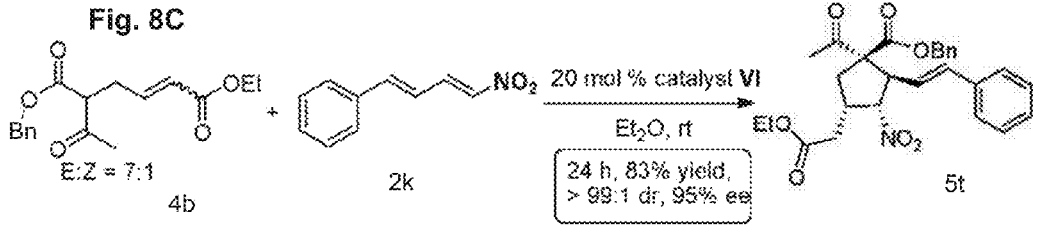

With optimized reaction conditions established, a series of nitroolefins were reacted with unsaturated ester substrates to investigate the generality of the domino double Michael process by using catalyst VI in diethyl ether. It was observed that most of the reactions are completed within 36 h with good to excellent yields (81-92%), excellent enantioselectivities (90-97% ee) and diastereoselectivities (95:5→99:1 dr). A majority of the examples (shown in FIG. 7) indicate that the position and electronic property of the substituents on aromatic rings have a very limited effect on the stereoselectivities. Regardless of the types of substituents on the aromatic rings, be it electron-withdrawing (FIG. 7, entries 6, 7, 13), -donating (entries 2-5), neutral (entry 1, 8, 9) groups and substrates containing a variety of substitution (para, meta, and ortho) groups participated in this reaction efficiently. The heterocyclic thienyl and furanyl groups (FIG. 7, entries 10-12) also participated in this process, giving good yields and enantioselectivities. Surprisingly, the presence of the nitro group on the aromatic ring did not cause a decrease in the enantiomeric excess. Without being bound by theory, this may be attributed to the primary amine group in the catalyst that can selectively capture the two nitro groups. Interestingly, the ratio (E:Z) 10:1) of 4a had no effect on reactivity and selectivity (FIG. 8A). The domino reaction also proceeded smoothly when 4a was replaced by 4b, giving excellent stereoselectivities (95% ee) as displayed in FIG. 8B. Notably, only one double Michael adduct was obtained from the reaction of nitrodiene 2k in 95% ee value (FIG. 8C). Theoretically, both β- and δ-positions of 2k can possibly be attacked due to the congruous two double bonds. This demonstrates the high regioselectivity and enantioselectivity of this method.

Without being bound by theory, according to experimental results and the dual activation model (Okino, T, et al., J. Am. Chem. Soc. (2005) 127, 119) the two substrates involved in the reaction are activated by catalyst VI as shown in FIG. 15. Nitroolefins are assumed to interact with the primary amine moiety of VI via multiple H-bonds. In this case, both the nitro group and β-ketoester group interact with multiple H-bonds so that these two groups are on the same side, thus enhancing the electrophilic character of the reacting carbon center and controlling stereochemistry. The carboanion (adjacent to the nitro group) generated from the Michael addition then attacks the double bond of α,β-unsaturated esters to afford double Michael products (FIG. 2).

Figure 9:
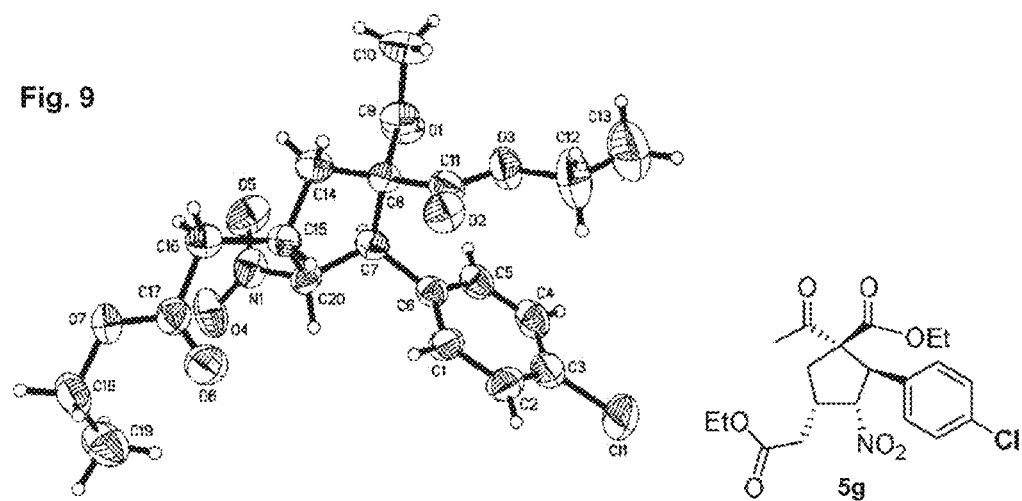
FIG. 9 depicts the X-ray crystal structure of compound 5g.

The stereochemistry was established by X-ray crystallographic determination of 5g (FIG. 9) and analysis of NMR data of the products.

Typical Procedure for Double-Michael Reactions

To a solution of diethyl 5-acetylhex-2-enedioate (4a, 0.3 mmol, 1.0 eq) and nitro olefin (0.45 mmol, 1.5 eq) in diethyl ether (0.4 mL) was added catalyst VI (Q-NH$_2$) (0.045 mmol, 0.15 eq) at room temperature (22° C.). The resulting mixture was stirred vigorously for 16-36 hours. After the reaction was completed (monitored by TLC and crude NMR), the product was afforded by flash chromatography over silica gel (Et$_2$O: Hexane=1:10 to 1:4).

(1R,2R,3R,4S)-ethyl 4-((ethoxycarbonyl)methyl)-1-acetyl-3-nitro-2-phenylcyclopentanecarboxylate (5a)

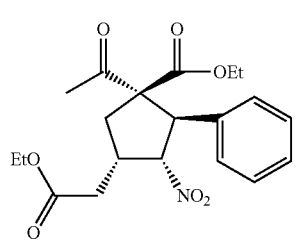

5a

The title compound was prepared according to the typical procedure, as described above in 91% yield.

$^1$H-NMR (400 MHz, CDCl$_3$) δ 7.31-7.21 (m, 5H), 5.49 (dd, J=5.2, 7.6 Hz, 1H), 5.10 (d, J=4.8 Hz, 1H), 4.26-4.14 (m, 2H), 3.80-3.72 (m, 1H), 3.68-3.58 (m, 1H), 3.41-3.33 (m, 1H), 2.88 (dd, J=6.8, 12.8 Hz, 1H), 2.50 (dd, J=7.2, 16.8 Hz, 1H), 2.40 (dd, J=7.6, 16.8 Hz, 1H), 2.20 (s, 3H), 2.01 (dd, J=10.8, 12.8 Hz, 1H), 1.30 (t, J=7.2 Hz, 3H), 0.76 (t, J=7.2 Hz, 3H).

$^{13}$C-NMR (100 MHz, CDCl$_3$) δ 200.09, 170.87, 170.29, 137.16, 128.52, 128.48, 127.80, 94.26, 71.28, 61.77, 61.05, 51.54, 40.27, 37.74, 34.20, 26.98, 14.16, 13.26.

HPLC: Chiralcel OD-H (hexane/i-PrOH=80/20, flow rate 1 mL/min, λ=230 nm), t$_R$ (major)=6.2 min, t$_R$ (minor)=8.9 min; 97% ee.

[α]$_D^{22}$=−3.1 (c=1.0, CH$_2$Cl$_2$).

HRMS (ESI) calcd for C$_{20}$H$_{26}$NO$_6$+H, m/z 392.1709. found 392.1707.

(1R,2R,3R,4S)-ethyl 4-((ethoxycarbonyl)methyl)-1-acetyl-2-(4-methoxylphenyl)-3-nitro-cyclopentanecarboxylate (5b)

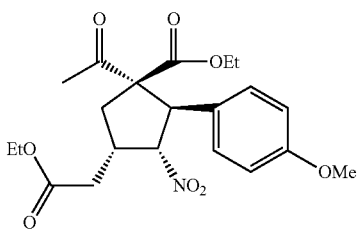

5b

To a solution of diethyl 5-acetylhex-2-enedioate (4a, 0.3 mmol, 1.0 eq) and 1-methoxy-4-((E)-2-nitrovinyl)benzene (0.6 mmol, 2.0 eq) in diethyl ether (0.4 mL) was added catalyst VI (Q-NH$_2$) (0.06 mmol, 0.2 eq) at room temperature (22° C.). The resulting mixture was stirred vigorously for 24 hours, then the reaction was continued for about 6 hours after removal of the solvent. After the reaction was completed (monitored by TLC and crude NMR), the title product was afforded by flash chromatography over silica gel (Et$_2$O:Hexane=1:10 to 1:3) in 83% yield.

$^1$H-NMR (400 MHz, CDCl$_3$) δ 7.15 (d, J=8.8 Hz, 2H), 6.82 (d, J=8.8, Hz, 2H), 5.44 (dd, J=5.6, 7.6 Hz, 1H), 5.02 (d, J=5.2 Hz, 1H), 4.24-4.15 (m, 2H), 3.83-3.76 (m, 1H), 3.78 (s, 3H), 3.63-3.57 (m, 1H), 3.51-3.43 (m, 1H), 2.86 (dd, J=6.8, 12.8 Hz, 1H), 2.48 (dd, J=7.6, 16.8 Hz, 1H), 2.40 (dd, J=7.6, 16.8 Hz, 1H), 2.19 (s, 3H), 2.00 (dd, J=10.8, 12.8 Hz, 1H), 1.30 (t, J=7.2 Hz, 3H), 0.83 (t, J=7.2 Hz, 3H).

$^{13}$C-NMR (100 MHz, CDCl$_3$) δ 200.36, 170.90, 170.42, 159.14, 129.59, 128.96, 113.85, 94.32, 71.02, 61.77, 61.03, 55.31, 50.97, 39.88, 37.72, 34.27, 27.06, 14.15, 13.39.

HPLC: Chiralcel OD-H (hexane/i-PrOH=80/20, flow rate 1 mL/min, λ=220 nm), t$_R$ (major)=8.1 min, t$_R$ (minor)=12.2 min; 96% ee.

[α]$_D^{22}$=−9.0 (c=1.3, CH$_2$Cl$_2$).

HRMS (ESI) calcd for C$_{21}$H$_{27}$NO$_8$+H, m/z 422.1815. found 422.1810.

(1R,2R,3R,4S)-ethyl 4-((ethoxycarbonyl)methyl)-1-acetyl-3-nitro-2-p-tolylcyclopentanecarboxylate (5c)

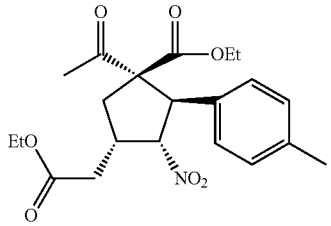

5c

The title compound was prepared according to the typical procedure, as described above in 89% yield.

$^1$H-NMR (400 MHz, CDCl$_3$) δ 7.09 (m, 4H), 5.44 (dd, J=5.2, 7.6 Hz, 1H), 5.04 (d, J=5.2 Hz, 1H), 4.24-4.15 (m, 2H), 3.80-3.75 (m, 1H), 3.63-3.57 (m, 1H), 3.45-3.41 (m, 1H), 2.87 (dd, J=6.8, 12.8 Hz, 1H), 2.46 (dd, J=7.2, 16.8 Hz, 1H), 2.40 (dd, J=7.6, 17.2 Hz, 1H), 2.30 (s, 3H), 2.19 (s, 3H), 2.00 (dd, J=10.8, 12.8 Hz, 1H), 1.29 (t, J=7.2 Hz, 3H), 0.78 (t, J=7.2 Hz, 3H).

$^{13}$C-NMR (100 MHz, CDCl$_3$) δ 200.25, 170.89, 170.12, 137.52, 133.97, 129.12, 128.32, 94.28, 71.13, 61.74, 61.02, 51.29, 40.04, 37.77, 34.26, 27.04, 20.99, 14.15, 13.25.

HPLC: Chiralcel OD-H (hexane/i-PrOH=80/20, flow rate 1 mL/min, λ=220 nm), t$_R$ (major)=6.1 min, t$_R$ (minor)=8.7 min; 96% ee.

[α]$_D^{22}$=−5.7 (c=1.3, CH$_2$Cl$_2$).

HRMS (ESI) calcd for C$_{21}$H$_{27}$NO$_7$+H, m/z 406.1866. found 406.1867.

(1R,2R,3R,4S)-ethyl 4-((ethoxycarbonyl)methyl)-1-acetyl-3-nitro-2-m-tolylcyclopentanecarboxylate (5d)

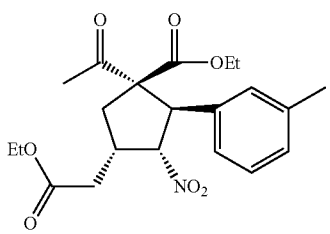

5d

The title compound was prepared according to the typical procedure, as described above in 85% yield.

$^1$H-NMR (400 MHz, CDCl$_3$) δ 7.20-7.17 (m, 1H), 7.10-6.97 (m, 3H), 5.46 (m, 1H), 5.05 (d, J=5.2 Hz, 1H), 4.24-4.16 (m, 2H), 3.80-3.72 (m, 1H), 3.64-3.58 (m, 1H), 3.45-3.36 (m, 1H), 2.87 (dd, J=6.8, 12.8 Hz, 1H), 2.48 (dd, J=6.4, 17.2 Hz, 1H), 2.36 (dd, J=7.6, 16.8 Hz, 1H), 2.32 (s, 3H), 2.19 (s, 3H), 2.00 (dd, J=10.8, 12.8 Hz, 1H), 1.30 (t, J=7.2 Hz, 3H), 0.77 (t, J=7.2 Hz, 3H).

$^{13}$C-NMR (100 MHz, CDCl$_3$) δ 200.13, 170.88, 170.31, 138.13, 137.06, 129.33, 128.48, 128.41, 125.29, 94.36, 71.24, 61.71, 61.02, 51.53, 40.21, 37.77, 34.23, 26.99, 21.32, 14.16, 13.23.

HPLC: Chiralpak AD-H (hexane/i-PrOH=90/10, flow rate 1 mL/min, λ=210 nm), $t_R$ (minor)=10.6 min, $t_R$ (major)=12.0 min; 94% ee.

$[\alpha]_D^{22}$=−4.2 (c=1.2, $CH_2Cl_2$).

HRMS (ESI) calcd for $C_{21}H_{27}NO_7$+H, m/z 406.1866. found 406.1858.

(1R,2R,3R,4S)-ethyl 4-((ethoxycarbonyl)methyl)-1-acetyl-2-(4-bromophenyl)-3-nitro-cyclopentanecarboxylate (5e)

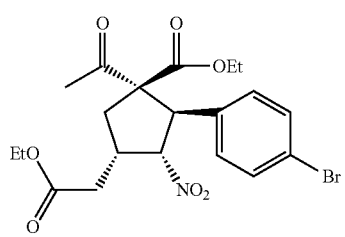

5e

The title compound was prepared according to the typical procedure, as described above in 92% yield.

$^1$H-NMR (400 MHz, $CDCl_3$) δ 7.43 (d, J=8.4 Hz, 1H), 7.11 (dd, J=8.4 Hz, 1H), 5.44 (dd, J=5.6, 7.2 Hz, 1H), 5.04 (d, J=5.2 Hz, 1H), 4.24-4.16 (m, 2H), 3.86-3.78 (m, 1H), 3.63-3.57 (m, 1H), 3.53-3.45 (m, 1H), 2.86 (dd, J=6.8, 13.2 Hz, 1H), 2.49 (dd, J=7.2, 16.8 Hz, 1H), 2.39 (dd, J=7.6, 17.0 Hz, 1H), 2.19 (s, 3H), 2.00 (dd, J=10.4, 12.4 Hz, 1H), 1.30 (t, J=7.2 Hz, 3H), 0.84 (t, J=7.2 Hz, 3H).

$^{13}$C-NMR (100 MHz, $CDCl_3$) δ 199.77, 170.81, 170.12, 136.02, 131.62, 130.21, 121.94, 93.72, 70.99, 61.96, 61.10, 50.93, 39.99, 37.70, 34.17, 26.96, 14.15, 13.33.

HPLC: Chiralcel OD-H (hexane/i-PrOH=80/20, flow rate 1 mL/min, λ=220 nm), $t_R$ (major)=7.6 min, $t_R$ (minor)=11.7 min; 97% ee.

$[\alpha]_D^{22}$=−19.0 (c=0.8, $CH_2Cl_2$).

HRMS (ESI) calcd for $C_{20}H_{24}BrNO_7$+H, m/z 470.0814. found 470.0808.

(1R,2R,3R,4S)-ethyl 4-((ethoxycarbonyl)methyl)-1-acetyl-2-(4-chlorophenyl)-3-nitro-cyclopentanecarboxylate (5g)

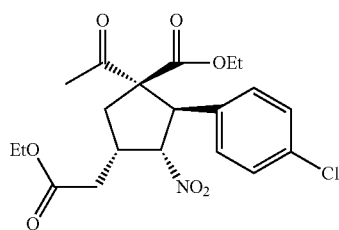

5g

The title compound was prepared according to the typical procedure, as described above in 88% yield.

$^1$H-NMR (400 MHz, $CDCl_3$) δ 7.28 (d, J=6.8 Hz, 1H), 7.16 (dd, J=2.0, 7.8 Hz, 1H), 5.44 (dd, J=5.6, 7.6 Hz, 1H), 5.05 (d, J=5.2 Hz, 1H), 4.24-4.16 (m, 2H), 3.86-3.78 (m, 1H), 3.64-3.57 (m, 1H), 3.52-3.44 (m, 1H), 2.86 (dd, J=6.8, 12.8 Hz, 1H), 2.48 (dd, J=7.4, 17.0 Hz, 1H), 2.39 (dd, J=7.6, 17.0 Hz, 1H), 2.19 (s, 3H), 2.00 (dd, J=10.4, 12.4 Hz, 1H), 1.30 (t, J=7.2 Hz, 3H), 0.84 (t, J=7.2 Hz, 3H).

$^{13}$C-NMR (100 MHz, $CDCl_3$) δ 200.03, 170.81, 170.14, 135.49, 133.82, 129.88, 128.64, 93.79, 71.02, 61.92, 61.09, 50.86, 39.97, 37.70, 34.17, 26.97, 14.15, 13.33.

HPLC: Chiralcel OD-H (hexane/i-PrOH=80/20, flow rate 1 mL/min, λ=254 nm), $t_R$ (major)=7.1 min, $t_R$ (minor)=11.1 min; 96% ee.

$[\alpha]_D^{22}$=−11.4 (c=1.0, $CH_2Cl_2$).

HRMS (ESI) calcd for $C_{20}H_{24}ClNO_7$+H, m/z 426.1320. found 426.1322.

(1R,2R,3R,4S)-ethyl 4-((ethoxycarbonyl)methyl)-1-acetyl-2-(2-methoxylphenyl)-3-nitro-cyclopentanecarboxylate (5l)

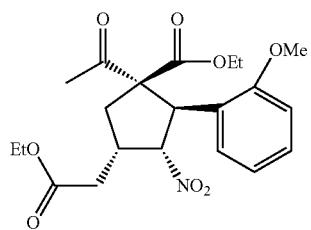

5l

To a solution of diethyl 5-acetylhex-2-enedioate (4a, 0.3 mmol, 1.0 eq) and 1-methoxy-2-((E)-2-nitrovinyl)benzene (0.6 mmol, 2.0 eq) in diethyl ether (0.4 mL) was added catalyst VI (Q-NH₂) (0.06 mmol, 0.2 eq) at room temperature (22° C.). The resulting mixture was stirred vigorously for 24 hours, then the reaction was continued for about 6 hours after removal of the solvent. After the reaction was completed (monitored by TLC and crude NMR), the title product was afforded by flash chromatography over silica gel ($Et_2O$:Hexane=1:10 to 1:3) in 81% yield.

$^1$H-NMR (400 MHz, $CDCl_3$) δ 7.30-7.21 (m, 2H), 6.90-6.89 (m, 1H), 6.78 (d, J=8.0 Hz, 1H), 5.55 (dd, J=4.0, 7.2 Hz, 1H), 5.13 (d, J=4.0 Hz, 1H), 4.21-4.13 (m, 2H), 3.90-3.84 (m, 1H), 3.77 (s, 3H), 3.65-3.59 (m, 1H), 3.53-3.45 (m, 1H), 2.89 (dd, J=6.4, 12.4 Hz, 1H), 2.48 (dd, J=6.4, 17.2 Hz, 1H), 2.34 (dd, J=8.4, 16.8 Hz, 1H), 2.14 (s, 3H), 1.95 (m, 1H), 1.28 (t, J=7.2 Hz, 3H), 0.78 (t, J=7.2 Hz, 3H).

$^{13}$C-NMR (100 MHz, $CDCl_3$) δ 200.09, 171.03, 170.20, 157.31, 132.03, 129.12, 125.88, 120.85, 110.10, 94.46, 70.76, 61.39, 60.87, 54.90, 50.54, 39.78, 37.88, 34.10, 26.50, 14.19, 13.23.

HPLC: Chiralpak AD-H (hexane/i-PrOH=90/10, flow rate 1 mL/min, λ=210 nm), $t_R$ (minor)=12.4 min, $t_R$ (major)=14.6 min; 95% ee.

$[\alpha]_D^{22}$=−5.5 (c=1.0, $CH_2Cl_2$).

HRMS (ESI) calcd for $C_{21}H_{27}NO_8$+H, m/z 422.1815. found 422.1823.

(1R,2R,3R,4S)-ethyl 4-((ethoxycarbonyl)methyl)-1-acetyl-2-(naphthalen-3-yl)-3-nitro-cyclopentanecarboxylate (5m)

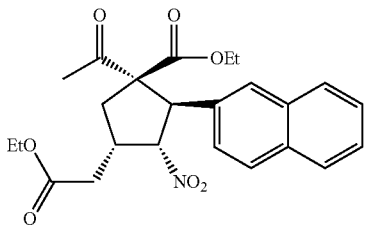

The title compound was prepared according to the typical procedure, as described above in 84% yield.

$^1$H-NMR (400 MHz, CDCl$_3$) δ 7.82-7.76 (m, 3H), 7.69 (s, 1H), 7.49-7.47 (m, 2H), 7.34 (d, J=8.4 Hz, 1H), 5.64-5.61 (m, 1H), 5.27 (d, J=5.2 Hz, 1H), 4.26-4.18 (m, 2H), 3.75-3.63 (m, 2H), 3.26-3.18 (m, 1H), 2.93 (dd, J=6.8, 12.8 Hz, 1H), 2.53 (dd, J=7.6, 16.8 Hz, 1H), 2.45 (dd, J=7.6, 16.8 Hz, 1H), 2.21 (s, 3H), 2.45 (dd, J=10.8, 12.8 Hz, 1H), 1.32 (t, J=7.2 Hz, 3H), 0.52 (t, J=7.2 Hz, 3H).

$^{13}$C-NMR (100 MHz, CDCl$_3$) δ 200.22, 170.91, 170.32, 128.17, 127.89, 127.48, 127.43, 126.40, 126.28, 126.26, 94.23, 71/30, 61.74, 61.08, 51.71, 40.19, 37.86, 34.29, 27.02, 14.18, 13.03.

HPLC: Chiralpak AD-H (hexane/i-PrOH=80/20, flow rate 1 mL/min, λ=254 nm), t$_R$ (minor)=20.5 min, t$_R$ (major)=33.5 min; 95% ee.

[α]$_D^{22}$=−31.9 (c=0.6, CH$_2$Cl$_2$).

HRMS (ESI) calcd for C$_{24}$H$_{27}$NO$_7$+H, m/z 442.1866. found 442.1861.

(1R,2R,3R,4S)-ethyl 4-((ethoxycarbonyl)methyl)-1-acetyl-2-(naphthalen-1-yl)-3-nitro-cyclopentanecarboxylate (5n)

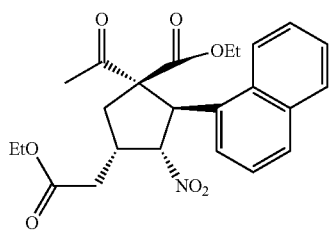

The title compound was prepared according to the typical procedure, as described above in 87% yield.

$^1$H-NMR (400 MHz, CDCl$_3$) δ 8.58 (d, J=7.6 Hz, 1H), 7.82 (d, J=8.4 Hz, 1H), 7.77 (d, J=8.4 Hz, 1H), 7.62-7.59 (m, 1H), 7.52-7.49 (m, 1H), 7.44-7.40 (m, 1H), 7.23 (d, J=7.2 Hz, 1H), 6.03 (d, J=2.4 Hz, 1H), 5.60-5.58 (m, 1H), 4.30-4.17 (m, 2H), 3.76-3.68 (m, 1H), 3.51-3.45 (m, 1H), 3.01 (dd, J=6.8, 12.8 Hz, 1H), 2.88-2.83 (m, 1H), 2.62 (dd, J=6.4, 17.2 Hz, 1H), 2.43 (dd, J=8.4, 17.2 Hz, 1H), 2.19 (s, 3H), 1.16-2.10 (m, 1H), 1.32 (t, J=7.2 Hz, 3H), 0.19 (t, J=7.2 Hz, 3H).

$^{13}$C-NMR (100 MHz, CDCl$_3$) δ 199.62, 170.91, 170.19, 135.23, 133.55, 132.51, 128.57, 126.75, 126.04, 124.99, 124.75, 124.57, 96.98, 72.47, 61.48, 61.11, 46.43, 37.98, 33.91, 26.81, 14.19, 12.51.

HPLC: Chiralcel OD-H (hexane/i-PrOH=80/20, flow rate 1 mL/min, λ=220 nm), t$_R$ (major)=7.7 min, t$_R$ (minor)=10.2 min; 95% ee.

[α]$_D^{22}$=−29.0 (c=1.0, CH$_2$Cl$_2$).

HRMS (ESI) calcd for C$_{24}$H$_{27}$NO$_7$+H, m/z 442.1866. found 442.1861.

(1R,2R,3R,4S)-ethyl 4-((ethoxycarbonyl)methyl)-1-acetyl-2-(furan-3-yl)-3-nitro-cyclopentanecarboxylate (5o)

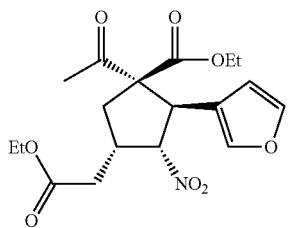

The title compound was prepared according to the typical procedure, as described above in 86% yield.

$^1$H-NMR (400 MHz, CDCl$_3$) δ 7.36-7.34 (m, 2H), 6.28 (s, 1H), 5.34-5.31 (m, 1H), 4.82 (d, J=6.8 Hz, 1H), 4.22-4.14 (m, 2H), 4.03-3.95 (m, 1H), 3.88-3.81 (m, 1H), 3.58-3.52 (m, 1H), 2.83 (dd, J=7.2, 13.2 Hz, 1H), 2.41 (d, J=7.6 Hz, 1H), 2.21 (s, 3H), 1.96 (dd, J=10.4, 12.8 Hz, 1H), 1.28 (t, J=7.2 Hz, 3H), 1.02 (t, J=7.2 Hz, 3H).

$^{13}$C-NMR (100 MHz, CDCl$_3$) δ 200.61, 170.86, 170.57, 143.15, 140.79, 120.66, 109.98, 93.37, 69.47, 61.91, 61.04, 43.71, 38.29, 37.85, 34.55, 27.21, 14.14, 13.48.

HPLC: Chiralpak AD-H (hexane/i-PrOH=90/10, flow rate 1 mL/min, λ=254 nm), t$_R$ (minor)=17.9 min, t$_R$ (major)=19.0 min; 94% ee.

[α]$_D^{22}$=5.7 (c=1.2, CH$_2$Cl$_2$).

HRMS (ESI) calcd for C$_{18}$H$_{23}$NO$_8$+H, m/z 382.1502. found 382.1499.

(1R,2R,3R,4S)-ethyl 4-((ethoxycarbonyl)methyl)-1-acetyl-2-(furan-2-yl)-3-nitro-cyclopentanecarboxylate (5p)

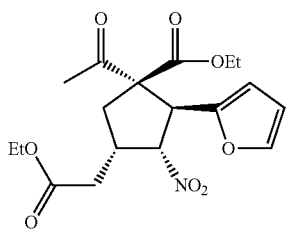

The title compound was prepared according to the typical procedure, as described above in 87% yield.

$^1$H-NMR (400 MHz, CDCl$_3$) δ 7.31-7.28 (m, 1H), 6.31-6.26 (m, 2H), 5.45 (dd, J=5.6, 7.6 Hz, 1H), 5.09 (d, J=5.6 Hz, 1H), 4.22-4.15 (m, 2H), 4.04-3.99 (m, 1H), 3.80-3.75 (m, 1H), 3.60-3.53 (m, 1H), 2.88 (dd, J=6.8, 13.2 Hz, 1H), 2.41 (d, J=7.6 Hz, 1H), 2.20 (s, 3H), 1.96-1.90 (m, 1H), 1.28 (t, J=7.2 Hz, 3H), 1.03 (t, J=7.2 Hz, 3H).

$^{13}$C-NMR (100 MHz, CDCl$_3$) δ 199.80, 170.76, 169.98, 149.81, 142.32, 110.73, 108.96, 92.07, 69.40, 62.32, 61.03, 46.32, 38.99, 37.50, 34.29, 26.73, 14.14, 13.60.

HPLC: Chiralcel OD-H (hexane/i-PrOH=80/20, flow rate 1 mL/min, λ=220 nm), $t_R$ (major)=7.2 min, $t_R$ (minor)=11.1 min; 94% ee.

$[α]_D^{22}$=−6.3 (c=1.1, CH$_2$Cl$_2$).

HRMS (ESI) calcd for C$_{18}$H$_{23}$NO$_8$+Na, m/z 404.1321. found 404.1326.

(1R,2R,3R,4S)-ethyl 4-((ethoxycarbonyl)methyl)-1-acetyl-3-nitro-2-(thiophen-2-yl)cyclopentanecarboxylate (5q)

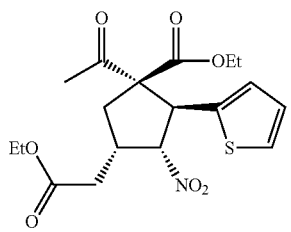

The title compound was prepared according to the typical procedure, as described above in 91% yield.

$^1$H-NMR (400 MHz, CDCl$_3$) δ 7.21-7.20 (m, 1H), 6.93-6.92 (m, 2H), 5.52-4.48 (m, 1H), 5.21 (d, J=7.2 Hz, 1H), 4.226-4.14 (m, 2H), 3.96-3.89 (m, 1H), 3.75-3.68 (m, 1H), 3.66-3.57 (m, 1H), 2.89 (dd, J=7.2, 12.8 Hz, 1H), 2.41 (d, J=7.6 Hz, 1H), 2.21 (s, 3H), 1.96 (dd, J=10.0, 13.2 Hz, 1H), 1.29 (t, J=7.2 Hz, 3H), 0.94 (t, J=7.2 Hz, 3H).

$^{13}$C-NMR (100 MHz, CDCl$_3$) δ 200.36, 170.76, 170.21, 138.64, 126.82, 126.27, 125.36, 94.23, 70.46, 62.10, 61.07, 47.35, 38.31, 37.70, 34.55, 27.14, 14.15, 13.48.

HPLC: Chiralpak AS-H (hexane/i-PrOH=95/5, flow rate 1 mL/min, λ=210 nm), $t_R$ (minor)=25.0 min, $t_R$ (major)=28.1 min; 94% ee.

$[α]_D^{22}$=−4.3 (c=1.2, CH$_2$Cl$_2$).

HRMS (ESI) calcd for C$_{18}$H$_{23}$NO$_7$S+Na, m/z 420.1093. found 420.1100.

(1R,2R,3R,4S)-ethyl 4-((ethoxycarbonyl)methyl)-1-acetyl-3-nitro-2-(4-nitrophenyl)cyclopentanecarboxylate (5r)

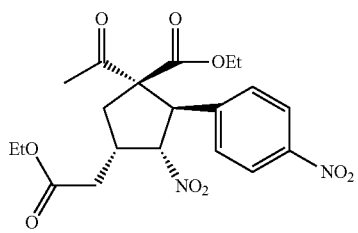

To a solution of diethyl 5-acetylhex-2-enedioate (4a, 0.3 mmol, 1.0 eq) and 1-nitro-4-((E)-2-nitrovinyl)benzene (0.6 mmol, 2.0 eq) in diethyl ether (0.4 mL) was added catalyst VI (Q-NH$_2$) (0.06 mmol, 0.2 eq) at room temperature (22° C.). The resulting mixture was stirred vigorously for 24 hours, then the reaction was continued for about 6 hours after removal of the solvent. After the reaction was completed (monitored by TLC and crude NMR), the title product was afforded by flash chromatography over silica gel (Et$_2$O:Hexane=1:10 to 1:3) in 81% yield.

$^1$H-NMR (400 MHz, CDCl$_3$) δ 8.17 (d, J=8.8 Hz, 1H), 7.44 (d, J=8.8 Hz, 1H), 5.52-5.49 (m, 1H), 5.19 (d, J=5.6 Hz, 1H), 4.25-4.16 (m, 2H), 3.86-3.80 (m, 1H), 3.69-3.62 (m, 1H), 3.49-3.43 (m, 1H), 2.89 (dd, J=6.8, 13.2 Hz, 1H), 2.51 (dd, J=7.2, 17.2 Hz, 1H), 2.40 (dd, J=7.6, 17.2 Hz, 1H), 2.22 (s, 3H), 2.02 (dd, J=10.8, 12.8 Hz, 1H), 1.30 (t, J=7.2 Hz, 3H), 0.82 (t, J=7.2 Hz, 3H).

$^{13}$C-NMR (100 MHz, CDCl$_3$) δ 199.79, 170.73, 169.82, 147.41, 144.35, 129.64, 123.60, 93.20, 71.10, 62.07, 61.21, 51.02, 40.01, 37.73, 34.09, 26.91, 14.15, 13.42.

HPLC: Chiralpak AS-H (hexane/i-PrOH=80/20, flow rate 1 mL/min, λ=210 nm), $t_R$ (major)=20.9 min, $t_R$ (minor)=25.4 min; 97% ee.

$[α]_D^{22}$=−9.7 (c=1.0, CH$_2$Cl$_2$).

(1R,2R,3R,4S)-benzyl 4-((ethoxycarbonyl)methyl)-1-acetyl-3-nitro-2-phenylcyclopentanecarboxylate (5s)

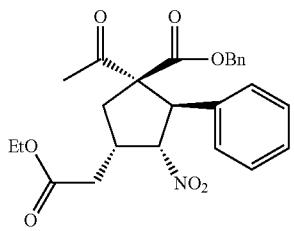

To a solution of 6-benzyl 1-ethyl 5-acetylhex-2-enedioate 4b (0.3 mmol, 1.0 eq) and 1-((E)-2-nitrovinyl)benzene (0.45 mmol, 1.5 eq) in diethylether (0.4 mL) was added catalyst VI (Q-NH$_2$) (0.045 mmol, 0.15 eq) at room temperature (22° C.). The resulting mixture was stirred vigorously for 16 hours, then the reaction was continued for about 6 hours after removal of the solvent. After the reaction was completed (monitored by TLC and crude NMR), the title product was afforded by flash chromatography over silica gel (Ethyl acetate:Hexane=1:10 to 1:4) in 91% yield.

$^1$H-NMR (400 MHz, CDCl$_3$) δ 7.54-7.14 (m, 8H), 6.96-6.94 (m, 2H), 5.51 (dd, J=5.2, 7.2 Hz, 1H), 5.11 (d, J=5.2 Hz, 1H), 4.83 (d, J=12.0 Hz, 1H), 4.25-4.16 (m, 2H), 4.10 (d, J=12.0 Hz, 1H), 3.69-3.63 (m, 1H), 2.89 (dd, J=6.8, 13.2 Hz, 1H), 2.49 (dd, J=7.6, 16.8 Hz, 1H), 2.40 (dd, J=7.6, 16.8 Hz, 1H), 2.11 (s, 3H), 2.02 (dd, J=10.8, 12.8 Hz, 1H), 1.30 (t, J=7.2 Hz, 3H).

$^{13}$C-NMR (100 MHz, CDCl$_3$) δ 199.84, 170.86, 170.18, 137.04, 134.09, 128.63, 128.49, 128.45, 128.28, 127.91, 94.23, 71.41, 67.57, 61.07, 51.69, 40.20, 37.81, 34.22, 27.07, 14.17.

HPLC: Chiralcel OD-H (hexane/i-PrOH=80/20, flow rate 1 mL/min, λ=220 nm), $t_R$ (major)=7.7 min, $t_R$ (minor)=11.5 min; 97% ee.

$[α]_D^{22}$=−5.0 (c=0.9, CH$_2$Cl$_2$).

HRMS (ESI) calcd for C$_{25}$H$_{27}$NO$_7$+H, m/z 454.1866. found 454.1861.

(1R,2R,3R,4S)-benzyl 4-((ethoxycarbonyl)methyl)-1-acetyl-3-nitro-2-styrylcyclopentanecarboxylate (5t)

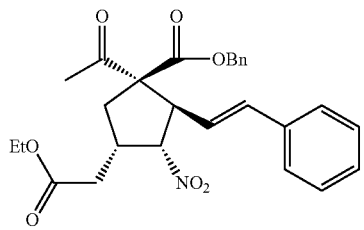

To a solution of 6-benzyl 1-ethyl 5-acetylhex-2-enedioate (4b, 0.3 mmol, 1.0 eq) and 1-((1E,3E)-4-nitrobuta-1,3-dienyl)benzene (0.6 mmol, 2.0 eq) in diethyl ether (0.4 mL) was added catalyst VI (Q-NH$_2$) (0.03 mmol, 0.2 eq) at room temperature (22° C.). The resulting mixture was stirred vigorously for 24 hours, and then the reaction was continued for about 6 hours after removal of the solvent. After the reaction was completed (monitored by TLC and crude NMR), the title product was afforded by flash chromatography over silica gel (Et$_2$O:Hexane=1:10 to 1:4) in 83% yield.

$^1$H-NMR (400 MHz, CDCl$_3$) δ 7.32-7.22 (m, 10H), 6.55 (d, J=16.0, 1H), 6.05 (dd, J=8.8, 16.0 Hz, 1H), 5.21-5.17 (m, 1H), 5.18 (d, J=12.0 Hz, 1H), 5.05 (d, J=12.0 Hz, 1H), 4.08 (d, J=12.4 Hz, 1H), 4.26-4.13 (m, 3H), 3.45-3.35 (m, 1H), 2.72 (dd, J=7.2, 13.2 Hz, 1H), 2.43-2.40 (m, 2H), 2.18 (s, 3H), 2.07 (dd, J=10.8, 13.2 Hz, 1H), 1.28 (t, J=7.2 Hz, 3H).

$^{13}$C-NMR (100 MHz, CDCl$_3$) δ 200.66, 170.89, 170.50, 135.91, 135.07, 134.36, 128.75, 128.73, 128.62, 128.60, 128.13, 126.55, 123.69, 92.81, 69.04, 67.85, 61.03, 51.55, 38.04, 37.63, 34.59, 27.64, 14.15.

HPLC: Chiralpak AD-H (hexane/i-PrOH=90/10, flow rate 1 mL/min, λ=254 nm), t$_R$ (major)=20.7 min, t$_R$ (minor)=22.8 min; 95% ee.

[α]$_D^{22}$=−5.3 (c=1.0, CH$_2$Cl$_2$).

HRMS (ESI) calcd for C$_{27}$H$_{29}$NO$_7$+H, m/z 480.2022. found 480.2017.

Figure 11:
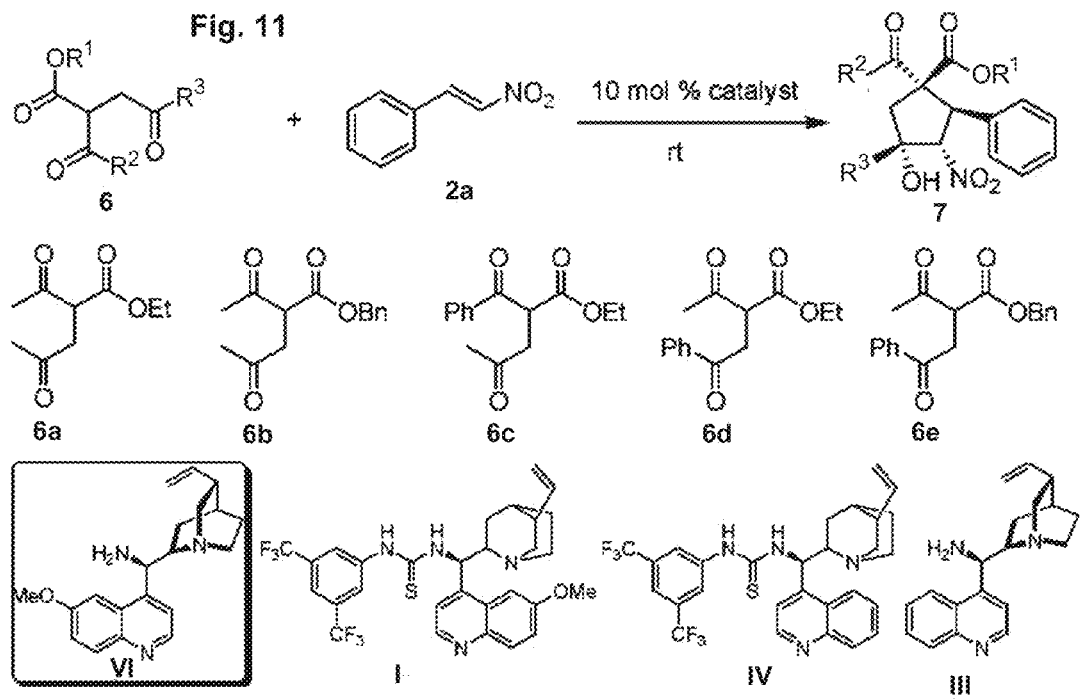
FIG. 11 depicts examples and data of domino Michael-Henry reactions of ethyl 2-acetyl-4-oxo-4-phenylbutanoate (6a) and trans-β-Nitrostyrene. Unless otherwise specified, all the reactions were carried out using 6 (1.0 mmol, 2.0 equiv) and 2a (0.5 mmol, 1.0 equiv) with 10 mol % of catalysts at room temperature. b: Isolated yields. c: Determined by chiral HPLC analysis. d: Reaction at 4° C. e: No reaction. f: Not applicable.

As indicated above cinchona alkaloid and derivatives have been identified as efficient bifunctional organocatalysts in asymmetric Michael reactions, Henry reactions (nitroaldol reactions), and tandem Michael-Henry reactions (cf. also FIG. 10). Therefore the feasibility of the use of diamine catalyst VI was explored in the hope to be able to allow catalysis of tandem Michael-Henry reactions involving a nitroolefin and a rationally designed carbon nucleophile 6a to form chiral cyclopentanes FIG. 10, n=0). However, the enantioselectivity of the desired product was only 67% ee (FIG. 11, entry 1). Despite changing the reaction conditions such as catalysts, solvents, and temperature, the highest enantiomeric excess obtained was 82% (FIG. 11, entries 1-4). The investigation of various substrates demonstrated that the domino Michael-Henry reaction proceeded smoothly to afford the desired cyclopentane ring products in high yields (92-95%, FIG. 11, entries 5, 7-9) with the exception of the less reactive substrate 6c (FIG. 11, entry 6). Surprisingly, only one diastereomer was obtained in all of the cases investigated. Nevertheless, varied enantioselectivities were observed with different substituents on 6. For example, higher enantiomeric excesses (75% ee) were observed when 6a was substituted with 6d or 6e.

Figure 13:
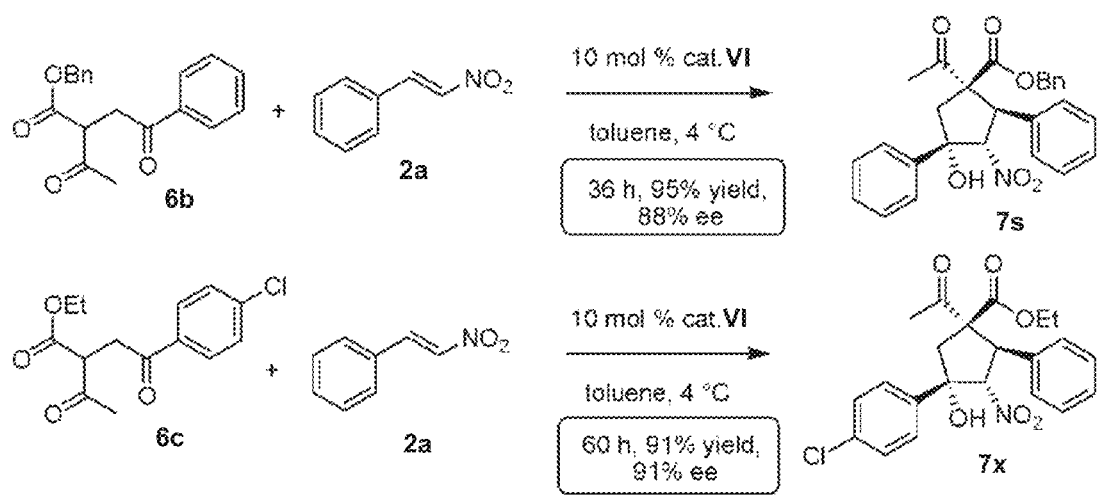
FIG. 13 depicts organocatalytic domino Michael-Henry reactions of trisubstituted carbon nucleophiles (6b or 6c) to trans-β-Nitrostyrene Catalyzed by Catalyst VI.

Despite many attempts, the best result achieved was only 83% ee with catalyst I. Therefore, it seemed essential to change the organocatalysts for much higher enantioselectivity. To our delight, the product was obtained in 93% yield with 90% ee (FIG. 11, entry 13) when catalyst VI was used. When catalyst IV was used, the lower enantiomeric excess indicated that the OMe group on the catalyst was critical for stereoselectivity (FIG. 11, entry 12). Although the reaction time was prolonged to 36 h, higher ee (95% ee) was afforded when the reaction temperature was lowered to 4° C. (FIG. 11, entry 15). The domino Michael-Henry reaction indeed proceeded smoothly to yield the desired cyclopentane ring product in excellent yield (95%) and good enantioselectivity (75% ee). With the optimized reaction conditions, the generality of the domino Michael-Henry process was investigated by using a variety of nitroalkenes. It was observed that all of the reactions were completed within 72 h, giving adducts in excellent yields (90-95%) and with complete diastereoselectivities and excellent enantioselectivities (88-96% ee). It appeared that the position and the electronic property of the substituents for aromatic rings had a very limited influence on the stereoselectivities of the reactions (FIG. 12, entries 2-7). Electron-withdrawing (entries 6, 7 and 11, 12), electron-donating (entries 2-5), and neutral (entries 1 and 10) groups, as well as substrates containing a variety of substitution patterns (para, meta and ortho), participated in this reaction efficiently. Among aromatic groups also heteroaromatic groups such as furyl and thienyl could be successfully employed to afford the respective cyclopentane derivatives with excellent enantioselectivity (entries 8 and 9). Surprisingly, the presence of the nitro group on the aromatic ring (entry 11) did not decrease the enantiomeric excess. Without being bound by theory this demonstrates that the primary amine group in the catalyst is able to capture one of the two nitro groups selectively. Furthermore, the domino reaction also proceeded smoothly when 6a was replaced with either 6b or 6c, as displayed in FIG. 13.

Figure 14:
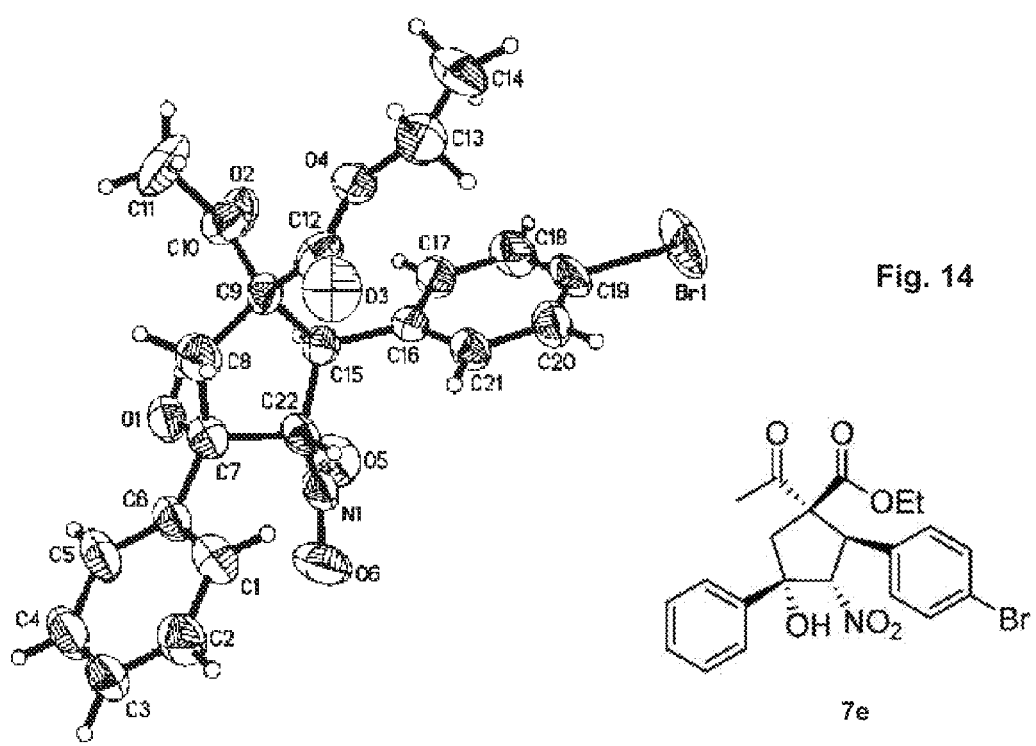
FIG. 14 depicts the X-ray crystal structure of compound 7f.
Figure 17:
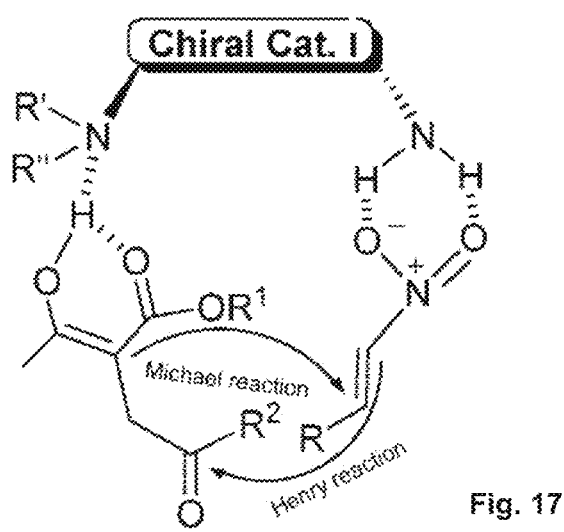
FIG. 17 illustrates the proposed action of the catalyst in a domino Michael-Henry reaction yielding a cyclopentane compound.
Figure 19A:
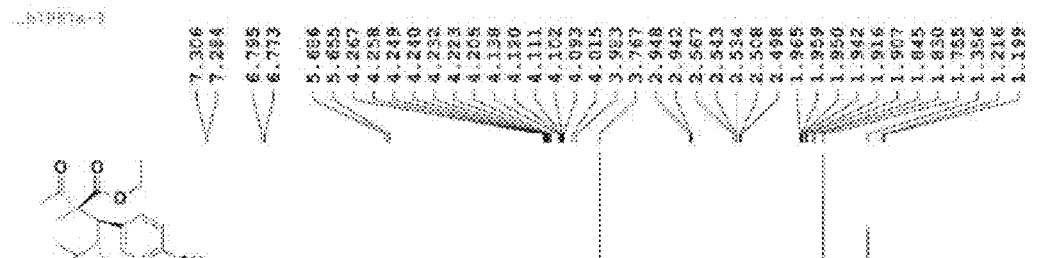
FIG. 19 depicts a $^1$H NMR spectrum (A) and a $^{13}$C NMR spectrum (B) of compound 3b.
Figure 19B:
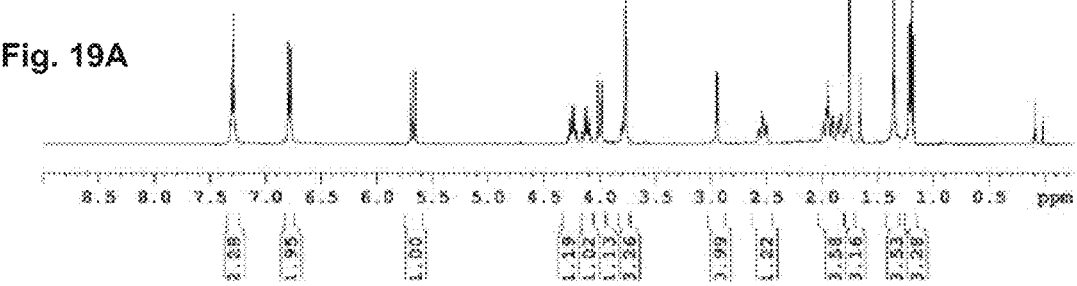
Figure 21A:
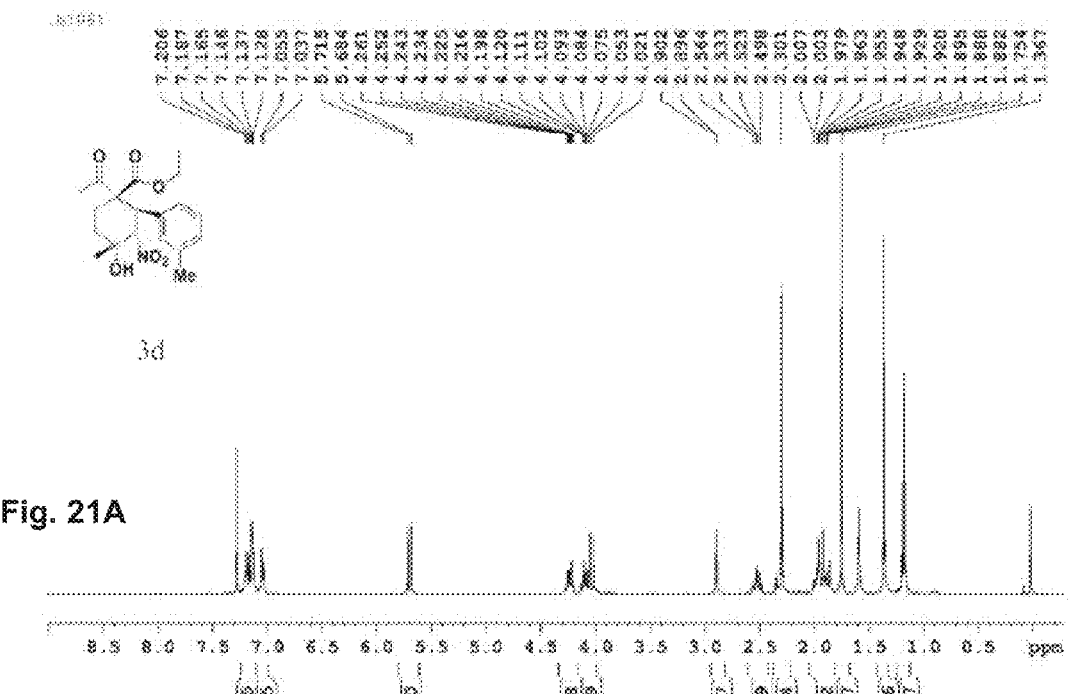
FIG. 21A depicts a $^1$H NMR spectrum and FIG. 21B a $^{13}$C NMR spectrum of compound 3d.
Figure 21B:
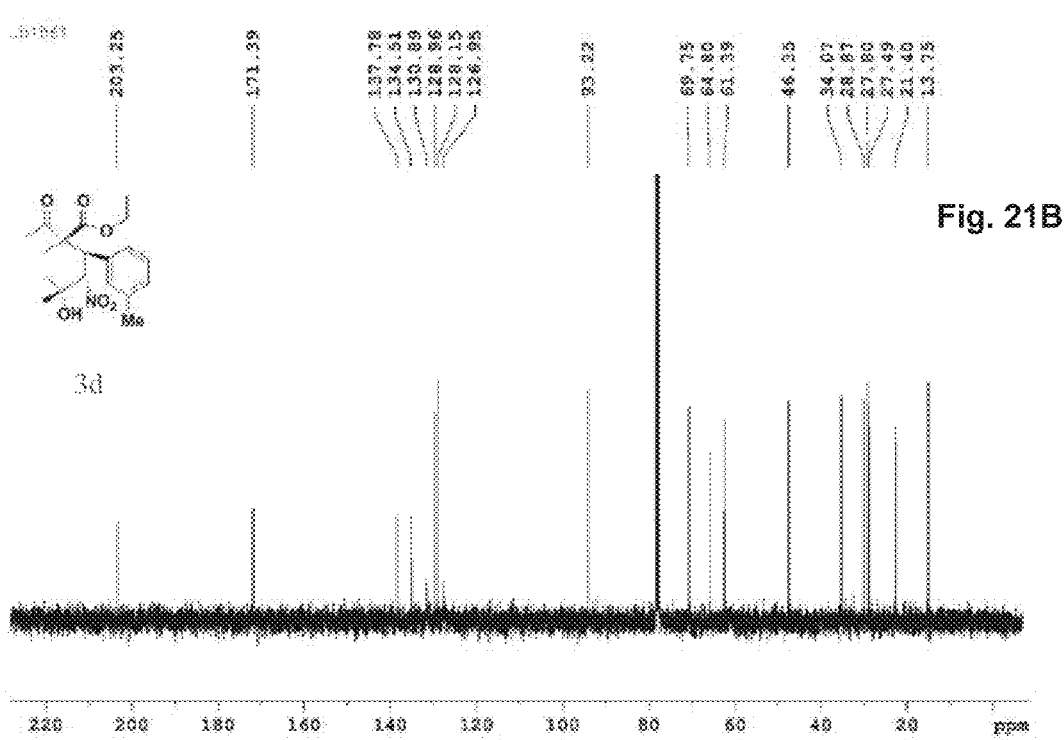
Figure 22A:
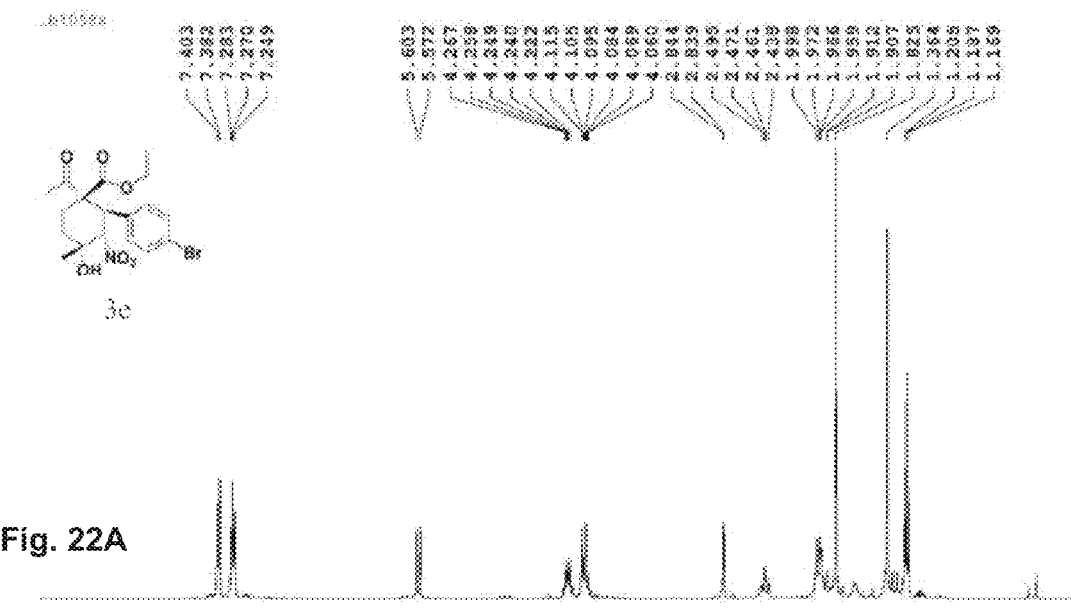
FIG. 22 depicts $^1$H NMR (A) and $^{13}$C NMR (B) spectra of compound 3e.
Figure 22B:
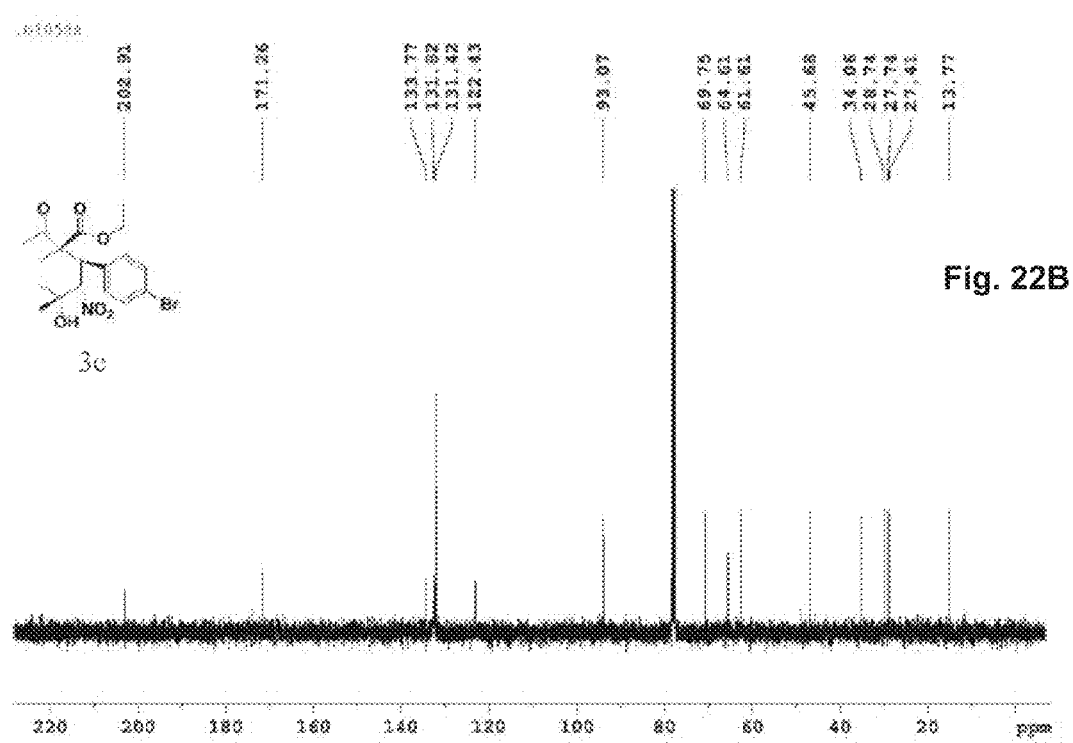
Figure 23A:
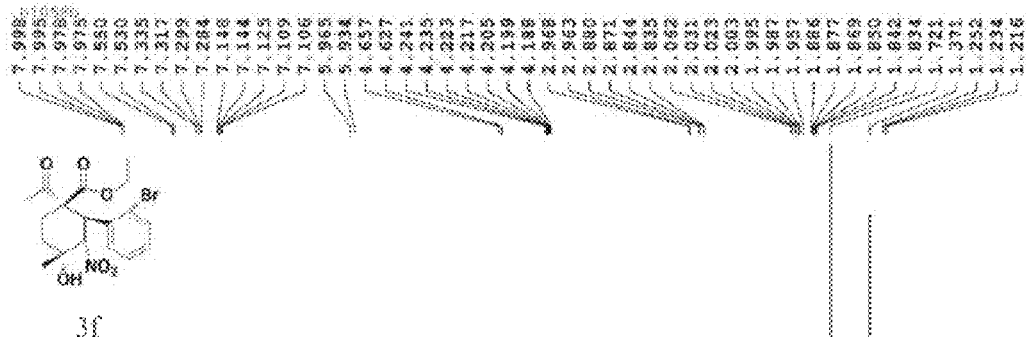
FIG. 23 depicts $^1$H NMR (A) and $^{13}$C NMR (B) spectra of compound 3f.
Figure 23B:
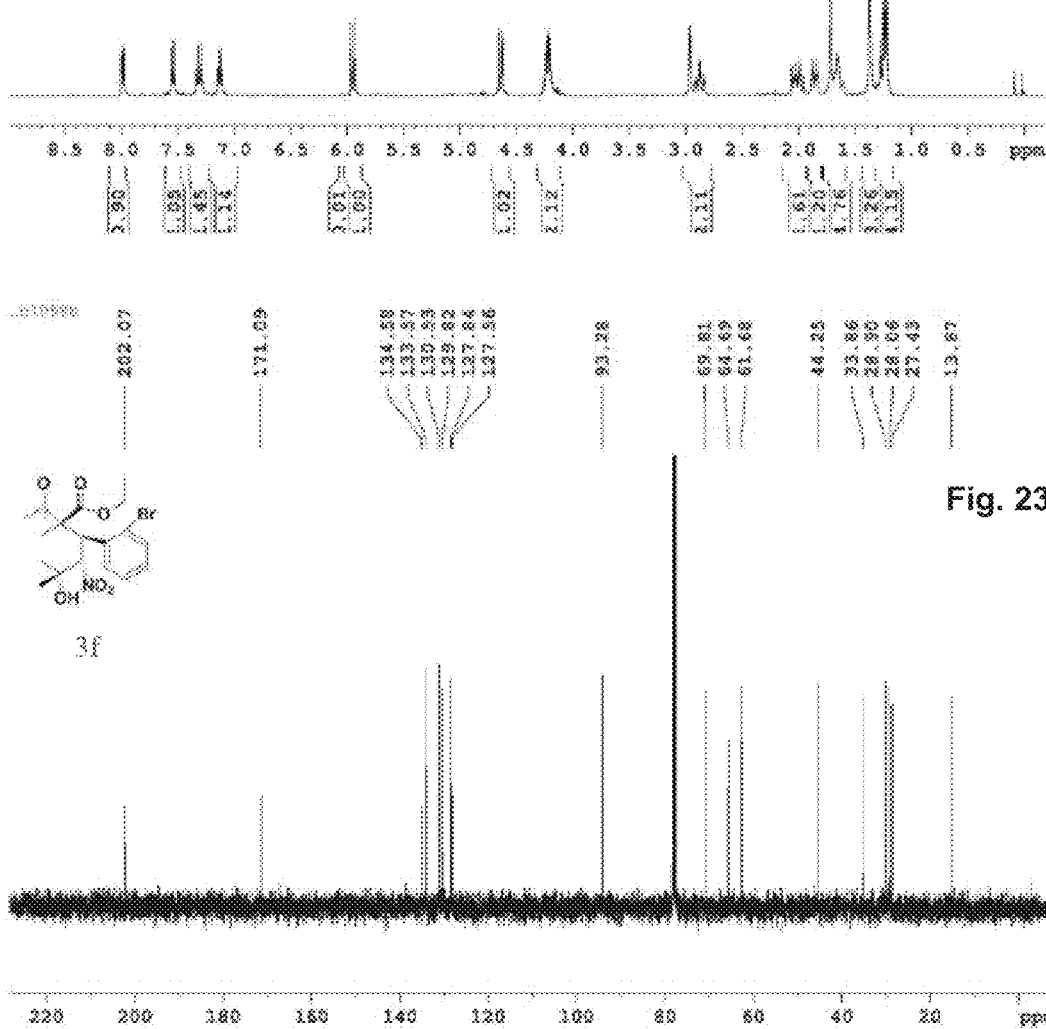
Figure 24A:
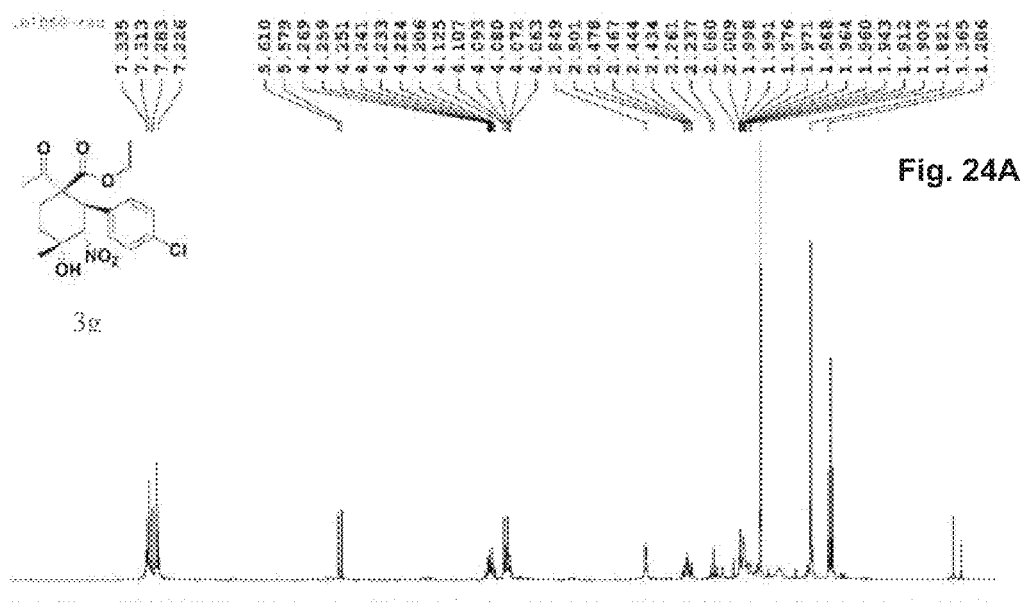
FIG. 24 depicts $^1$H NMR (A) and $^{13}$C NMR (B) spectra of compound 3g.
Figure 24B:
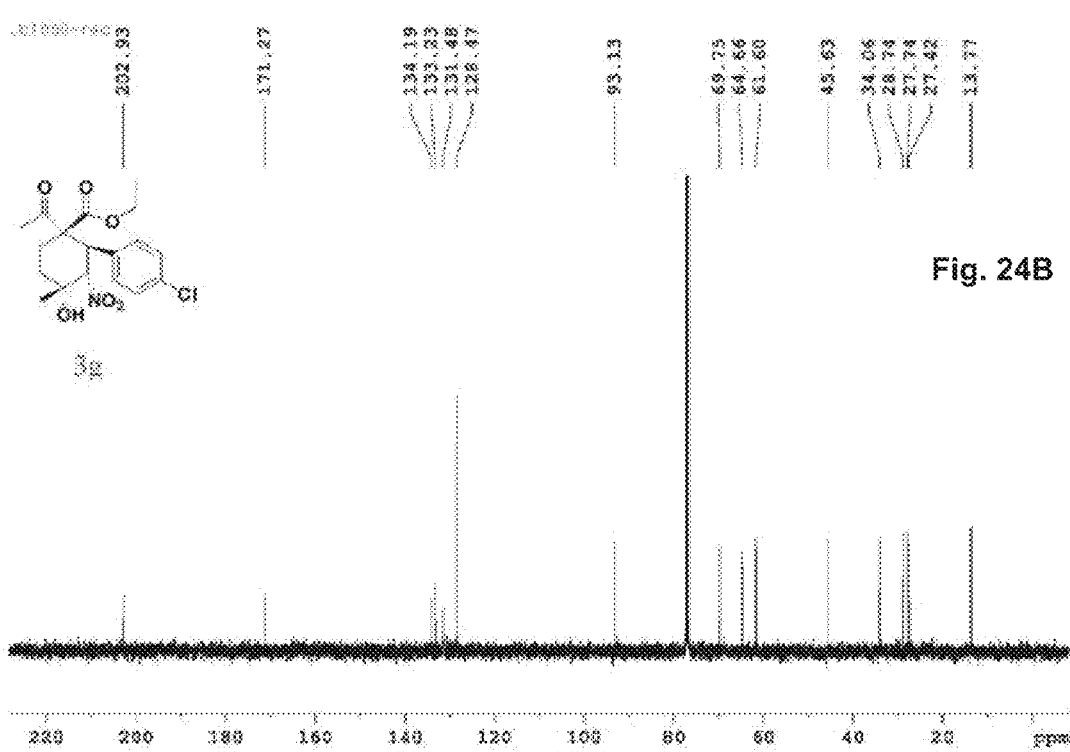
Figure 25A:
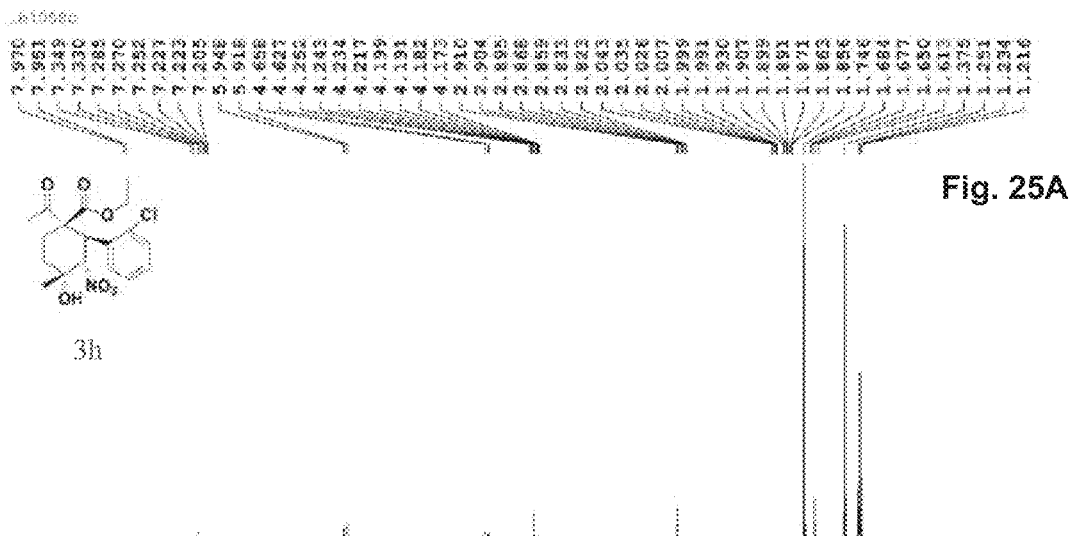
FIG. 25 depicts $^1$H NMR (A) and $^{13}$C NMR (B) spectra of compound 3h.
Figure 25B:
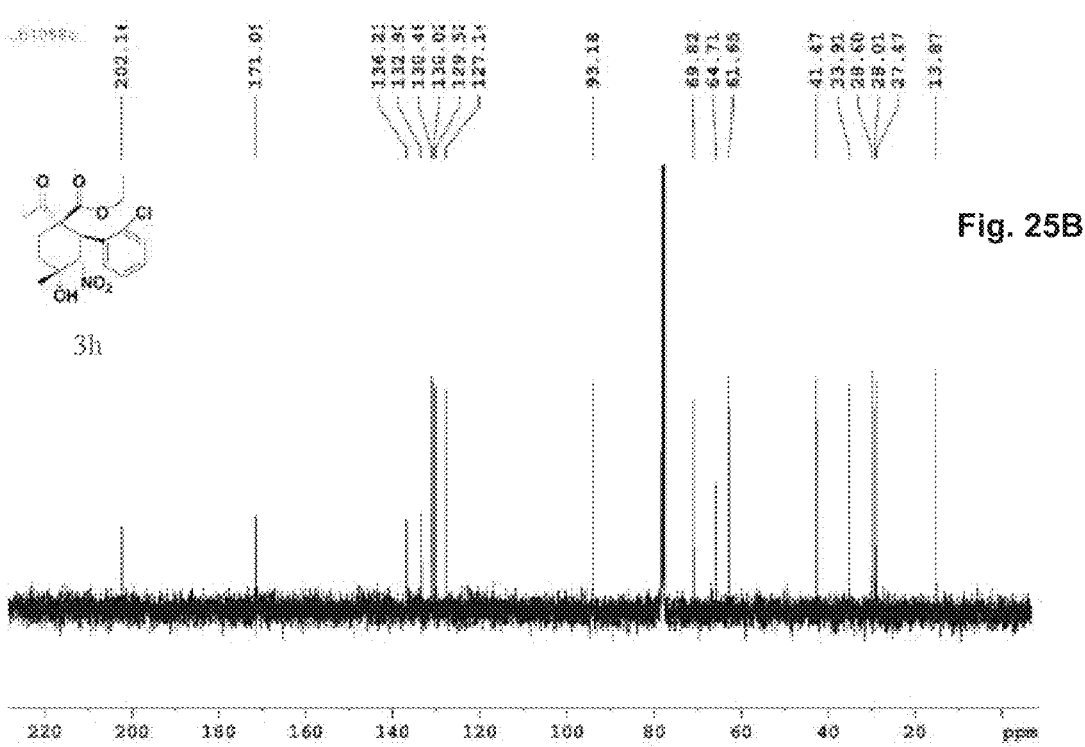
Figure 26A:
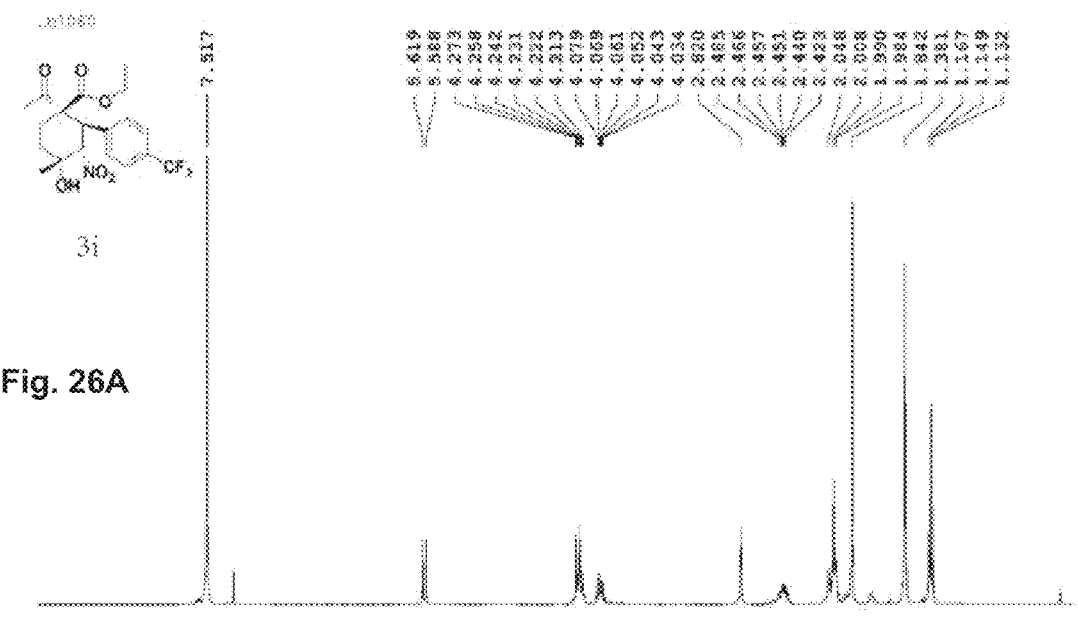
FIG. 26 depicts $^1$H NMR (A) and $^{13}$C NMR (B) spectra of compound 3l.
Figure 26B:
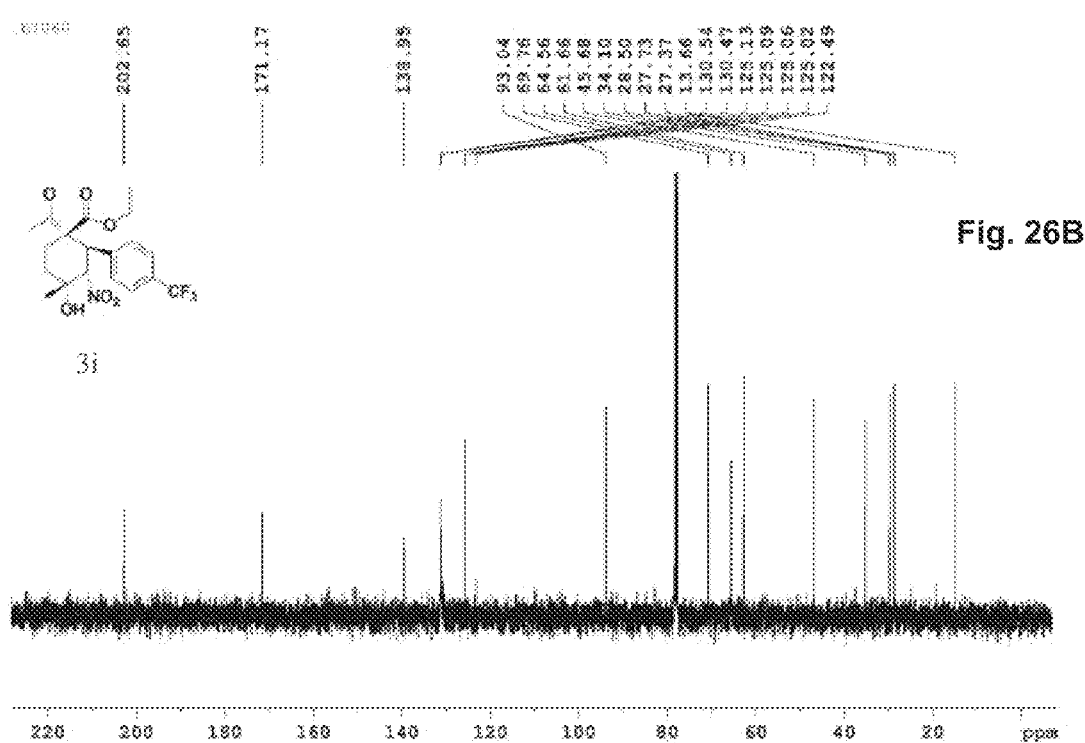
Figure 27A:
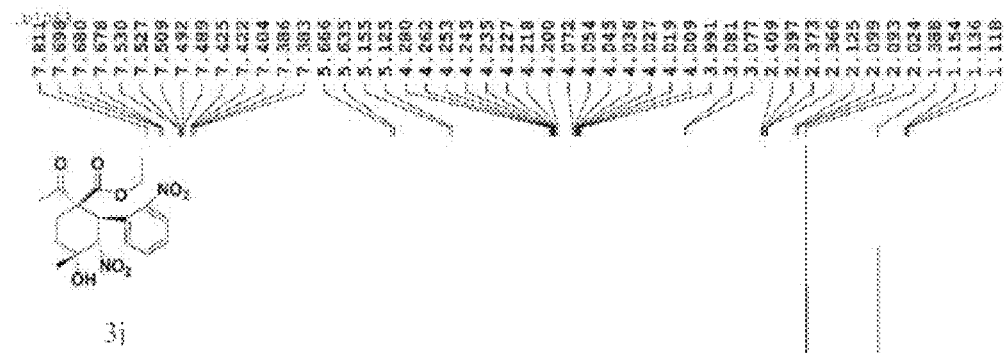
FIG. 27 depicts $^1$H NMR (A) and $^{13}$C NMR (B) spectra of compound 3j.
Figure 27B:
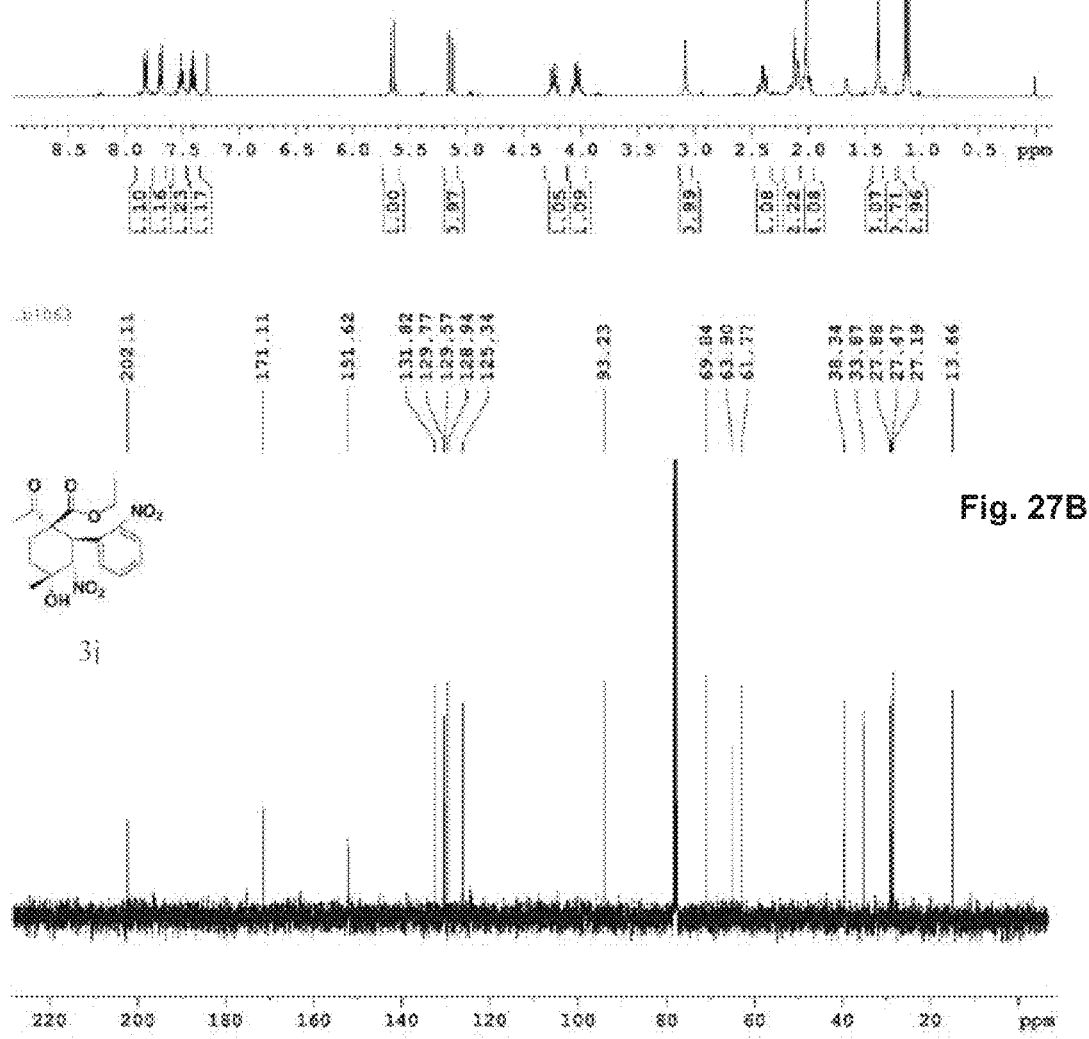
Figure 28A:
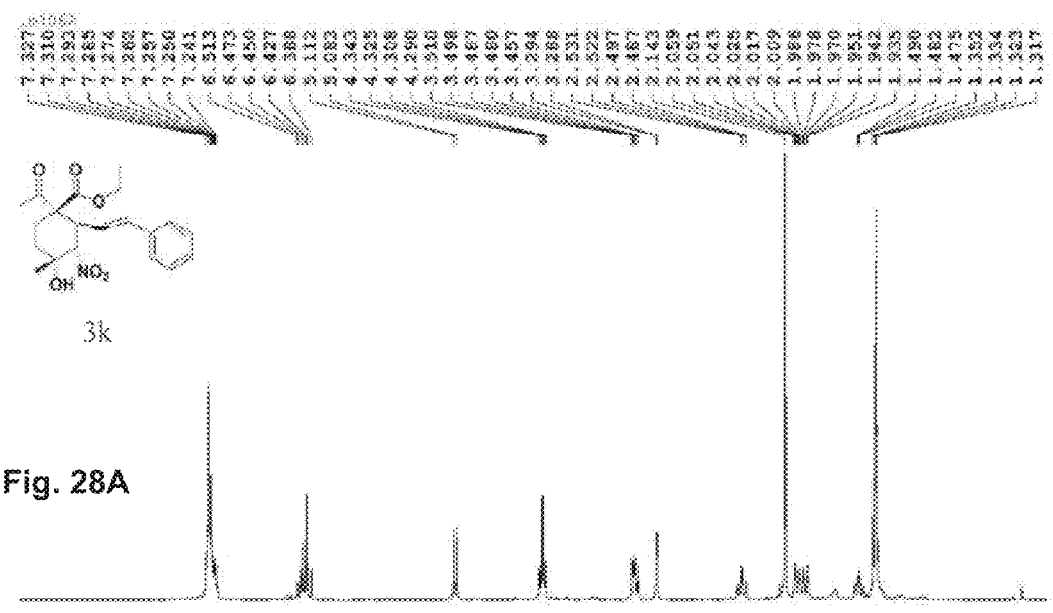
FIG. 28 depicts $^1$H NMR (A) and $^{13}$C NMR (B) spectra of compound 3k.
Figure 28B:
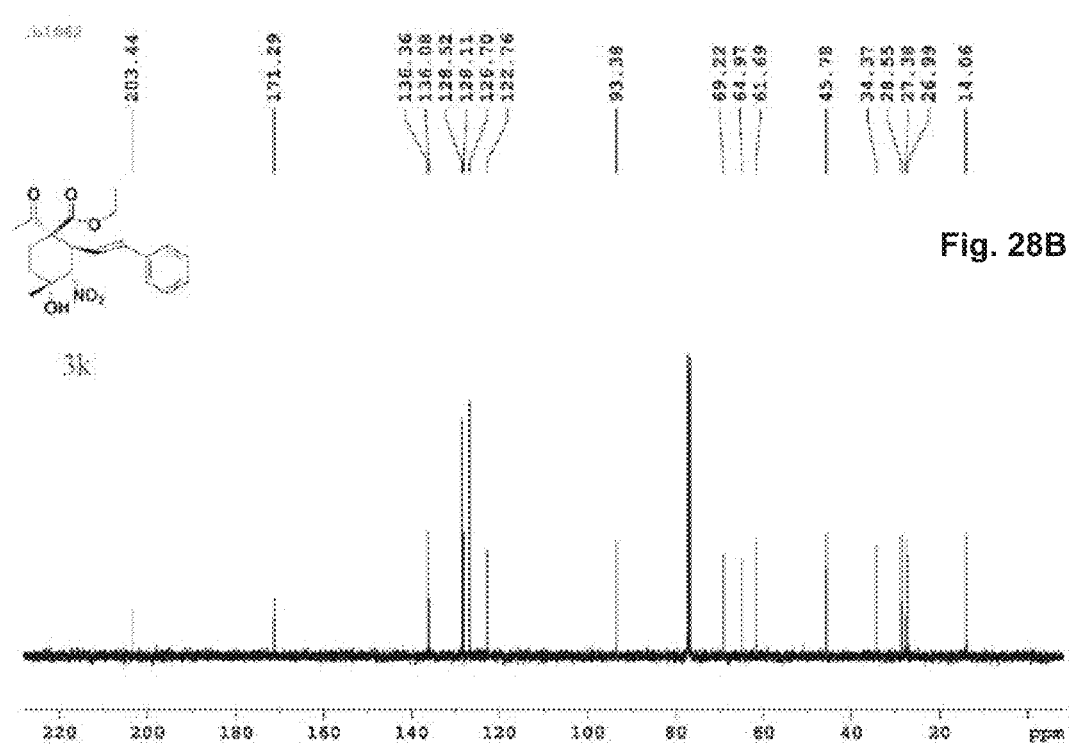
Figure 30A:
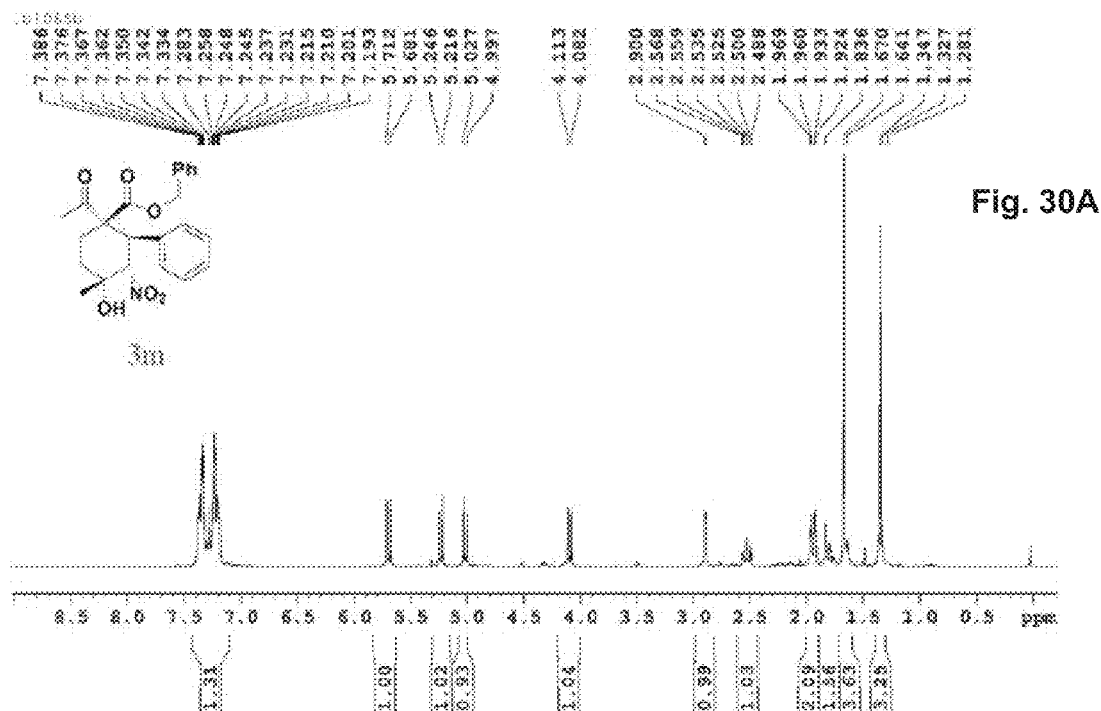
FIG. 30 depicts $^1$H NMR (A) and $^{13}$C NMR (B) spectra of compound 3m.
Figure 30B:
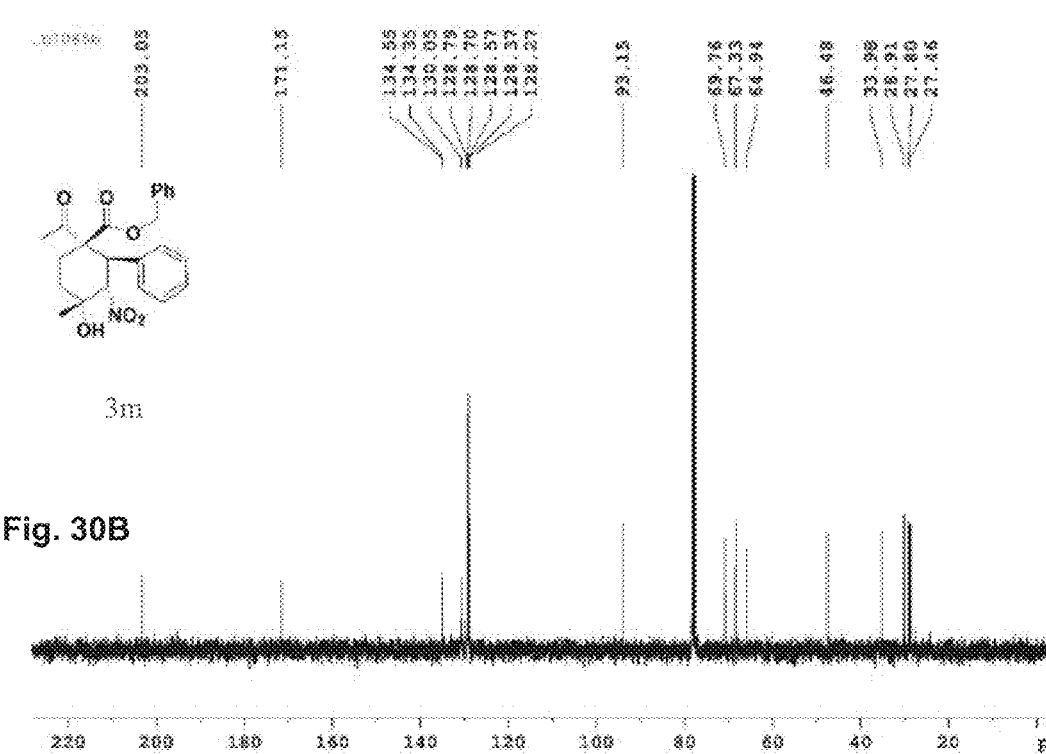
Figure 31A:
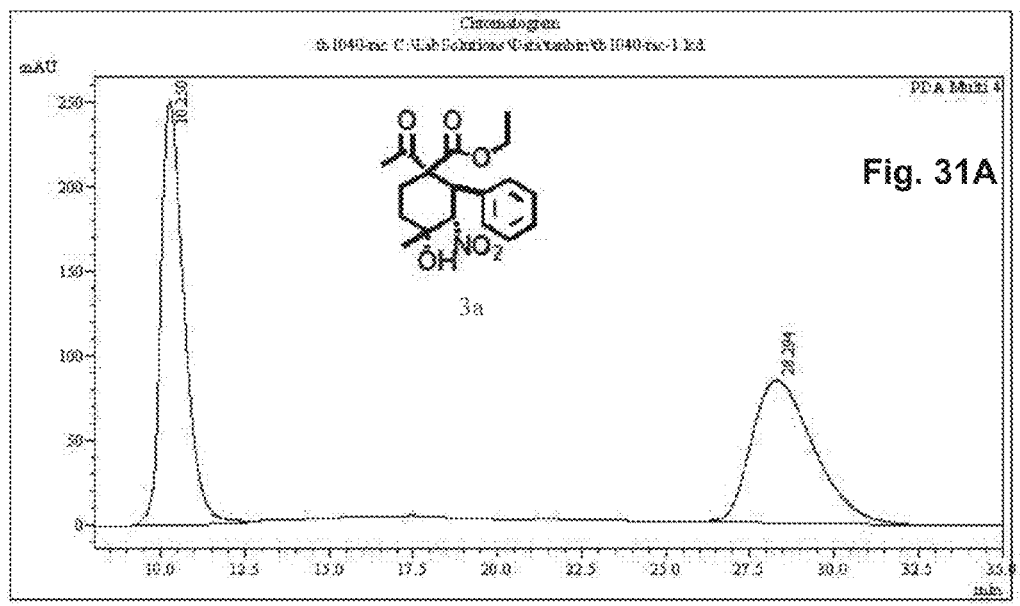
FIG. 31 depicts an HPLC spectrum of a racemic mixture of compound 3a (A) in comparison to the obtained product 3a (B).
Figure 31B:
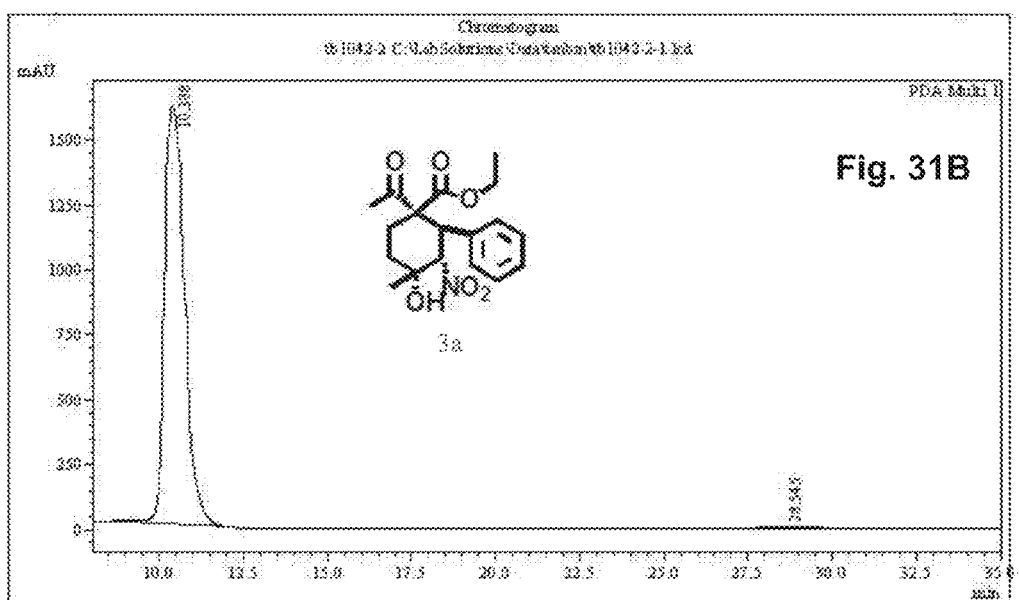
Figure 32A:
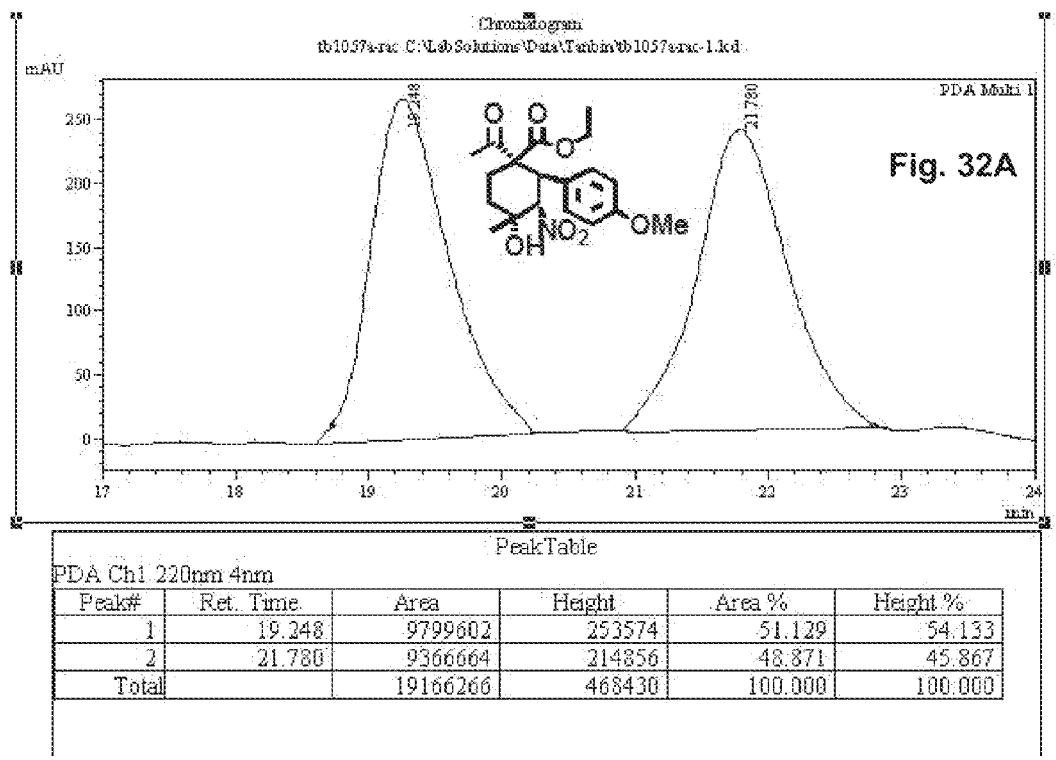
FIG. 32 depicts an HPLC spectrum of a racemic mixture of compound 3b (A) in comparison to the obtained product 3b (B).
Figure 32B:
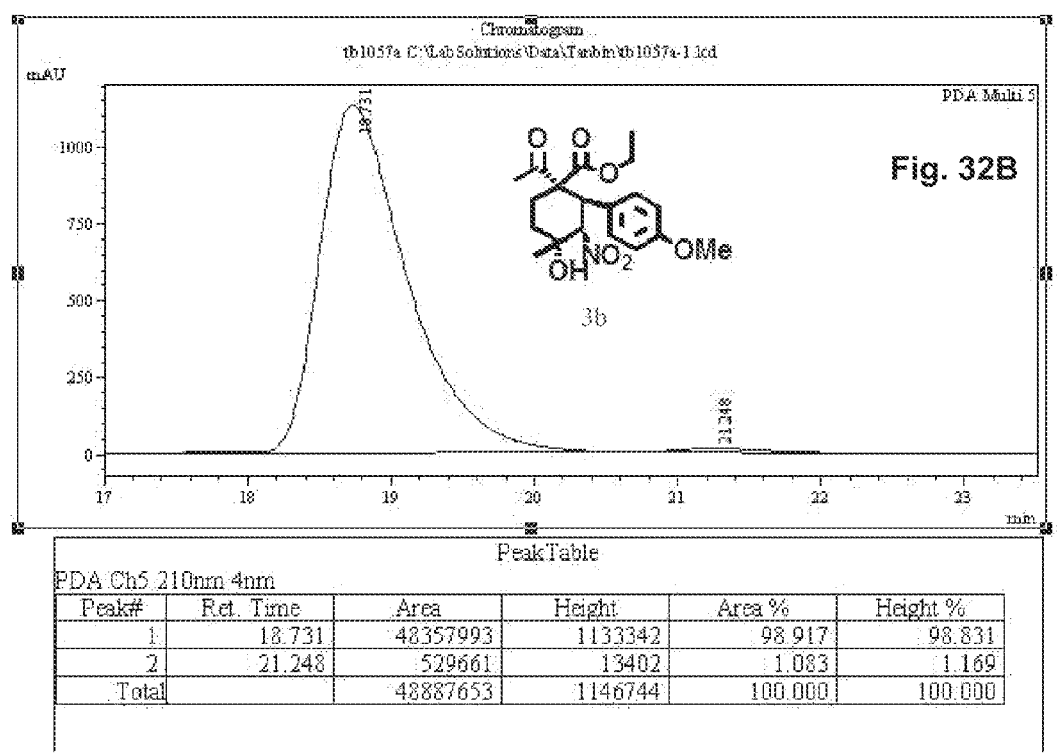
Figure 33A:
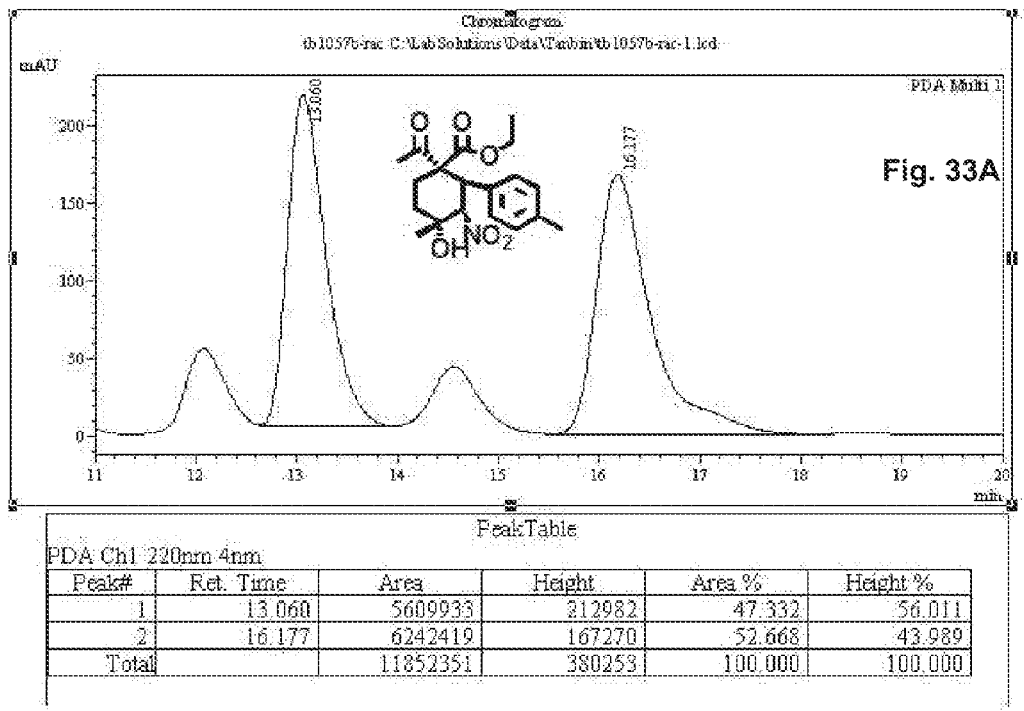
FIG. 33 depicts an HPLC spectrum of a racemic mixture of compound 3c (A) in comparison to the obtained product 3c (B).
Figure 33B:
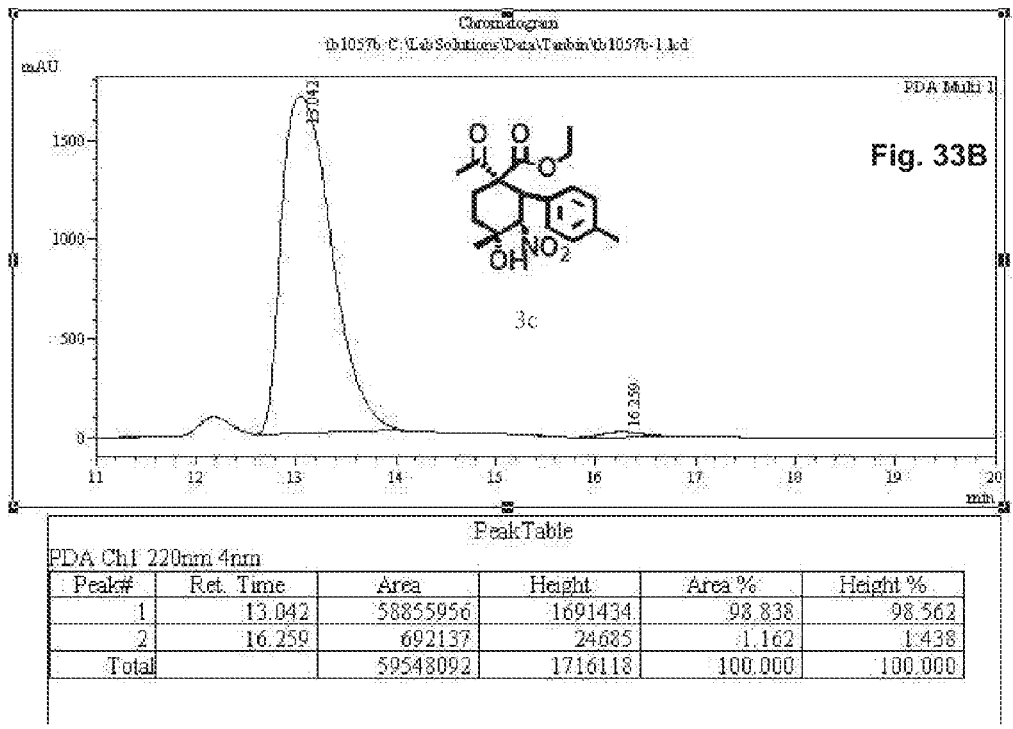
Figure 35A:
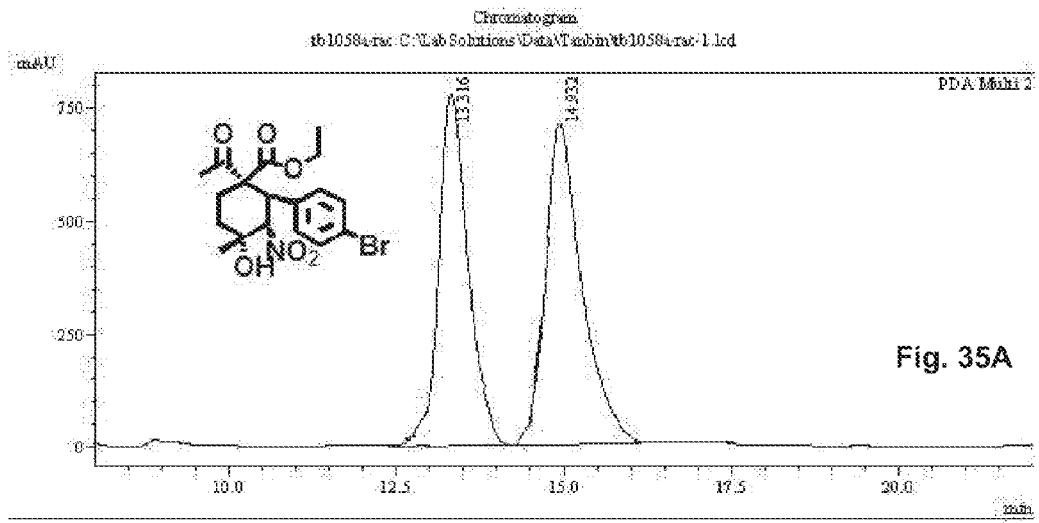
FIG. 35 depicts an HPLC spectrum of a racemic mixture of compound 3e (A), and in comparison the obtained product 3e (B).
Figure 35B:
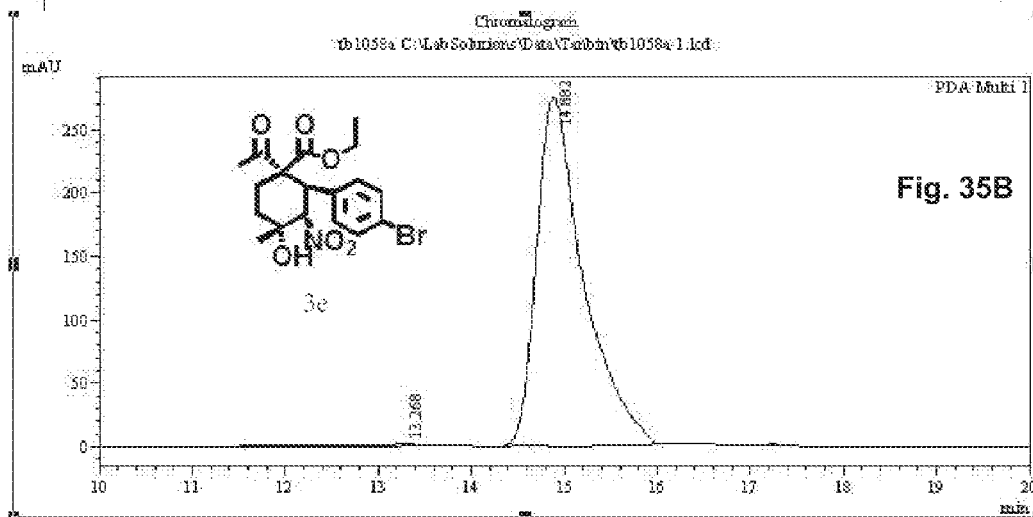
Figure 36A:
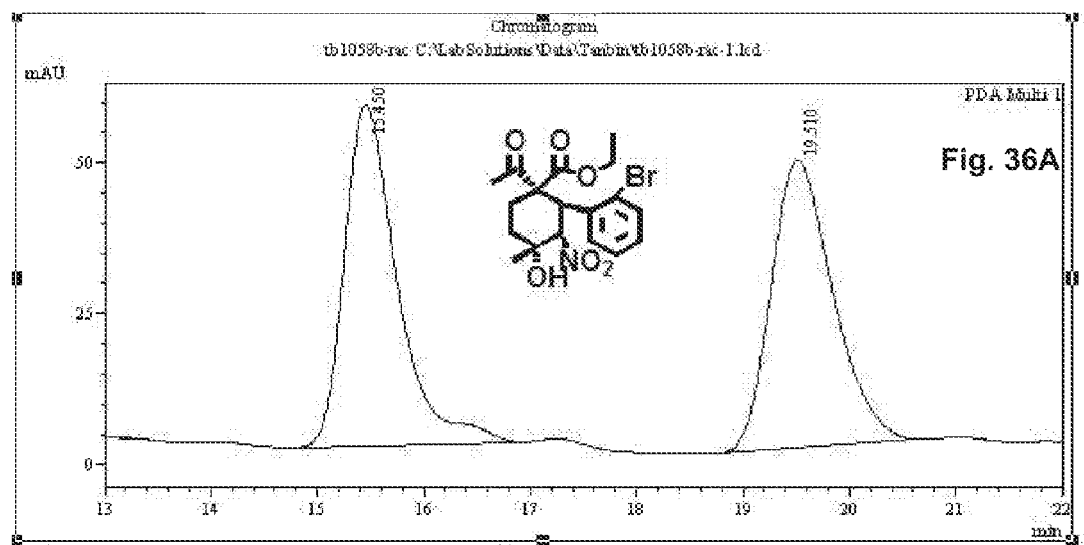
FIG. 36 depicts an HPLC spectrum of a racemic mixture of compound 3f (A), and in comparison the obtained product 3f (B).
Figure 36B:
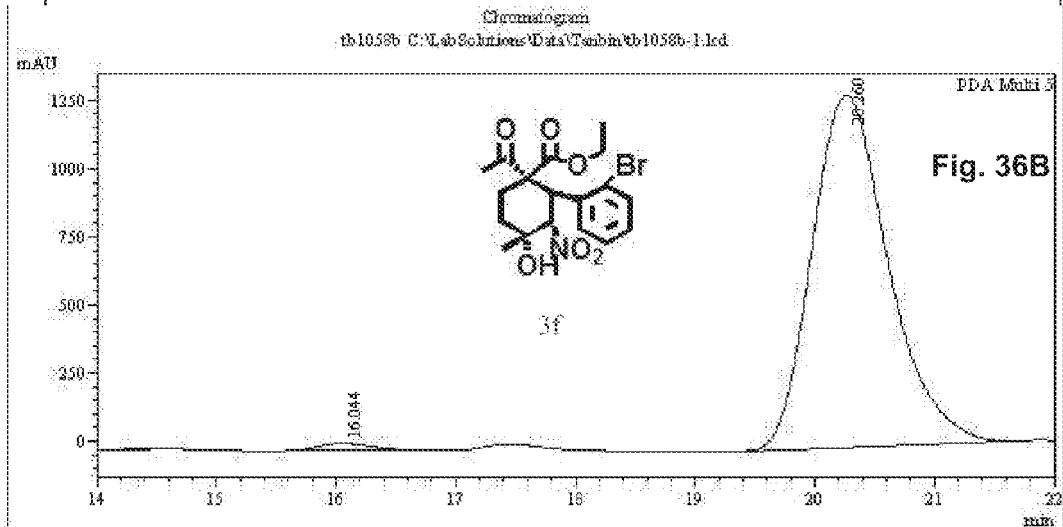
Figure 37A:
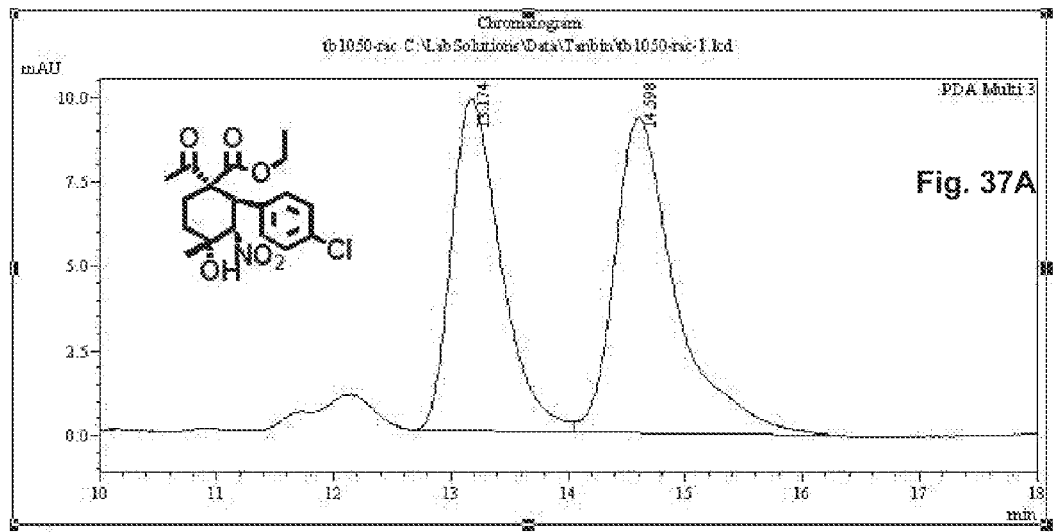
FIG. 37 depicts an HPLC spectrum of a racemic mixture of compound 3g (A), and in comparison the obtained product 3g (B).
Figure 37B:
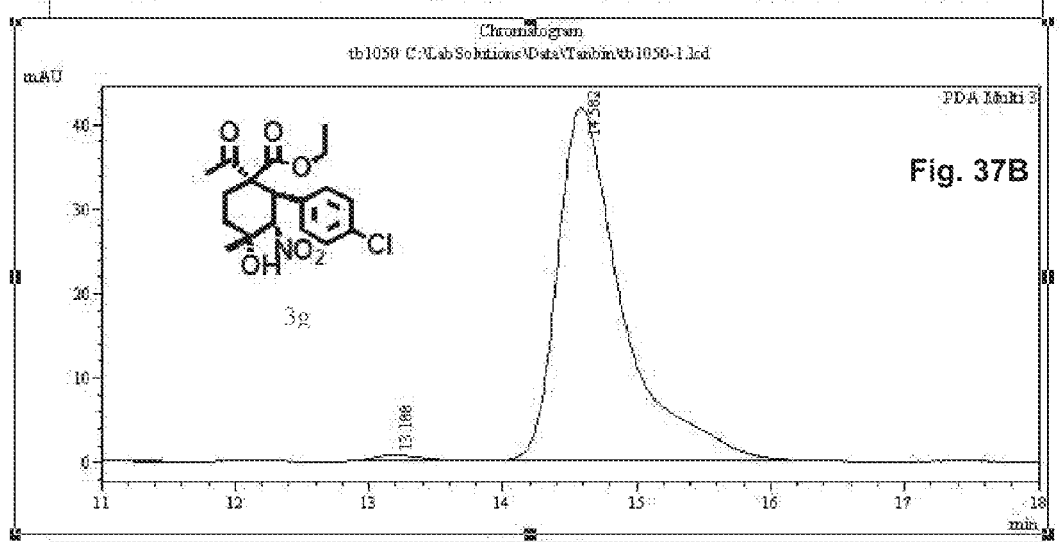
Figures 38A, 38B:
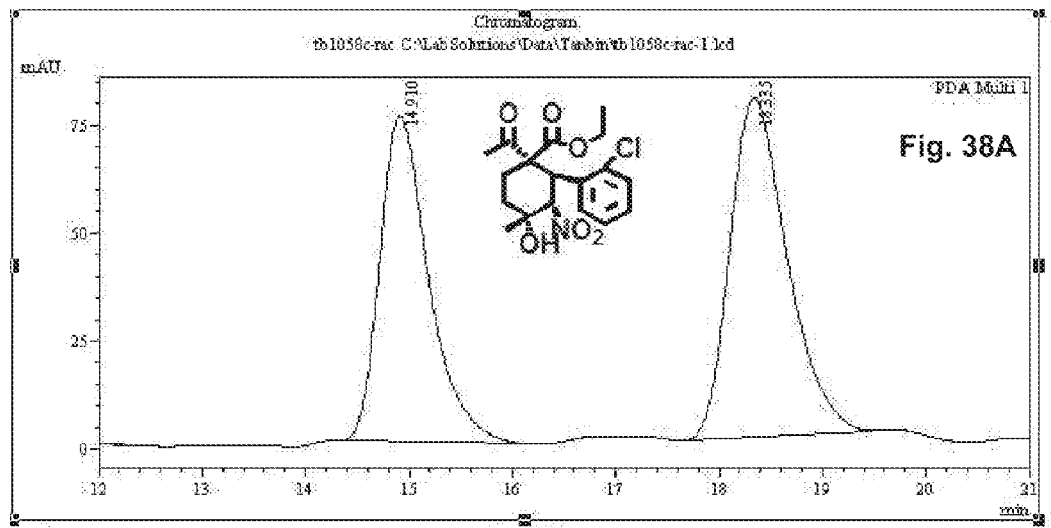
FIG. 38 depicts an HPLC spectrum of a racemic mixture of compound 3h (A), and in comparison the obtained product 3h (B).
Figure 39A:
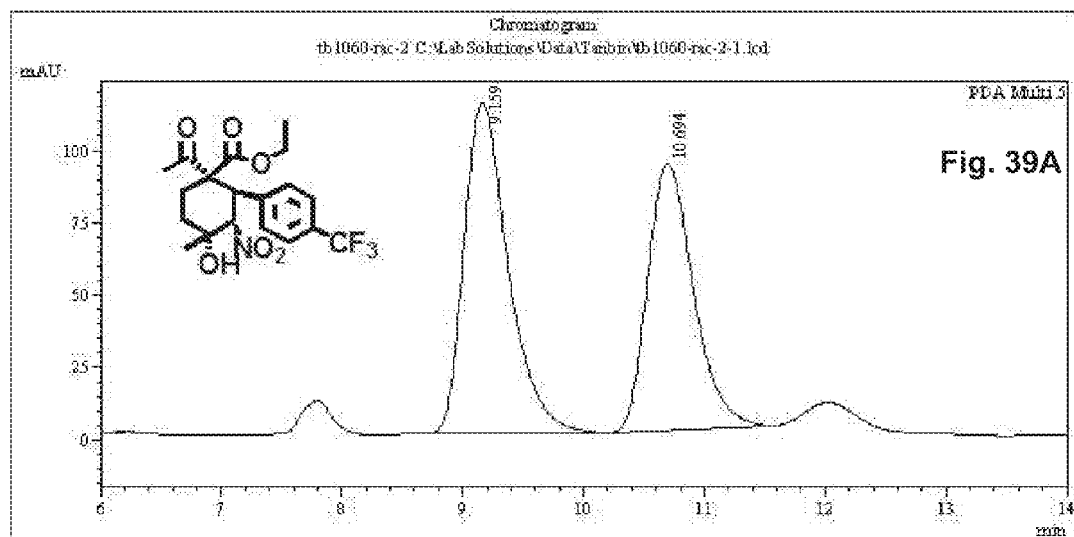
FIG. 39 depicts an HPLC spectrum of a racemic mixture of compound 3l (A), and in comparison the obtained product 3l (B).
Figure 39B:
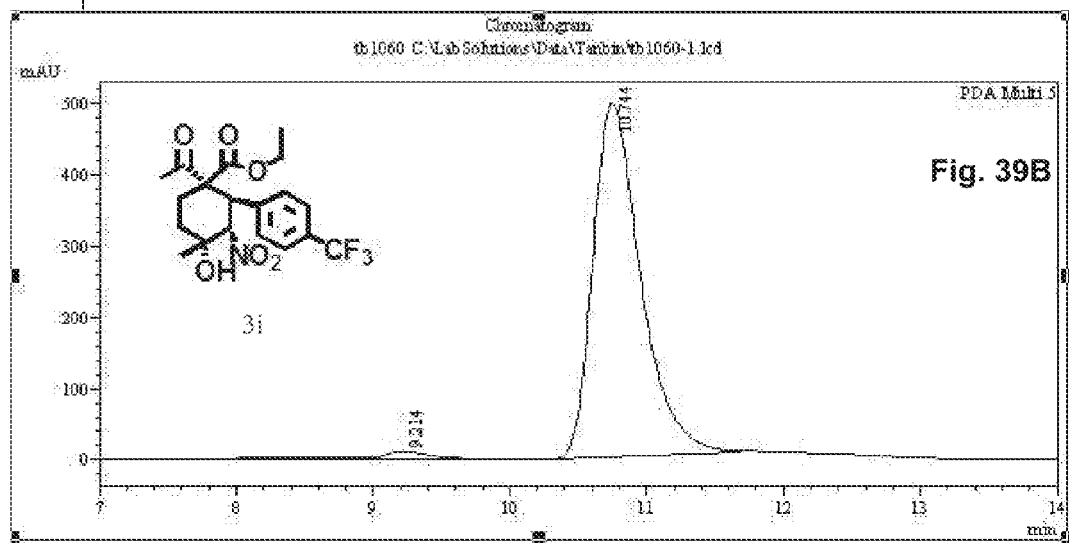
Figure 40A:
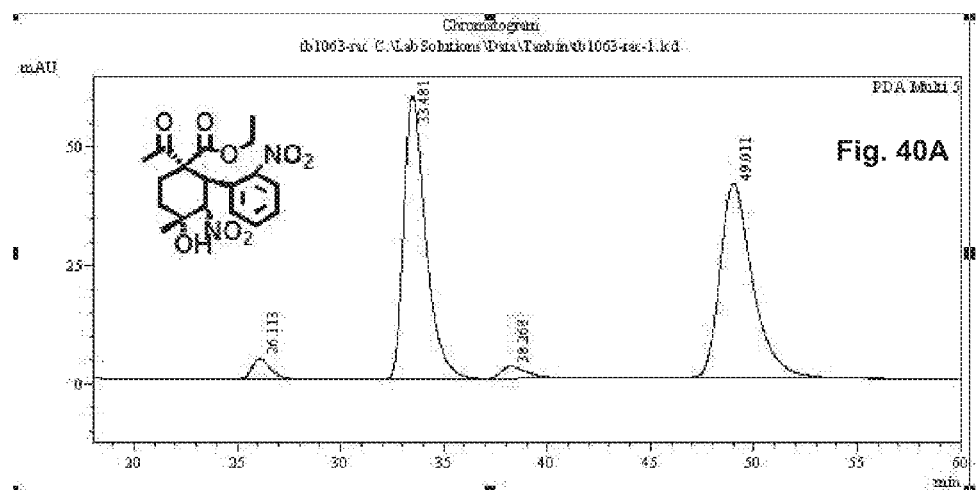
FIG. 40 depicts an HPLC spectrum of a racemic mixture of compound 3j (A), and in comparison the obtained product 3j (B).
Figure 40B:
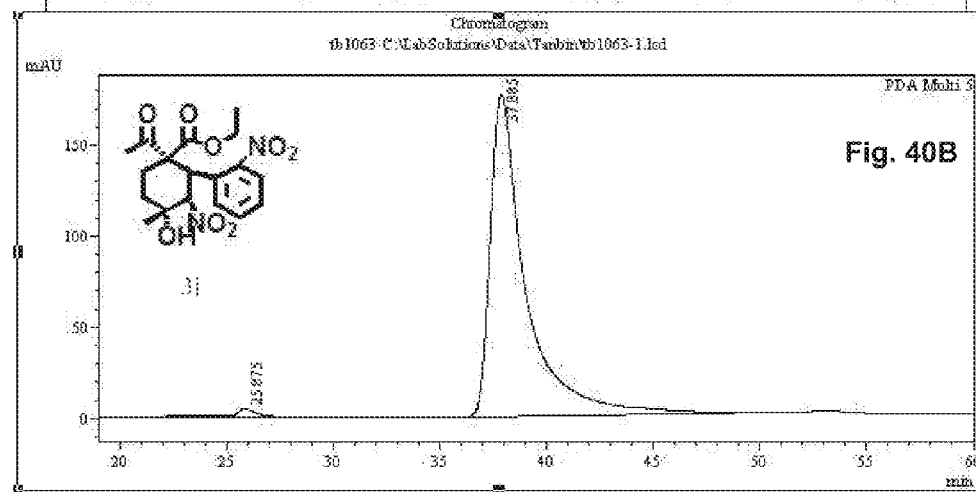
Figure 41A:
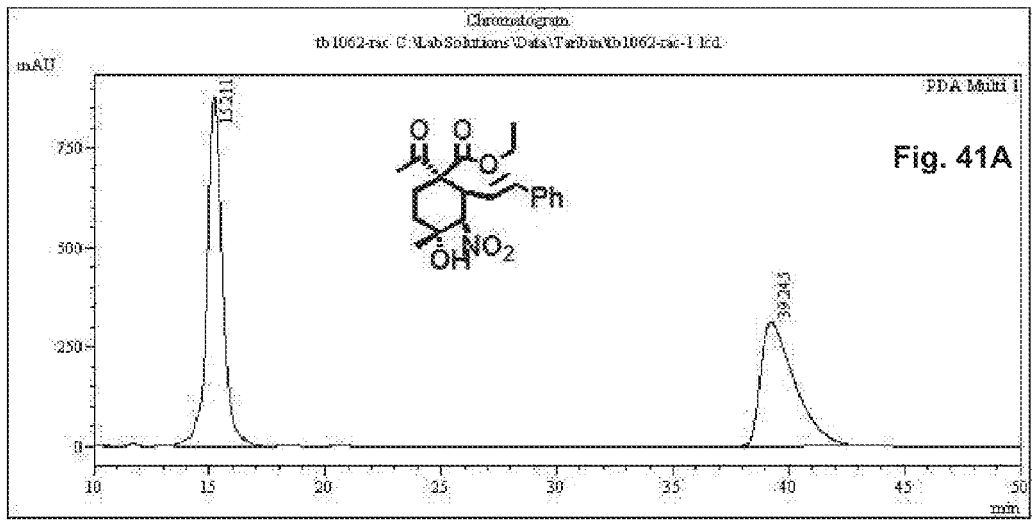
FIG. 41 depicts an HPLC spectrum of a racemic mixture of compound 3k (A), and in comparison the obtained product 3k (B).
Figure 41B:
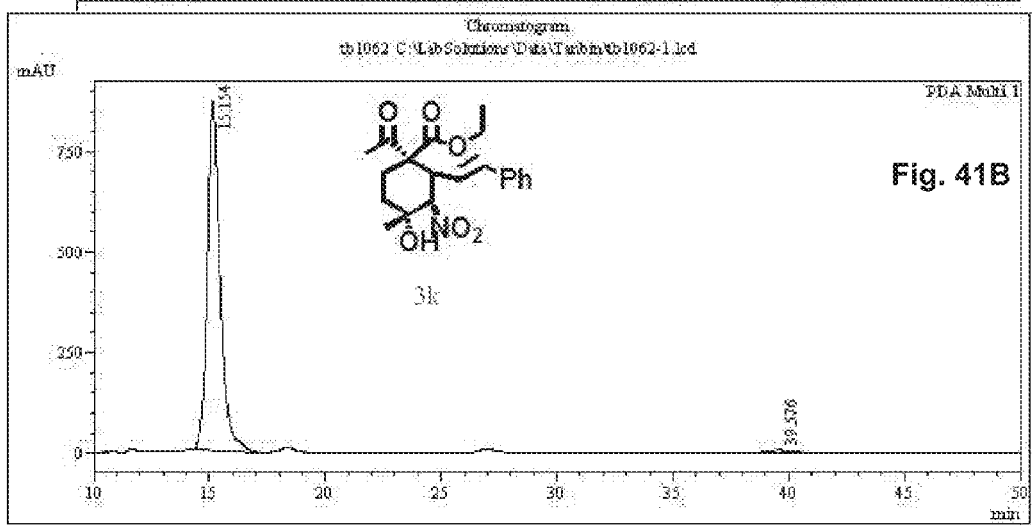
Figure 42A:
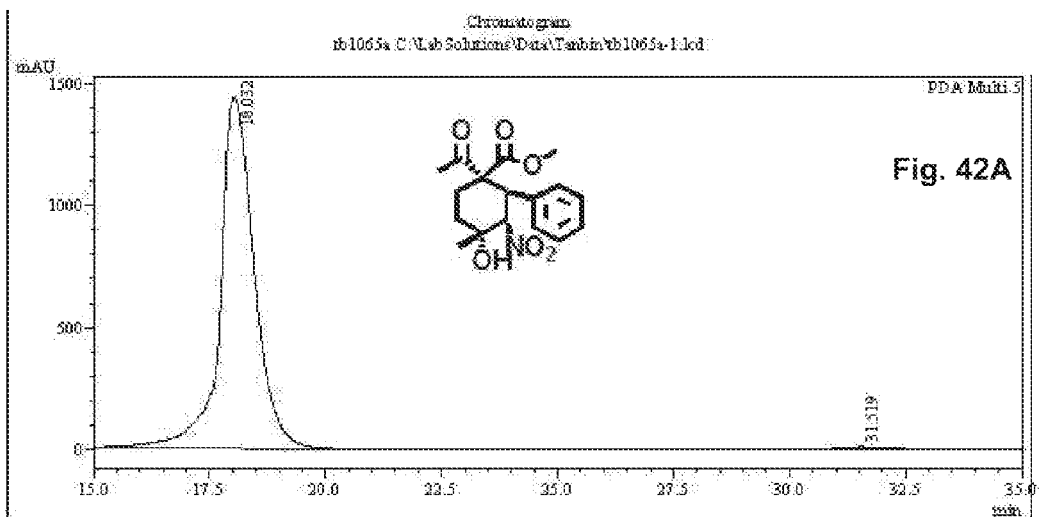
FIG. 42 depicts an HPLC spectrum of a racemic mixture of compound 3l (A), and in comparison the obtained product 3l (B).
Figure 42B:
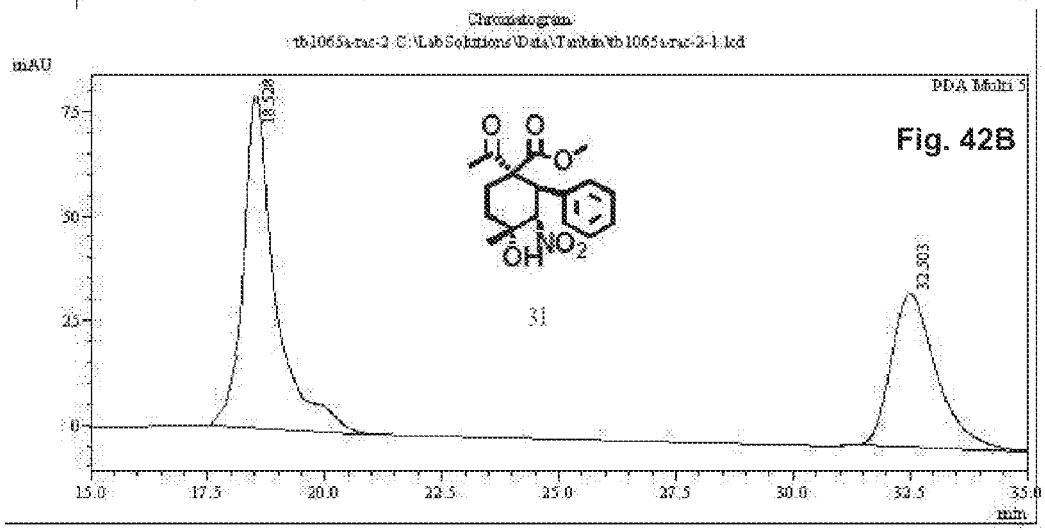
Figure 43A:
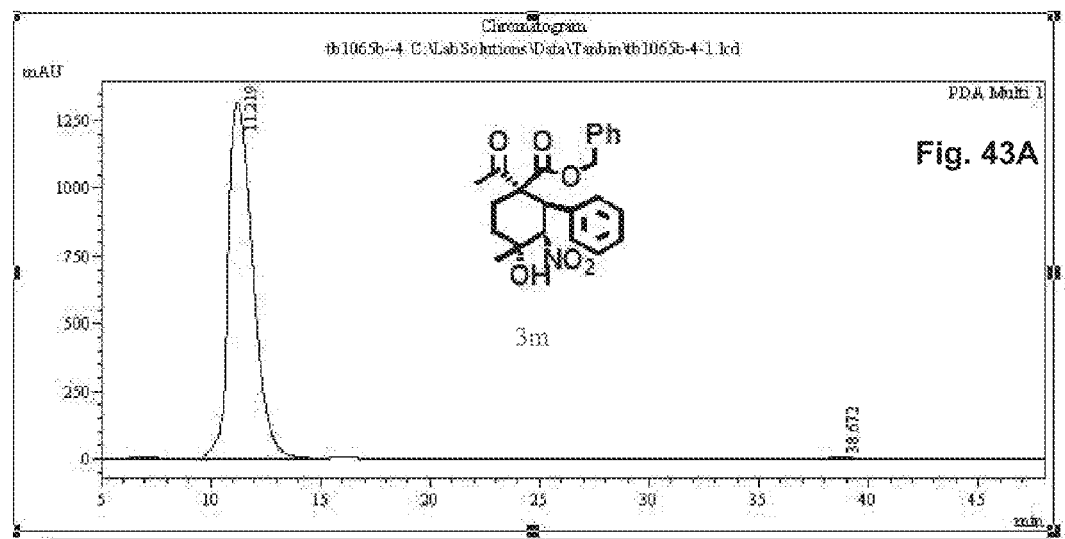
FIG. 43 depicts an HPLC spectrum of a racemic mixture of compound 3m (A), and in comparison the obtained product 3m (B).
Figure 43B:
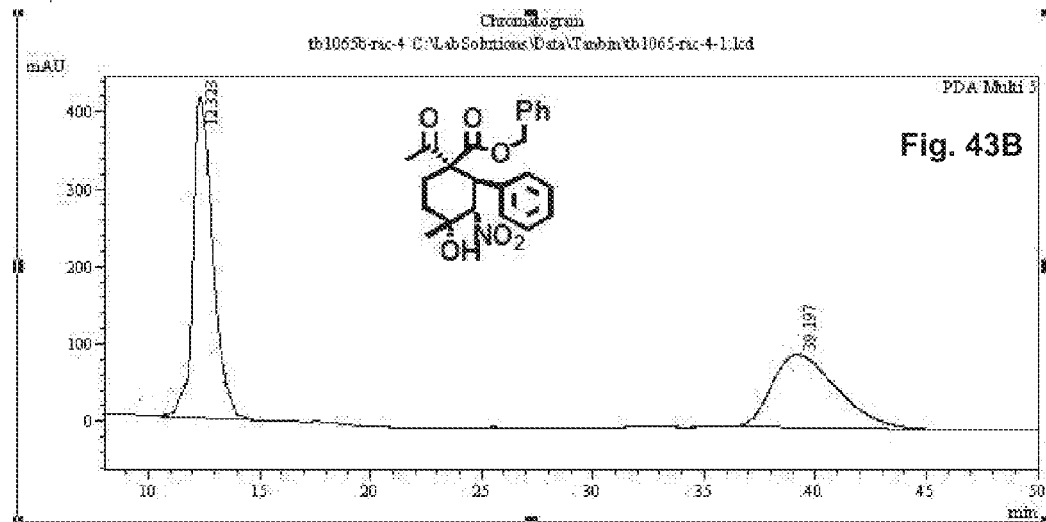
Figure 44A:
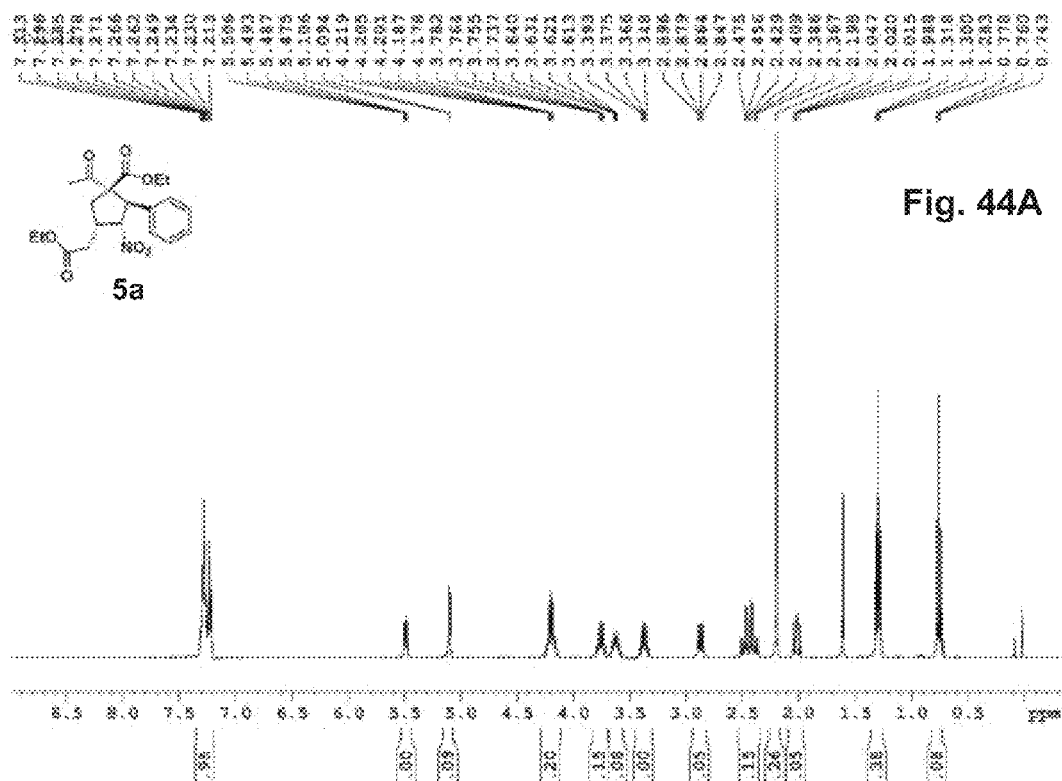
Figure 44B:
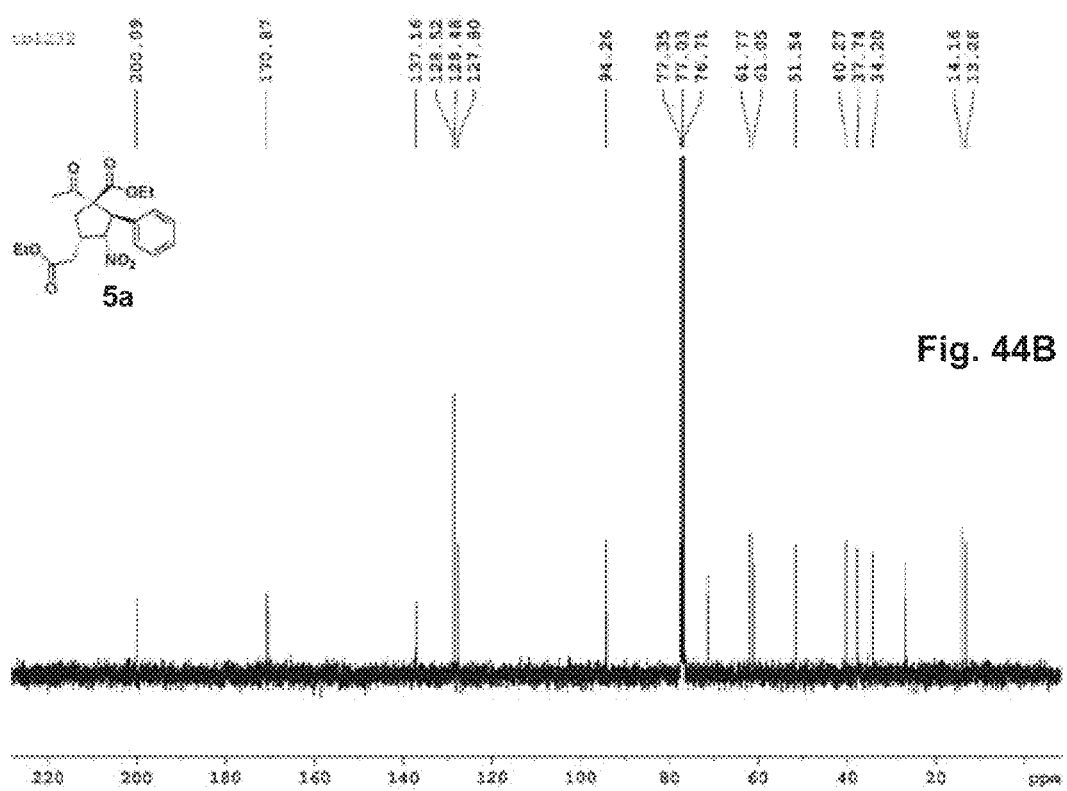
Figure 45A:
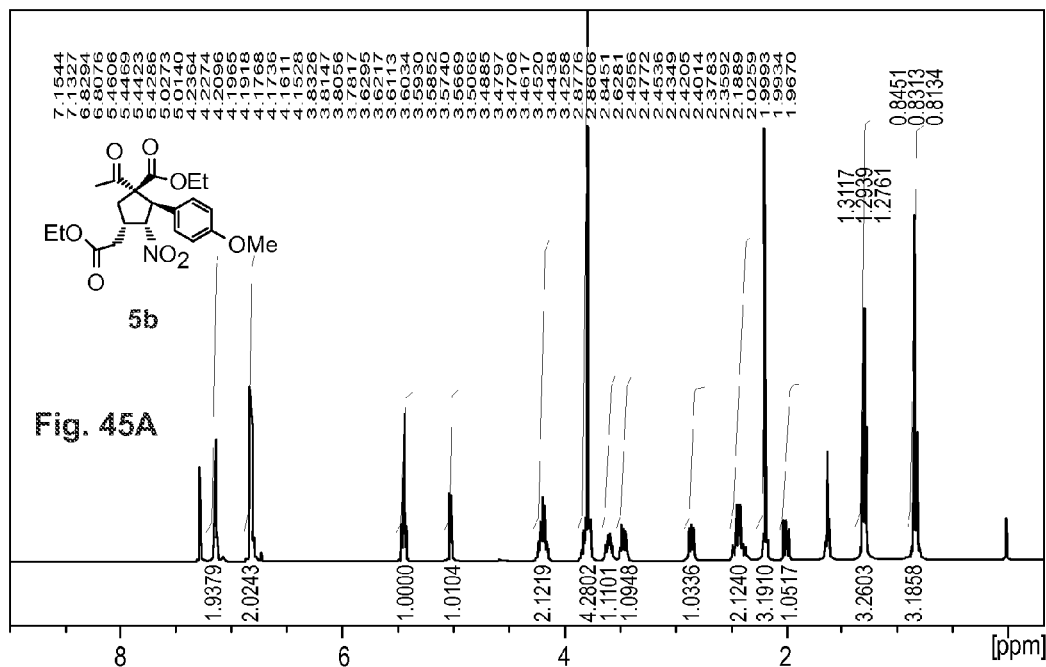
FIG. 45 depicts $^1$H NMR (A) and $^{13}$C NMR (B) spectra of compound 5b.
Figure 45B:
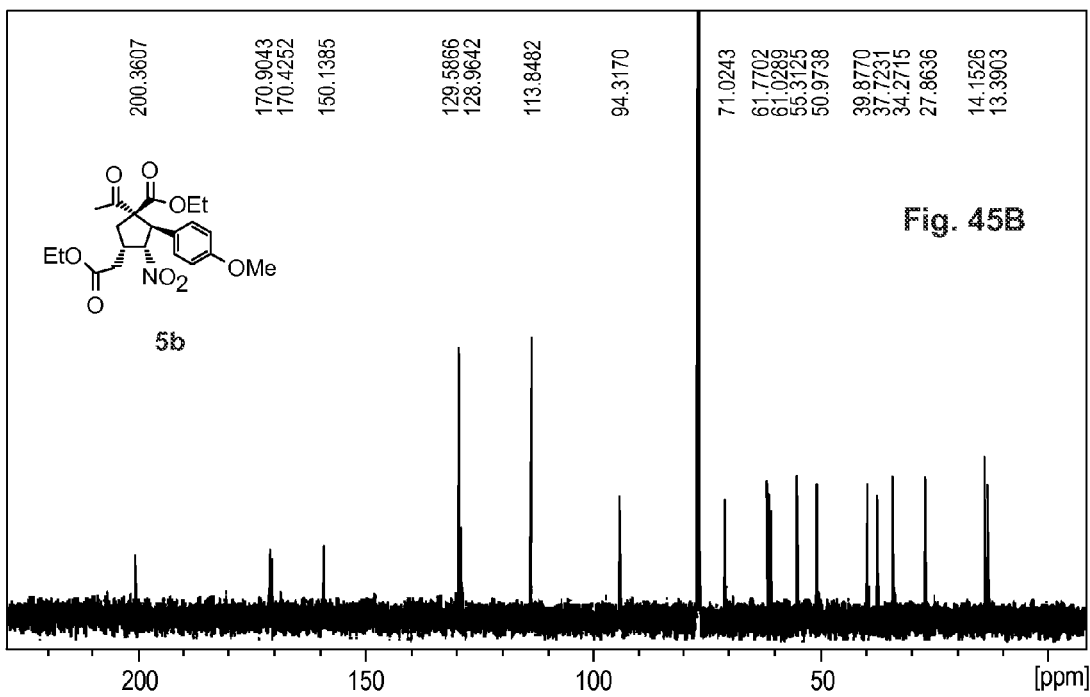
Figure 46A:
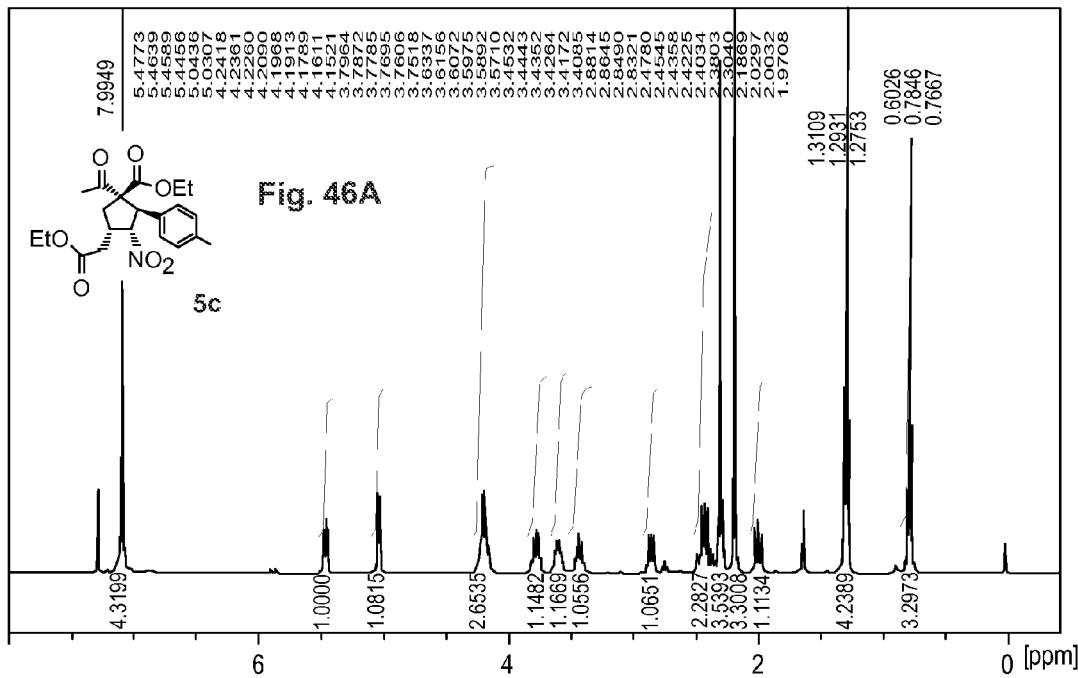
FIG. 46 depicts $^1$H NMR (A) and $^{13}$C NMR (B) spectra of compound 5c.
Figure 46B:
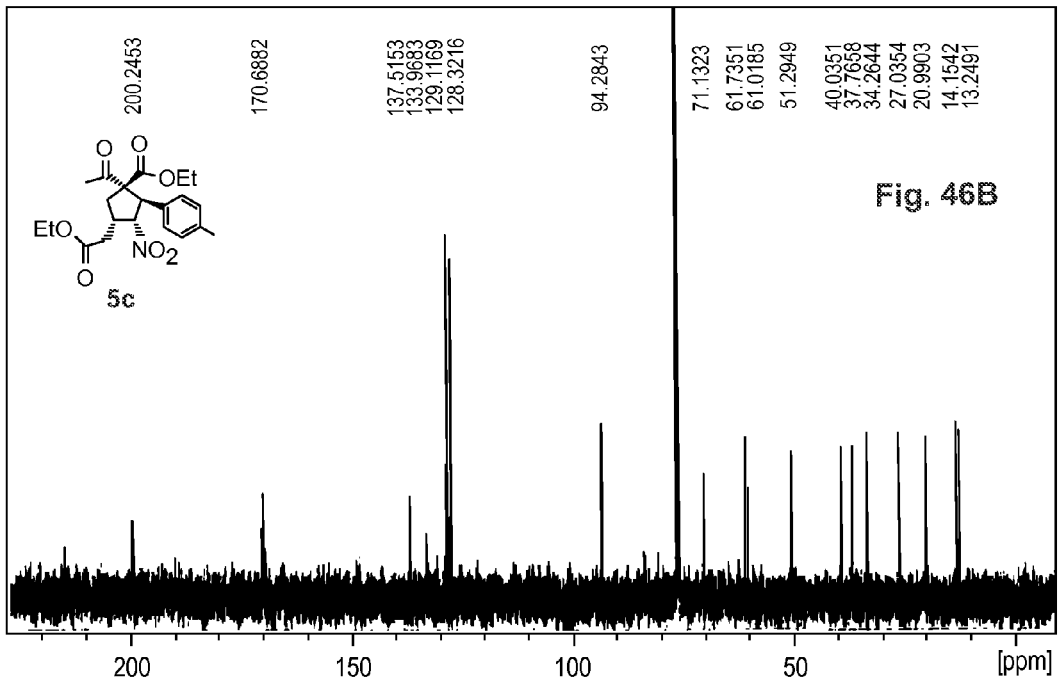
Figure 48A:
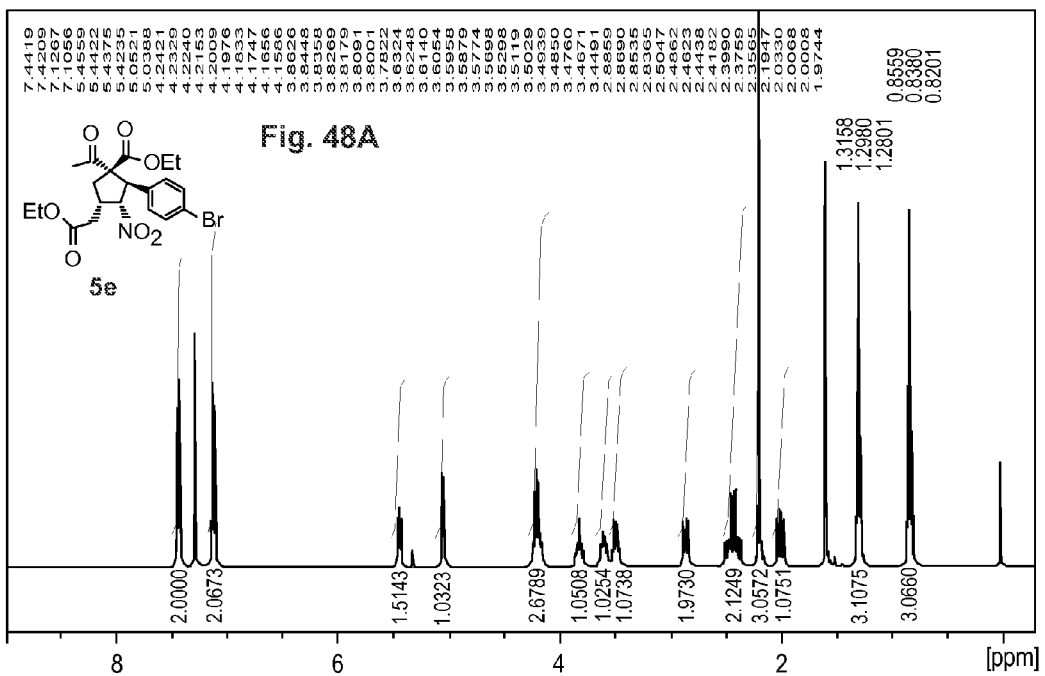
FIG. 48 depicts $^1$H NMR (A) and $^{13}$C NMR (B) spectra of compound 5e.
Figure 48B:
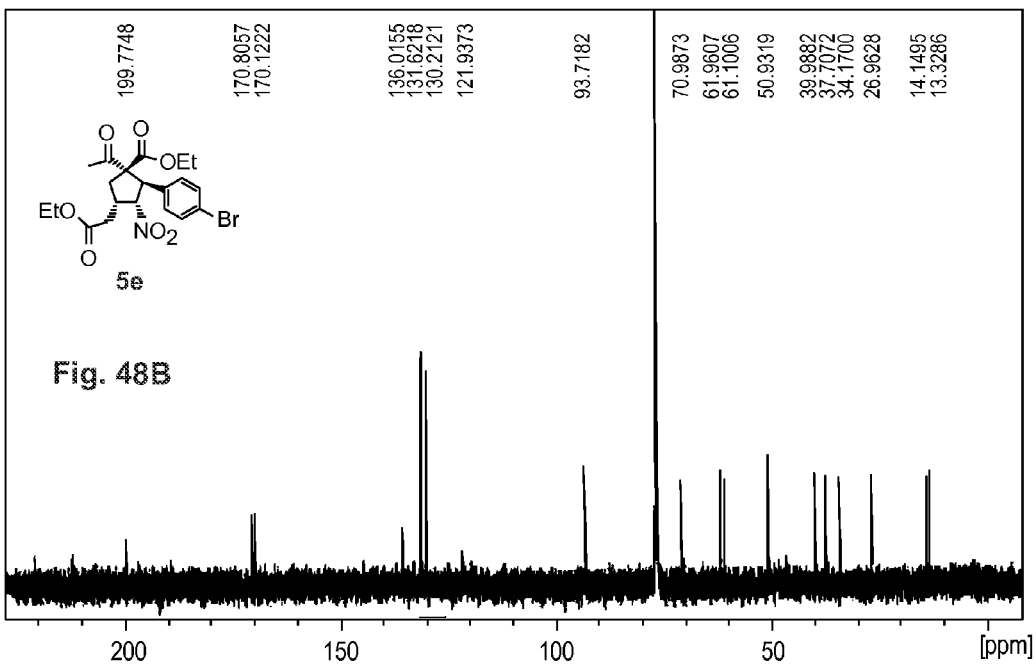
Figure 49A:
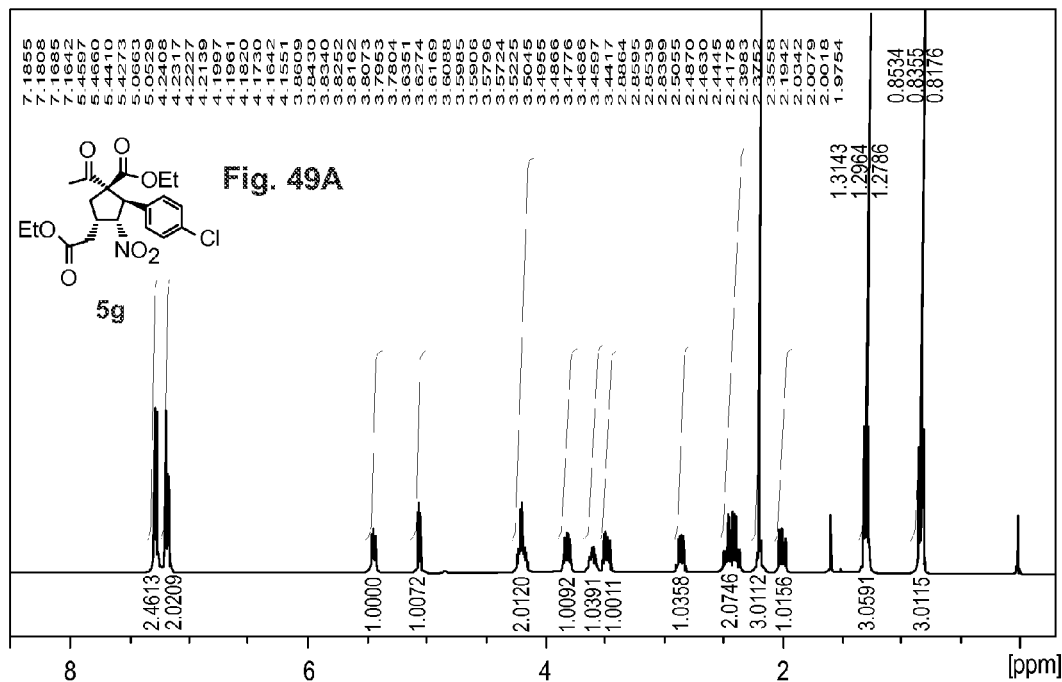
FIG. 49 depicts $^1$H NMR (A) and $^{13}$C NMR (B) spectra of compound 5g.
Figure 49B:
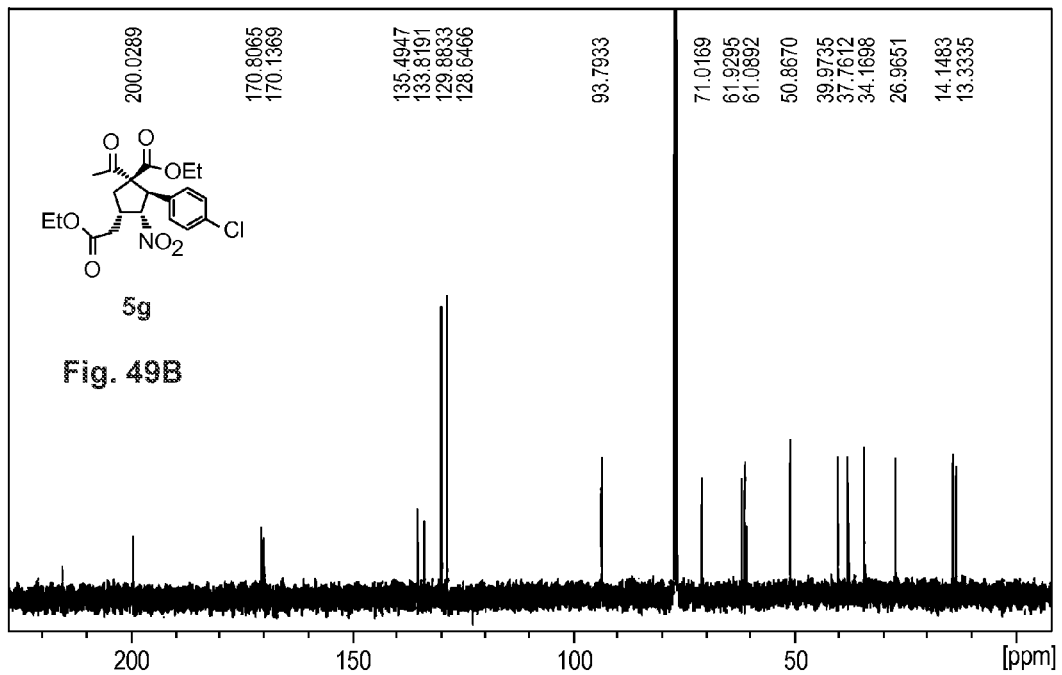
Figure 51A:
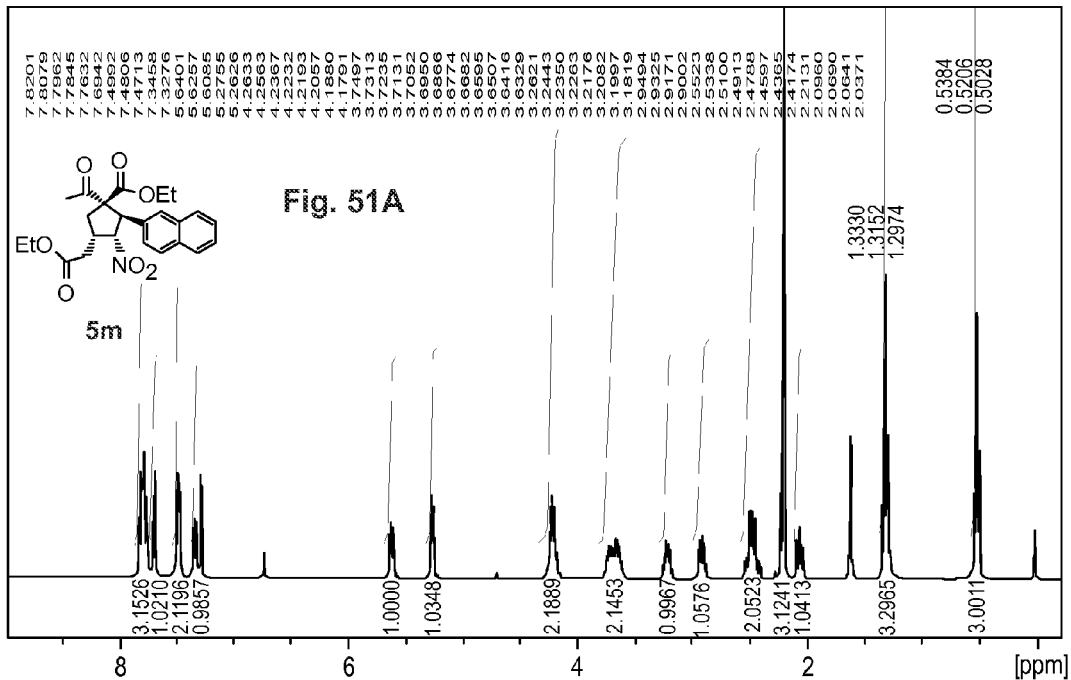
FIG. 51 depicts $^1$H NMR (A) and $^{13}$C NMR (B) spectra of compound 5m.
Figure 51B:
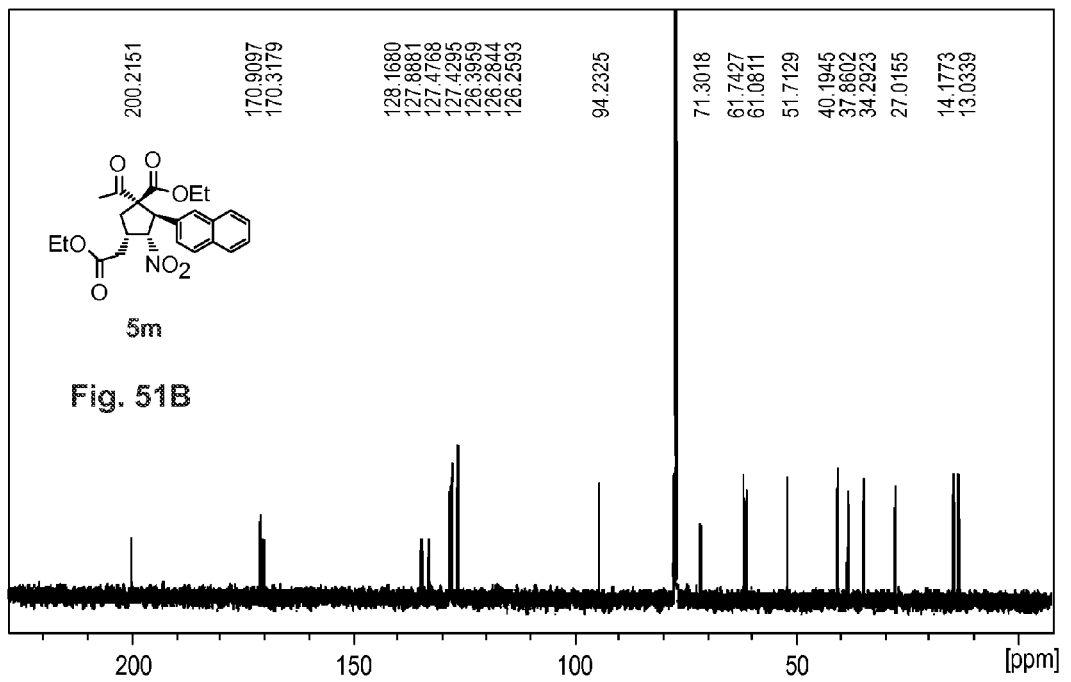
Figure 52A:
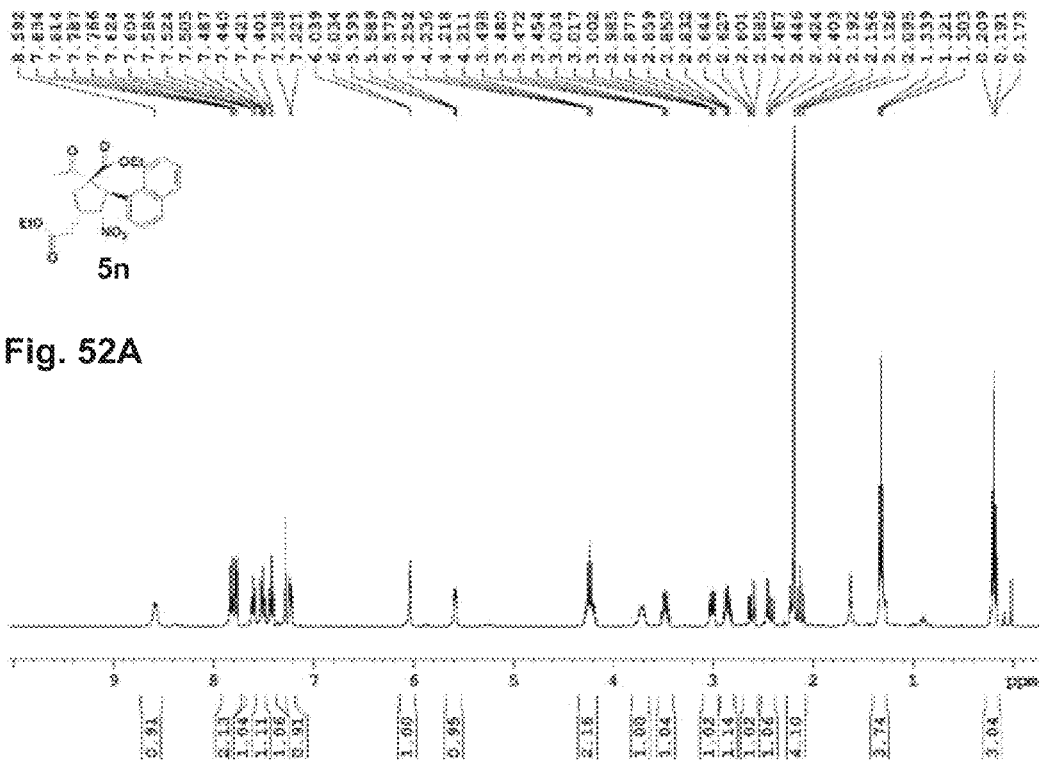
FIG. 52 depicts $^1$H NMR (A) and $^{13}$C NMR (B) spectra of compound 5n.
Figure 52B:
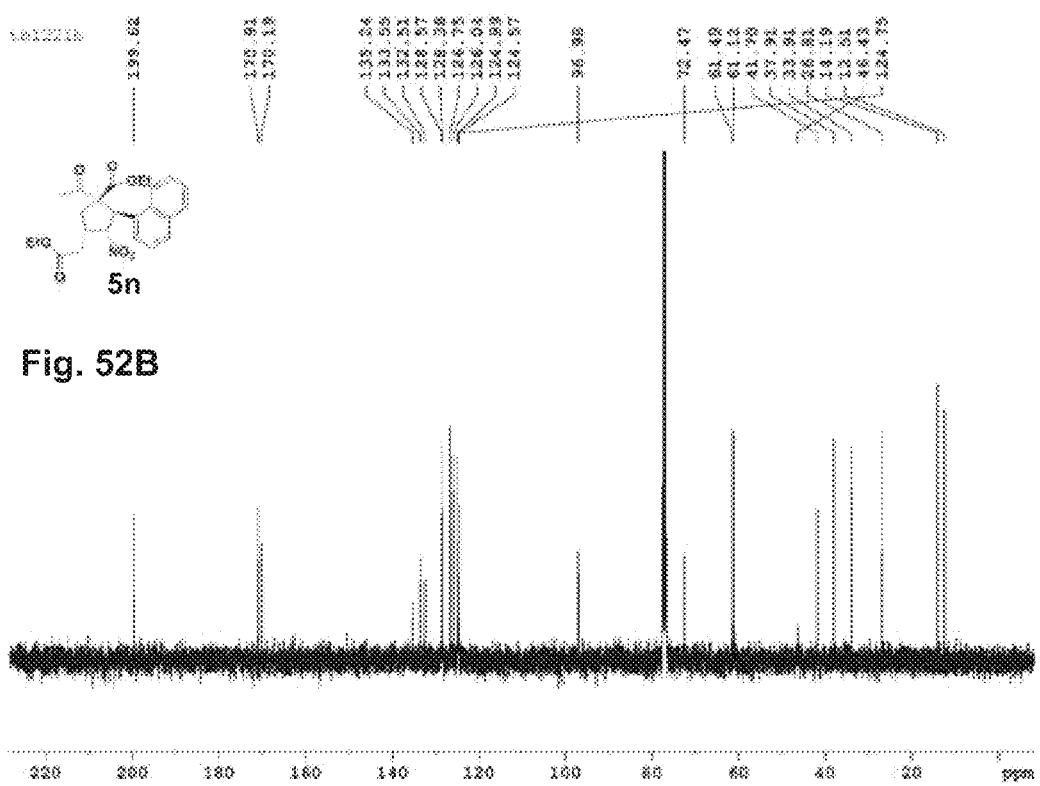
Figure 53A:
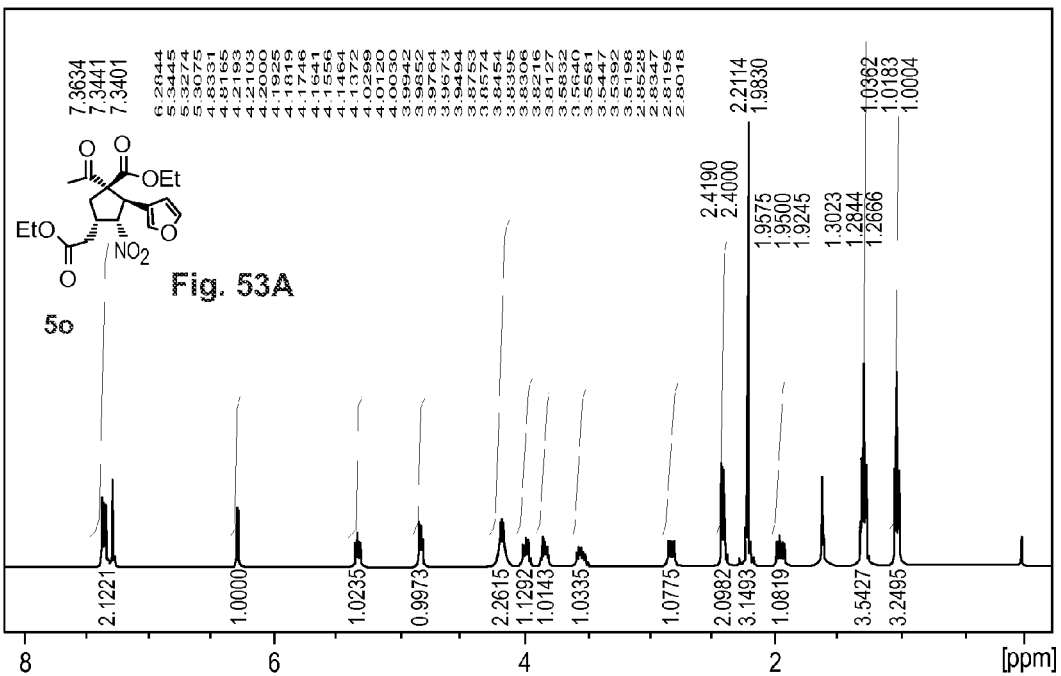
FIG. 53 depicts $^1$H NMR (A) and $^{13}$C NMR (B) spectra of compound 5o.
Figure 53B:
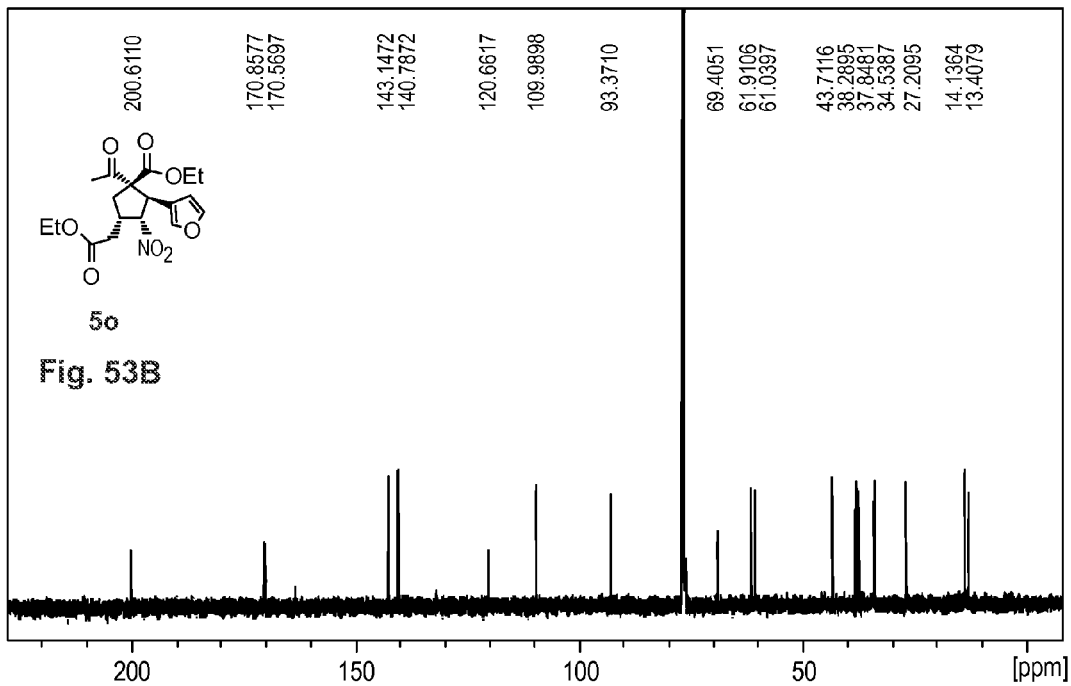
Figure 56A:
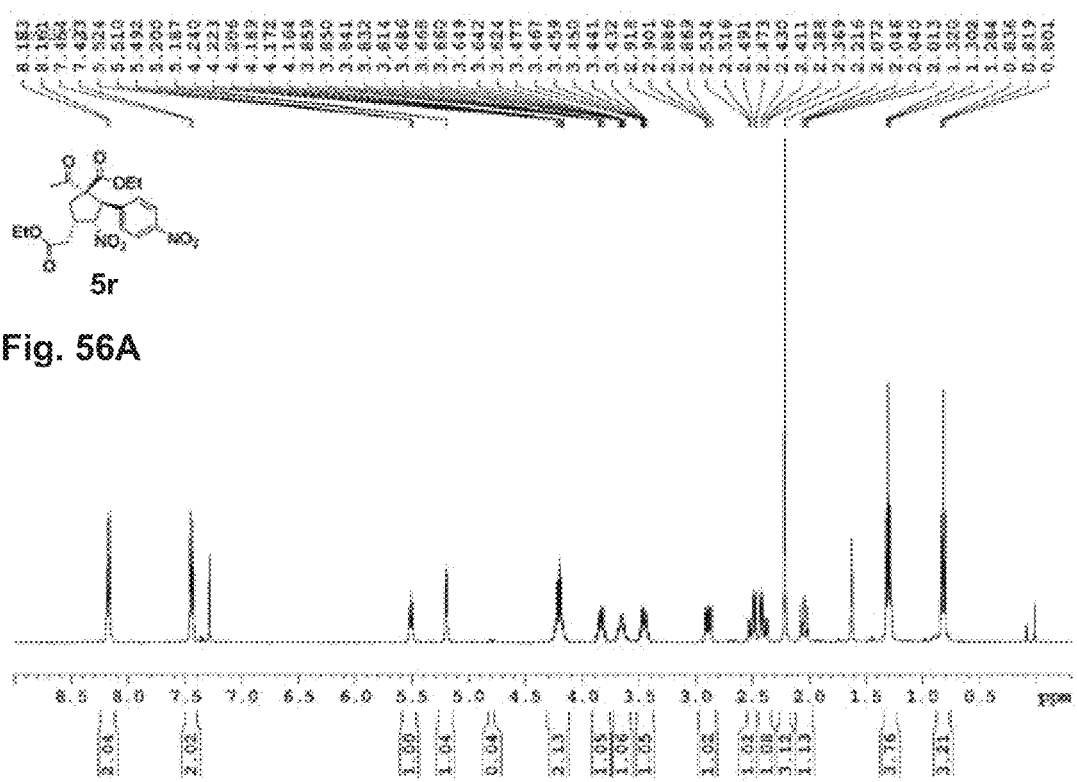
FIG. 56 depicts $^1$H NMR (A) and $^{13}$C NMR (B) spectra of compound 5r.
Figure 56B:
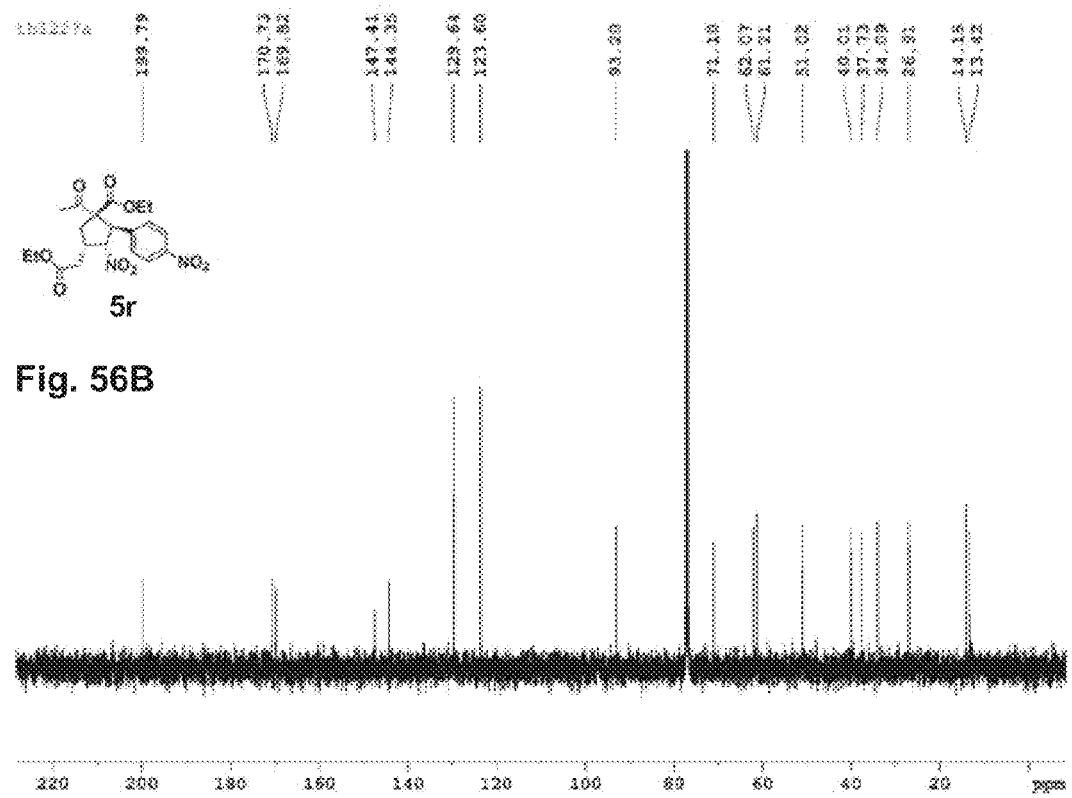
Figure 57A:
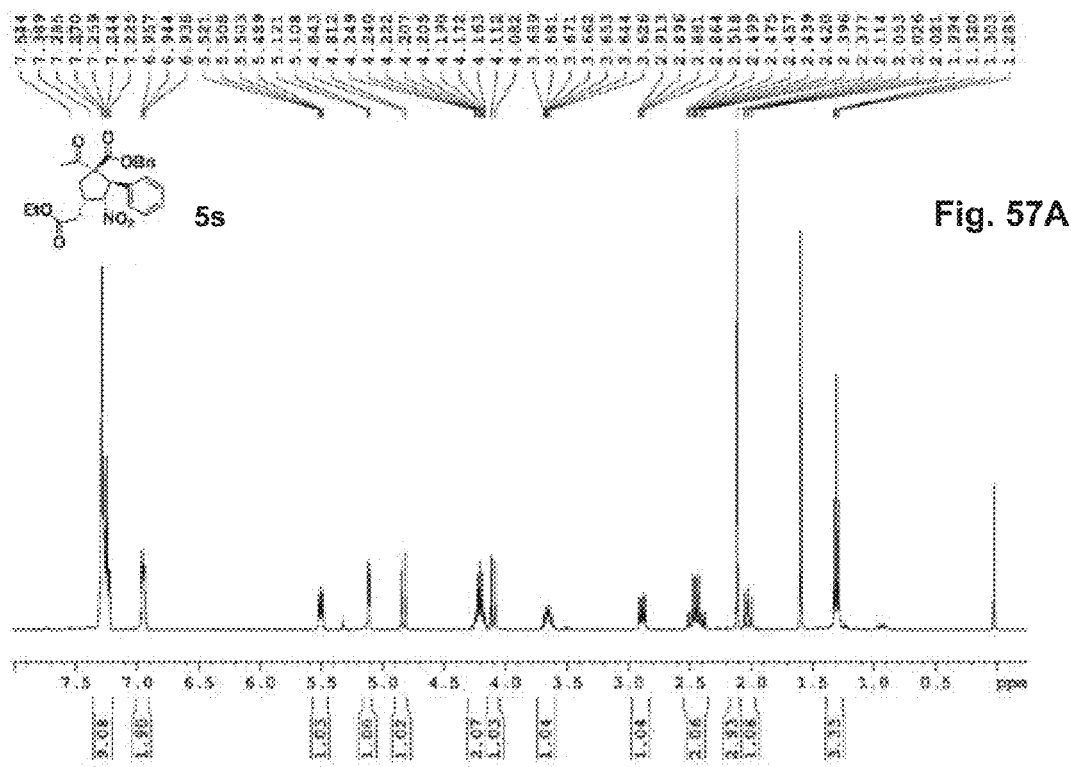
FIG. 57 depicts $^1$H NMR (A) and $^{13}$C NMR (B) spectra of compound 5s.
Figure 57B:
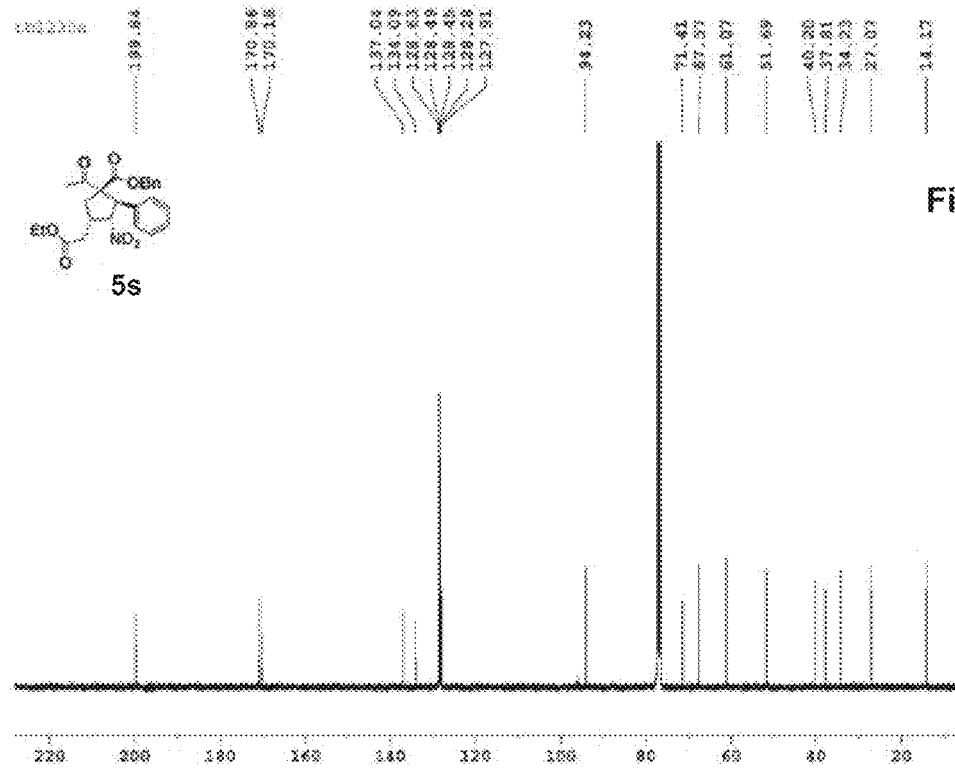
Figure 58A:
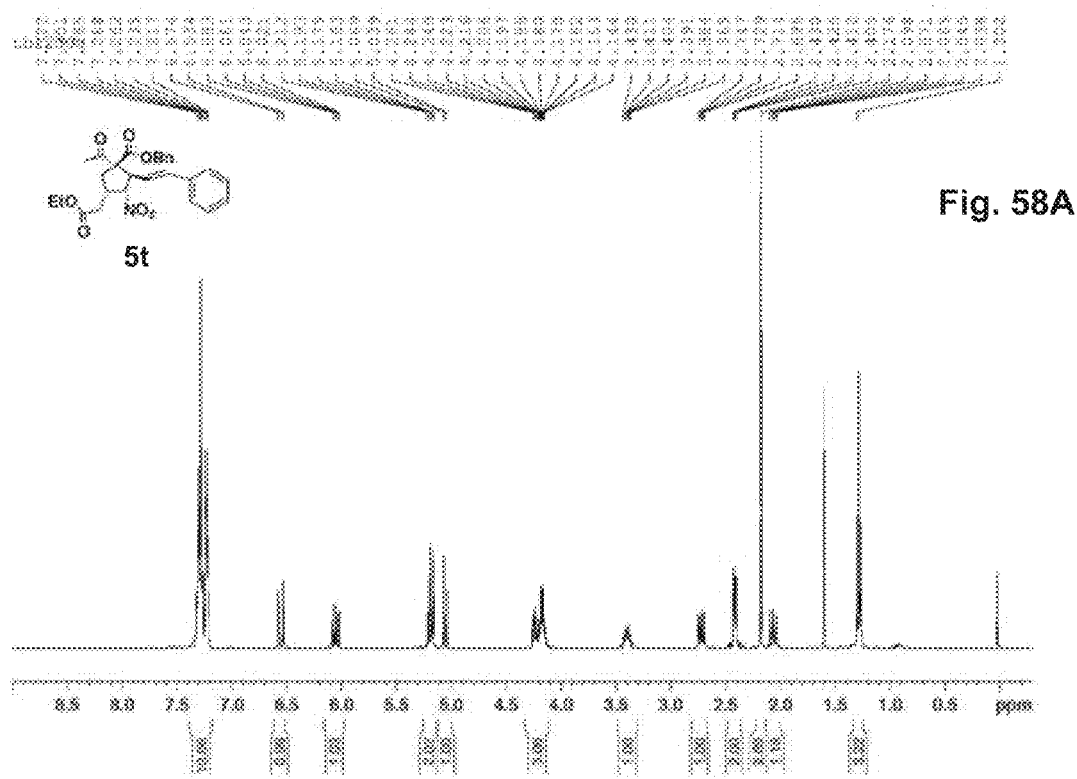
FIG. 58 depicts $^1$H NMR (A) and $^{13}$C NMR (B) spectra of compound 5t.
Figure 58B:
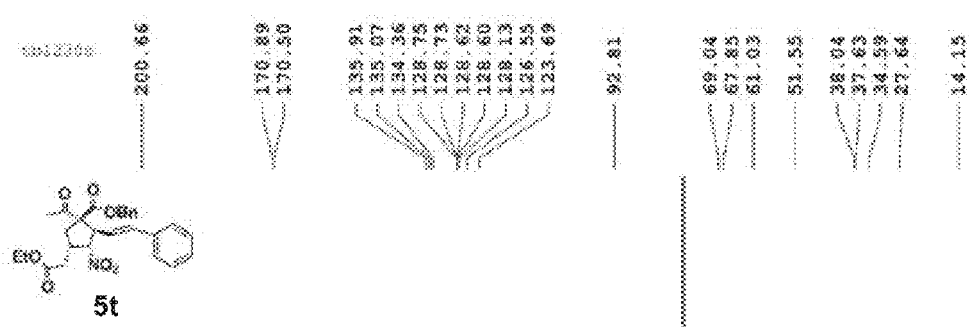
Figure 59A:
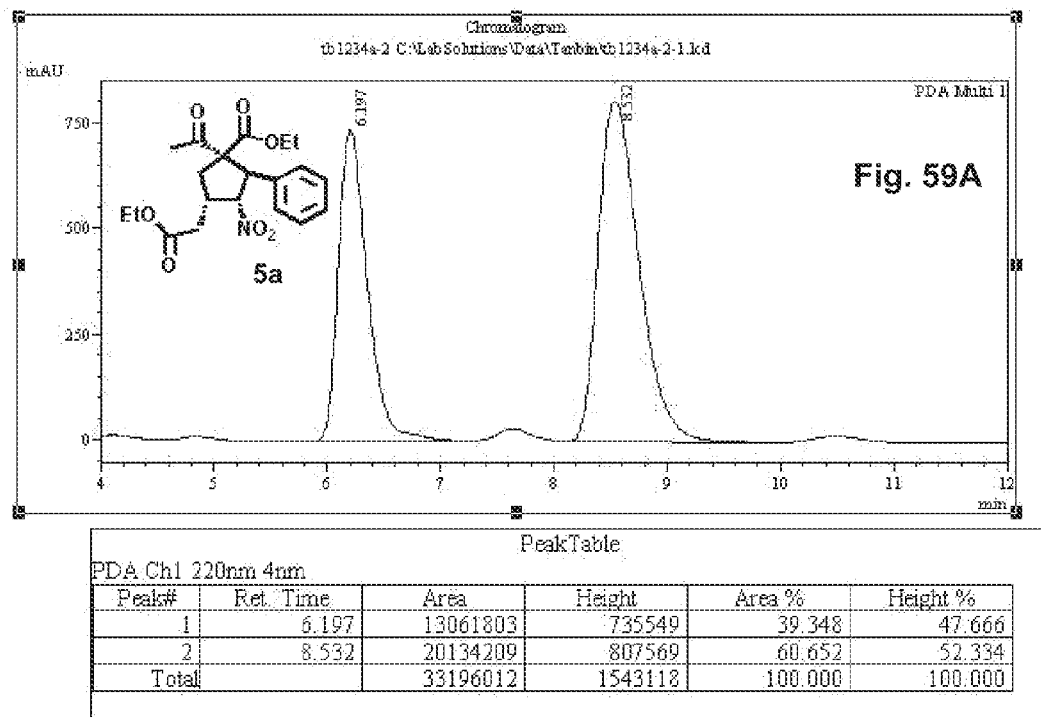
FIG. 59 depicts an HPLC spectrum of a racemic mixture of compound 5a (A), and in comparison the obtained product 5a (B).
Figure 59B:
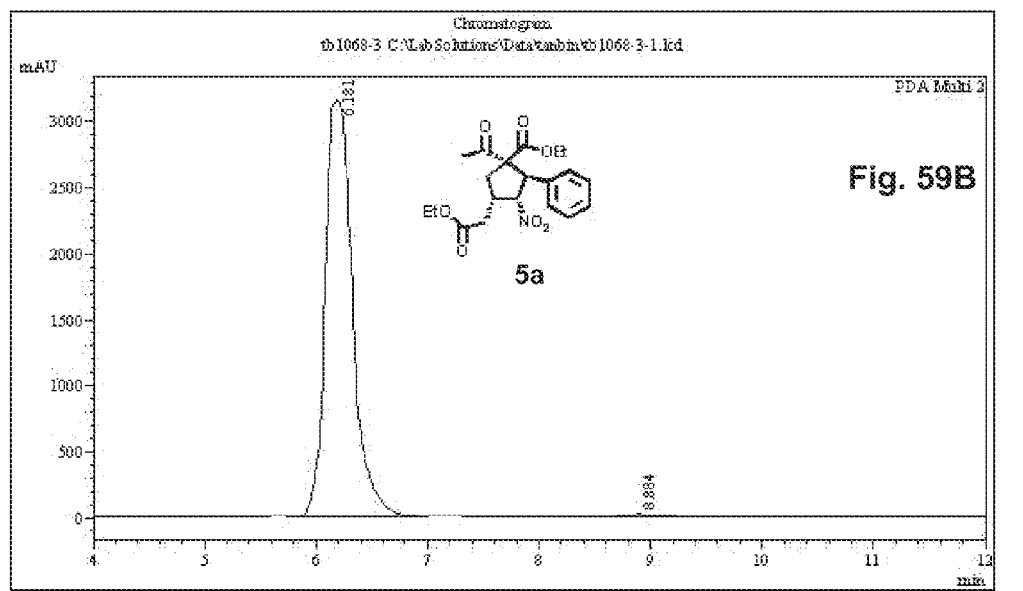
Figure 60A:
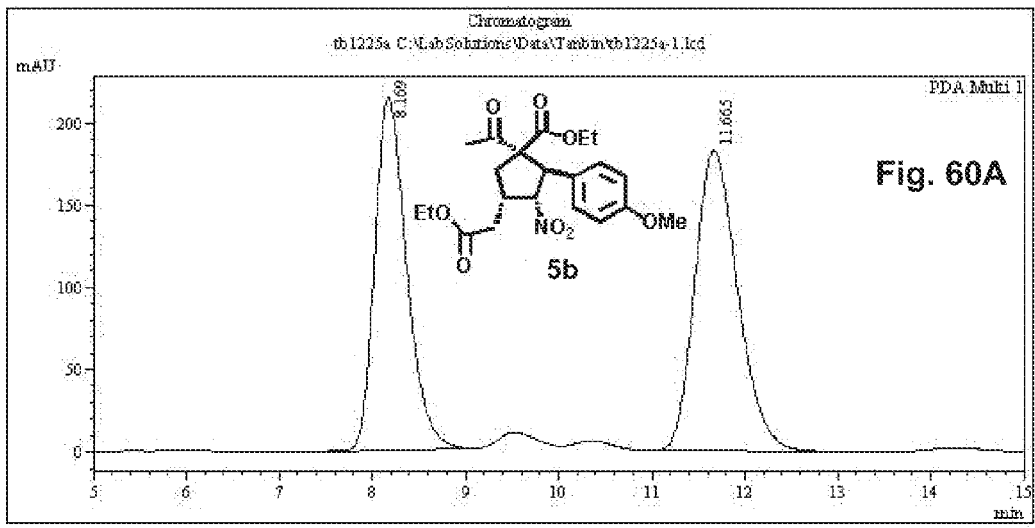
FIG. 60 depicts an HPLC spectrum of a racemic mixture of compound 5b (A), and in comparison the obtained product 5b (B).
Figure 60B:
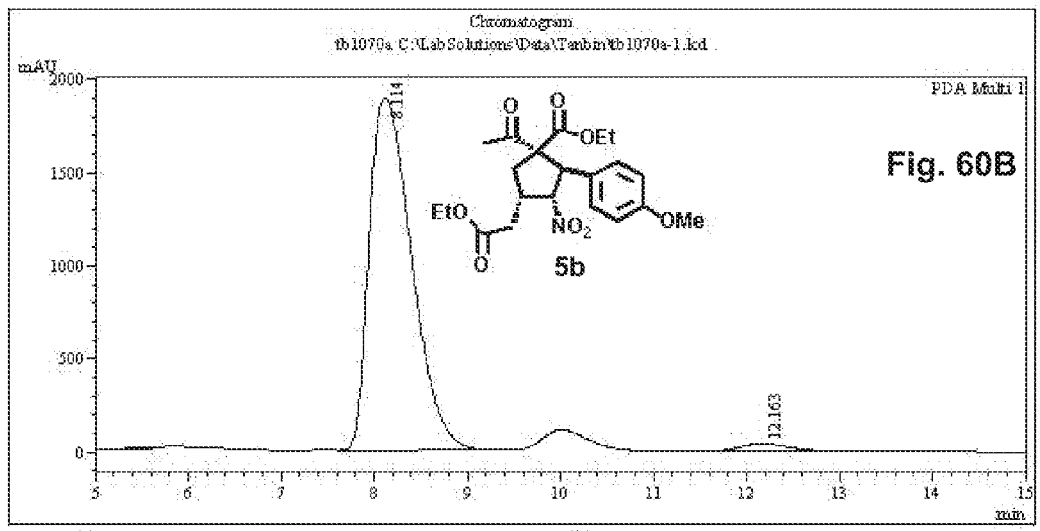
Figure 61A:
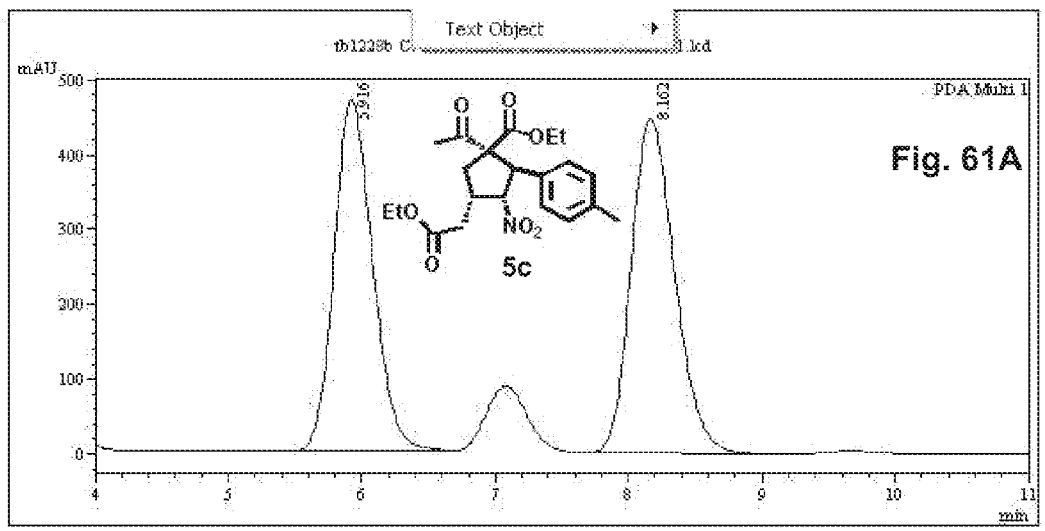
FIG. 61 depicts an HPLC spectrum of a racemic mixture of compound 5c (A), and in comparison the obtained product 5c (B).
Figure 61B:
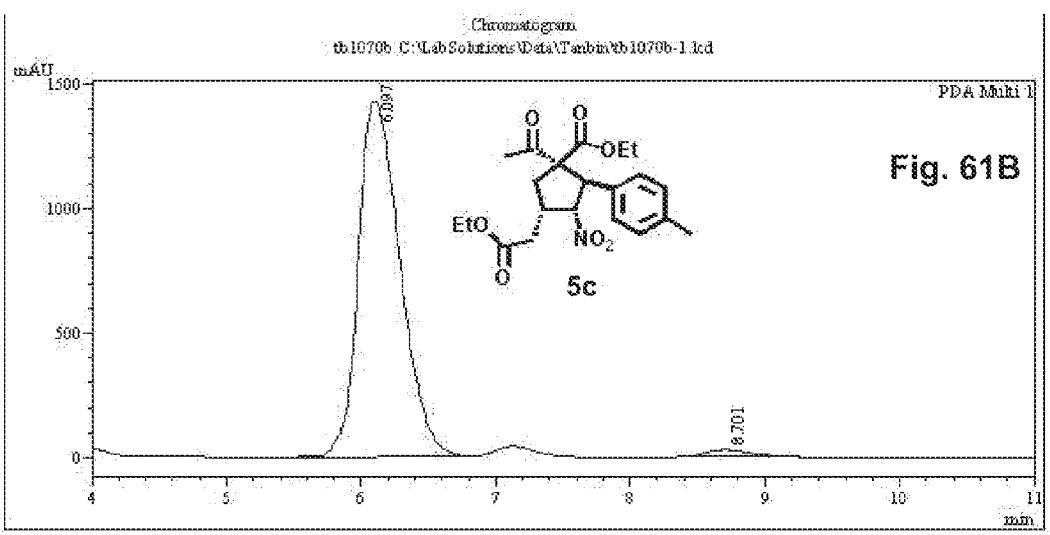
Figure 62A:
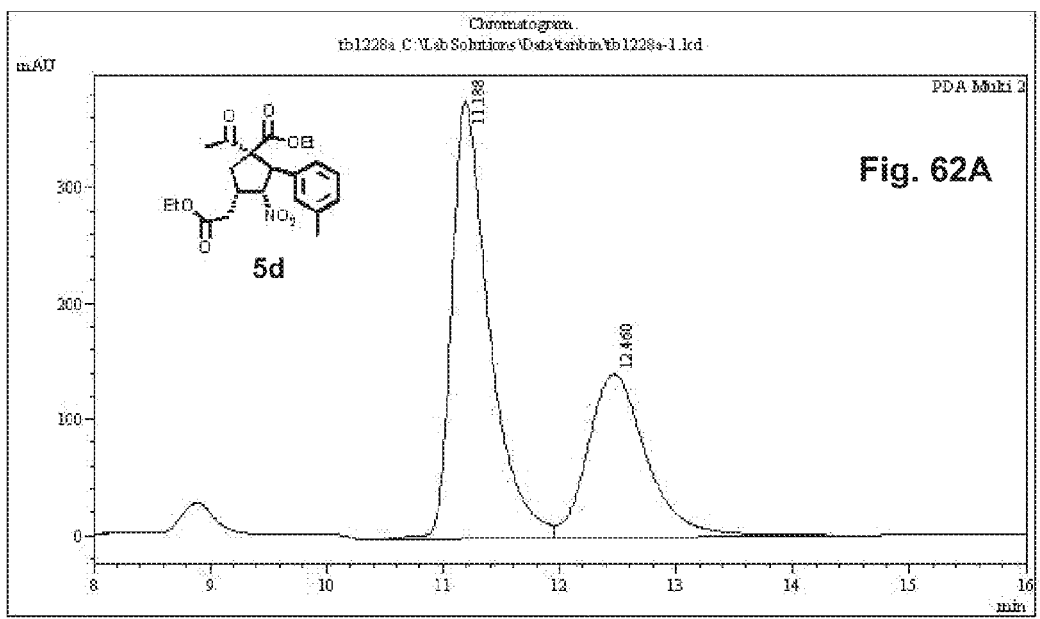
FIG. 62 depicts an HPLC spectrum of a racemic mixture of compound 5d (A), and in comparison the obtained product 5d (B).
Figure 62B:
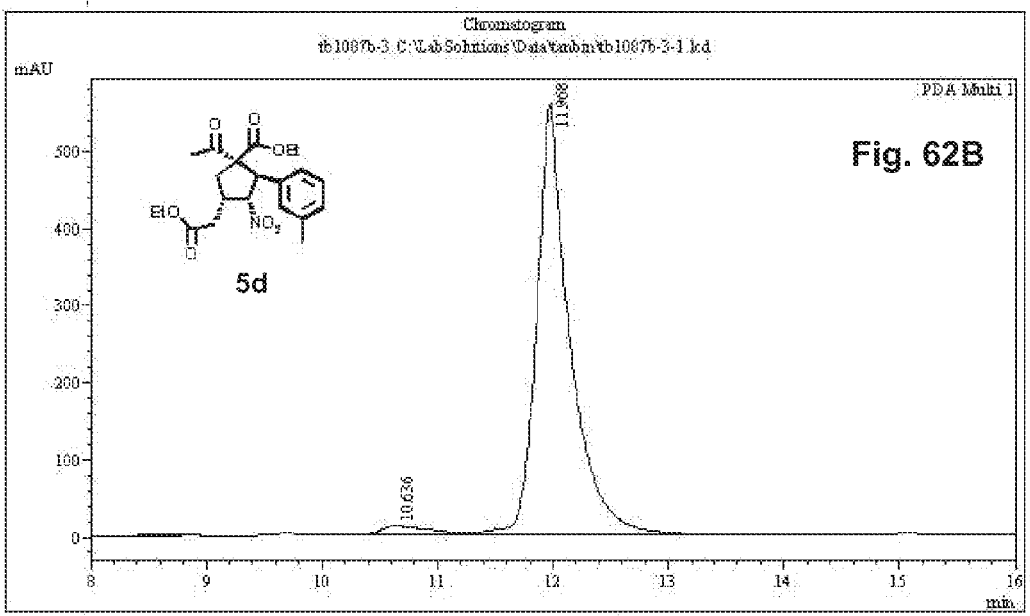
Figure 63A:
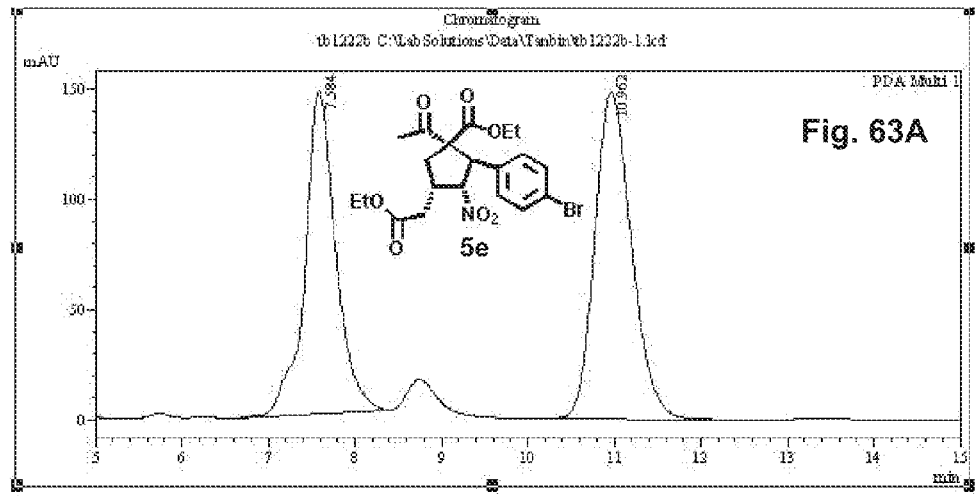
FIG. 63 depicts an HPLC spectrum of a racemic mixture of compound 5e (A), and in comparison the obtained product 5e (B).
Figure 63B:
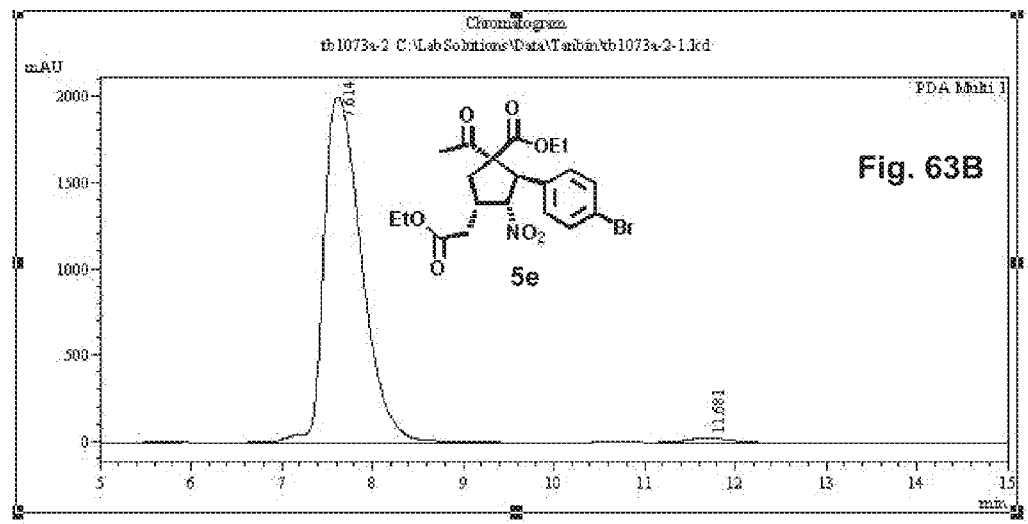
Figure 64A:
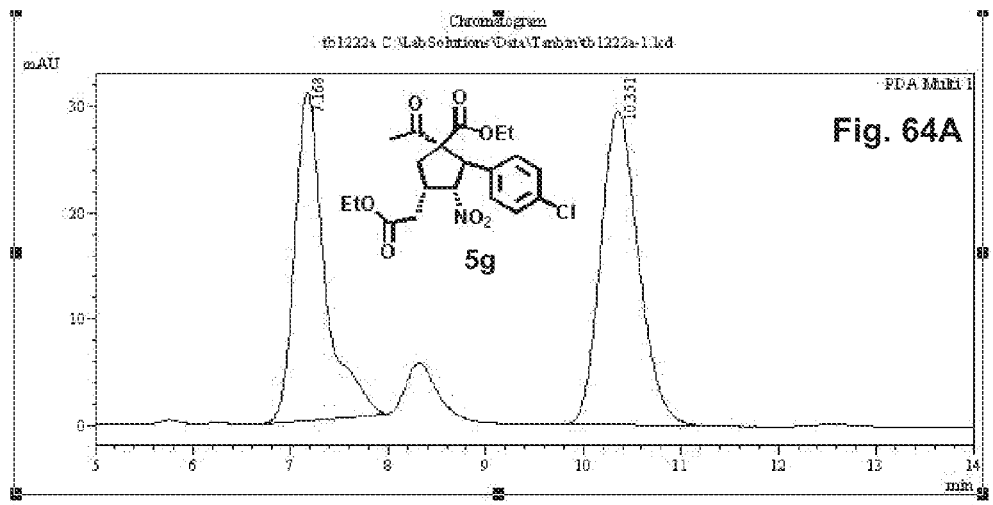
FIG. 64 depicts an HPLC spectrum of a racemic mixture of compound 5g (A), and in comparison the obtained product 5g (B).
Figure 64B:
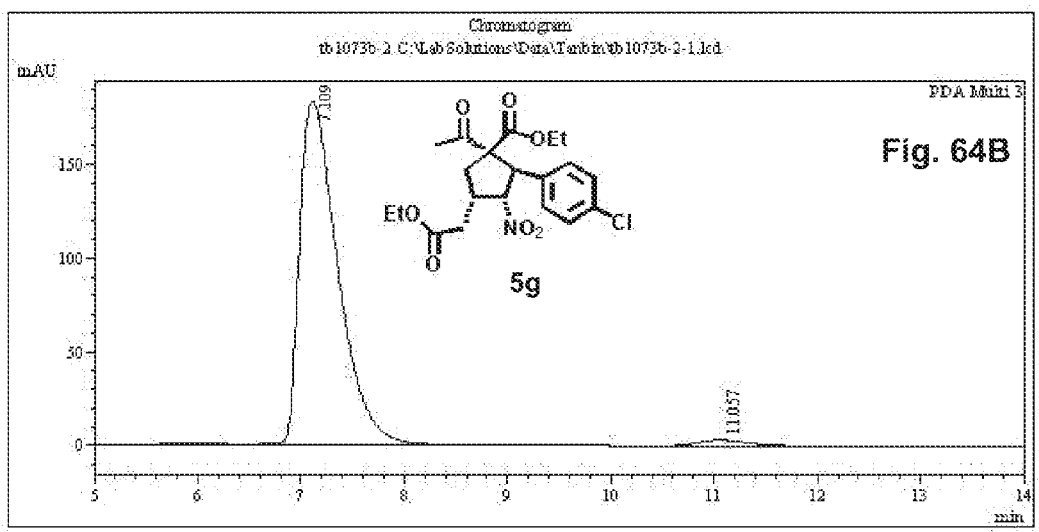
Figure 65A:
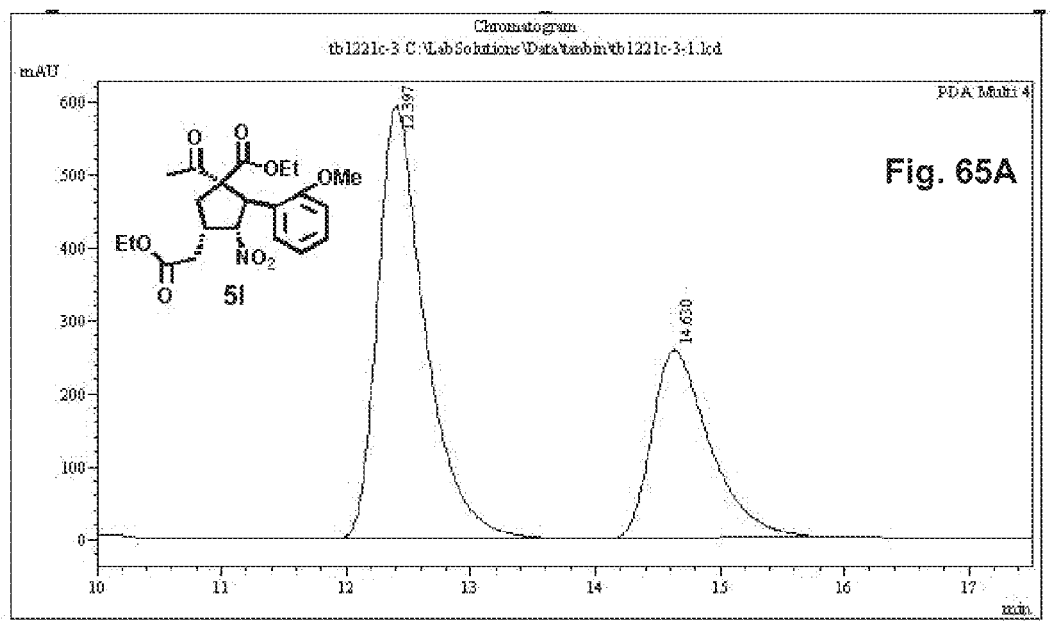
FIG. 65 depicts an HPLC spectrum of a racemic mixture of compound 5l (A), and in comparison the obtained product 5l (B).
Figure 65B:
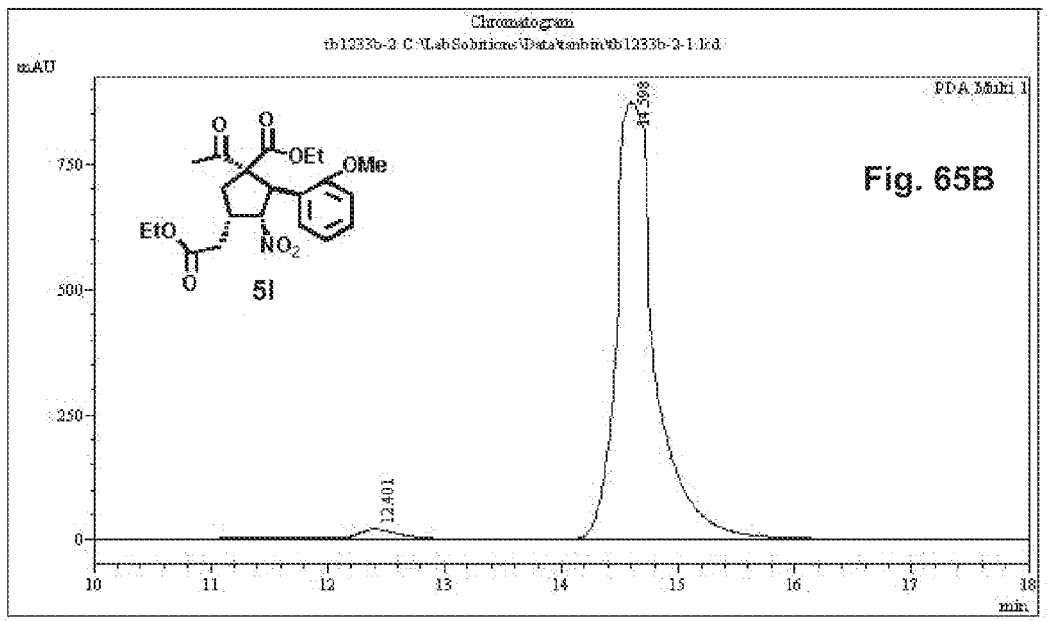
Figure 66A:
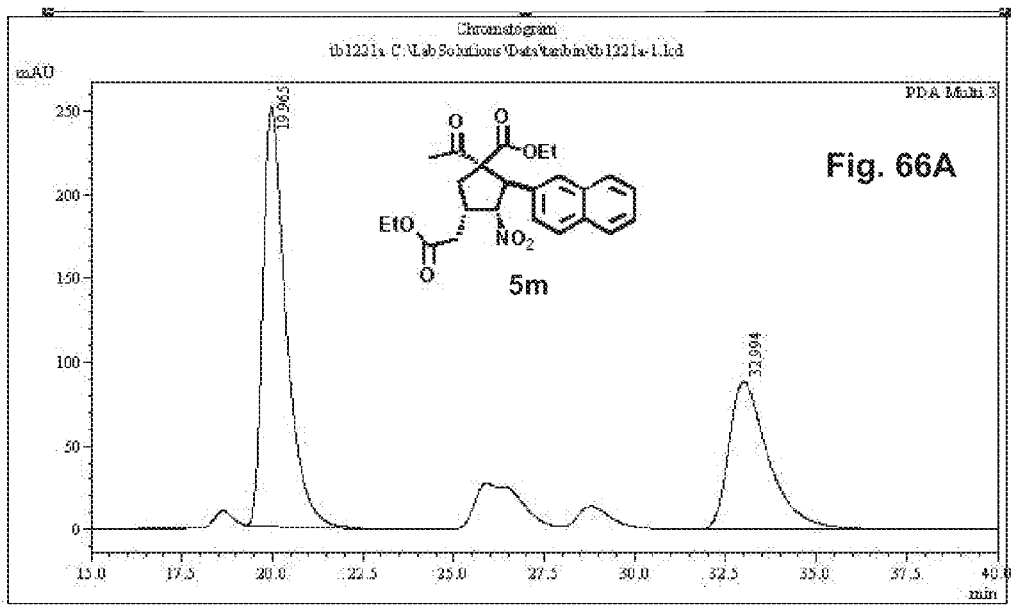
FIG. 66 depicts an HPLC spectrum of a racemic mixture of compound 5m (A), and in comparison the obtained product 5m (B).
Figure 66B:
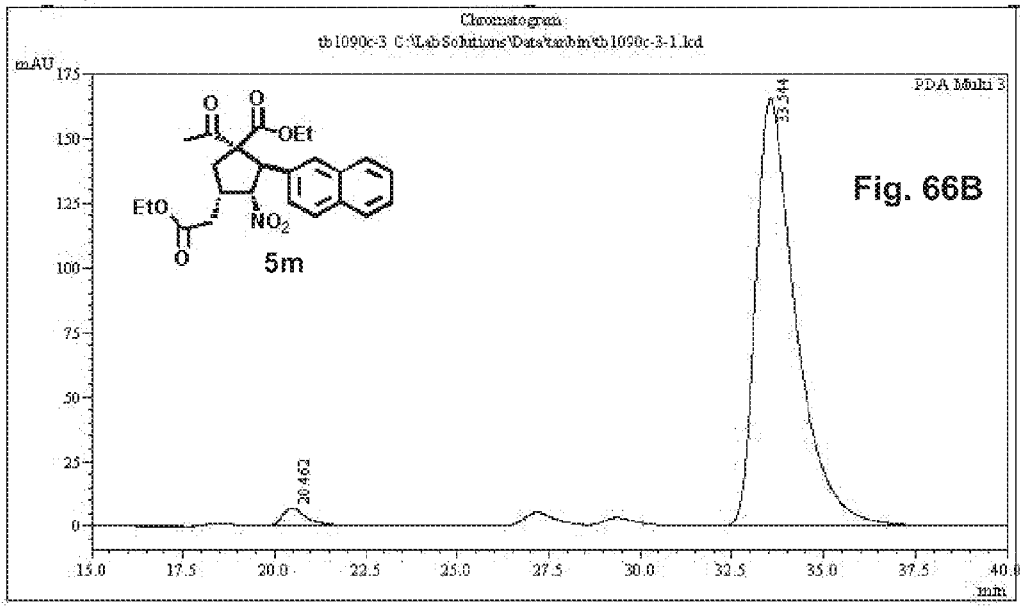
Figure 67A:
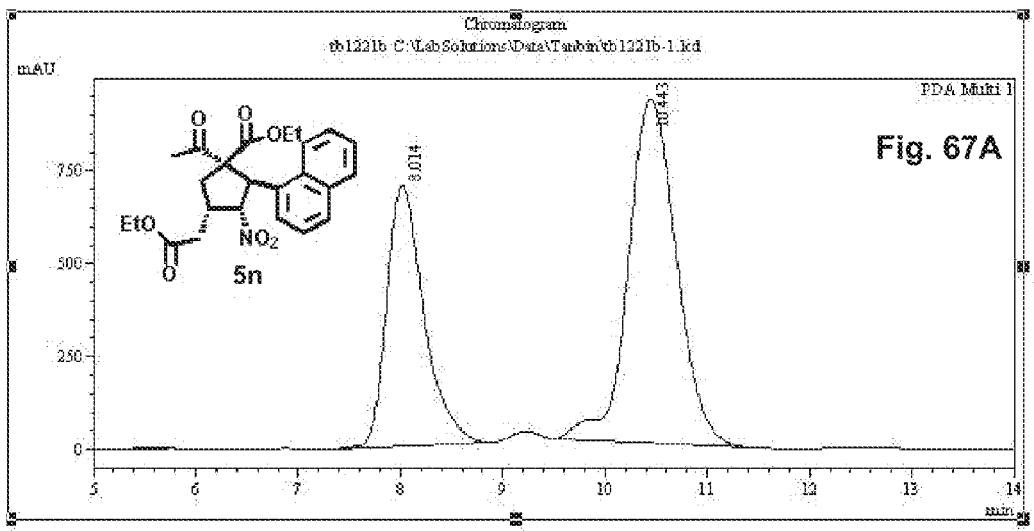
FIG. 67 depicts an HPLC spectrum of a racemic mixture of compound 5n (A), and in comparison the obtained product 5n (B).
Figure 67B:
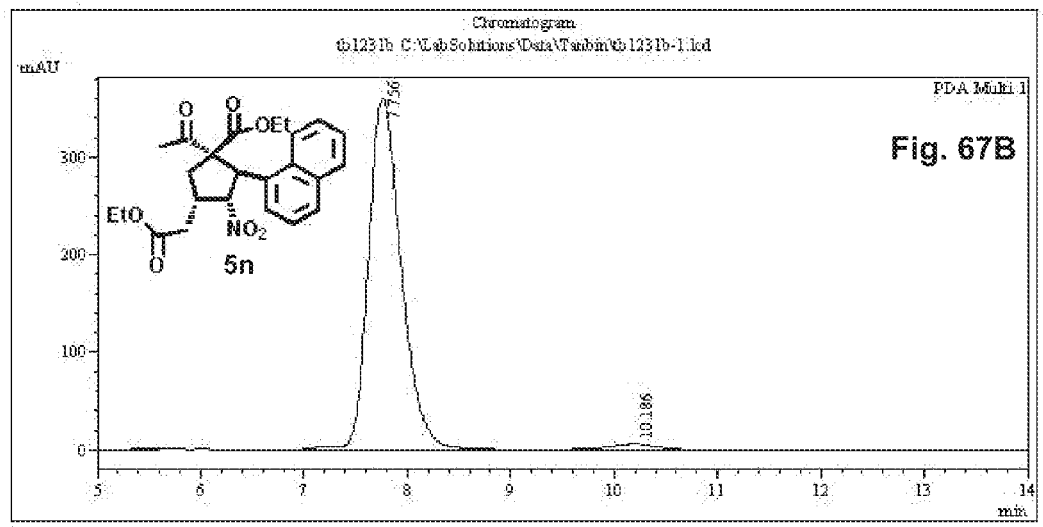
Figure 68A:
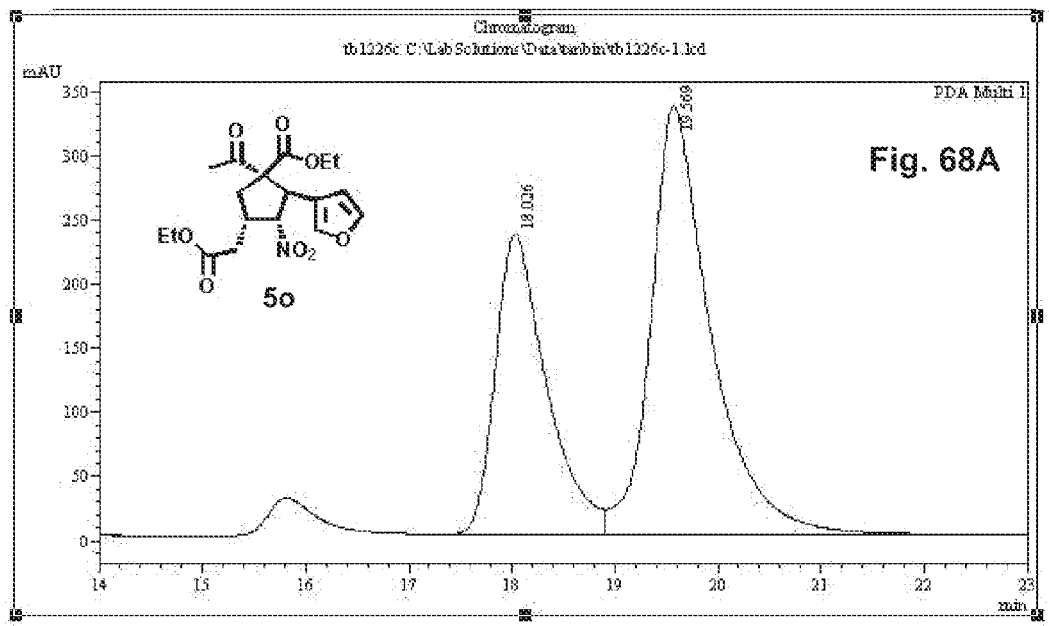
FIG. 68 depicts an HPLC spectrum of a racemic mixture of compound 5o (A), and in comparison the obtained product 5o (B).
Figure 68B:
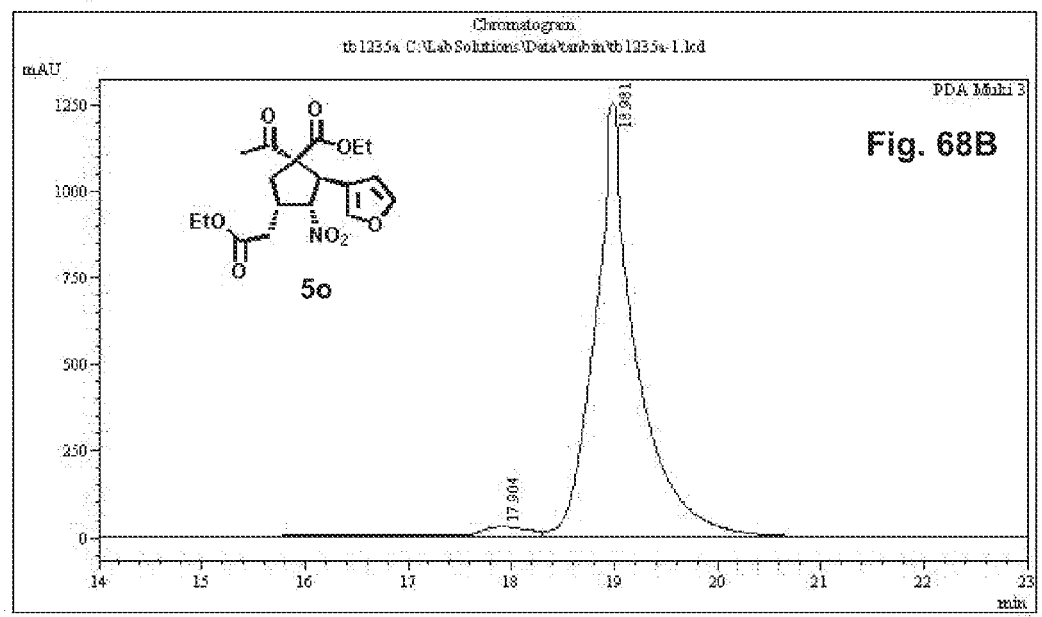
Figure 69A:
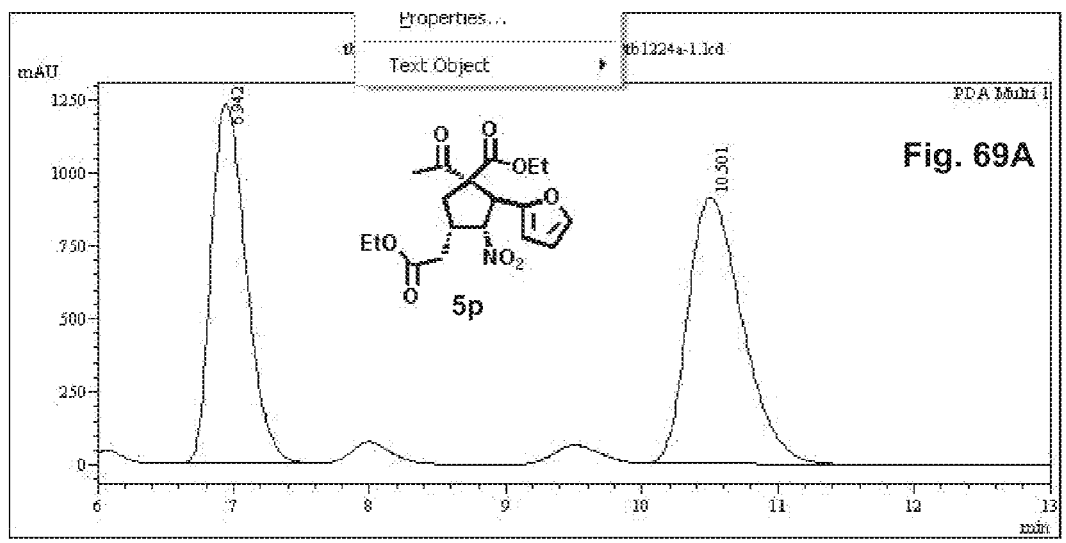
FIG. 69 depicts an HPLC spectrum of a racemic mixture of compound 5p (A), and in comparison the obtained product 5p (B).
Figure 69B:
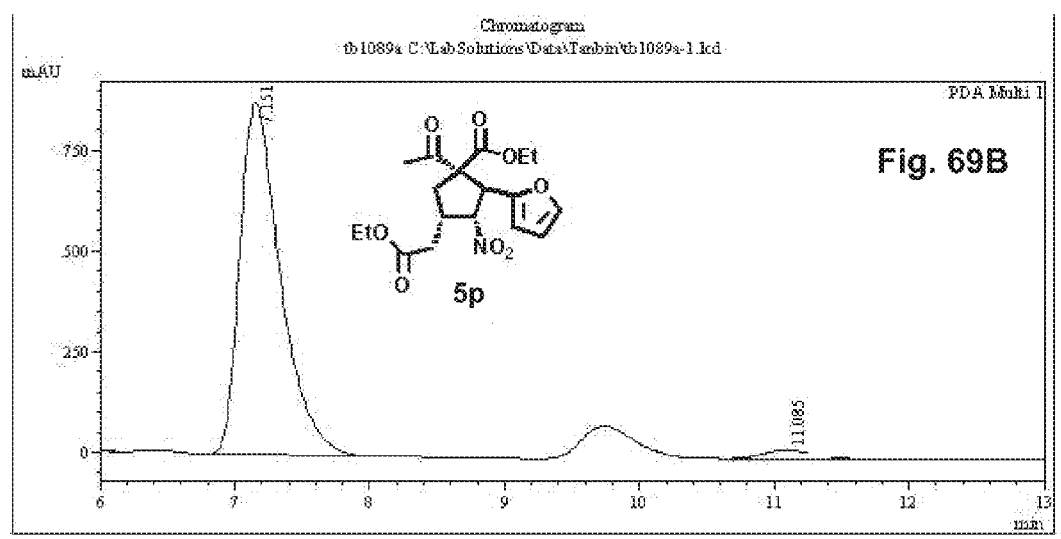
Figure 70A:
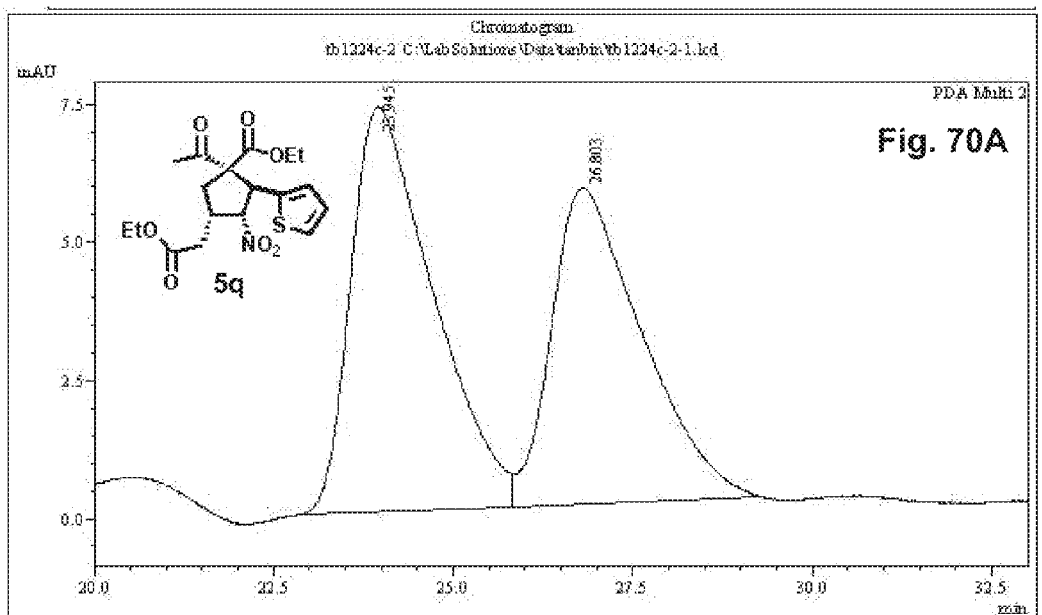
FIG. 70 depicts an HPLC spectrum of a racemic mixture of compound 5q (A), and in comparison the obtained product 5q (B).
Figure 70B:
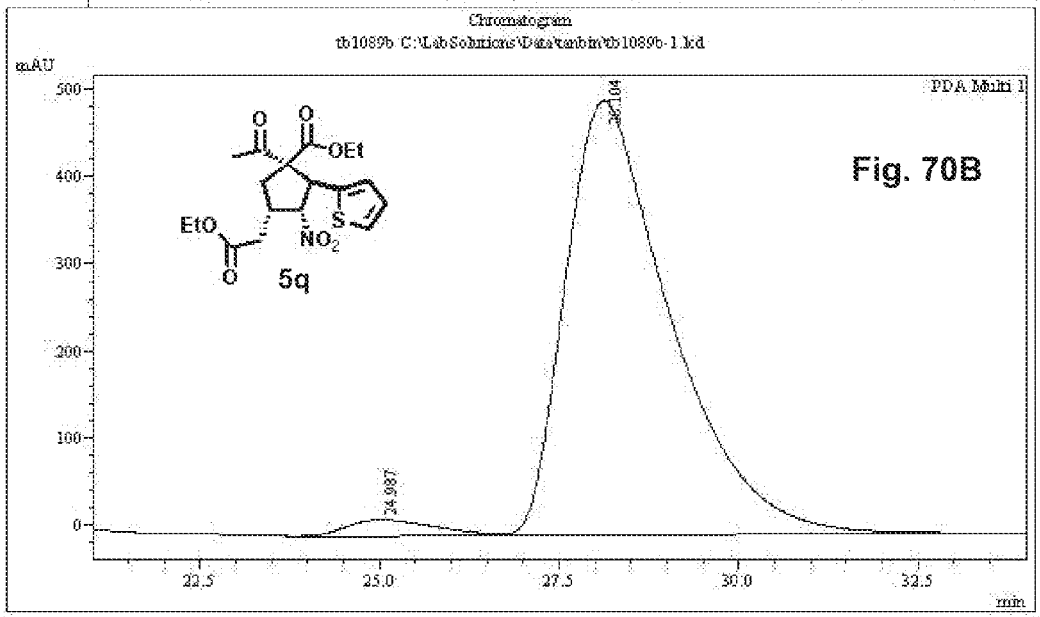
Figure 71A:
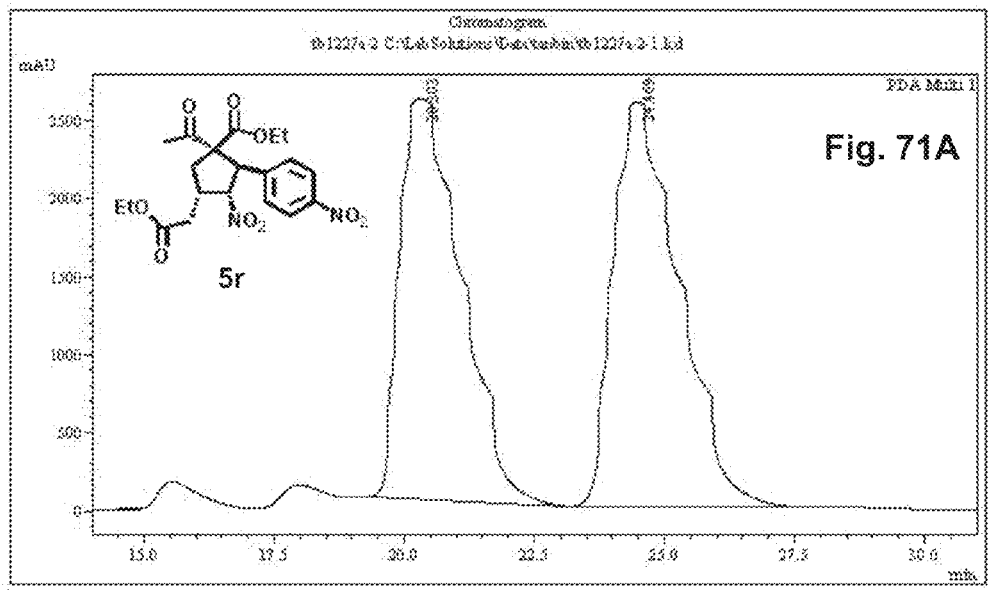
FIG. 71 depicts an HPLC spectrum of a racemic mixture of compound 5r (A), and in comparison the obtained product 5r (B).
Figure 71B:
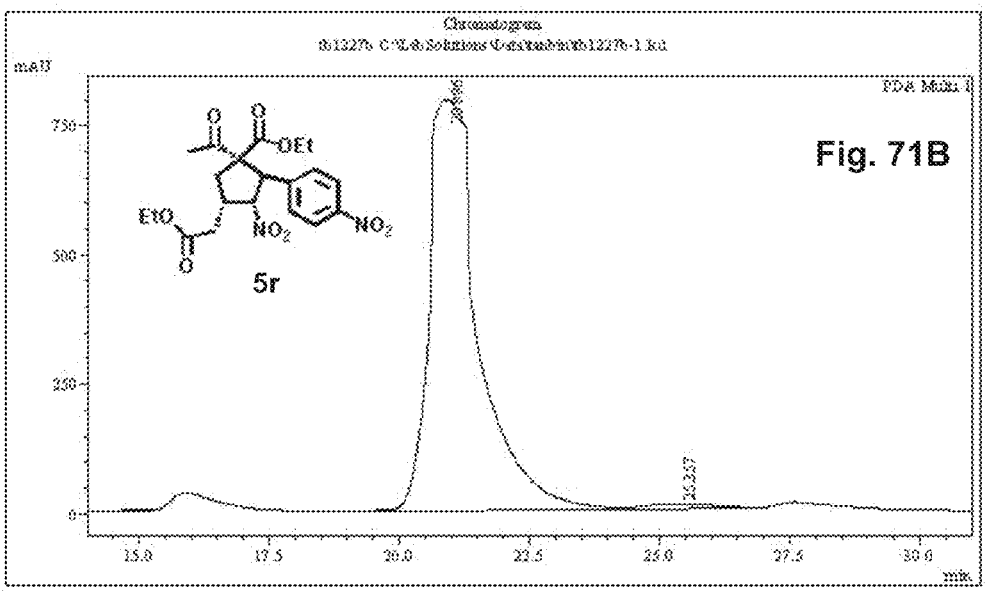
Figure 72A:
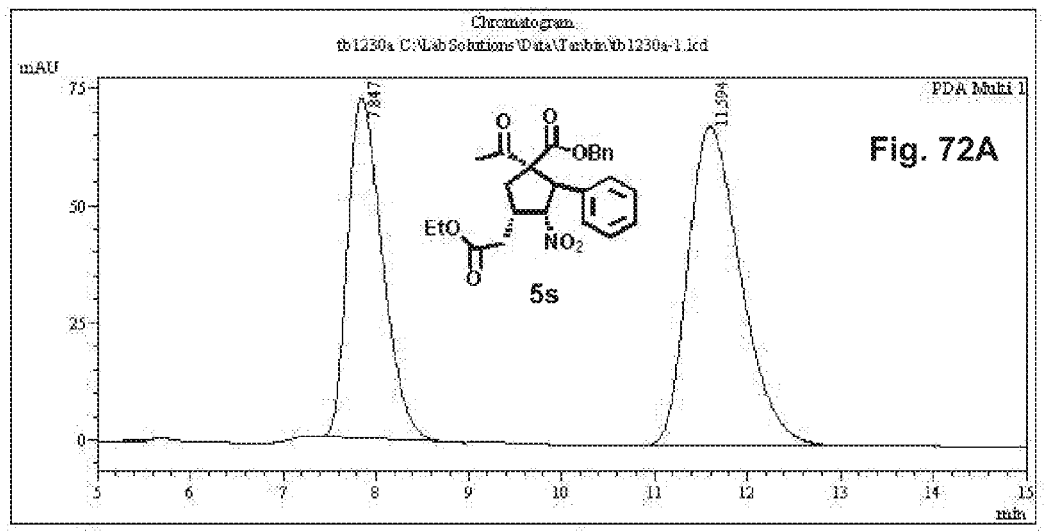
FIG. 72 depicts an HPLC spectrum of a racemic mixture of compound 5s (A), and in comparison the obtained product 5s (B).
Figure 72B:
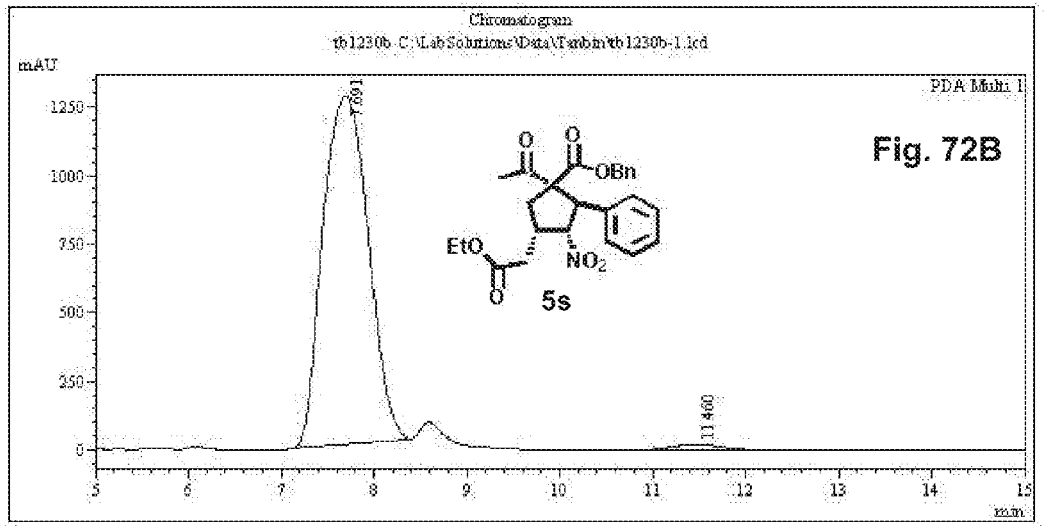
Figure 73A:
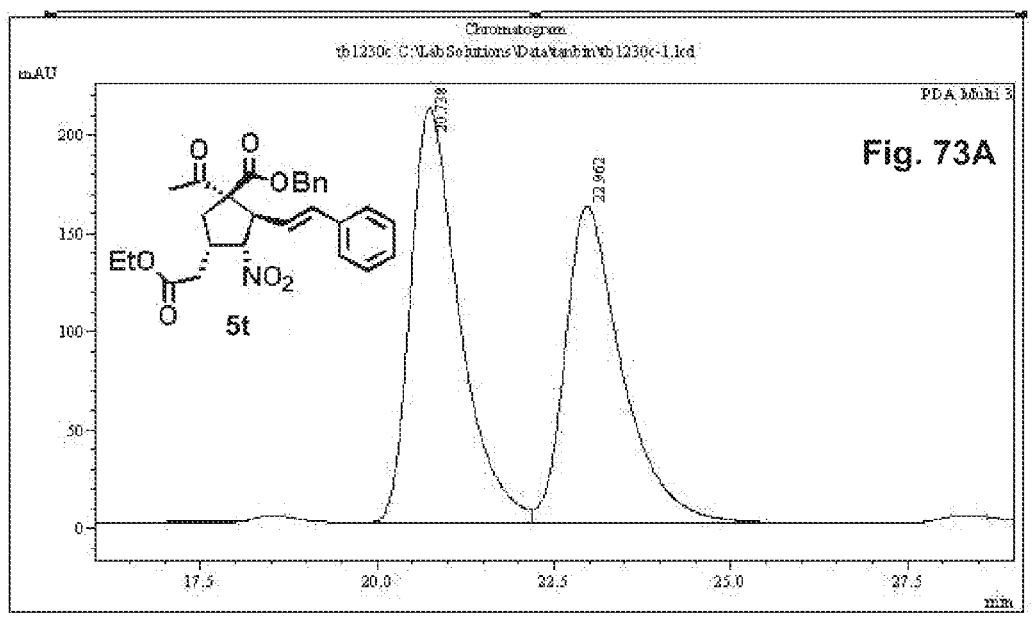
FIG. 73 depicts an HPLC spectrum of a racemic mixture of compound 5t (A), and in comparison the obtained product 5t (B).
Figure 73B:
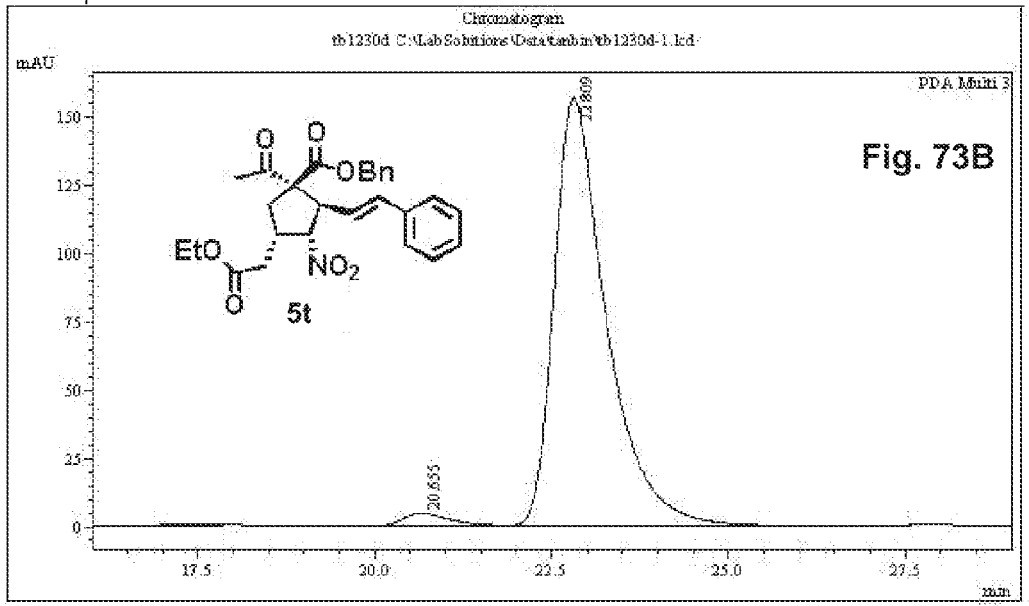
Figure 74A:
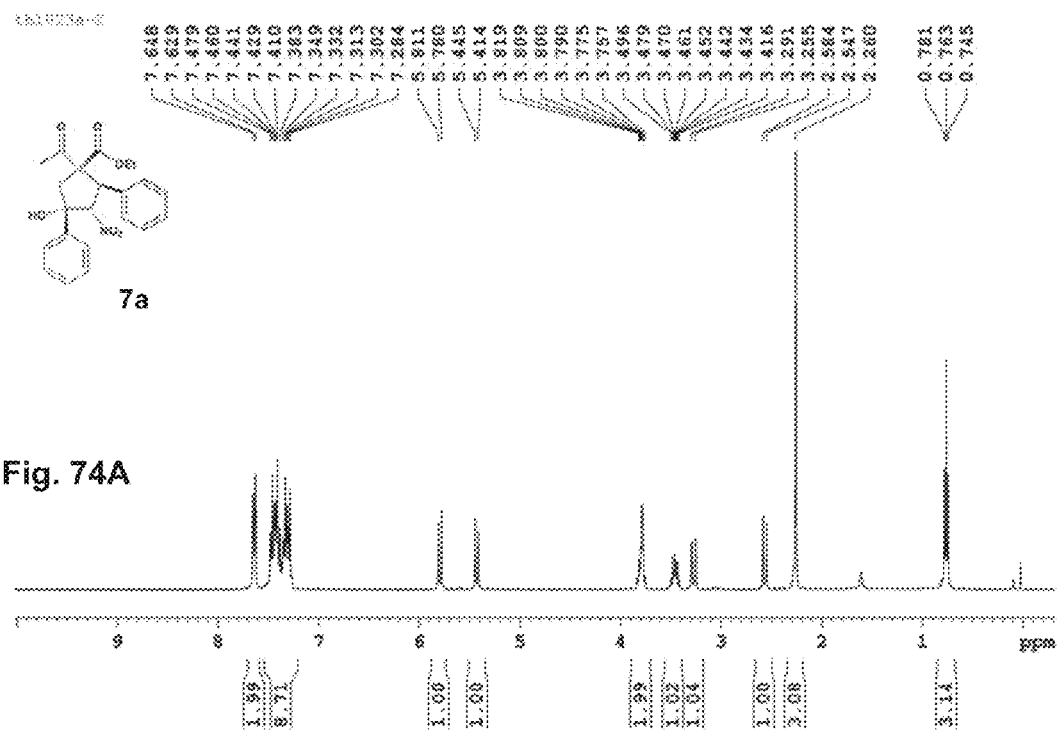
Figure 74B:
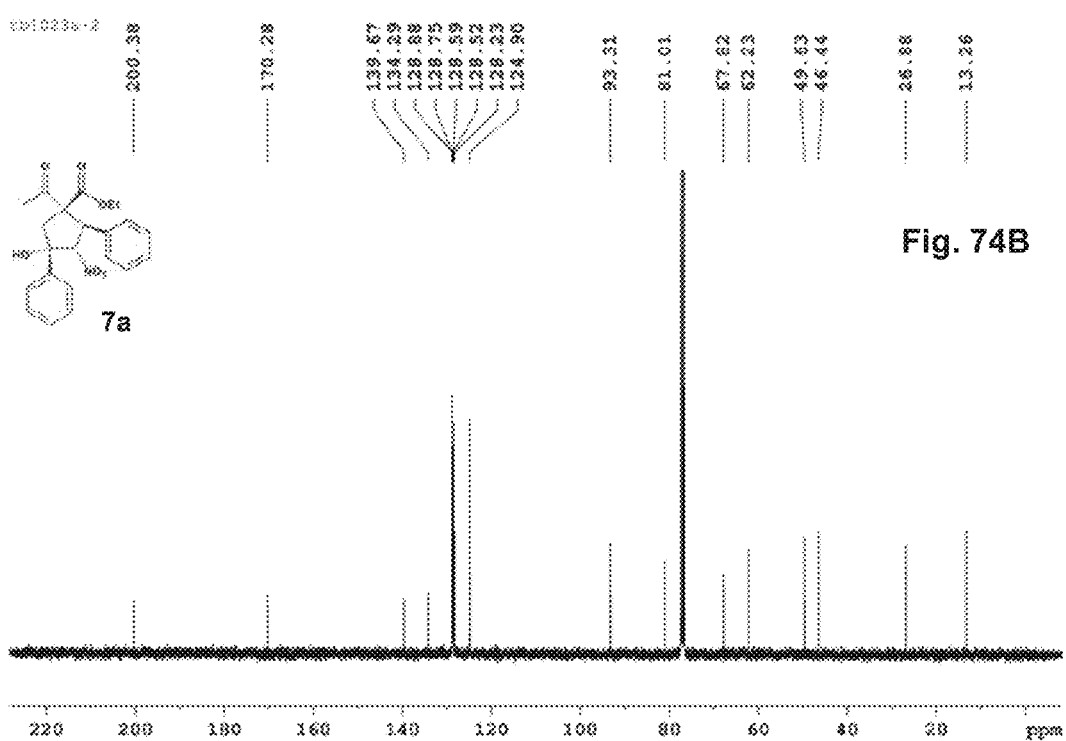
Figure 76A:
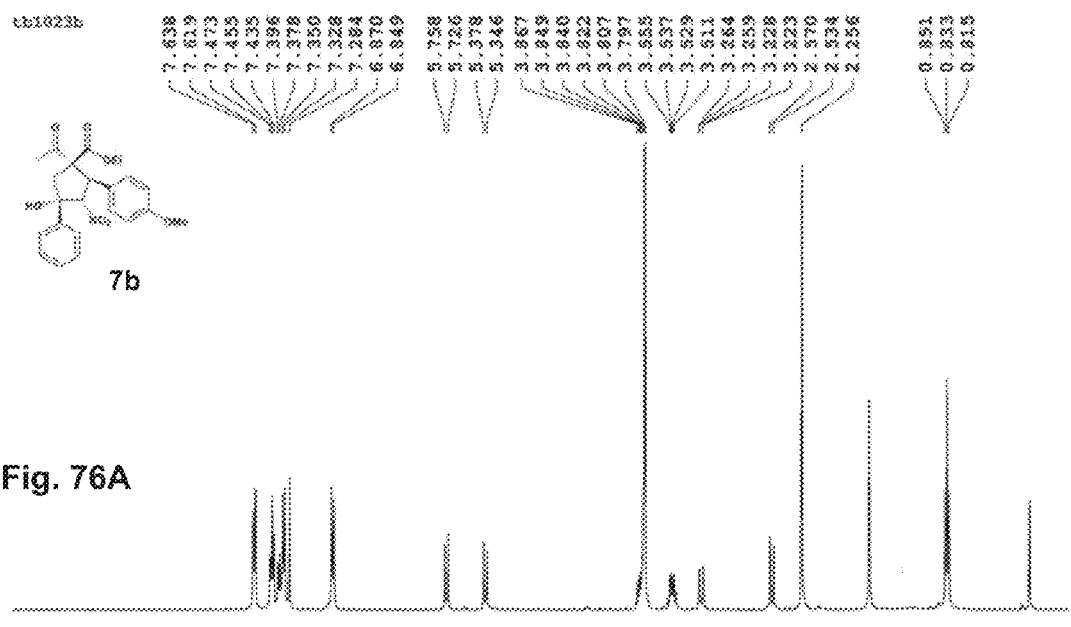
FIG. 76 depicts $^1$H NMR (A) and $^{13}$C NMR (B) spectra of compound 7b.
Figure 76B:
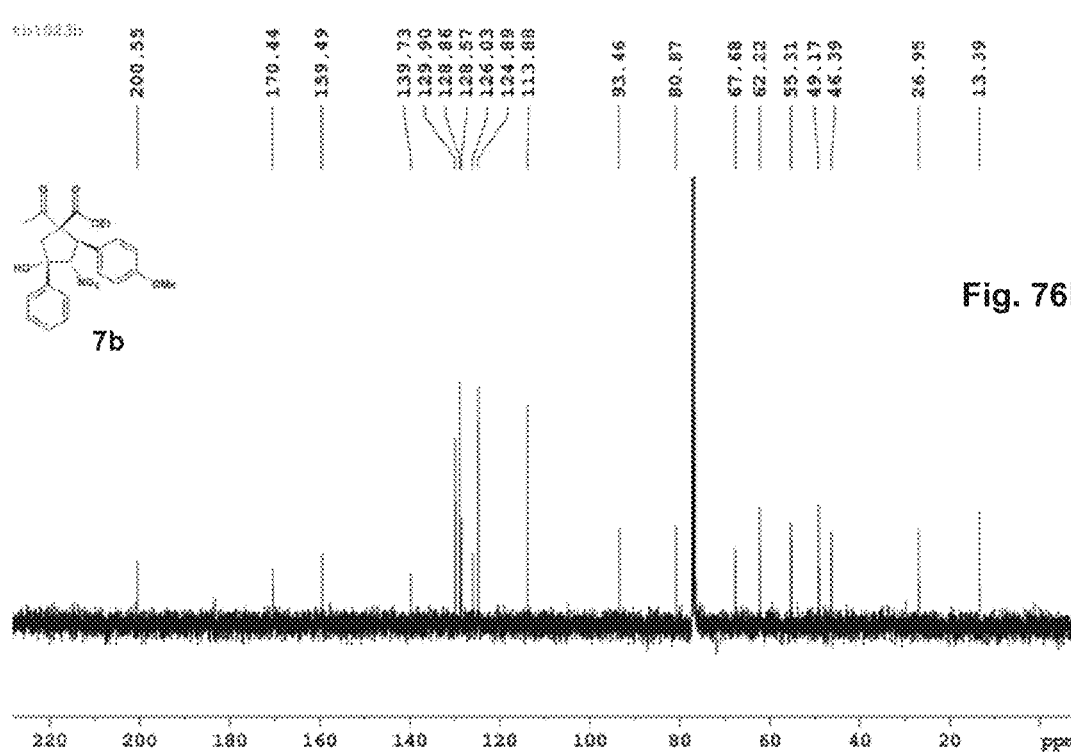
Figure 77A:
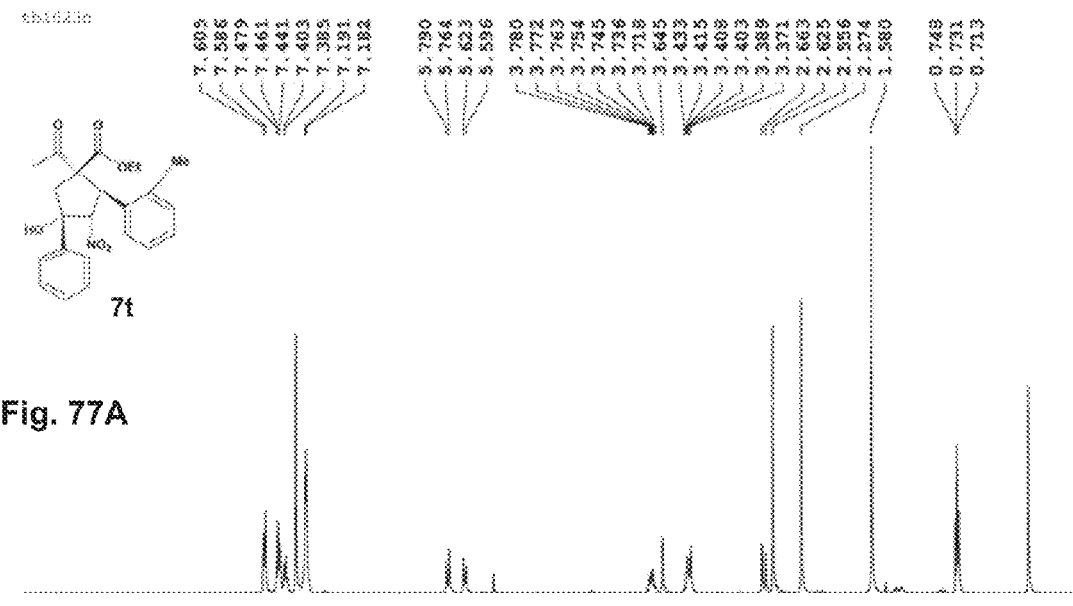
FIG. 77 depicts $^1$H NMR (A) and $^{13}$C NMR (B) spectra of compound 7t.
Figure 77B:
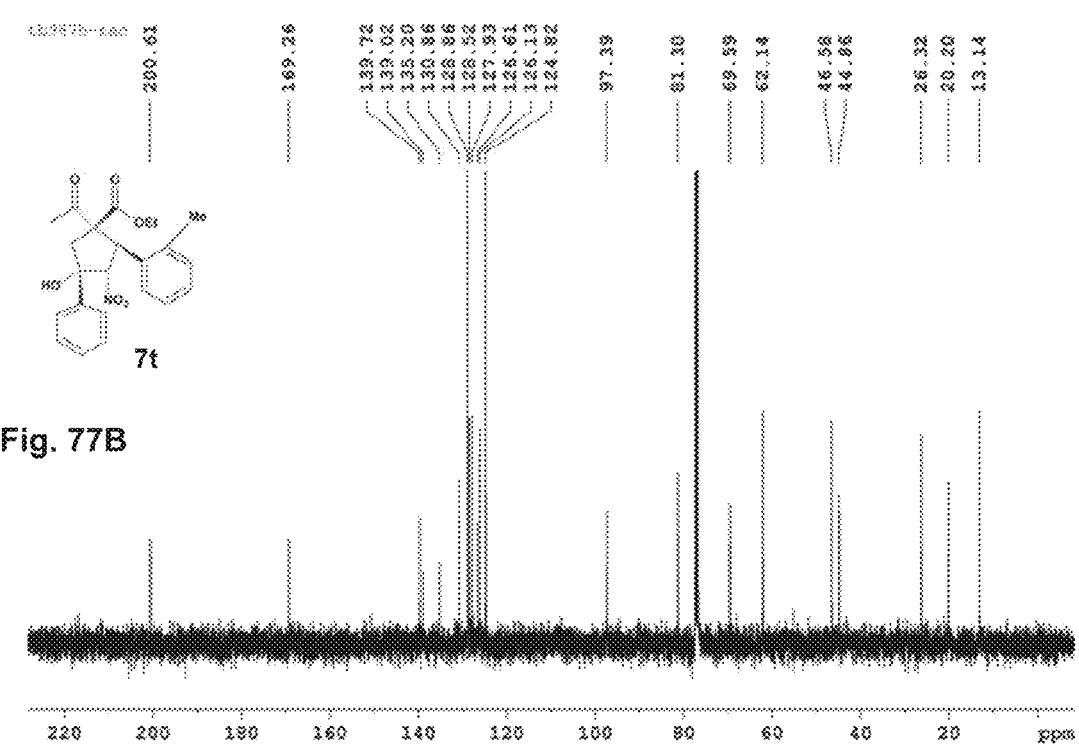
Figure 81A:
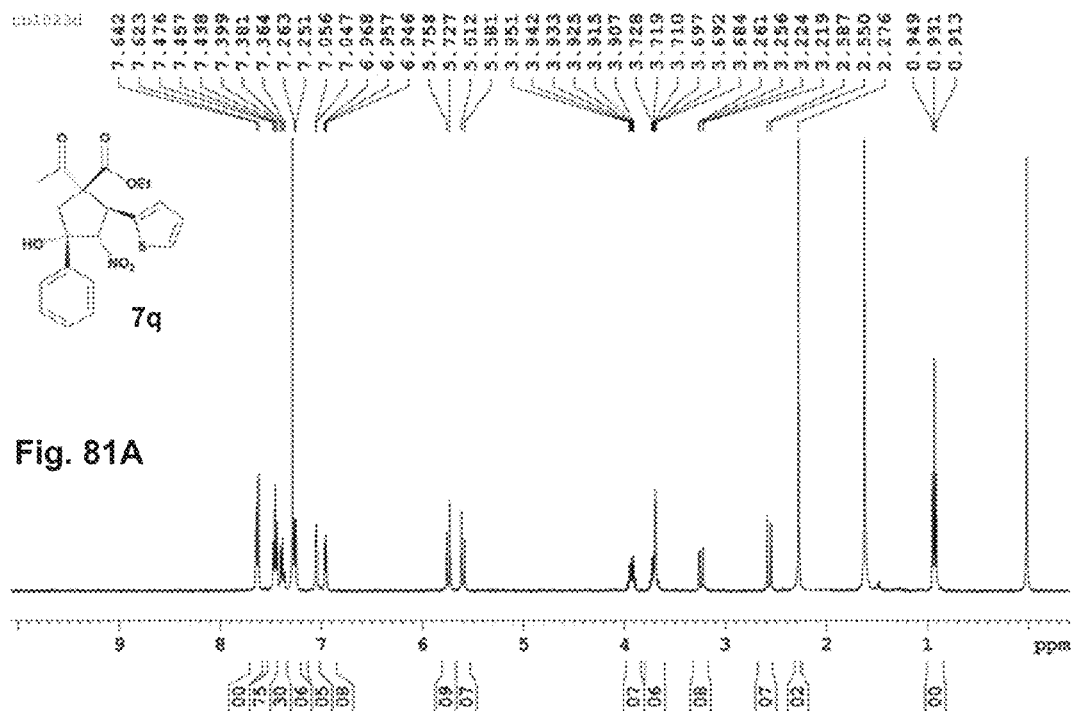
FIG. 81 depicts $^1$H NMR (A) and $^{13}$C NMR (B) spectra of compound 7q.
Figure 81B:
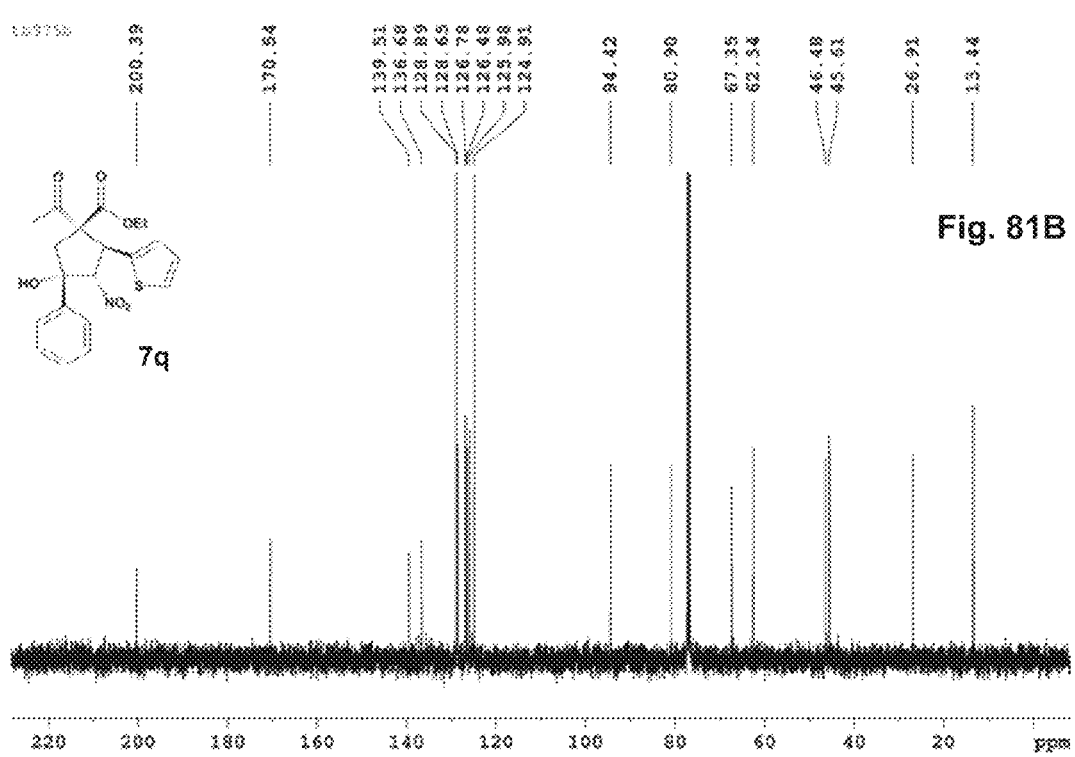
Figure 83A:
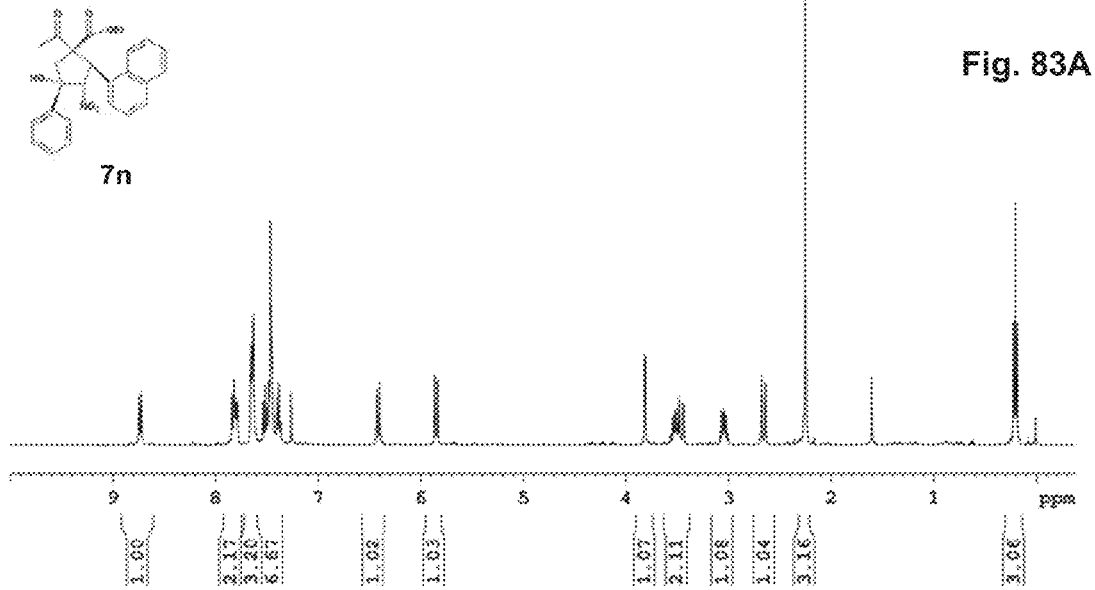
FIG. 83 depicts $^1$H NMR (A) and $^{13}$C NMR (B) spectra of compound 7n.
Figure 83B:
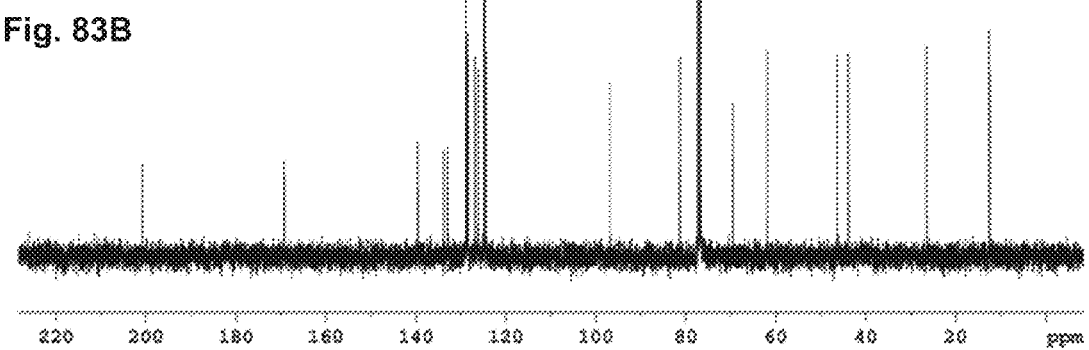
Figure 84A:
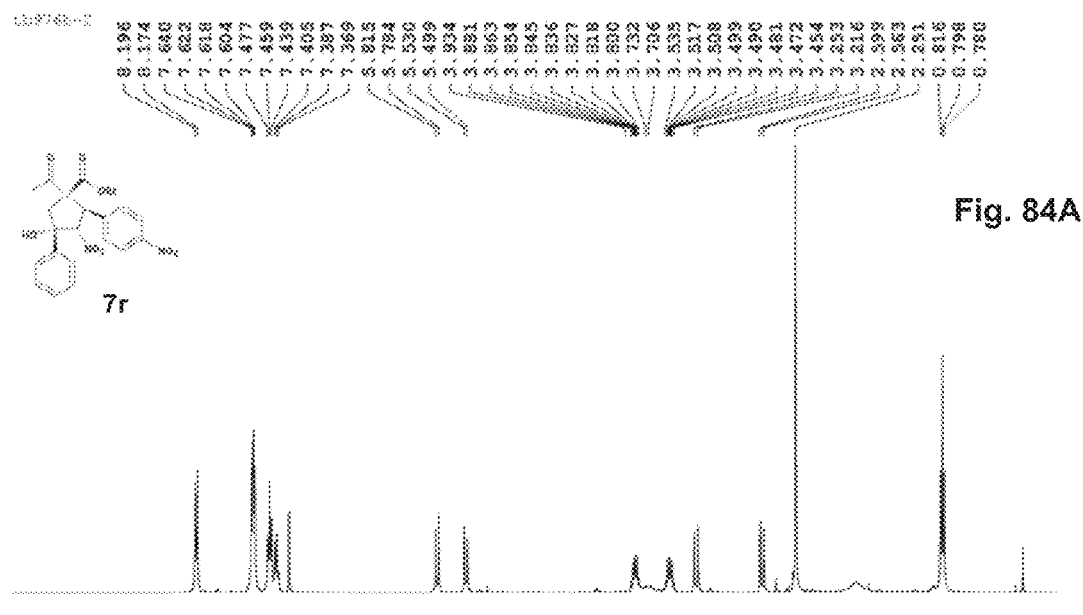
FIG. 84 depicts $^1$H NMR (A) and $^{13}$C NMR (B) spectra of compound 7r.
Figure 84B:
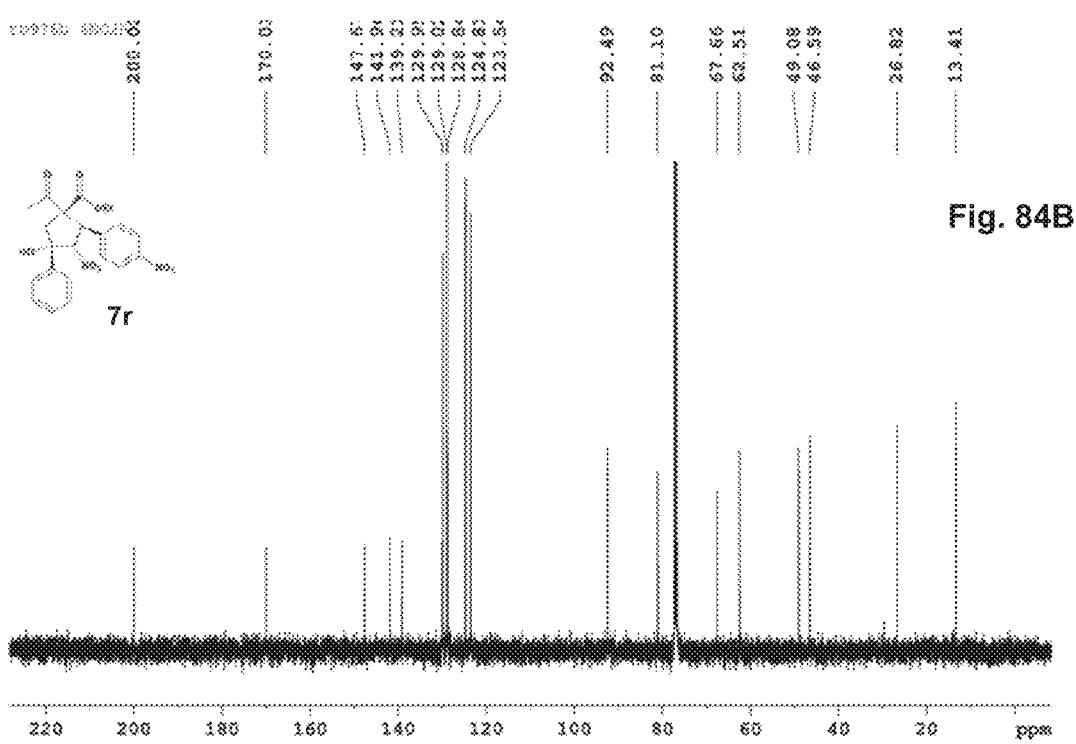
Figure 85A:
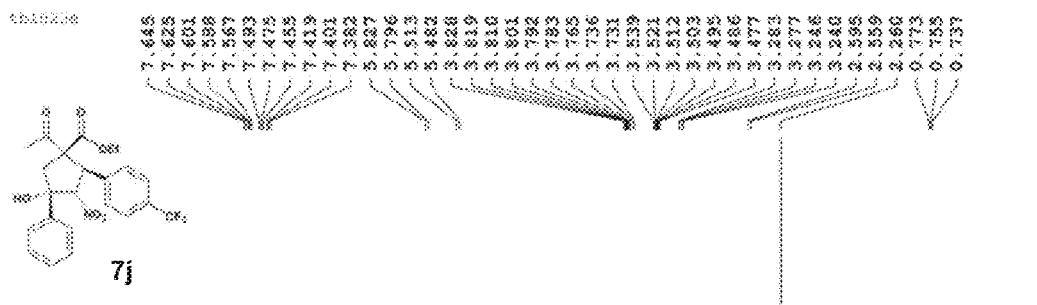
FIG. 85 depicts $^1$H NMR (A) and $^{13}$C NMR (B) spectra of compound 7j.
Figure 85B:
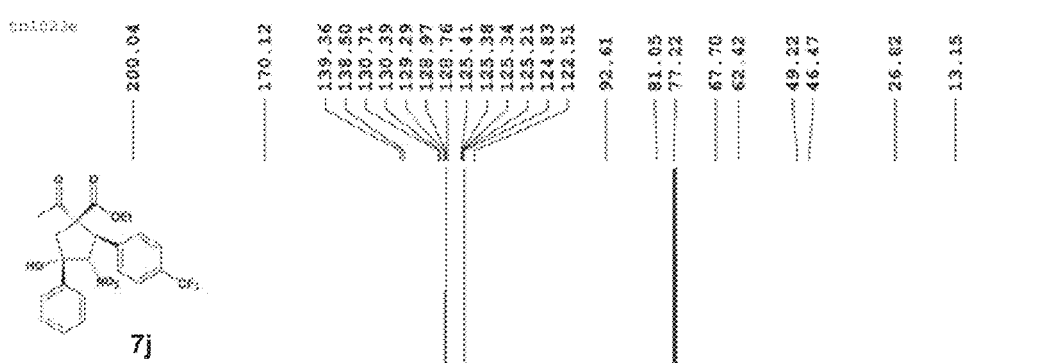
Figure 86A:
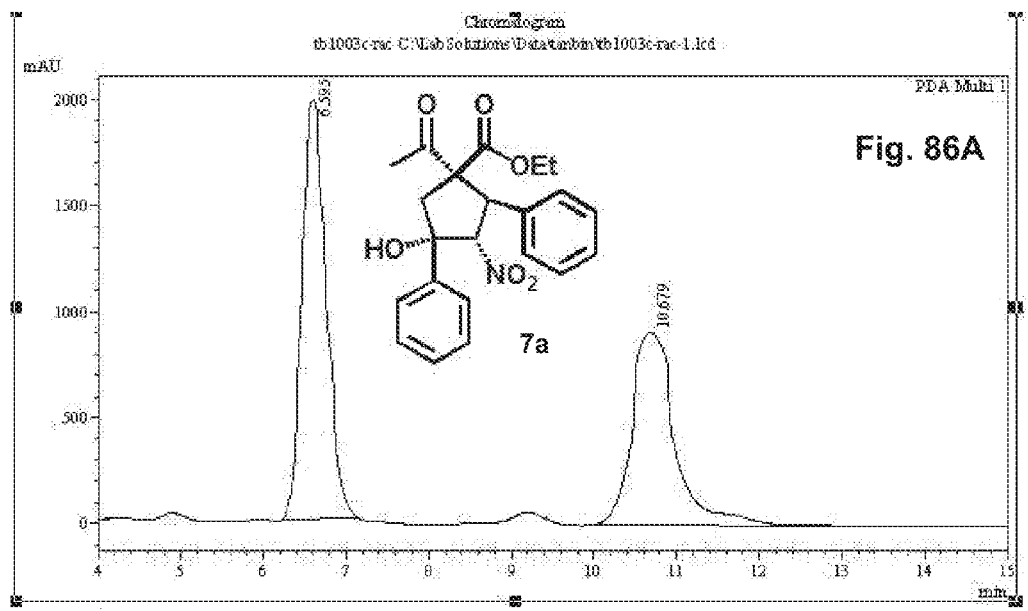
FIG. 86 depicts an HPLC spectrum of a racemic mixture of compound 7a (A), and in comparison the obtained product 7a (B).
Figure 86B:
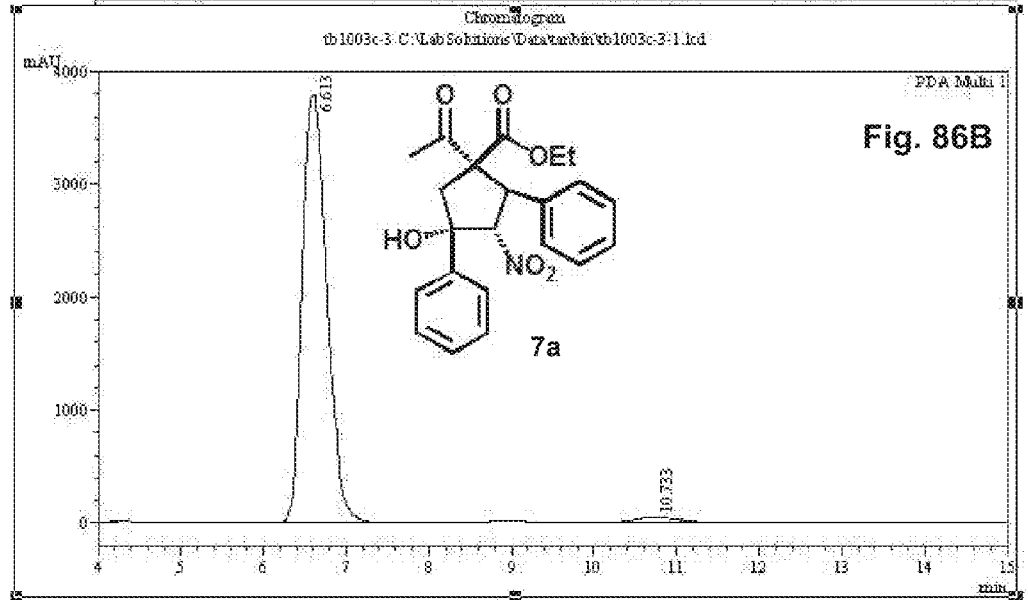
Figure 87A:
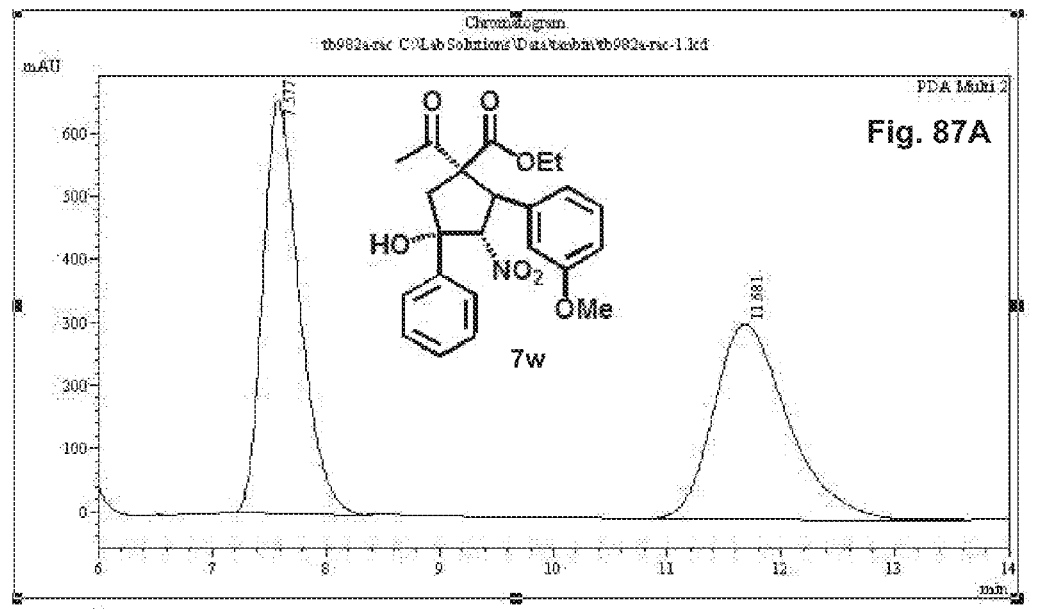
FIG. 87 depicts an HPLC spectrum of a racemic mixture of compound 7w (A), and in comparison the obtained product 7w (B).
Figure 87B:
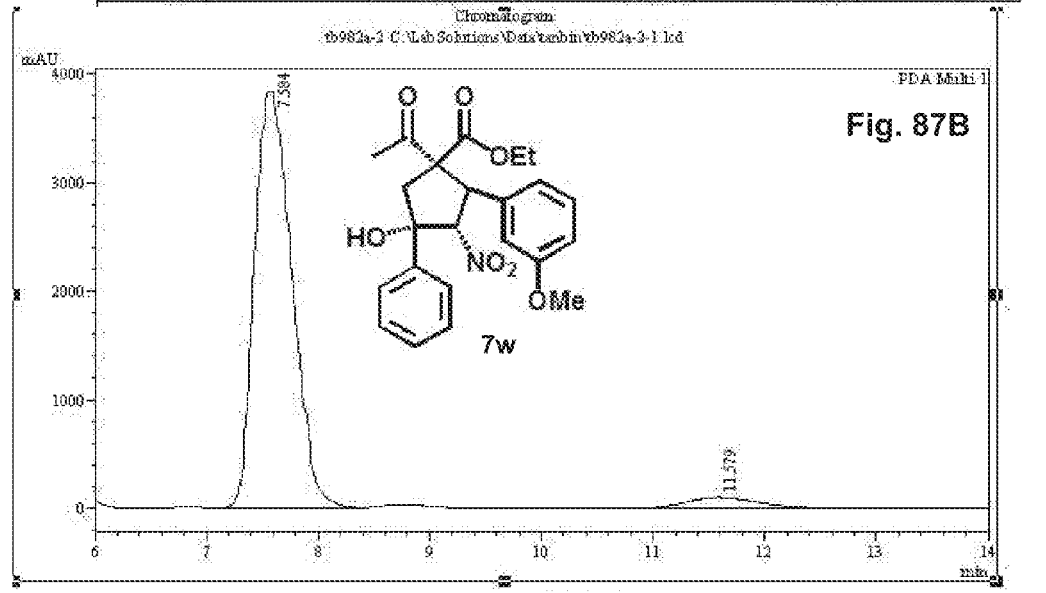
Figure 88A:
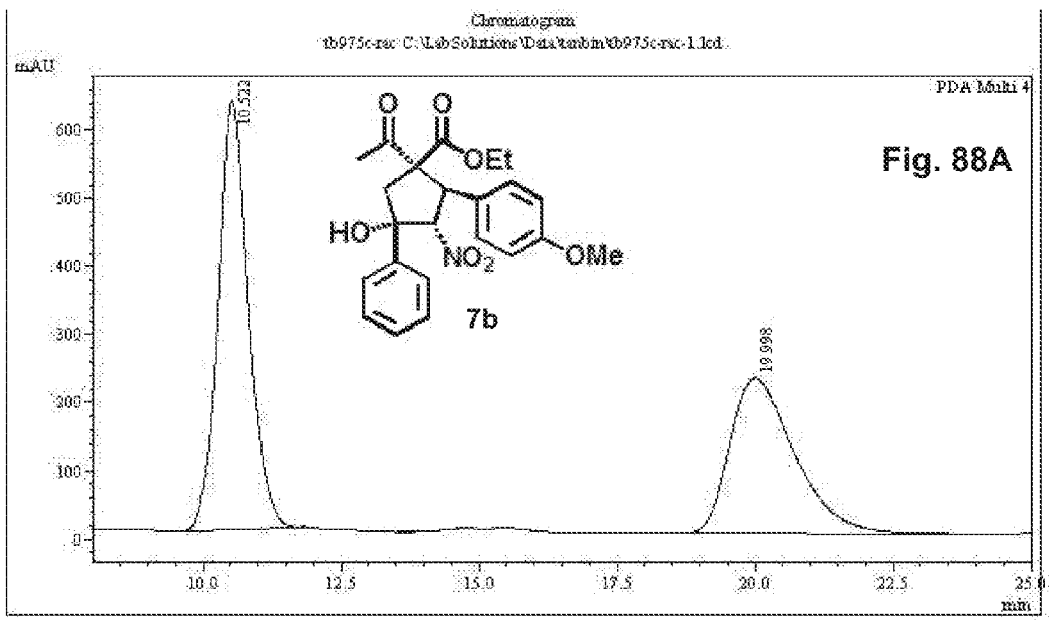
FIG. 88 depicts an HPLC spectrum of a racemic mixture of compound 7b (A), and in comparison the obtained product 7b (B).
Figure 88B:
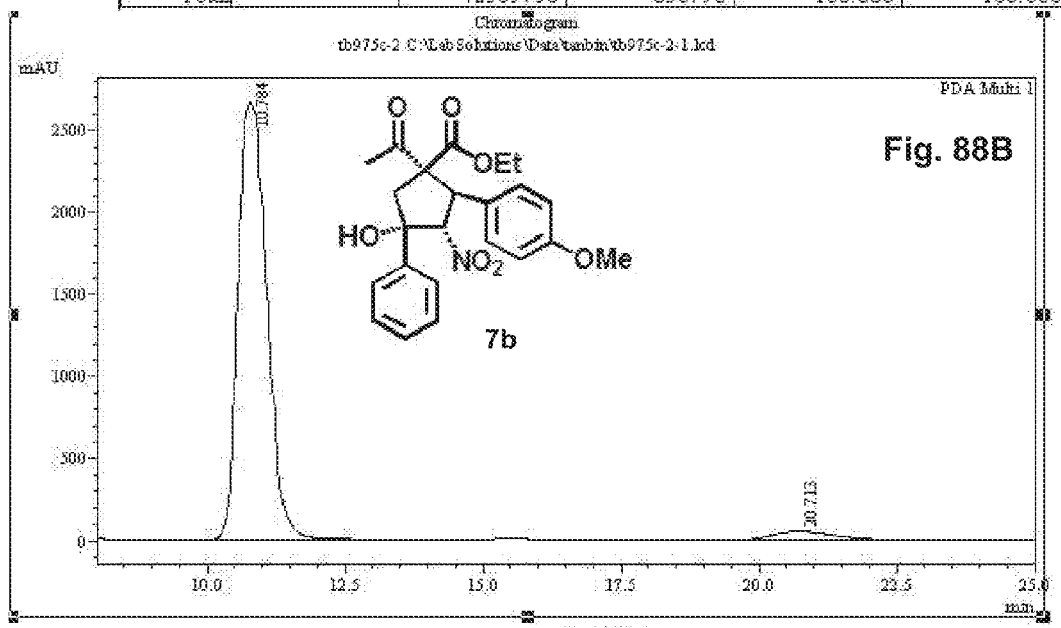
Figure 89A:
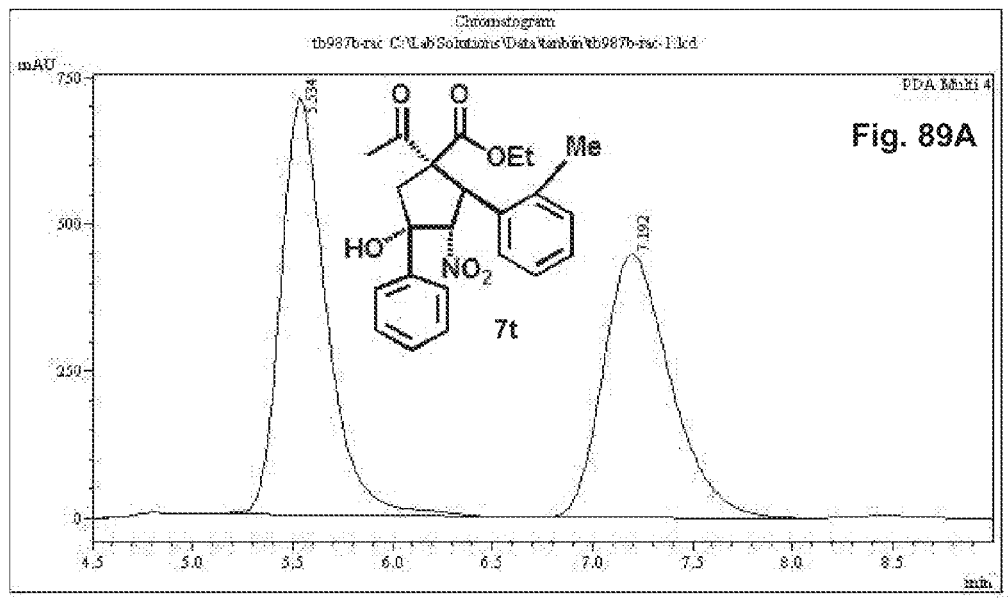
FIG. 89 depicts an HPLC spectrum of a racemic mixture of compound 7t (A), and in comparison the obtained product 7t (B).
Figure 89B:
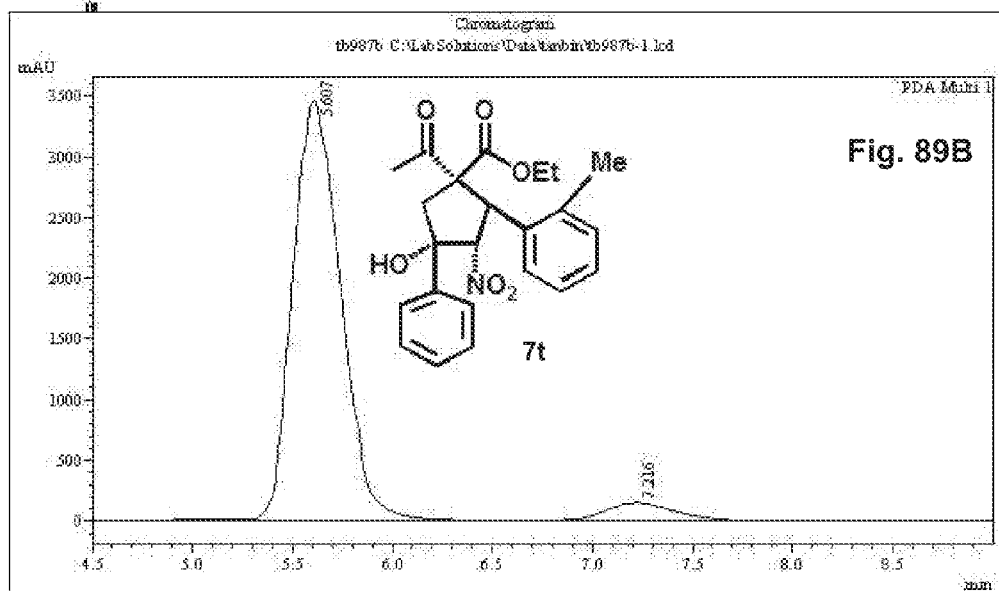
Figure 90A:
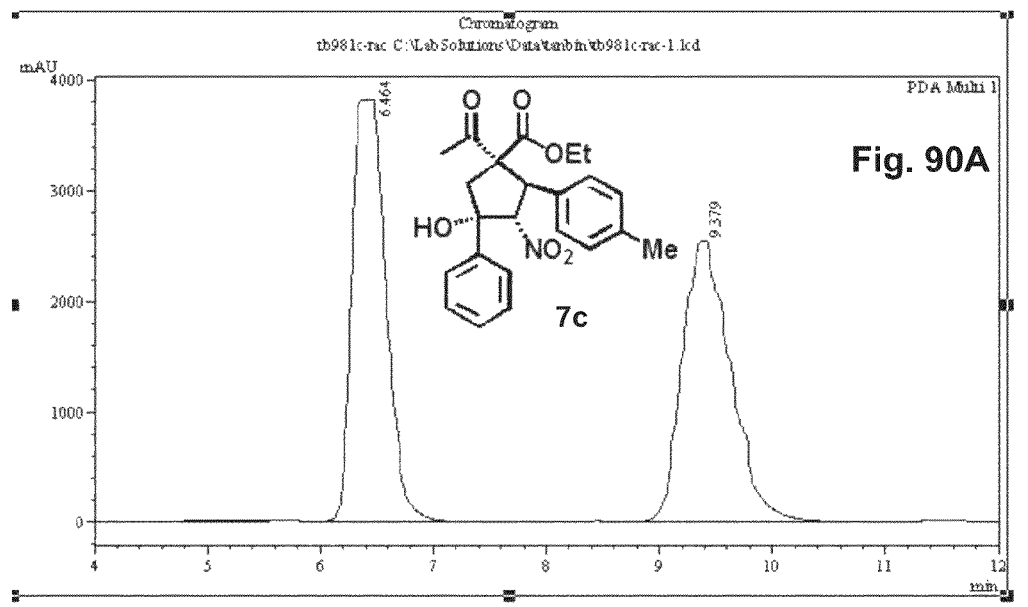
FIG. 90 depicts an HPLC spectrum of a racemic mixture of compound 7c (A), and in comparison the obtained product 7c (B).
Figure 90B:
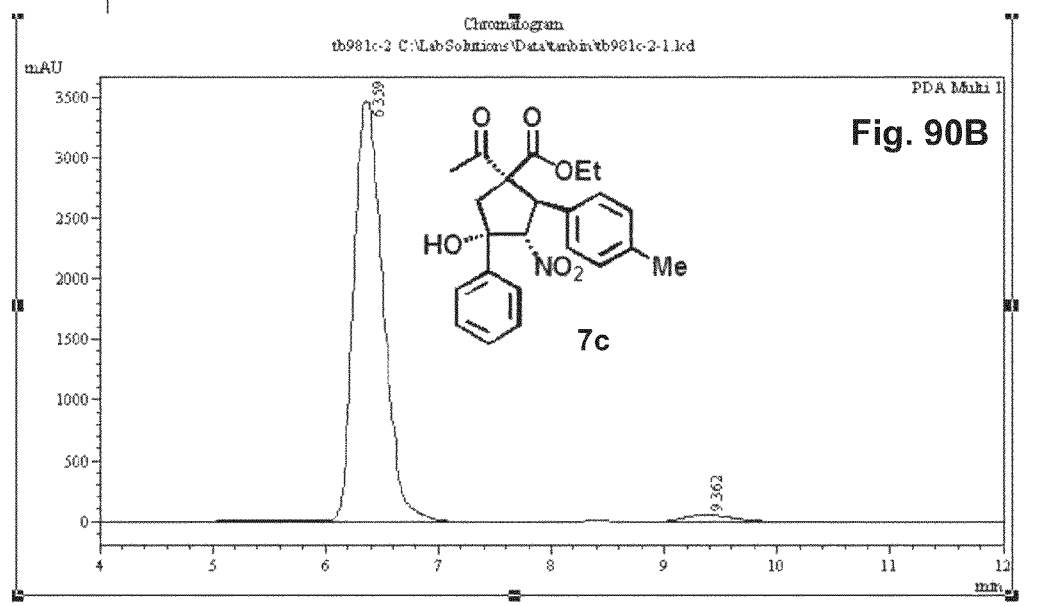
Figure 91A:
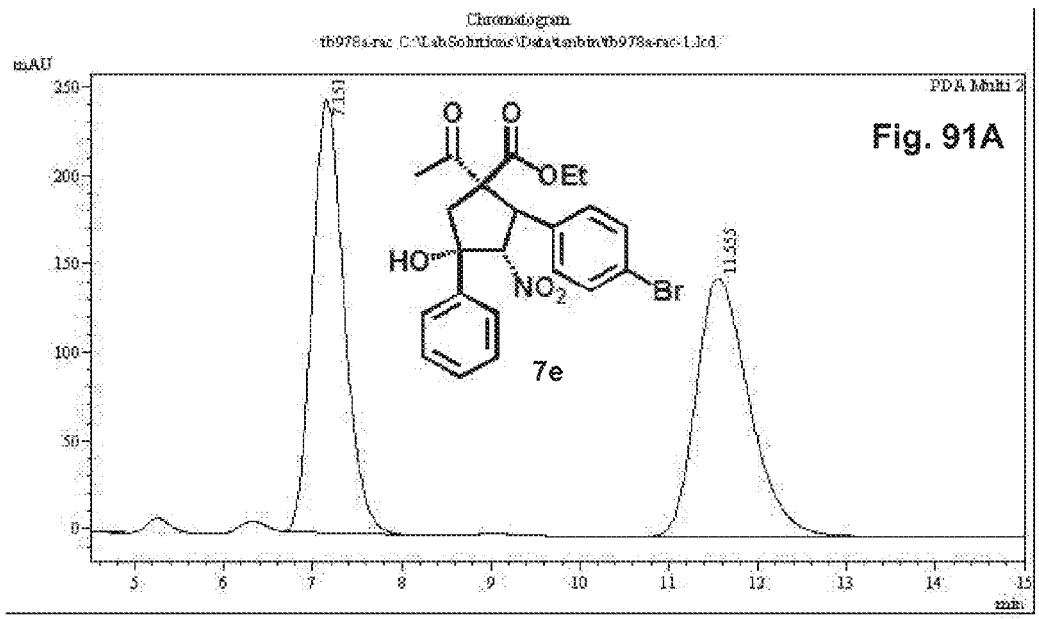
FIG. 91 depicts an HPLC spectrum of a racemic mixture of compound 7e (A), and in comparison the obtained product 7e (B).
Figure 91B:
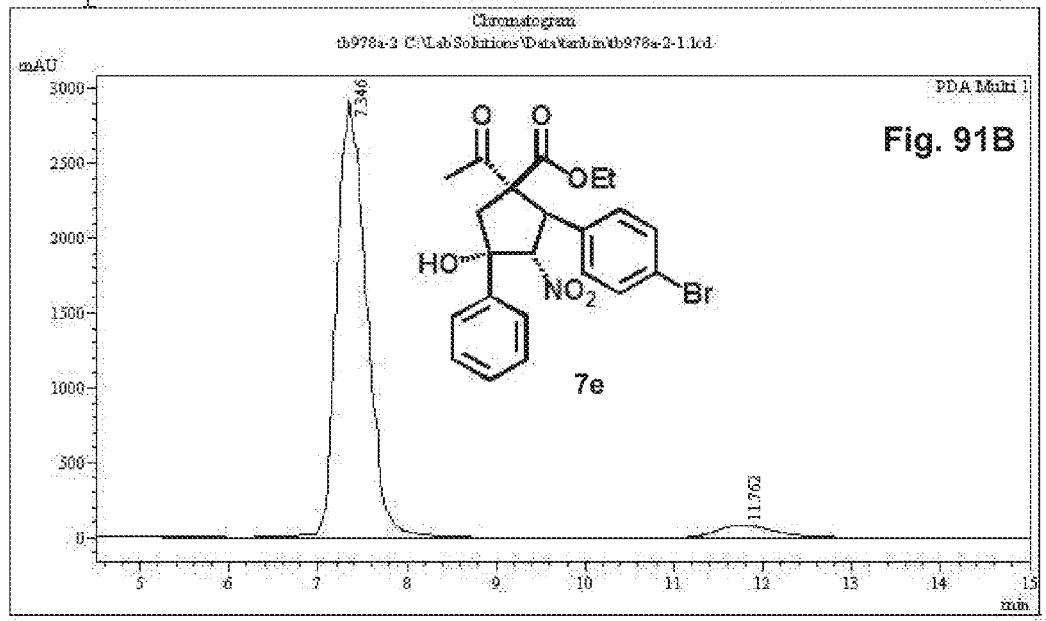
Figure 93A:
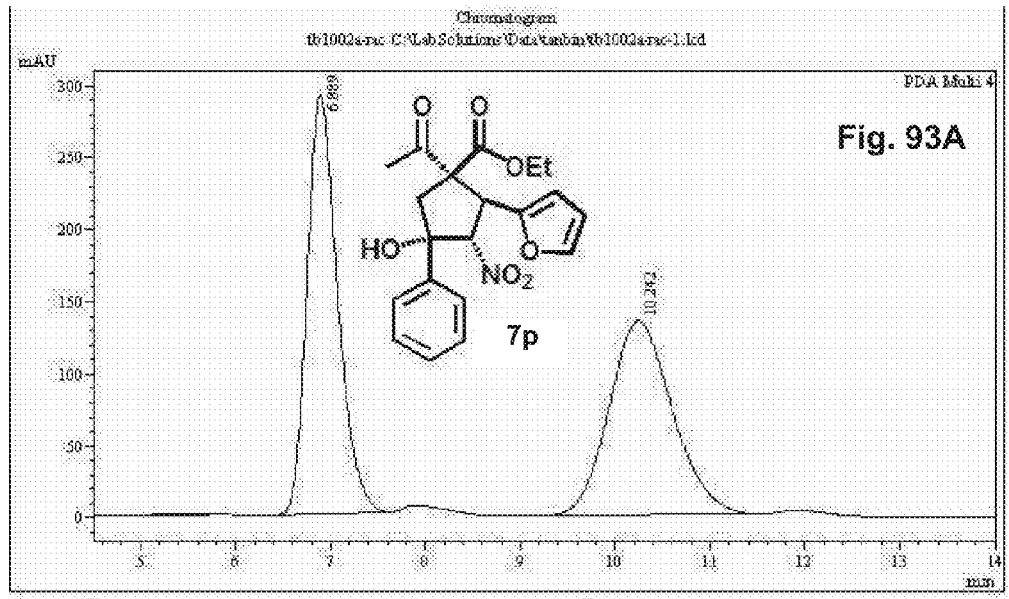
FIG. 93 depicts an HPLC spectrum of a racemic mixture of compound 7p (A), and in comparison the obtained product 7p (B).
Figure 93B:
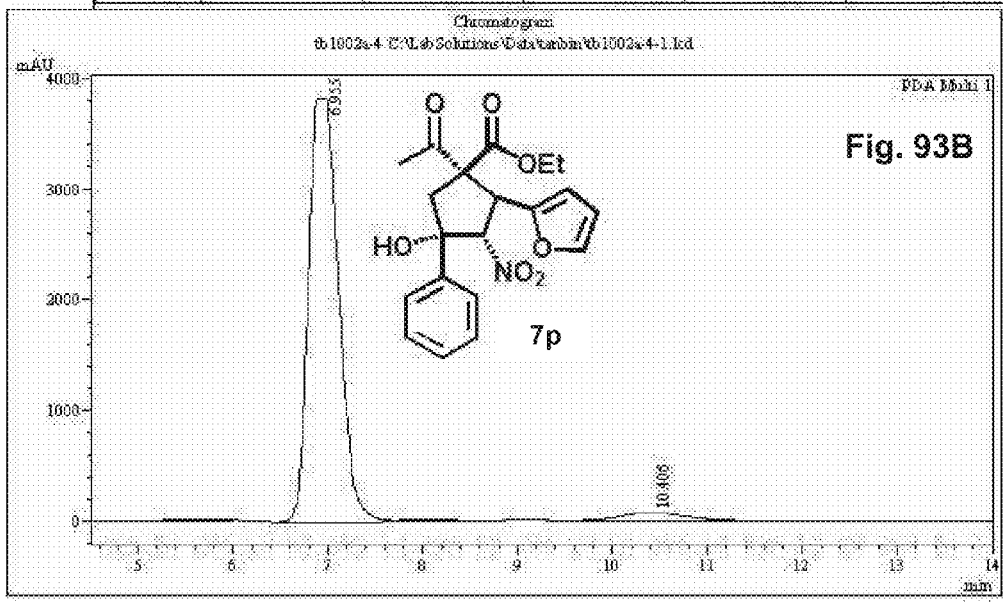
Figure 94A:
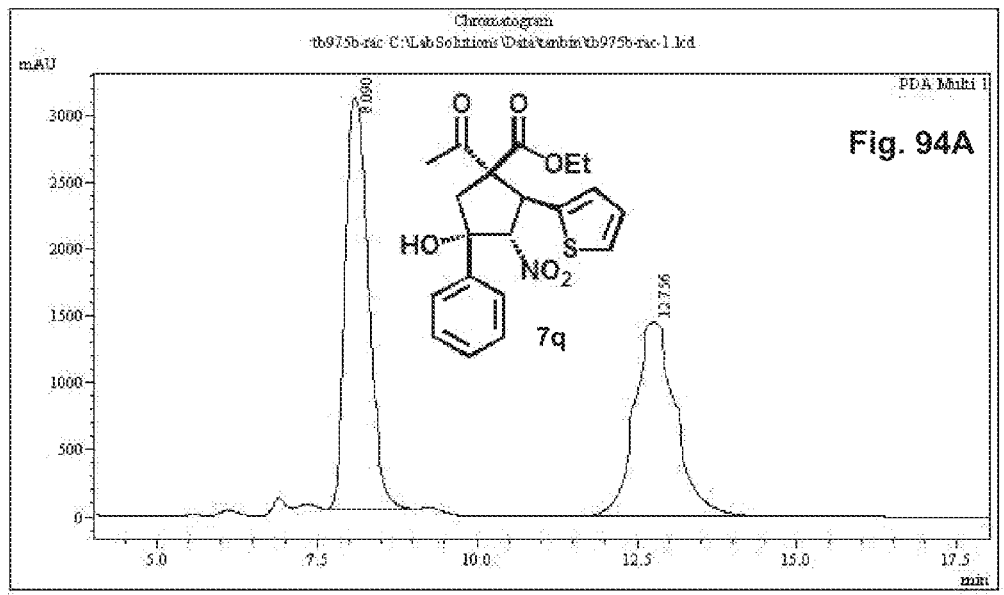
FIG. 94 depicts an HPLC spectrum of a racemic mixture of compound 7q (A), and in comparison the obtained product 7q (B).
Figure 94B:
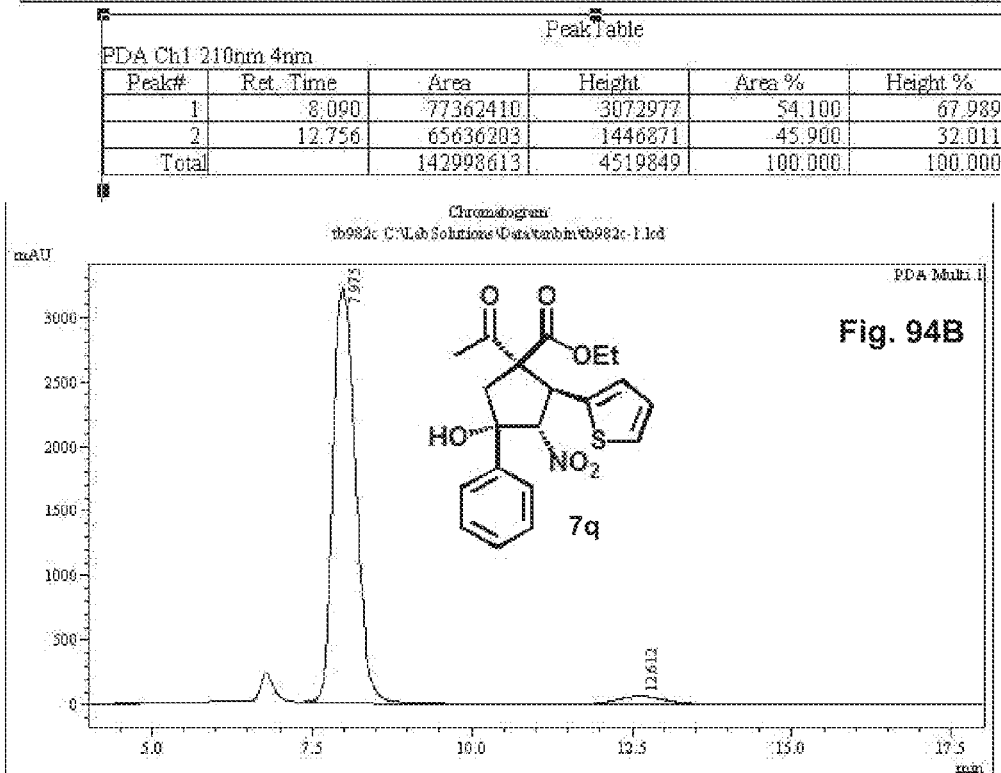
Figures 95A, 95B:
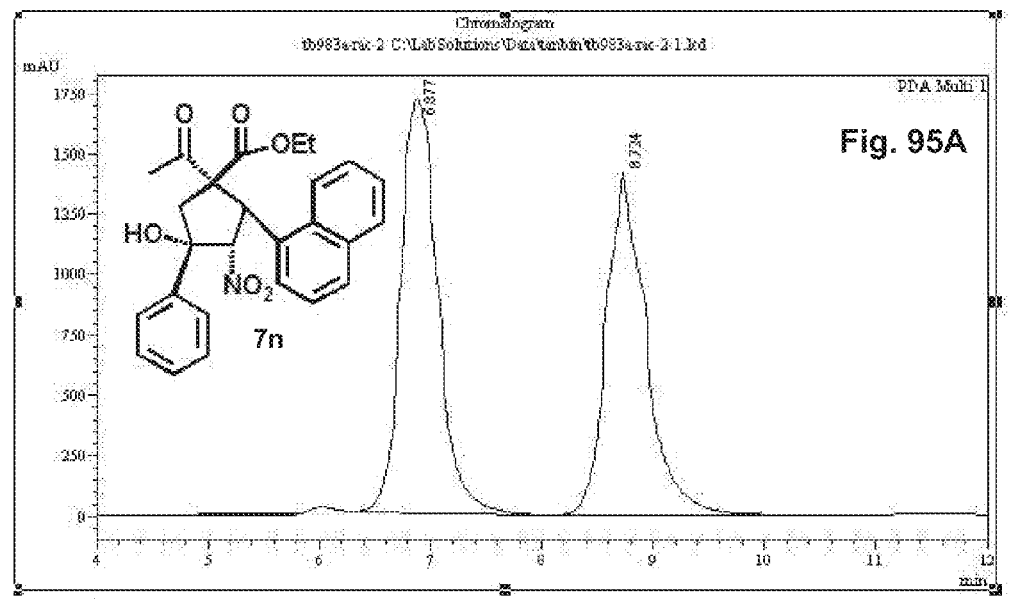
FIG. 95 depicts an HPLC spectrum of a racemic mixture of compound 7n (A), and in comparison the obtained product 7n (B).
Figure 97A:
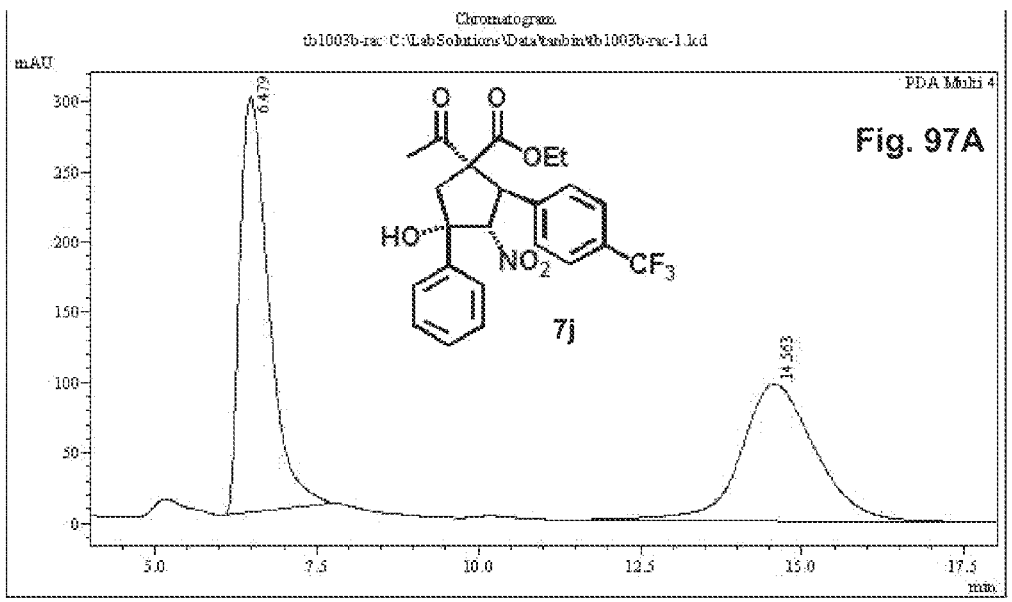
FIG. 97 depicts an HPLC spectrum of a racemic mixture of compound 7j (A), and in comparison the obtained product 7j (B).
Figure 97B:
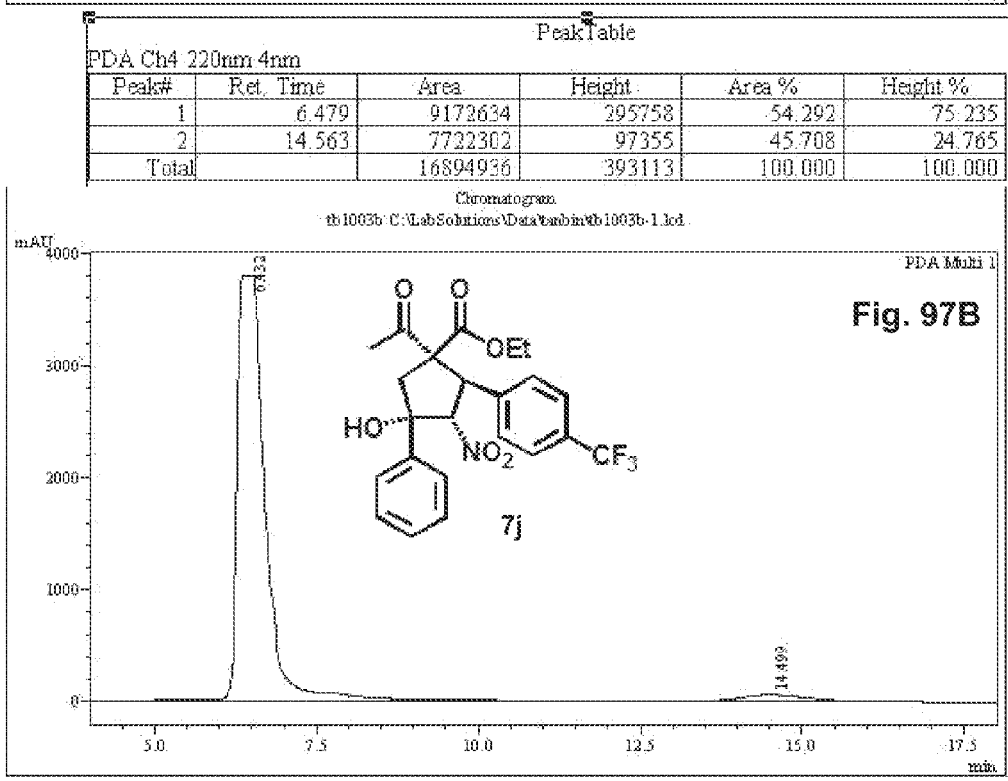
Figure 98A:
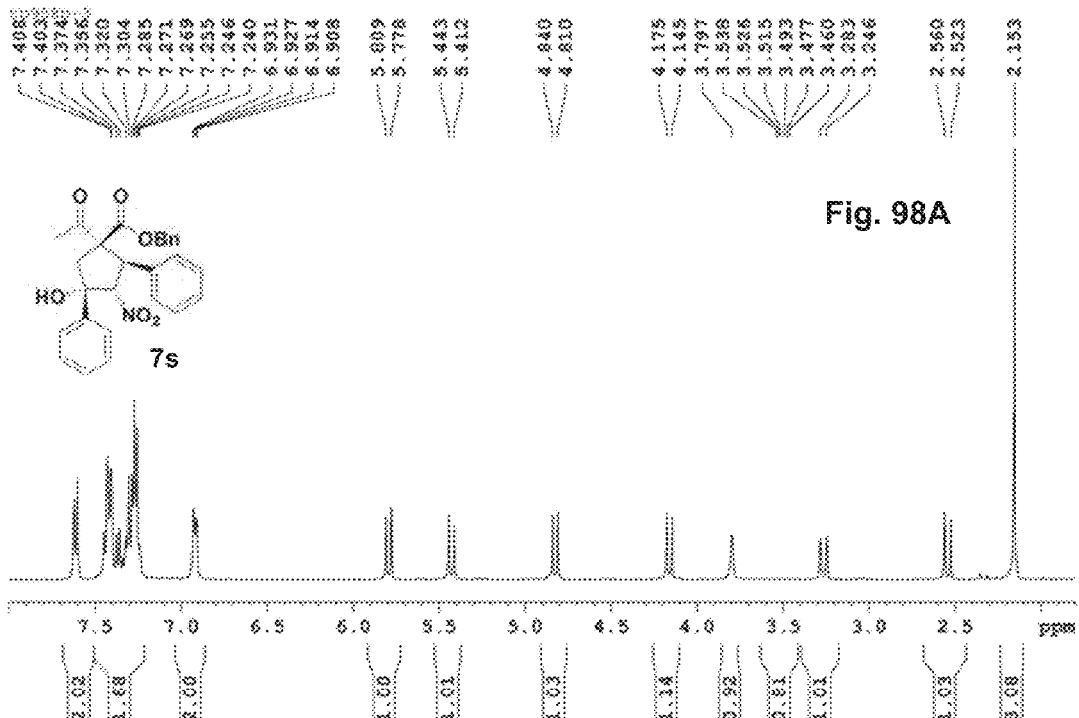
FIG. 98 depicts $^1$H NMR (A) and $^{13}$C NMR (B) spectra of compound 7s.
Figure 98B:
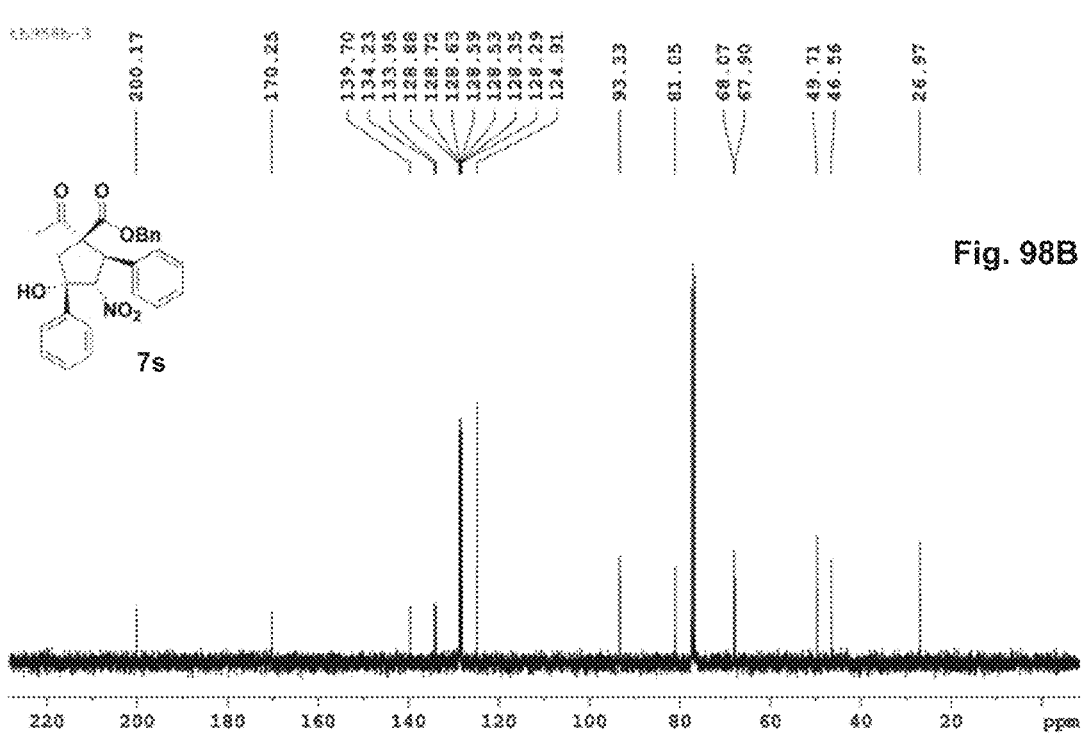
Figure 101A:
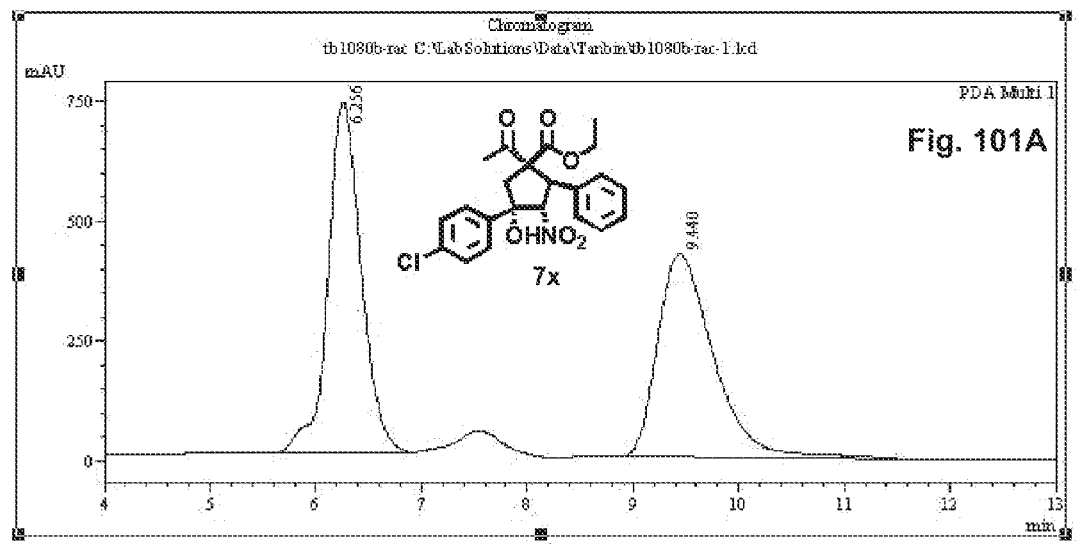
FIG. 101 depicts an HPLC spectrum of a racemic mixture of compound 7x (A), and in comparison the obtained product 7x (B).
Figure 101B:
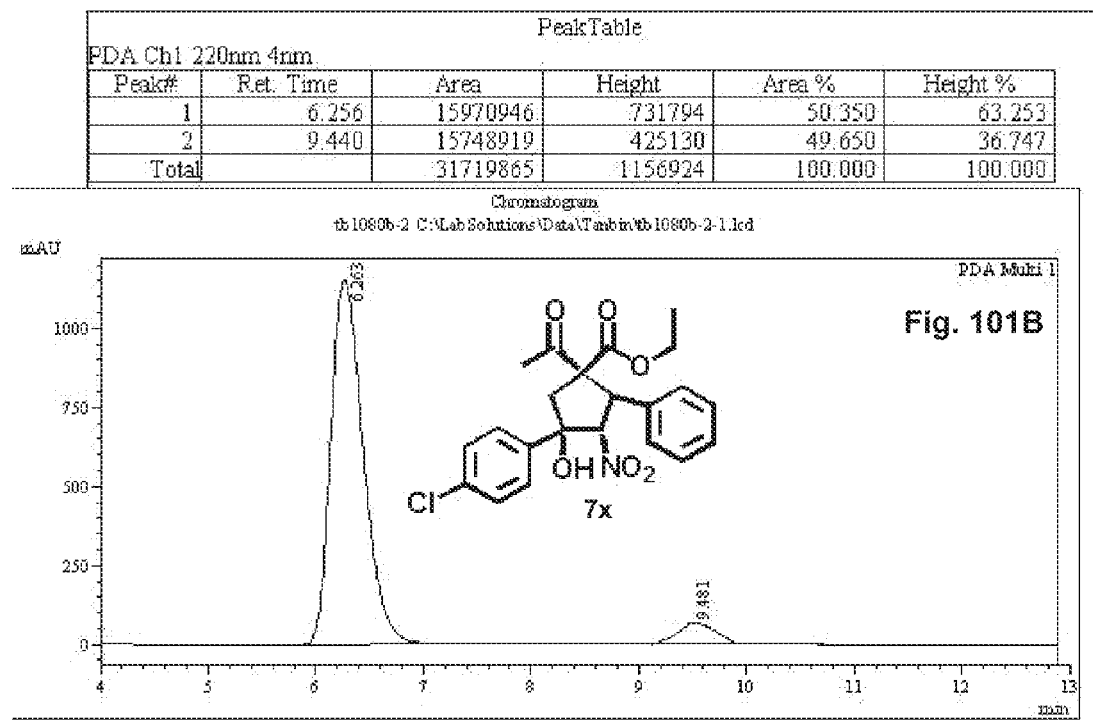

The dual activation model was proposed (Okino et al., 2005, supra) where the two substrates involved in the reaction are activated simultaneously by catalyst VI as shown in the FIG. 17. Nitroolefins have been assumed to interact with the primary amine moiety of VI via multiple H-bonds, thus enhancing the electrophilic character of the reacting carbon center. However, the enolic form of 6 is assumed to interact with the tertiary amine group and a subsequent deprotonation results in a highly nucleophilic enolate species. The carbonanion adjacent to the nitro group then attacks the carbonyl group to afford Henry products. The absolute configuration of 7f was determined by X-ray crystallography (FIG. 14, see the data below). The stereochemistry of this domino reaction was then established by analysis of the X-ray crystal structures together with analysis of the NMR data.

Typical Procedure for the Michael-Henry Reactions Yielding Cyclopentane Products To a solution of ethyl 2-acetyl-4-oxo-4-phenylbutanoate 6d (1.0 mmol, 2 eq) and nitroolefins (0.5 mmol, 1 eq) in toluene (0.5 mL) was added catalyst VI (Q-NH$_2$) (0.05 mmol, 0.1 eq) at 4° C. The resulting mixture was stirred vigorously at 4° C. After the reaction was complete (monitored by TLC), the products were afforded by flash column chromatography over silica gel (EtOAc:Hexane=1:10 to 1:6).

(1R,2R,3S,4S)-ethyl-1-acetyl-4-hydroxy-3-nitro-2,4-diphenylcyclopentanecarboxylate (7a)

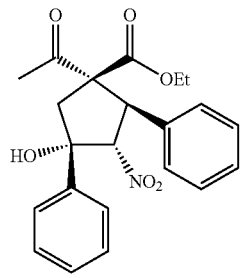

The title compound was prepared according to the typical procedure, as described above in 93% yield.

$^1$H-NMR (400 MHz, CDCl$_3$) δ 7.64 (d, J=7.6, 2H), 7.47-7.28 (m, 8H), 5.80 (d, J=12.4 Hz, 1H), 5.43 (d, J=12.4 Hz, 1H), 3.82-3.76 (m, 2H), 3.50-3.42 (m, 1H), 3.27 (d, J=14.4 Hz, 1H), 2.57 (d, J=14.8 Hz, 1H), 2.26 (s, 3H), 0.76 (t, J=7.2 Hz, 3H).

$^{13}$C-NMR (100 MHz, CDCl$_3$) δ 200.38, 170.28, 139.67, 134.29, 128.88, 128.75, 128.59, 128.52, 128.23, 124.90, 93.31, 81.01, 67.82, 62.23, 49.63, 46.44, 26.88, 13.26.

HPLC: Chiralcel OD-H (hexane/i-PrOH=80/20, flow rate 1 mL/min, λ=210 nm), $t_R$ (major)=6.6 min, $t_R$ (minor)=10.7 min; 95% ee.

$[α]_D^{25}$=23.1 (c=1.0, CHCl$_3$).

HRMS (EI) calcd for C$_{22}$H$_{23}$NO$_6$, m/z 397.1520. found 397.1524.

(1R,2R,3S,4S)-ethyl-1-acetyl-4-hydroxy-2-(4-methoxyphenyl)-3-nitro-4-phenylcyclopentane carboxylate (7b)

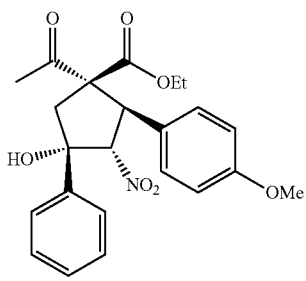 [SMILES: CCOC(=O)[C@]1(C(C)=O)C[C@](O)(c2ccccc2)[C@@H]([N+](=O)[O-])[C@@H]1c1ccc(OC)cc1]

The title compound was prepared according to the typical procedure, as described above in 93% yield.

$^1$H-NMR (400 MHz, CDCl$_3$) δ 7.63 (d, J=7.6, 2H), 7.48-7.28 (m, 8H), 5.74 (d, J=12.8 Hz, 1H), 5.36 (d, J=12.8 Hz, 1H), 3.86-3.80 (m, 2H), 3.79 (s, 3H), 3.56-3.51 (m, 1H), 3.25 (dd, J=7.2, 14.4 Hz, 1H), 2.56 (d, J=14.4 Hz, 1H), 2.27 (s, 3H), 0.83 (t, J=7.2 Hz, 3H).

$^{13}$C-NMR (100 MHz, CDCl$_3$) δ 200.55, 170.44, 159.49, 139.73, 129.90, 128.86, 128.57, 126.03, 124.89, 113.88, 93.46, 88.87, 67.68, 62.22, 55.31, 49.17, 46.39, 26.95, 13.39.

HPLC: Chiralcel OD-H (hexane/i-PrOH=80/20, flow rate 1 mL/min, λ=210 nm), $t_R$ (major)=10.8 min, $t_R$ (minor)=20.7 min; 92% ee.

$[α]_D^{25}$=23.3 (c=1.2, CHCl$_3$).

HRMS (EI) calcd for C$_{23}$H$_{25}$NO$_7$, m/z 427.1626. found 427.1629.

(1R,2R,3S,4S)-ethyl-1-acetyl-4-hydroxy-3-nitro-4-phenyl-2-p-tolylcyclopentane carboxylate (7c)

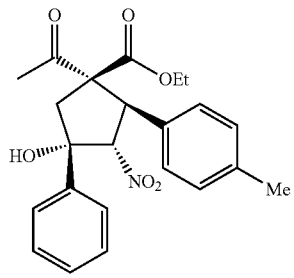

The title compound was prepared according to the typical procedure, as described above in 91% yield.

$^1$H-NMR (400 MHz, CDCl$_3$) δ 7.61 (d, J=7.6, 2H), 7.45-7.34 (m, 3H), 7.29-7.27 (m, 2H), 7.11 (d, J=8.0 Hz, 2H), 5.75 (d, J=12.4 Hz, 1H), 5.36 (d, J=12.4 Hz, 1H), 3.83-3.75 (m, 2H), 3.53-3.45 (m, 1H), 3.24 (dd, J=2.0, 14.4 Hz, 1H), 2.54 (d, J=14.8 Hz, 1H), 2.30 (s, 3H), 2.24 (s, 3H), 0.77 (t, J=7.2 Hz, 3H).

$^{13}$C-NMR (100 MHz, CDCl$_3$) δ 200.49, 170.35, 139.74, 137.98, 131.10, 129.16, 128.86, 128.60, 128.56, 124.90, 93.42, 80.95, 67.76, 62.20, 49.42, 46.43, 26.93, 21.04, 13.24.

HPLC: Chiralcel OD-H (hexane/i-PrOH=80/20, flow rate 1 mL/min, λ=210 nm), $t_R$ (major)=6.4 min, $t_R$ (minor)=9.4 min; 95% ee.

$[α]_D^{25}$=12.1 (c=1.5, CHCl$_3$).

HRMS (EI) calcd for C$_{23}$H$_{25}$NO$_6$, m/z 411.1678. found 411.1682.

(1R,2R,3S,4S)-ethyl-1-acetyl-2-(4-bromophenyl)-4-hydroxy-3-nitro-4-phenylcyclopentane carboxylate (7e)

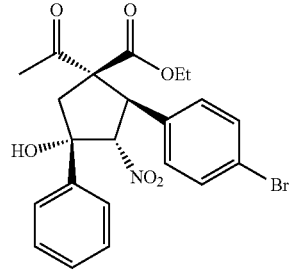 [SMILES: CCOC(=O)[C@]1(C(C)=O)C[C@](O)(c2ccccc2)[C@@H]([N+](=O)[O-])[C@@H]1c1ccc(C)cc1]

The title compound was prepared according to the typical procedure, as described above in 94% yield.

$^1$H-NMR (400 MHz, CDCl$_3$) δ 7.61 (d, J=7.6, 2H), 7.46-7.42 (m, 4H), 7.38-7.37 (m, 1H), 7.30-7.27 (m, 2H), 5.72 (d, J=12.4 Hz, 1H), 5.37 (d, J=12.4 Hz, 1H), 3.87-3.79 (m, 1H), 3.76 (d, J=2.4 Hz, 1H), 3.56-3.51 (m, 1H), 3.22 (dd, J=2.0, 14.4 Hz, 1H), 2.53 (d, J=14.8 Hz, 1H), 2.23 (s, 3H), 0.82 (t, J=7.2 Hz, 3H).

$^{13}$C-NMR (100 MHz, CDCl$_3$) δ 200.28, 170.23, 139.51, 133.35, 131.64, 130.50, 128.92, 128.68, 124.86, 122.35, 92.85, 80.98, 67.55, 62.42, 49.02, 46.46, 26.87, 13.33.

HPLC: Chiralcel OD-H (hexane/i-PrOH=80/20, flow rate 1 mL/min, λ=210 nm), $t_R$ (major)=7.1 min, $t_R$ (minor)=11.6 min; 91% ee.

$[α]_D^{25}$=8.1 (c=1.0, CHCl$_3$).

HRMS (EI) calcd for C$_{22}$H$_{22}$BrNO$_6$, m/z 475.0626. found 475.0629.

(1R,2R,3S,4S)-ethyl-1-acetyl-2-(4-chlorophenyl)-4-hydroxy-3-nitro-4-phenylcyclopentane carboxylate (7g)

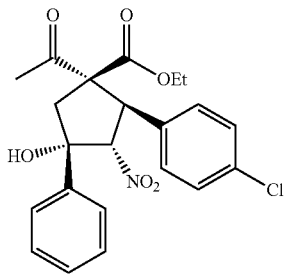 [SMILES: CCOC(=O)[C@]1(C(C)=O)C[C@](O)(c2ccccc2)[C@@H]([N+](=O)[O-])[C@@H]1c1ccc(Br)cc1]

The title compound was prepared according to the typical procedure, as described above in 95% yield.

$^1$H-NMR (400 MHz, CDCl$_3$) δ 7.62 (d, J=7.6, 2H), 7.46-7.42 (m, 2H), 7.38-7.35 (m, 3H), 7.30-7.26 (m, 2H), 5.73 (d, J=12.4 Hz, 1H), 5.38 (d, J=12.4 Hz, 1H), 3.87-3.79 (m, 1H), 3.75 (d, J=3.2 Hz, 1H), 3.57-3.49 (m, 1H), 3.23 (dd, J=2.0, 14.4 Hz, 1H) 2.53 (d, J=14.8 Hz, 1H), 2.23 (s, 3H), 0.82 (t, J=7.2 Hz, 3H).

$^{13}$C-NMR (100 MHz, CDCl$_3$) δ 200.29, 170.24, 139.51, 134.22, 132.80, 130.18, 128.92, 128.67, 124.86, 92.93, 80.98, 67.59, 62.40, 48.98, 46.45, 26.87, 13.33.

HPLC: Chiralcel OD-H (hexane/i-PrOH=80/20, flow rate 1 mL/min, λ=210 nm), t$_R$ (major)=7.2 min, t$_R$ (minor)=11.2 min; 95% ee.

[α]$_D^{25}$=10.4 (c=1.8, CHCl$_3$).

HRMS (EI) calcd for C$_{22}$H$_{22}$ClNO$_6$, m/z 431.1132. found 431.1135.

(1R,2R,3S,4S)-ethyl-1-acetyl-4-hydroxy-3-nitro-4-phenyl-2-(thiophen-2-yl)cyclopentane carboxylate (7q)

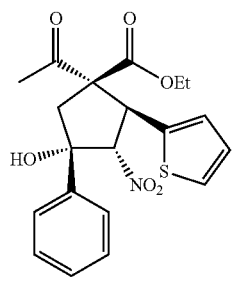 [SMILES: CCOC(=O)[C@]1(C(C)=O)C[C@](O)(c2ccccc2)[C@@H]([N+](=O)[O-])[C@@H]1c1cccs1]

The title compound was prepared according to the typical procedure, as described above in 93% yield.

$^1$H-NMR (400 MHz, CDCl$_3$) δ 7.63 (d, J=3.6, 2H), 7.48-7.36 (m, 3H), 7.26 (d, J=4.8 Hz, 1H), 7.05 (d, J=3.6 Hz, 1H), 6.96 (t, J=4.4 Hz, 1H), 5.74 (d, J=12.4 Hz, 1H), (m, 2H), 5.60 (d, J=12.4 Hz, 1H), 3.95-3.91 (m, 1H), 3.73-3.68 (m, 2H), 3.26 (dd, J=2.0, 14.8 Hz, 1H), 2.57 (d, J=14.8 Hz, 1H), 2.27 (s, 3H), 0.93 (t, J=7.2 Hz, 3H).

$^{13}$C-NMR (100 MHz, CDCl$_3$) δ 200.39, 170.54, 139.51, 136.68, 128.89, 128.65, 126.78, 126.48, 125.98, 124.91, 94.42, 80.91, 67.35, 62.54, 46.48, 45.61, 26.91, 13.44.

HPLC: Chiralcel OD-H (hexane/i-PrOH=80/20, flow rate 1 mL/min, λ=210 nm), t$_R$ (major)=8.0 min, t$_R$ (minor)=12.6 min; 93% ee.

[α]$_D^{25}$=21.6 (c=1.8, CHCl$_3$).

HRMS (EI) calcd for C$_{20}$H$_{21}$NO$_6$S, m/z 403.1086. found 403.1088.

(1R,2R,3S,4S)-ethyl-1-acetyl-2-(furan-2-yl)-4-hydroxy-3-nitro-4-phenylcyclopentane carboxylate (7p)

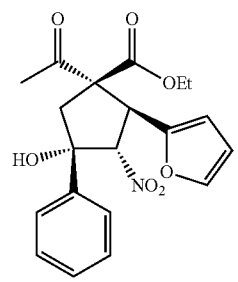 [SMILES: CCOC(=O)[C@]1(C(C)=O)C[C@](O)(c2ccccc2)[C@@H]([N+](=O)[O-])[C@@H]1c1ccco1]

The title compound was prepared according to the typical procedure, as described above in 91% yield.

$^1$H-NMR (400 MHz, CDCl$_3$) δ 7.61 (d, J=8.0, 2H), 7.47-7.39 (m, 4H), 6.38-6.35 (m, 2H), 5.74 (d, J=11.6 Hz, 1H), 5.41 (d, J=12.0 Hz, 1H), 4.07-4.01 (m, 1H), 3.86-3.80 (m, 1H), 3.66 (s, 1H), 3.25 (d, J=14.8 Hz, 1H), 2.58 (d, J=14.8 Hz, 1H), 2.29 (s, 3H), 1.04 (t, J=7.2 Hz, 3H).

$^{13}$C-NMR (100 MHz, CDCl$_3$) δ 200.15, 169.93, 148.62, 142.79, 139.58, 128.85, 128.57, 124.88, 110.84, 109.99, 92.67, 80.85, 66.18, 62.72, 46.29, 44.31, 26.51, 13.62.

HPLC: Chiralcel OD-H (hexane/i-PrOH=80/20, flow rate 1 mL/min, λ=210 nm), t$_R$ (major)=7.0 min, t$_R$ (minor)=10.4 min; 92% ee.

[α]$_D^{25}$=26.0 (c=1.5, CHCl$_3$).

HRMS (EI) calcd for C$_{20}$H$_{21}$NO$_7$, m/z 387.1314. found 387.1318.

(1R,2R,3S,4S)-ethyl-1-acetyl-4-hydroxy-3-nitro-4-phenyl-2-o-tolylcyclopentanecarboxylate (7t)

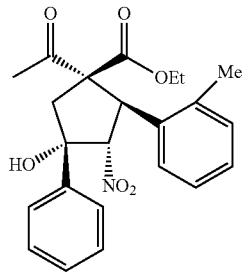 [SMILES: CCOC(=O)[C@]1(C(C)=O)C[C@](O)(c2ccccc2)[C@@H]([N+](=O)[O-])[C@@H]1c1ccccc1C]

The title compound was prepared according to the typical procedure, as described above in 90% yield.

$^1$H-NMR (400 MHz, CDCl$_3$) δ 7.60 (d, J=7.6, 2H), 7.48-7.39 (m, 3H), 7.19-7.18 (m, 4H), 5.78 (d, J=10.4 Hz, 1H), 5.61 (d, J=10.8 Hz, 1H), 3.78-3.72 (m, 1H), 3.65 (s, 1H), 3.43-3.37 (m, 2H), 2.65 (d, J=15.2 Hz, 1H), 2.56 (s, 3H), 2.27 (s, 3H), 0.73 (t, J=6.8 Hz, 3H).

$^{13}$C-NMR (100 MHz, CDCl$_3$) δ 200.61, 169.26, 139.72, 139.02, 135.20, 130.86, 128.86, 128.52, 127.93, 126.61, 126.13, 124.82, 97.39, 81.30, 69.59, 62.14, 46.58, 44.86, 26.32, 20.20, 13.14.

HPLC: Chiralcel OD-H (hexane/i-PrOH=80/20, flow rate 1 mL/min, λ=210 nm), $t_R$ (major)=5.6 min, $t_R$ (minor)=7.2 min; 90% ee.

$[α]_D^{25}$=18.1 (c=1.0, CHCl$_3$).

HRMS (EI) calcd for C$_{23}$H$_{25}$NO$_6$, m/z 411.1678. found 411.1679.

(1R,2R,3S,4S)-ethyl-1-acetyl-4-hydroxy-2-(3-methoxyphenyl)-3-nitro-4-phenylcyclopentane carboxylate (7w)

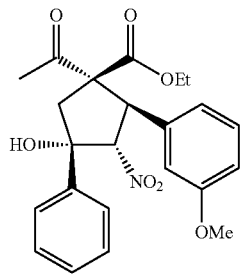 [SMILES: CCOC(=O)[C@]1(C(C)=O)C[C@](O)(c2ccccc2)[C@@H]([N+](=O)[O-])[C@@H]1c1cccc(OC)c1]

The title compound was prepared according to the typical procedure, as described above in 91% yield.

$^1$H-NMR (400 MHz, CDCl$_3$) δ 7.60 (d, J=8.4, 1H), 7.45-7.35 (m, 3H), 7.65-7.63 (m, 3H), 7.24-7.20 (m, 2H), 6.96-6.95 (m, 2H), 6.81 (dd, J=1.6, 8.4 Hz, 1H), 5.74 (d, J=12.4 Hz, 1H), 5.37 (d, J=12.4 Hz, 1H), 3.85-3.76 (m, 3H), 3.74 (d, J=2.0 Hz, 1H), 3.56-3.48 (m, 1H), 3.25 (dd, J=2.0, 14.4 Hz, 1H), 2.54 (d, J=14.4 Hz, 1H), 2.24 (s, 3H), 0.79 (t, J=7.2 Hz, 3H).

$^{13}$C-NMR (100 MHz, CDCl$_3$) δ 200.36, 159.65, 139.65, 135.84, 129.49, 128.87, 128.59, 124.89, 120.53, 114.72, 113.90, 93.43, 81.00, 67.73, 62.25, 55.32, 49.62, 46.48, 26.86, 13.30.

HPLC: Chiralcel OD-H (hexane/i-PrOH=80/20, flow rate 1 mL/min, λ=210 nm), $t_R$ (major)=7.6 min, $t_R$ (minor)=11.6 min; 92% ee.

$[α]_D^{25}$=28.1 (c=1.0, CHCl$_3$).

HRMS (EI) calcd for C$_{23}$H$_{25}$NO$_7$, m/z 427.1626. found 427.1628.

(1R,2R,3S,4S)-ethyl-1-acetyl-4-hydroxy-2-(naphthalen-1-yl)-3-nitro-4-phenylcyclopentane carboxylate (7n)

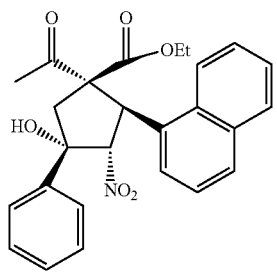 [SMILES: CCOC(=O)[C@]1(C(C)=O)C[C@](O)(c2ccccc2)[C@@H]([N+](=O)[O-])[C@@H]1c1cccc2ccccc12]

The title compound was prepared according to the typical procedure, as described above in 91% yield.

$^1$H-NMR (400 MHz, CDCl$_3$) δ 8.73 (d, J=8.4, 1H), 7.84-7.79 (m, 2H), 7.65-7.63 (m, 3H), 7.53-7.37 (m, 6H), 6.42 (d, J=10.8 Hz, 1H), 5.85 (d, J=10.8 Hz, 1H), 3.82 (d, J=2.4 Hz, 1H), 3.55-3.44 (m, 2H), 3.07-3.02 2.66 (d, J=14.8 Hz, 1H), 2.26 (s, 3H), 0.21 (t, J=7.2 Hz, 3H).

$^{13}$C-NMR (100 MHz, CDCl$_3$) δ 200.86, 169.30, 139.62, 133.83, 132.95, 128.98, 128.91, 128.62, 128.42, 126.89, 126.16, 124.88, 124.74, 124.35, 96.86, 81.38, 69.59, 61.91, 46.41, 43.93, 26.54, 12.60.

HPLC: Chiralcel OD-H (hexane/i-PrOH=80/20, flow rate 1 mL/min, λ=210 nm), $t_R$ (major)=6.9 min, $t_R$ (minor)=8.7 min; 96% ee.

$[α]_D^{25}$=22.1 (c=1.0, CHCl$_3$).

HRMS (EI) calcd for C$_{26}$H$_{25}$NO$_6$, m/z 447.1677. found 447.1678.

(1R,2R,3S,4S)-ethyl-1-acetyl-4-hydroxy-3-nitro-2-(4-nitrophenyl)-4-phenylcyclopentane carboxylate (7r)

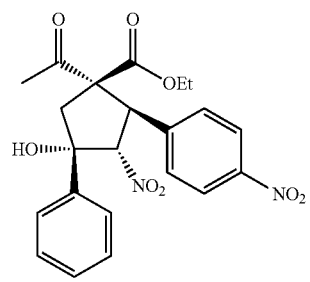 [SMILES: CCOC(=O)[C@]1(C(C)=O)C[C@](O)(c2ccccc2)[C@@H]([N+](=O)[O-])[C@@H]1c1ccc([N+](=O)[O-])cc1]

The title compound was prepared according to the typical procedure, as described above in 90% yield.

$^1$H-NMR (400 MHz, CDCl$_3$) δ 7.18 (d, J=8.0, 2H), 7.64-7.60 (m, 4H), 7.48-7.447 (m, 2H), 7.41-7.37 (m, 1H), 5.80 (d, J=12.4 Hz, 1H), 5.52 (d, J=12.4 Hz, 1H), 3.93-3.80 (m, 1H), 3.54-3.45 (m, 1H), 3.23 (d, J=14.8 Hz, 1H), 2.58 (d, J=14.4 Hz, 1H), 2.25 (s, 3H), 0.80 (t, J=7.2 Hz, 3H).

$^{13}$C-NMR (100 MHz, CDCl$_3$) δ 200.02, 170.01, 147.67, 141.96, 139.21, 129.95, 129.02, 128.84, 124.81, 123.54, 92.49, 81.10, 67.66, 62.51, 49.08, 46.59, 26.82, 13.41.

HPLC: Chiralcel OD-H (hexane/i-PrOH=65/35, flow rate 1 mL/min, λ=210 nm), $t_R$ (major)=6.8 min, $t_R$ (minor)=15.6 min; 91% ee.

$[α]_D^{25}$=19.3 (c=1.2, CHCl$_3$).

HRMS (EI) calcd for C$_{22}$H$_{22}$N$_2$O$_8$, m/z 442.1371. found 442.1375.

(1R,2R,3S,4S)-ethyl-1-acetyl-4-hydroxy-3-nitro-4-phenyl-2-(4-(trifluoromethyl)phenyl)-cyclopentanecarboxylate (7j)

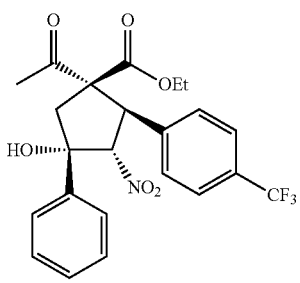 [SMILES: CCOC(=O)[C@]1(C(C)=O)C[C@](O)(c2ccccc2)[C@@H]([N+](=O)[O-])[C@@H]1c1ccc(C(F)(F)F)cc1]

The title compound was prepared according to the typical procedure, as described above in 95% yield.

$^1$H-NMR (400 MHz, CDCl$_3$) δ 7.65-7.58 (m, 6H), 7.49-7.46 (m, 2H), 7.42-7.38 (m, 1H), 5.81 (d, J=12.4 Hz, 1H), 5.50 (d, J=12.4 Hz, 1H), 3.83-3.77 (m, 1H), 3.73 (d, J=2.0 Hz, 1H), 3.54-3.48 (m, 1H), 3.26 (dd, J=2.4, 14.8 Hz, 1H), 2.58 (d, J=14.8 Hz, 1H), 2.26 (s, 3H), 0.76 (t, J=7.2 Hz, 3H).

$^{13}$C-NMR (100 MHz, CDCl$_3$) δ 200.04, 170.12, 139.36, 138.50, 130.45 (q), 129.29, 128.97, 128.76, 125.38 (q), 124.83, 92.61, 81.05, 77.22, 67.70, 62.42, 49.22, 46.47, 26.82, 13.15.

HPLC: Chiralpak AS-H (hexane/i-PrOH=80/20, flow rate 1 mL/min, λ=210 nm), $t_R$ (major)=6.4 min, $t_R$ (minor)=14.5 min; 92% ee.

$[\alpha]_D^{25}$=23.8 (c=1.0, CHCl$_3$).

HRMS (EI) calcd for C$_{23}$H$_{22}$F$_3$NO$_6$, m/z 465.1394. found 465.1395.

(1R,2R,3S,4S)-benzyl-1-acetyl-4-hydroxy-3-nitro-2,4-diphenylcyclopentanecarboxylate (7s)

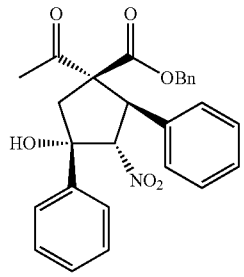 [SMILES: CC(=O)[C@@]1(C(=O)OCc2ccccc2)C[C@](O)(c2ccccc2)[C@@H]([N+](=O)[O-])[C@@H]1c1ccccc1]

To a solution of benzyl 2-acetyl-4-oxo-4-phenylbutanoate (1.0 mmol, 2 eq) and (E)-(2-nitrovinyl)benzene (0.5 mmol, 1 eq) in toluene (0.5 mL) was added catalyst VI (0.05 mmol, 0.1 eq) at 4° C. The resulting mixture was stirred for 36 hours. The product was afforded by flash column chromatography over silica gel (EtOAc:exane=1:5) in 95% yield.

$^1$H-NMR (400 MHz, CDCl$_3$) δ 7.40 (d, J=2.0 Hz, 1H), 7.37-7.24 (m, 11H), 6.90-6.87 (dd, J=2.4, 7.6 Hz, 2H), 5.79 (d, J=12.4 Hz, 1H), 5.43 (d, J=12.4 Hz, 1H), 4.83 (d, J=12.0 Hz, 1H), 4.16 (d, J=12.0 Hz, 1H), 3.80 (s, 1H), 3.26 (d, J=14.8 Hz, 1H), 2.54 (d, J=14.8 Hz, 1H), 2.15 (s, 3H).

$^{13}$C-NMR (100 MHz, CDCl$_3$) δ 200.17, 170.24, 139.70, 134.23, 133.95, 128.88, 128.72, 128.63, 128.59, 128.53, 128.35, 128.29, 124.91, 93.33, 81.05, 68.07, 67.90, 49.71, 46.56, 26.97.

HPLC: Chiralcel OD-H (hexane/i-PrOH=85/15, flow rate 1 mL/min, λ=210 nm), $t_R$ (major)=10.4 min, $t_R$ (minor)=13.2 min; 88% ee.

$[\alpha]_D^{25}$=15.5 (c=1.0, CHCl$_3$).

HRMS (EI) calcd for C$_{27}$H$_{25}$NO$_6$, m/z 459.1677. found 459.1681.

(1R,2R,3S,4S)-ethyl-1-acetyl-4-(4-chlorophenyl)-4-hydroxy-3-nitro-2-phenylcyclopentane carboxylate (7x)

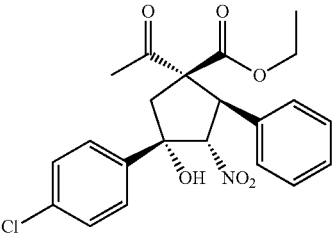 [SMILES: CCOC(=O)[C@]1(C(C)=O)C[C@](O)(c2ccc(Cl)cc2)[C@@H]([N+](=O)[O-])[C@@H]1c1ccccc1]

To a solution of ethyl 2-acetyl-4-oxo-4-(4-chlorophenyl)-butanoate (1.0 mmol, 2 eq) and (E)-(2-nitrovinyl)benzene (0.5 mmol, 1 eq) in toluene (0.5 mL) was added catalyst VI (0.05 mmol, 0.1 eq) at 4° C. The resulting mixture was stirred for 60 hours. The product was afforded by flash column chromatography over silica gel (EtOAc:Hexane=1:5) in 91% yield.

$^1$H-NMR (400 MHz, CDCl$_3$) δ 7.59 (d, J=8.8 Hz, 2H), 7.43-7.28 (m, 7H), 5.74 (d, J=12.4 Hz, 1H), 5.41 (d, J=12.4 Hz, 1H), 3.84 (d, J=1.2 Hz, 1H), 3.82-3.78 (m, 1H), 3.49-3.41 (m, 1H), 3.22 (d, J=15.2 Hz, 1H), 2.54 (d, J=15.2 Hz, 1H), 2.25 (s, 3H), 0.76 (s, 3H).

$^{13}$C-NMR (100 MHz, CDCl$_3$) δ 200.33, 170.30, 138.38, 134.59, 134.09, 129.03, 128.67, 128.57, 128.32, 126.52, 93.23, 80.68, 67.62, 62.34, 49.50, 46.52, 26.90, 13.24.

HPLC: Chiralcel OD-H (hexane/i-PrOH=85/15, flow rate 1 mL/min, λ=220 nm), $t_R$ (major)=6.3 min, $t_R$ (minor)=9.5 min; 91% ee.

$[\alpha]_D^{25}$=40.6 (c=1.5, CHCl$_3$).

HRMS (EI) calcd for C$_{22}$H$_{22}$ClNO$_6$, m/z 431.1132. found 431.1137.

In summary, several cyclization processes based on the use of unsaturated nitro compounds are provided herein. The first is based on an organocatalytic tandem Michael-Henry reaction. The reaction is efficiently catalyzed by readily available 9-amino-9-deoxyepiquinine (VI) to give synthetically useful, highly functionalized chiral cyclohexanes with four stereogenic centers containing two quaternary stereocenters in good to excellent yields (85-94%), excellent enantioselectivities (97% to >99% ee) and high diastereoselectivities (93:7-99:1 dr). The first highly enantioselective Michael addition of α-substituted β-ketoesters to nitroolefins catalyzed by VI is presented and, in particular, the first organocatalytic Henry reaction of common ketones used as acceptors with excellent results. This strategy of developing a practical and efficient tandem Michael-Henry reaction will hopefully spark more efforts into the designing of such organocatalytic reactions.

The second process is based on a highly enantioselective and diastereoselective organocatalytic domino double Michael reaction that provides expedited access toward highly functionalized cyclopentane derivatives. The structure was confirmed by X-ray analysis of adduct 5g. Simple operational procedures, high yields (81-91%), excellent enantioselectivity (90-97% ee), diastereoselectivities (95:5→99:1 dr), and immense potential of synthetic versatility of the products render this new methodology highly appealing for asymmetric synthesis. Further applications of this methodology toward total synthesis of natural products and pharmaceutical agents are currently under active investigation.

The third process provides a facile organocatalytic, enantioselective synthesis of highly functionalized chiral cyclopentanes with four stereogenic centers (two quaternary and two tertiary stereocenters) in excellent yields (90-95%), enantioselectivities (88-96% ee), and complete diastereoselectivities by a domino Michael-Henry reaction strategy. The domino reaction is efficiently catalyzed by readily available catalyst VI (9-amino-9-deoxyepiquinine) to give synthetically valuable multifunctionalized chiral cyclopentanes, where the organocatalytic intramolecular Henry reaction of common ketones is employed for the cyclopentane ring-closing step in excellent stereoselectivities. This domino synthesis is particularly useful in natural product synthesis since many types of biologically active natural substances are known that bear optically active cyclopentane derivatives. This strategy of developing a practical and efficient domino Michael-Henry reaction is expected to spark further efforts into the designing of such organocatalytic domino reactions.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of forming a compound of general formula (33)

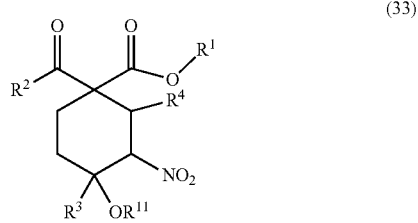

wherein $R^1$ and $R^2$ are independently from one another one of a silyl group, an aliphatic group and an alicyclic group with a main chain having 1 to 20 carbon atoms and 0 to 7 heteroatoms selected from the group consisting of N, O, S, Se and Si, $R^3$ is one of H, a silyl group, an aliphatic group, an alicyclic group, an aromatic group, an arylaliphatic group and an arylalicyclic group with a main chain having 1 to 20 carbon atoms and 0 to 7 heteroatoms selected from the group consisting of N, O, S, Se and Si, and $R^4$ is one of (i) the group —CH=CH—$R^9$, wherein $R^9$ is one of H, a silyl group, an aliphatic group, an alicyclic group, an aromatic group, an arylaliphatic group and an arylalicyclic group with a main chain having 1 to 20 carbon atoms and 0 to 7 heteroatoms selected from the group consisting of N, O, S, Se and Si, (ii) an aromatic group, (iii) an arylaliphatic group and (iv) an arylalicyclic group, the aromatic, arylaliphatic or arylalicyclic group comprising a main chain having 1 to 20 carbon atoms and 0 to 7 heteroatoms selected from the group consisting of N, O, S, Se and Si, $R^{11}$ is one of (i) H, (ii) a silyl group, (iii) an aliphatic group, (iv) an alicyclic group, (v) an aromatic group, (vi) an arylaliphatic group, (vii) an arylalicyclic, the aliphatic, alicyclic, aromatic, arylaliphatic or arylalicyclic group comprising a main chain having 1 to 20 carbon atoms and 0 to 7 heteroatoms selected from the group consisting of N, O, S, Se and Si, (viii) a carbonate group —O—C(O)—O—$R^{17}$, and (ix) a carbamoyl group —O—C(O)—N($R^{17}$)—$R^{18}$, wherein $R^{17}$ and $R^{18}$ are independent from one another H or one of an aliphatic, an alicyclic, an aromatic, an arylaliphatic, and an arylalicyclic group with a main chain of a length of 1 to 20 carbon atoms, comprising 0 to 6 heteroatoms selected from the group consisting of N, O, S, Se and Si, the process comprising:
providing a first compound of the general formula (1),

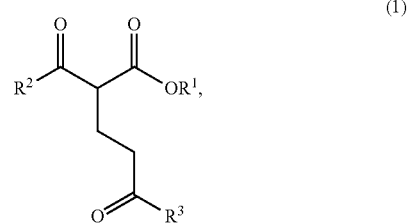

providing a second compound of the general formula (2)

contacting the first compound of formula (1) and the second compound of formula (2) in the presence of a compound of general formula (X),

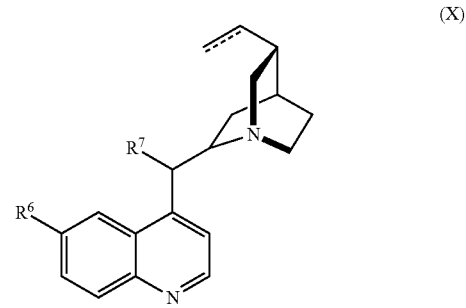

wherein $R^6$ is one of H, OMe, OH, OTf, SH, and NH$_2$, $R^7$ is one of OH and —N($R^8$)H, wherein $R^8$ is one of H, a carbamoyl group, and a thiocarbamoyl group and ≡ represents one of a single and a double bond, and allowing the first and the second compound to undergo a reaction for a sufficient period of time to allow the formation of a compound of general formula (23)

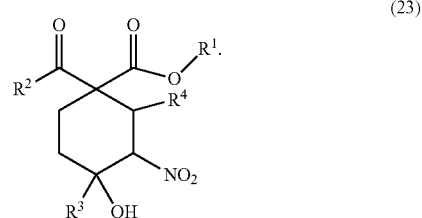

2. The process of claim 1, further comprising contacting the compound of general formula (23) with a compound of general formula $R^{11}$—X, wherein X is one of H, halogen, —CN, —COO$R^{13}$, —COS$R^{13}$ —COSe$R^{13}$ and —CONR$^{14}$R$^{15}$ wherein $R^{13}$ is one of halogen, —CN, an aliphatic, an alicyclic, an aromatic, an arylaliphatic, and an arylalicyclic group with a main chain of a length of 1 to 20 carbon atoms, comprising 0 to 6 heteroatoms selected from the group consisting of N, O, S, Se and Si, and $R^{14}$ and $R^{15}$ are independent from one another one of H, an aliphatic, an alicyclic, an aromatic, an arylaliphatic, and an arylalicyclic group with a main chain of a length of 1 to 20 carbon atoms, comprising 0 to 6 heteroatoms selected from the group consisting of N, O, S, Se and Si, thereby allowing the formation of a compound of general formula (33).

3. The process of claim 1, wherein the compound of general formula (X) is present in a catalytical amount.

4. The process of claim 1, wherein the process is carried out in a suitable solvent.

5. The process of any one of claims 1-4, wherein contacting the first compound of formula (1) and the second compound of formula (2) is carried out at a temperature selected in the range from –40° C. to 40° C.

6. The process of claim 5, wherein contacting the first compound of formula (1) and the second compound of formula (2) is carried out at ambient temperature.

7. The process of claim 1, wherein the process is a process of carrying out an asymmetric reaction, and wherein the compound of general formula (X) is of one of formulas (XA) and (XB),

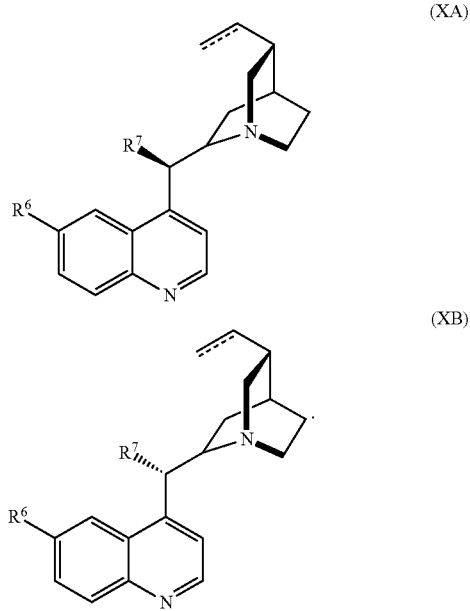

8. The process of claim 7, wherein the compound of general formula (X) is of formula (XA), wherein the compound of general formula (33) is a compound of general formula (34)

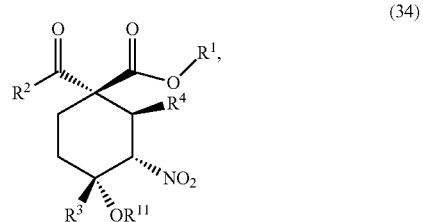

and wherein allowing the first and the second compound to undergo a reaction for a sufficient period of time comprises allowing the formation of a compound of general formula (3)

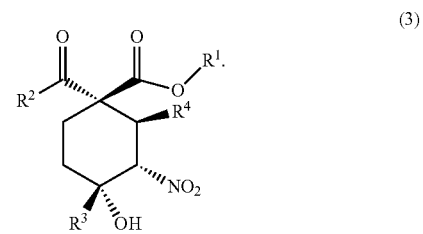

9. The process of claim 4, wherein the process is carried out in a polar liquid.

10. The process of claim 4, wherein the process is carried out in a non-polar liquid.

11. The process of claim 1, wherein the formed compound of general formula (33) is (1R,2R,3S,4R)-ethyl-1-acetyl-4-hydroxy-4-methyl-3-nitro-2-phenyl cyclohexane carboxylate represented by the following structure:

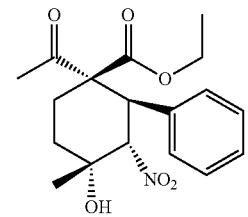

* * * * *